United States Patent [19]
Fukumi et al.

[11] Patent Number: 5,470,851
[45] Date of Patent: Nov. 28, 1995

[54] THIAZOLIDINECARBOXYLIC ACID AMIDE DERIVATIVES AND THEIR THERAPEUTIC USES

[75] Inventors: Hiroshi Fukumi; Toshiaki Sakamoto; Mitsuo Sugiyama; Takeshi Yamaguchi; Takeshi Oshima; Fumitoshi Asai; Yasuteru Iijima, all of Hiromachi, Japan

[73] Assignee: Sankyo Company, Limited, Tokyo, Japan

[21] Appl. No.: 129,774

[22] Filed: Sep. 30, 1993

Related U.S. Application Data

[63] Continuation-in-part of Ser. No. 997,357, Dec. 28, 1992, abandoned, Ser. No. 95,313, Jul. 21, 1993, abandoned, and Ser. No. 974,187, Nov. 10, 1992, abandoned, said Ser. No. 95,313, is a continuation of Ser. No. 3,850, Jan. 11, 1993, abandoned, which is a continuation of Ser. No. 720,639, Jun. 25, 1991, abandoned.

[30] Foreign Application Priority Data

| Jun. 27, 1990 | [JP] | Japan | 2-169479 |
| Dec. 27, 1991 | [JP] | Japan | 3-345736 |
| Mar. 13, 1992 | [JP] | Japan | 4-054698 |

[51] Int. Cl.⁶ ................ C07D 417/04; C07D 417/14; C07D 487/04; A61K 31/55

[52] U.S. Cl. ............. 514/214; 514/218; 514/219; 514/252; 514/318; 514/333; 514/342; 540/555; 540/575; 540/578; 540/579; 544/364; 546/193; 546/194; 546/280; 546/256

[58] Field of Search .................... 540/555, 575, 540/578, 579; 544/364; 546/193, 194, 256, 280; 514/214, 218, 219, 252, 318, 333, 342

[56] References Cited

U.S. PATENT DOCUMENTS

| 4,788,205 | 11/1988 | Copper et al. | 514/333 |
| 4,948,795 | 8/1990 | Mase et al. | 514/252 |
| 4,987,132 | 1/1991 | Mase et al. | 514/252 |

FOREIGN PATENT DOCUMENTS

| 0258033 | 8/1987 | European Pat. Off. | 546/210 |
| 0279681 | 8/1988 | European Pat. Off. | 544/364 |
| 0350145 | 3/1989 | European Pat. Off. | 544/364 |
| 0421823 | 4/1991 | European Pat. Off. | |
| 0447857 | 9/1991 | European Pat. Off. | |
| 463873 | 1/1992 | European Pat. Off. | |
| WO89/10363 | 11/1989 | WIPO | |

OTHER PUBLICATIONS

Fukimi et al, Chemical Abstract 116: 194335v (1992).

Primary Examiner—Philip I. Datlow
Attorney, Agent, or Firm—Frishauf, Holtz, Goodman, Langer & Chick

[57] ABSTRACT

Thiazolidinecarboxylic acid amides having combined anti-allergic and antiasthmatic activities with an antagonist activity against platelet Activating Factor and having the following general formula (I)

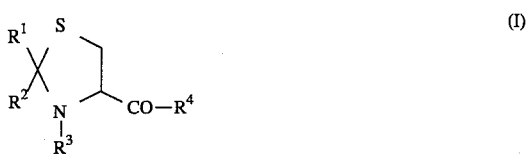

wherein R⁴ is

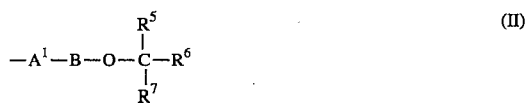

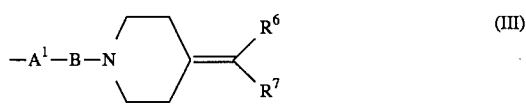

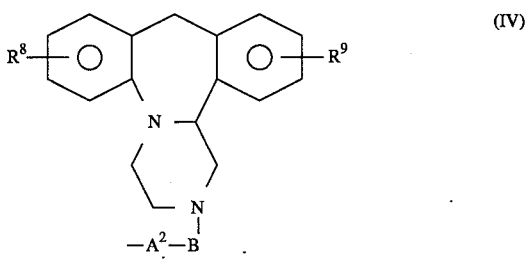

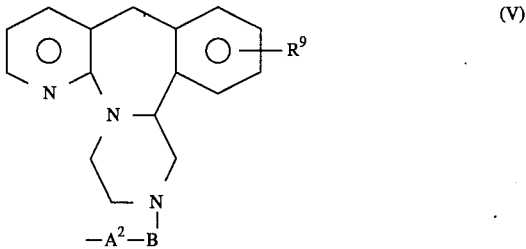

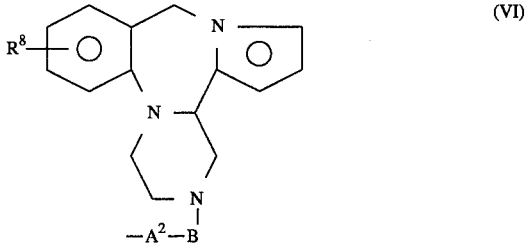

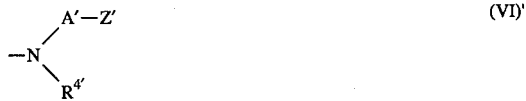

90 Claims, No Drawings

THIAZOLIDINECARBOXYLIC ACID AMIDE DERIVATIVES AND THEIR THERAPEUTIC USES

This is (1) a continuation-in-part of U.S. application Ser. No. 07/997,357 filed Dec. 28, 1992 now abandoned the entire disclosure of which is hereby incorporated by reference; and (2) a continuation-in-part of U.S. application Ser. No. 08/095,313 filed Jul. 21, 1993 now abandoned which is a continuation of Ser. No. 08/003,850 filed Jan. 11, 1993 now abandoned which is a continuation application of U.S. application Ser. No. 07/720,639 filed Jun. 25, 1991, now abandoned the entire disclosure of which is hereby incorporated by reference. This application is a continuation-in-part of U.S. application Ser. No. 07/974,187 filed Nov. 10, 1992, now abandoned.

BACKGROUND OF THE INVENTION

The present invention relates to a series of new pyridylthiazolinecarboxylic acid amide compounds which we have found to have a valuable combination of antiallergic and antiasthmatic activities with an antagonist activity against Platelet Activating Factor (PAF).

A number of compounds having anti-allergic activities are known, and it is also known that compounds having a heterocyclylalkylamide structure have anti-allergic activity (see, for example, U.S. Pat. No. 4,965,266, Chemical Pharmaceutical Bulletin, 37, p. 1256 (1989), etc.).

PAF (platelet activating factor) exhibits a strong platelet activating and aggregating effect, from which is derives its name. It has, however, in recent years been seen to be a potentially crucial mediator in a wide variety of pathological processes. Thus, it also has a hypotensive effect and increases vasopermeability; it is believed to be an active agent in the induction of the shock state (for example endotoxin-induced shock or anaphylactic shock) and to act as a mediator of inflammatory disease. It has also been found to play an important role in nephritis, myocardial infarction, angina pectoris, asthma, cardiac and systemic anaphylaxis, gastric and intestinal ulceration, psoriasis and immune and renal disorders. In addition, PAF inhibitors also inhibit eosinophile accumulation and could, therefore, be used for the treatment of late allergic reaction.

However, although it has recently appeared to us that it would be desirable to develop anti-allergic agents which not only have anti-allergic activity but also have activities which cooperate with the anti-allergic activity, such as PAF antagonism, no drugs satisfying this demand have yet been put on the market.

For example, while is known that certain thiazolidine derivatives, for example Compound (A) shown below (which is described in U.S. Pat. No. 4,987,132), have PAF antagonism, their anti-allergic activity is very weak. Other prior art compounds described in the same US Patent have anti-PAF activities, but their anti-allergic activity is either also very weak or effectively non-existent.

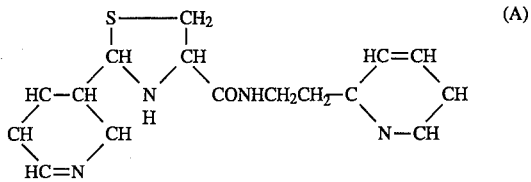

Japanese Patent Application Kokai No. Hei 2-179 (equivalent to Australian Patent No. 9214013) discloses a number of pyridylthiazolinecarboxylic acid amide compounds which are said to be PAF antagonists, such as the compound of formula (A):

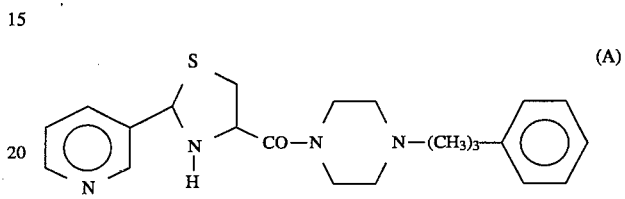

However, the antiallergic activity of these compounds is very weak.

We have now surprisingly found a series of compounds which combine strong anti-allergic, anti-asthmatic and anti-PAF activities, all in the same compound, a combination of activities that, so far as we are aware, has not hitherto been known. Moreover, the compounds of the invention have sufficiently low toxicities to render them of potential value for the treatment and prophylaxis of disorders in, *inter alia,* human beings.

BRIEF SUMMARY OF INVENTION

It is, accordingly, an object of the invention to provide a series of new pyridlthiazolidinecarboxylic acide amide derivatives.

It is further, and more specific, object of the invention to provide such compounds which not only have anti-allergic and anti-asthmatic activities but also have anti-PAF activity.

Other objects and advantages will become apparent as the description proceeds.

The compounds of the present invention are those pyridlthiazolidinecarboxylic acid amide derivatives of formula (I):

wherein
$R^1$ represents a pyridyl group which is unsubstituted or is substituted by at least one substituent selected from the group consisting of alkyl groups having from 1 to 4 carbon atoms and alkoxy groups having from 1 to 4 carbon atoms;
$R^2$ represents a hydrogen atom, or a pyridyl group which is unsubstituted or is substituted by at least one substituent selected from the group consisting of alkyl groups having from 1 to 4 carbon atoms and alkoxy groups having from 1 to 4 carbon atoms;
$R^3$ represents a hydrogen atom or an alkyl group having from 1 to 4 carbon atoms;

$R^4$ represents a group of formula (II), (III), (IV), (V) (VI) or (VI):

$$-A^1-B-O-\underset{\underset{R^7}{|}}{\overset{\overset{R^5}{|}}{C}}-R^6 \qquad (II)$$

$$-A^1-B-N\diagup\diagdown=\overset{R^6}{\underset{R^7}{\diagup}} \qquad (III)$$

(IV) [tricyclic structure with $R^8$, $R^9$, N, and $-A^2-B$]

(V) [tricyclic structure with $R^9$, N, N, and $-A^2-B$]

(VI) [tricyclic structure with $R^8$, N, N, and $-A^2-B$]

$$-N\diagdown\underset{R^{4'}}{\diagup}\overset{A'-Z'}{} \qquad (VI)'$$

wherein:
$R^5$ represents a hydrogen atom or an alkyl group having from 1 to 4 carbon atoms;
$R^6$ and $R^7$ are independently selected from the group consisting of:
  unsubstituted phenyl groups,
  substituted phenyl groups which are substituted by at least one substituent selected from the group consisting of alkyl groups having from 1 to 4 carbon atoms, haloalkyl groups having from 1 to 4 carbon atoms and having at least one halogen atom, alkoxy groups having from 1 to 4 carbon atoms and halogen atoms,
  cycloalkyl groups having from 3 to 6 ring carbon atoms, and
  aromatic heterocyclic groups having 5 to 6 ring atoms of which from 1 to 3 are hetero-atoms selected from the group consisting of nitrogen, oxygen and sulfur atoms and the remainder are carbon atoms;
$R^8$ and $R^9$ are independently selected from the group consisting of hydrogen atoms, alkyl groups having from 1 to 4 carbon atoms, haloalkyl groups having from 1 to 4 carbon atoms and having at least one halogen atom, alkoxy groups having from 1 to 4 carbon atoms, hydroxy groups and halogen atoms;
$A^1$ represents a group of formula (VII) or (VIII):

$$-N-D-N- \qquad (VII)$$
$$\phantom{-N-}\underset{R^{10}}{|}\phantom{-D-}\underset{R^{11}}{|}$$

$$-N\diagdown\underset{(CH_2)_n}{\diagup}N- \qquad (VIII)$$

where:
$R^{10}$ and $R^{11}$ are independently selected from the group consisting of hydrogen atoms and alkyl groups having from 1 to 4 carbon atoms;
D represents an alkylene or alkylidene group having from 2 to 5 carbon atoms; and
n is 2 or 3;
$A^2$ represents a group of formula (VIII), above, or (IX):

$$-\underset{\underset{R^{10}}{|}}{N}- \qquad (IX)$$

where $R^{10}$ is as defined above; and
B represents an alkylene or alkylidene group having from 2 to 4 carbon atoms; or
—$A^2$—B— represents a single bond;
$R^{4'}$ represents a hydrogen atom or an alkyl group having from 1 to 4 carbon atoms;
A' represents an alkylene or alkylidene group having from 2 to 7 carbon atoms; and
Z' represents a group of formula:

$$-N\diagdown\underset{(CH_2)_m}{\diagup}N-CH\diagup\overset{R^{7'}}{\diagdown_{R^{8'}}} \qquad (II)'$$
with $H_2C-CH_2$ bridging $$-N\diagdown\underset{H_2C-CH_2}{\overset{H_2C-CH_2}{\diagup}}CH-E'-CH\diagup\overset{R^{7'}}{\diagdown_{R^{8'}}} \qquad (III)'$$

$$-N\diagdown\underset{H_2C-CH_2}{\overset{H_2C-CH_2}{\diagup}}C=C\diagup\overset{R^{7'}}{\diagdown_{R^{8'}}} \qquad (IV)'$$

$$-N\diagdown\underset{H_2C-CH_2}{\overset{H_2C-CH_2}{\diagup}}CH-\underset{\underset{R^{7'}}{|}}{\overset{\overset{OH}{|}}{C}}-R^{8'} \qquad (V)'$$

and groups of formulae (II)', (III)', (IV)' and (V)' in which one or more of the ring atoms is substituted by an alkyl group having from 1 to 4 carbon atoms;
in which:
$R^{7'}$ and $R^{8'}$ are independently selected from the group consisting of unsubstituted phenyl groups, substituted phenyl groups which are substituted by at least one substituent selected from the group consisting of substituents (a), defined below, and aromatic heterocyclic groups which have 5 or 6 ring atoms of which 1 or 2 are hetero-atoms selected from the group consisting of nitrogen, oxygen and sulfur hetero-atoms, said aromatic heterocyclic groups being unsubstituted or being substituted by at least one substituent selected from the group consisting of substituents (a), defined below;

said substituents (a) are selected from the group consisting of alkyl groups having from 1 to 4 carbon atoms, alkoxy groups having from 1 to 4 carbon atoms, halogen atoms and haloalkyl groups having from 1 to 4 carbon atoms;

E' represents a direct carbon-carbon single bond or an oxygen atom (—O—); and m is 2 or 3;

with the proviso that when $R^4$ is (VI)', $R^2$ can also be an alkyl group having 1–4 carbon atoms; and $R^3$ can also be selected from the group consisting of an alkoxycarbonyl group having from 2 to 5 carbon atoms, an aralkyloxycarbonyl group in which the alkyl part has from 1 to 4 carbon atoms and the aryl part is as defined below, an aryloxycarbonyl group in which the aryl part is as defined below, an aliphatic carboxylic acyl group having from 1 to 5 carbon atoms, an aliphatic carboxylic acyl group which has from 2 to 5 carbon atoms and which is substituted by at least one halogen atom, an arylcarbonyl group in which the aryl part is as defined below, an alkylsulfonyl group having from 1 to 4 carbon atoms, an arylsulfonyl group in which the aryl part is as defined below, or a group of formula —B'—$NR^{5'}R^{6'}$, in which B' represents an alkylene or alkylidene group having from 2 to 4 carbon atoms; and $R^{5'}$ and $R^{6'}$ are independently selected from the group consisting of hydrogen atoms and alkyl groups having from 1 to 4 carbon atoms;

said aryl groups have from 6 to 10 ring atoms and are unsubstituted or are substituted by at least one substituent selected from the group consisting of alkyl groups having from 1 to 4 carbon atoms, alkoxy groups having from 1 to 4 carbon atoms and halogen atoms;

and pharmaceutically acceptable salts thereof.

The invention also provides a composition for the treatment or prophylaxis of histamine- or PAF- related disorders, such as allergies or asthma, in a mammal, e.g. a human being, which comprises an effective amount of an anti-histamine or anti-PAF agent in admixture with a pharmaceutically acceptable carrier or diluent, wherein the anti-histamine or anti-PAF agent is at least one compound selected from the group consisting of compounds of formula (I) and pharmaceutically acceptable salts thereof.

The invention also provides a method for the treatment or prophylaxis of histamine-related disorders, such as allergies or asthma, in a mammal, e.g. a human being, which comprises administering to said mammal an effective amount of an anti-histamine, wherein the anti-histamine is at least one compound selected from the group consisting of compounds of formula (I) and pharmaceutically acceptable salts thereof.

The invention also provides a novel process for the preparation of compounds of formula (I) and pharmaceutically acceptable salts thereof The invention also provides novel processes for the preparation of the compounds of the present invention, which processes are described in more detail hereafter.

DETAILED DESCRIPTION OF INVENTION

In the compounds of the present invention, when $R^4$ is a group of Formula (II)–(VI), where the substituent on the pyridyl group represented by $R^1$ or $R^2$ is an alkyl group, or where $R^3$, $R^5$, $R^8$, $R^9$, $R^{10}$ and $R^{11}$ represents an alkyl group, or where the substituent on the substituted phenyl group represented by $R^6$ and $R^7$ is an alkyl group, this may be a straight or branched chain alkyl group having from 1 to 4 carbon atoms. Examples of such groups include the methyl, ethyl, propyl, isopropyl, butyl, isobutyl, sec-butyl and t-butyl groups, of which the methyl, ethyl, propyl, isopropyl, butyl and sec-butyl groups are preferred, the methyl and ethyl group being more preferred, and the methyl group being most preferred.

Where the substituent on the pyridyl group represented by $R^1$ or $R^2$ is an alkoxy group, or where $R^8$ and $R^9$ represents an alkoxy group, or where the substituent on the substituted phenyl group represented by $R^6$ or $R^7$ is an alkoxy group, this may be a straight or branched chain alkoxy group having from 1 to 4 carbon atoms. Examples of such groups include the methoxy, ethoxy, propoxy, isopropoxy, butoxy, isobutoxy, sec-butoxy and t-butoxy groups, of which the methoxy, ethoxy, propoxy, isopropoxy, butoxy and isobutoxy groups are preferred, the methoxy and ethoxy groups being more preferred, and the methoxy group being most preferred.

Where $R^1$ or $R^2$ represents a substituted pyridyl group, the number of substituents is limited only by the number of positions capable of being substituted (i.e. 4), and possibly by steric constraints. In general, from 1 to 3 substituents are preferred, 1 or 2 substituents being more preferred.

The pyridyl group may be 2-, 3- and 4- pyridyl groups.

$R^1$ is preferably an unsubstituted pyridyl group or a substituted pyridyl group having at least one substituent selected from the group consisting of alkyl groups which have from 1 to 4 carbon atoms, and more preferably having 0 or 1 such substituent, and is most preferably an unsubstituted pyridyl group.

$R^2$ is preferably a hydrogen atom.

$R^3$ is preferably a hydrogen atom, a methyl group or an ethyl group, more preferably a hydrogen atom or a methyl group.

$R^5$ is preferably a hydrogen atom, a methyl group or an ethyl group, more preferably a hydrogen atom or a methyl group, and most preferably a hydrogen atom.

Where $R^8$ or $R^9$ or the substituent on the phenyl group represented by $R^6$ and $R^7$ is a haloalkyl group, the alkyl part may be a straight or branched chain alkyl group having from 1 to 4 carbon atoms. This is substituted by one or more halogen atoms, for example fluorine, chlorine, bromine or iodine atoms. There is no particular limitation on the number of halogen substituents, except such as may be imposed by the number of substitutable positions and possibly by steric constraints. Thus, the maximum number of halogen atoms is 3 for the methyl group, 5 for the ethyl group, 7 for the propyl groups and 9 for the butyl groups, However, in general, from 1 to 5 halogen atoms are preferred (except for halomethyl groups, where from 1 or 3 are preferred), from 1 to 3 halogen atoms being more preferred. Examples of such haloalkyl groups include the fluoromethyl, chloromethyl, bromomethyl, iodomethyl, 2-fluoroethyl, 2-chloroethyl, 3-fluoropropyl, 3-chloropropyl, 4-fluorobutyl, 4-chlorobutyl, trifluoromethyl, trichloromethyl, 2,2,2-trifluoroethyl and 2,2,2-trichloroethyl groups, of which we prefer the fluoromethyl, chloromethyl and trisfluoromethyl groups, more preferably the trifluoromethyl group.

$R^{10}$ and $R^{11}$ are the same or different and each is preferably a hydrogen atom, a methyl group or an ethyl group, more preferably a methyl group or an ethyl group.

Where $R^8$ or $R^9$ or the substituent on the phenyl group represented by $R^6$ or $R^7$ is a halogen atom, this may be, for example, a fluorine, chlorine, bromine or iodine atom, preferably a fluorine or chlorine atom.

$R^8$ and $R^9$ are the same or different and each is preferably a hydrogen atom, a halogen atom, a methyl group, a methoxy group, an ethyl group, an ethoxy group, a trifluoromethyl group or a hydroxy group. Where $R^8$ or $R^9$ is other than a hydrogen atom, it is preferably at the 7-, 8-, 12- or 13- position of the group of formula (IV), (V) or (VI).

Where $R^6$ or $R^7$ is a cycloalkyl group, this has from 3 to 6 ring carbon atoms, and examples include the cyclopropyl, cyclobutyl, cyclopentyl and cyclohexyl groups, of which we prefer the cyclopentyl and cyclohexyl groups.

Where $R^6$ and $R^7$ is a heterocyclic group, this is an aromatic heterocyclic group containing 5 or 6 ring atoms, of which from 1 to 3, preferably 1 or 2, are hetero-atoms selected from the group consisting of nitrogen, oxygen and sulfur atom. Where there are three hetero-atoms, these may be the same or different and they are selected from nitrogen, oxygen and sulfur atoms; however, more preferably one or two are nitrogen atoms and the other is a nitrogen, oxygen or sulfur atom. Where there are two hetero-atoms, these may be the same or different and they are selected from nitrogen, oxygen and sulfur atoms; however, more preferably one is a nitrogen atom and the other is a nitrogen, oxygen or sulfur atom. Most preferably, there is a single hetero-atom. Examples of such groups include the furyl, thienyl, pyrrolyl, pyridyl, thiazolyl, isothiazolyl, oxazolyl, isoxazolyl, imidazolyl, pyrazolyl, pyrazinyl, pyridazinyl, pyrimidinyl and furazanyl groups, preferably the pyrrolyl, pyridyl, pyrimidinyl, pyrazinyl, furyl, thienyl, oxazolyl, isoxazolyl, thiazolyl, isothiazolyl or imidazolyl groups, and more preferably the furyl, thienyl and pyridyl groups.

B represents an alkylene or alkylidene group having from 2 to 4 carbon atoms, which may be straight or branched chain group. Examples of such groups include the ethylene, ethylidene, trimethylene, propylene, isopropylidene, cetramethylene and 2-methyltrimethylene groups, preferably the ethylene, trimethylene, propylene, tetramethylene and 2-methyltrimethylene groups, more preferably the ethylene and trimethylene groups, most preferably the ethylene group.

D represents an alkylene or alkylidene group having from 2 to 5 carbon atoms, which may be a straight or branched chain group. Examples of such groups include the ethylene, ethylidine, trimethylene, propylene, isopropylidene, tetramethylene, 2-methyltrimethylene and pentamethylene groups, preferably the ethylene, trimethylene, propylene, tetramethylene, 2-methyltrimethylene and pentamethylene groups, more preferably the ethylene, trimethylene or tetramethylene group.

Where $R^4$ represents a group of Formula (II):

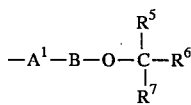
(II)

preferred examples of the group represented by the formula (X):

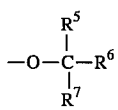
(X)

include the diphenylmethoxy, α-(o-,m- and p-fluorophenyl)benzyloxy, α-(o-, m- and p- chlorophenyl)benzyloxy, bis(o-, m- and p- fluorophenyl)methoxy, α-(o-, m- and p-fluorophenyl)- o-, m- and p- chlorobenzyloxy, α-(o-, m- and p- fluorophenyl)-o-, m- and methylbenzyloxy, α-(o-, m- and p- fluorophenyl)-o-, m- and p- methoxybenzyloxy, bis(o-, m- and p- chlorophenyl)methoxy, α- (o-, m- and p- chlorophenyl)-o-, m- and p- methylbenzyloxy, α- (o-, m- and p- chlorophenyl)-o-, m- and p- methoxybenzyloxy, α-(o-, m- and p- methoxyphenyl)benzyloxy, bis(o-, m- and p- methoxyphenyl)methoxy, α-(o-, m- and p- methylphenyl)benzyloxy, di(o-, m- and p- methylphenyl)methoxy, α-(2-, 3- or 4-pyridyl)benzyloxy, α-(2-, 3- or 4-pyridyl)-o-, m- and p-methylbenzyloxy, α-(2-, 3- or 4-pyridyl)-o-, m- and p-methoxybenzyloxy, α-(2-, 3- or 4-pyridyl)-o-, m- and p-trifluoromethylbenzyloxy, α-(2-, 3- or 4pyridyl)-o-, m- and p- chlorobenzyloxy, α-(2-, 3- or 4- pyridyl)-o-, m- and p-fluorobenzyloxy, α-(2- or 3- thienyl)benzyloxy, α-(2- or 3-thienyl)-o-, m- and p- methylbenzyloxy, α-(2- or 3- thienyl)-o-, m- and p- methoxybenzyloxy, α-(2- or 3- thienyl)-o-, m- and p- trifluoromethylbenzyloxy, α-(2- or 3- thienyl)-o-, m- and p- chlorobenzyloxy, α-(2- or 3- thienyl) -o-, m- and p-fluorobenzyloxy, α-(2- or 3- furyl)benzyloxy, α-(2- or 3-furyl)-o-, m- and p- methylbenzyloxy, α-(2- or 3- furyl)-o-, m- and p- methoxybenzyloxy, α-(2- or 3- furyl)-o-, m- and p- trifluoromethylbenzyloxy, α-(2- or 3- furyl)-o-, m- and p-chlorobenzyloxy, α-(2- or 3- furyl)-o-, m- and p- fluorobenzyloxy, α-(2-, 3- or 4- pyridyl)-α-(2- or 3- thienyl)methoxy, α,α-di(2-, 3- or 4- pyridyl)methoxy, α-(2-, 3- or 4- pyridyl)-α-(2- or 3- furyl)methoxy, α-cyclohexylbenzyloxy, α-cyclohexyl-o-, m- and p- methylbenzyloxy, α-cyclohexyl-o-, m- and p- methoxybenzyloxy, α-cyclohexyl-o-, m- and p- trifluoromethylbenzyloxy, α-cyclohexyl-o-, m- and p- chlorobenzyloxy, α-cyclohexyl-o-, m- and p- fluorobenzyloxy, α-cyclohexyl-α-(2- or 3- thienyl)methoxy, α-cyclohexyl-α-(2- or 3- furyl))methoxy, 4-(diphenylmethylene)- piperidinyl, 4-[α-(o-, m- and p- fluorophenyl)-α-phenylmethylene] piperidinyl, 4-[α,α- bis(o-, m- and p-fluorophenyl)methylene]piperidinyl, 4-[α-(o-, m- and p-chlorophenyl)-α-phenylmethylene]piperidinyl, 4-[α,α-bis(o-, m- and p- chlorophenyl)methylene]piperidinyl, 4-[α-(o-, m- and p- methylphenyl)-α-phenylmethylene]piperidinyl, 4-[α,α-di(o-, m- and p- methylphenylmethylene] piperidinyl, 4-(o-, m- and p- methoxyphenyl)-α-(o-, m- and p- methylphenyl)methylene]piperidinyl, 4-[α,α- bis(o-, m- and p- methoxyphenyl)- methylene]piperidinyl, 4-[α-(o-, m- and p- methoxyphenyl)-α-phenylmethylene]piperidinyl, 4-[α-(2-, 3- or 4- pyridyl)-α-phenylmethylene]piperidinyl, 4-[α-(2-, 3- or 4- pyridyl)-α-(o-, m- and p- methylphenyl)methylene]piperidinyl, 4-[α-(2-, 3- or 4- pyridyl)-α-(o-, m- and p- methoxyphenyl)methylene]piperidinyl, 4-[α-(2-, 3- or 4- pyridyl-α-(o-, m- and p- trifluoromethylphenyl)methylene]piperidinyl, 4-[α-(2-, 3- or 4- pyridyl)-α-(o-, m- and p- chlorophenyl)methylene]piperidinyl, 4-[α-(2-, 3- or 4-pyridyl)-α-(o-, m- and p- fluorophenyl)methylene]piperidinyl, 4-[α-(2- or 3- thienyl)-α-phenylmethylene]piperidinyl, 4-[α-(2- or 3- thienyl)-α-(o-, m- and p- methylphenyl)methylene]piperidinyl, 4-[α-(2- or 3- thienyl)-α-(o-, m- and p-methoxyphenyl)methylene]piperidinyl, 4-[α-(2- or 3- thienyl)-α-(o-, m- and p- trifluoromethylphenyl)methylene]piperidinyl, 4-[α-(2- or 3- thienyl)-α-(o-, m- and p- chlorophenyl)methylene]piperidinyl, 4-[α-(2- or 3- thienyl)-α-(o-, m- and p- fluorophenyl)methylene]piperidinyl, 4-[α-(2- or 3-furyl)-α-phenylmethylene]piperidinyl, 4-[α(2- or 3-furyl)-α-(o-, m- and p- methylphenyl)methylene]piperidinyl, 4-[α-(2- or 3-furyl)-α-(o-, m- and p- methoxyphenyl)methylene] piperidinyl, 4-[α-(2- or 3-furyl)-α-(o-, m- and p- trifluoromethylphenyl)methylene]piperidinyl, 4-(α-(2- or 3-furyl)-α-(o-, m- and p- chlorophenyl)methylene]piperidinyl, 4-[α-(2- or 3- furyl)-α-(o-, m- and p- fluorophenyl)methylene]piperidinyl, 4-[α-(2-, 3- or 4pyridyl)-α-(2-or 3- thienyl)methylene]piperidinyl, 4-[α,α-di(2-, 3- or 4- pyridyl)methylene]piperidinyl, 4-[α-(2-, 3- or 4- pyridyl)-α-(2- or 3-furyl)methylene]piperidinyl, 1,1-diphenylethoxy, 1,1-bis(o-, m- and p- fluorophenyl)ethoxy, α-(o-, m- and p- fluorophenyl)-α-methylbenzyloxy, α-(o-, m- and p- chlorophenyl)-α-methylbenzyloxy, α-(o-, m- and p- chlorophenyl)-α-methyl-o-, m- and p- chlorobenzyloxy, α-(o-, m- and p- methylphenyl)-α-methylbenzyloxy, α-(o-, m- and p- methylphenyl)-α-methyl-o-, m- and p- methylbenzyloxy, α-(o-, m- and p- methoxyphenyl)-α-methylbenzyloxy, α-(2-, 3- or 4-pyridyl)-α- methylbenzyloxy, α-(2-, 3- or 4-pyridyl)-α-methyl-o-, m- and p- chlorobenzyloxy, α-(2-, 3- or 4-pyridyl)-α-methyl-o-, m- and p- fluorobenzyloxy, α-(2- or 3- thienyl)-α-methylbenzyloxy, α-(2- or 3- thienyl)-α-methyl-o-, m- and p- chlorobenzyloxy, α-(2- or 3- thienyl)-α-methyl-o-, m- and p- fluorobenzyloxy, α-(2- or 3- furyl)-α-methylbenzyloxy, α-(2- or 3- furyl)-α-methyl-o-, m- and p- chlorobenzyloxy and α-(2- or 3- furyl)-α-methyl-o-, m- and p- fluorobenzyloxy groups.

More preferred groups which may be represented by the formula (X) include the diphenylmethoxy, bis(o-, m- and p- fluorophenyl)methoxy, α-(o-, m- and p- fluorophenyl)-o-, m- and p- chlorobenzyloxy, bis(o-, m- and p- chlorophenyl)methoxy, α-(o-, m- and p- chlorophenyl)benzyloxy, α-(o-, m- and p- fluorophenyl)benzyloxy, α-(o-, m- or p- methylphenyl)benzyloxy, α-(2-, 3- or 4- pyridyl)benzyloxy, (2-, 3- or 4- pyridyl)-o-, m- and p- chlorobenzyloxy, (2-, 3- or 4- pyridyl)-o-, m- and p- fluorobenzyloxy, 4-(diphenylmethylene)piperidinyl, 4-[α-(o-, m- and p-fluorophenyl)-α-phenylmethylene]piperidinyl, 4-(α,α-bis(o-, m- and p- fluorophenyl)-methylene]piperidinyl, 4-[α-(o-, m- and p-chlorophenyl)-α-phenylmethylene]piperidinyl, 4-[α-(2- or 3- thienyl)-α-phenylmethylene]piperidinyl, 4-(2- or 3- thienyl)-α-(o-, m- and p- fluorophenyl)methylene]piperidinyl, 1,1-diphenylethoxy, 1,1-bis(o-, m- and p- fluorophenyl)ethoxy, 1-(o-, m- and o- fluorophenyl)-1-phenylethoxy and α-(o-, m- and p- chlorophenyl)-α-methylbenzyloxy groups.

Still more preferred groups which may be represented by the formula (X) include the diphenylmethoxy, bis(o-, m- and p- fluorophenyl)methoxy, α-(o-, m- and p- fluorophenyl)-o-, m- and p- chlorobenzyloxy, bis(o-, m- and p- chlorophenyl)methoxy, α-(o-, m- and p- chlorophenyl)benzyloxy, α-(o-, m- and p- fluorophenyl)benzyloxy, α-(o-, m- or p- methylphenyl)benzyloxy, α-(2-, 3- or 4- pyridyl)benzyloxy, α-(2-, 3- or 4- pyridyl)-o-, m- and p- chlorobenzyloxy and α-(2-, 3- or 4- pyridyl)-o-, m- and p- fluorobenzyloxy groups.

The compounds of the present invention contain at least one basic nitrogen atom in their molecules, and can, therefore, form acid addition salts. There is no particular limitation on the nature of the acid employed to form such salts, provided that, where the salt is to be used for therapeutic purposes, it is pharmaceutically acceptable, that it is not more toxic (or unacceptably more toxic) or less active (or unacceptably less active) than the parent compound. On the other hand, where the salt is to be used for other purposes, e.g. for the preparation of other, and possibly more active, compounds, even this restriction does not apply. Examples of such acid addition salts include: salts with mineral acids, especially hydrohalic acids (such as hydrofluoric acid, hydrobromic acid, perchloric acid, hydroiodic acid or hydrochloric acid), nitric acid, carbonic acid, sulfuric acid of phosphoric acid; salts with lower alkylsulfonic acids, such as mechanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. Of these salts, we prefer the hydrochlorides, fumarates, oxalates and maleates.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. We particularly prefer those compounds in which the carbon atom at the 4-position of the thiazolidine ring has the R-configuration.

A preferred class of compounds of the present invention are those compounds of formula (I) in which:
$R^1$, $R^2$ and $R^3$ are as defined above;
$R^4$ represents a group of formula (II) or (III), wherein $R^5$, $R^6$, $R^7$, $A^1$ and 3 are as defined above;
and pharmaceutically acceptable salts thereof.

An alternative preferred class of compounds of the present invention are those compounds of formula (I) in which:
$R^1$, $R^2$ and $R^3$ are as defined above;
$R^4$ represents a group of formula (IV), (V) or (VI), wherein $R^8$, $R^9$, $A^2$ and B are as defined above;
and pharmaceutically acceptable salts thereof.

More preferred compounds of the present invention are those compounds of formula (I) and salts thereof in which:
(A) $R^1$ represents a pyridyl group.
(B) $R^2$ represents a hydrogen atom, a methyl group or a pyridyl group (particularly a hydrogen atom).
(C) $R^3$ represents a hydrogen atom or a methyl group (particularly a hydrogen atom).
(D) $A^1$ represents a group of formula (VII) or (VIII), wherein $R^{10}$ and $R^{11}$ are the same or different, and each represent a methyl group or an ethyl group; D represents an ethylene, trimethylene or tetramethylene group; and n is 2 or 3. More preferably: $R^{10}$ and $R^{11}$ are the same and each represents a methyl group; D represents an ethylene group or a trimethylene group; and n is 2.
(E) B represents an ethylene group or a trimethylene group, particularly an ethylene group.
(F) The group of formula (X) represents a bis(o-, m- or p- fluorophenyl)methoxy, α- (o-, m- or p- chlorophenyl)benzyloxy, bis(o-, m- or p- fluorophenyl)methoxy, α, α-diphenylmethoxy, α-(o-, m- or p- fluorophenyl)benzyloxy, α-(o-, m- or p- methylphenyl)benzyloxy, α-(2-, 3- or 4- pyridyl)benzyloxy, 4-[α-(2- or 3- thienyl) -α-phenylmethylene]-piperidinyl or 4- [α, α-bis(o-, m- or p- fluorophenyl)methylene]piperidinyl group, particularly, a bis(4-fluorophenyl)methoxy, α-(4-chlorophenyl)-benzyloxy, bis(4-fluorophenyl)methoxy, diphenylmethoxy or α-(2-pyridyl)benzyloxy group.
(G, $R^4$ represents a group of formula (IV) or (VI), wherein $R^8$ and $R^9$ are the same or different, and each represents a hydrogen atom or a halogen atom, particularly a group of formula (IV), wherein $R^8$ and $R^9$ are the same or different and each represents a hydrogen atom, a florine atom or a chlorine atom.

(H) $A^2$ represents a group of formula (IX) or (XI):

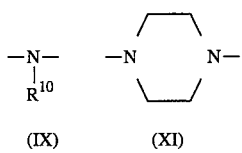

wherein $R^{10}$ represents a hydrogen atom or an alkyl group having from 1 to 4 carbon atoms, particularly a group of formula (IX), wherein $R^{10}$ represents a hydrogen atom or a methyl group.

(I) 3 represents an ethylene group of a trimethylene group, or —$A^2$—B—represents a single bond, in particular, we prefer that 3 should represent an ethylene group.

Still more preferred are those compounds in which $R^1$ is as defined in (A) above, $R^2$ is as defined in (B) above, $R^3$ is as defined in (C) above, $A^1$ is as defined in (D) above, B is as defined in (E) above, the group of formula (X) is as defined in (F) above, and $R^4$ is as defined in (G) above, or those compounds in which $R^1$ is as defined in (A) above, $R^2$ is as defined in (B) above, $R^3$ is as defined in(C) above, $A^2$ is as defined in (H) above, and B is as defined in (I) above.

Specific examples of compounds of the invention are those compounds having the following formulae (I-1) to (I-12), in which the substituents are as defined in the respective one of Tables 1 to 12, i.e. Table 1 relates to formula (I-1), Table 2 relates to formula (I-2), Table 3 relates to formula (I-3), and so on. In the Tables the following abbreviations are used are used for certain groups; otherwise, standard internationally recognised symbols are used to designate atoms:

| | |
|---|---|
| Dme | 5,6-dimethyl |
| Et | ethyl |
| cHx | cyclohexyl |
| Me | methyl |
| Ph | phenyl |
| Py | pyridyl |
| Tfm | trifluoromethyl |
| Tm | trimethylene |
| Thi | 2-thienyl |

(I-1)
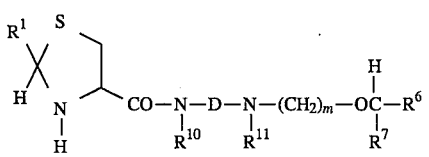

(I-2)
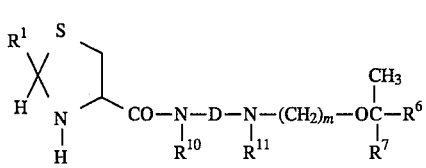

(I-3)
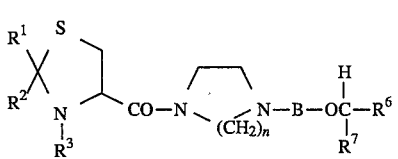

(I-4)
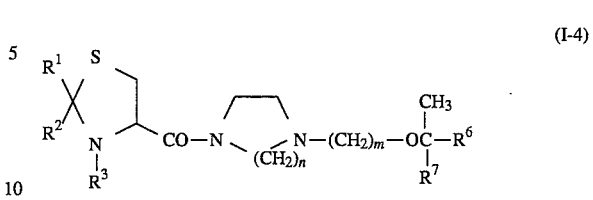

(I-5)
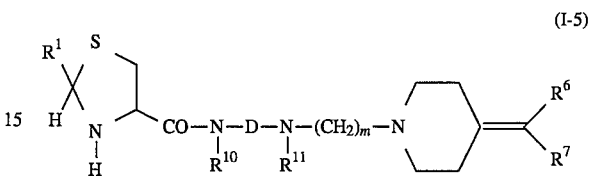

(I-6)
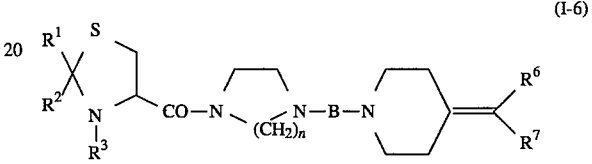

(I-7)
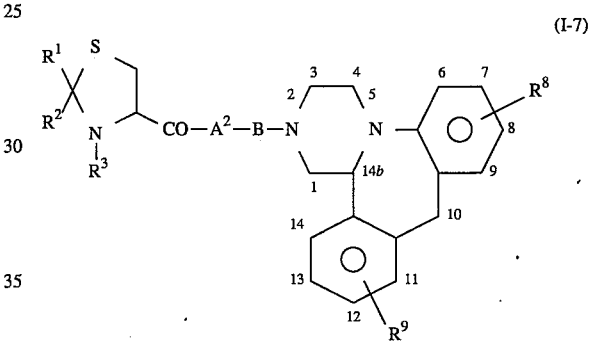

(I-8)
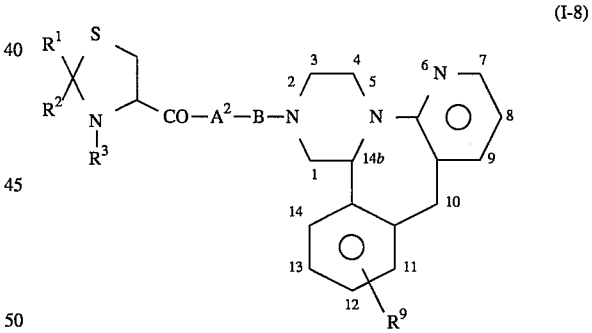

(I-9)
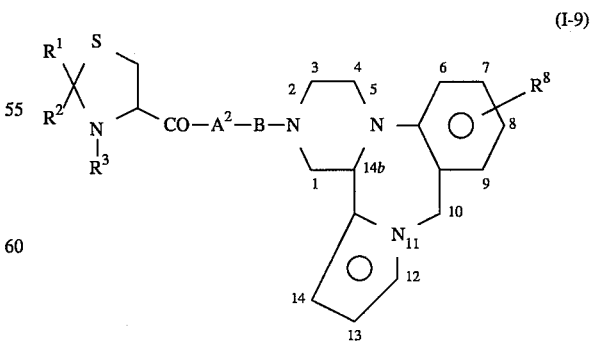

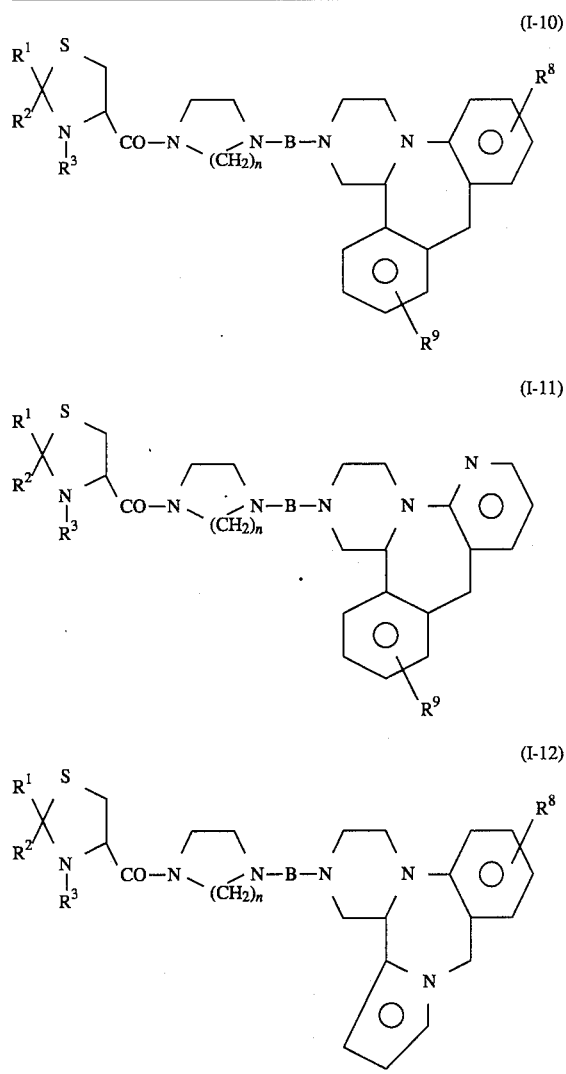

TABLE 1

| Cpd. No. | R¹ | R¹⁰ | R¹¹ | D | m | R⁶ | R⁷ |
|---|---|---|---|---|---|---|---|
| 1-1 | 3-Py | Me | Me | (CH$_2$)$_3$ | 2 | 4-FPh | 4-FPh |
| 1-2 | 3-Py | Me | Me | (CH$_2$)$_4$ | 2 | 4-FPh | 4-FPh |
| 1-3 | 3-Py | Me | Me | (CH$_2$)$_5$ | 2 | 4-FPh | 4-FPh |
| 1-4 | 3-Py | Me | Me | (CH$_2$)$_3$ | 2 | 4-FPh | 3-FPh |
| 1-5 | 2-Py | Me | Me | (CH$_2$)$_3$ | 2 | Ph | 4-FPh |
| 1-6 | 3-Py | Me | Me | (CH$_2$)$_2$ | 2 | 4-FPh | 4-ClPh |
| 1-7 | 3-Py | Me | Me | (CH$_2$)$_3$ | 2 | 4-FPh | 4-MePh |
| 1-8 | 3-Py | Me | Me | (CH$_2$)$_4$ | 2 | 4-FPh | 3-MeOPh |
| 1-9 | 4-Py | Me | Me | (CH$_2$)$_3$ | 2 | 4-ClPh | 3-ClPh |
| 1-10 | 3-Py | Me | Me | (CH$_2$)$_5$ | 2 | 3-ClPh | 3-ClPh |
| 1-11 | 3-Py | Me | Me | (CH$_2$)$_3$ | 2 | 4-ClPh | 4-MeOPh |
| 1-12 | 3-Py | Me | Me | (CH$_2$)$_2$ | 2 | Ph | 4-MeOPh |
| 1-13 | 2-Py | Me | Me | (CH$_2$)$_3$ | 2 | 4-MeOPh | 4-MeOPh |
| 1-14 | 4-Py | Me | Me | (CH$_2$)$_2$ | 2 | Ph | 4-MePh |
| 1-15 | 3-Py | Me | Me | (CH$_2$)$_4$ | 2 | 4-MePh | 4-MePh |
| 1-16 | Dme-3-Py | Me | Me | (CH$_2$)$_3$ | 2 | 4-FPh | 4-FPh |
| 1-17 | 3-Py | Et | Et | (CH$_2$)$_3$ | 2 | Ph | 2-FPh |
| 1-18 | 2-Me-3-Py | Me | Me | (CH$_2$)$_2$ | 2 | Ph | Ph |
| 1-19 | 2-Py | Me | Me | (CH$_2$)$_3$ | 2 | 4-FPh | 4-FPh |
| 1-20 | 2-Py | Me | Me | (CH$_2$)$_3$ | 2 | Ph | Ph |

TABLE 1-continued

| Cpd. No. | R¹ | R¹⁰ | R¹¹ | D | m | R⁶ | R⁷ |
|---|---|---|---|---|---|---|---|
| 1-21 | 3-Py | Me | Me | (CH$_2$)$_3$ | 2 | Ph | 3-ClPh |
| 1-22 | 2-Me-3-Py | Et | Et | (CH$_2$)$_3$ | 2 | 4-FPh | 4-FPh |
| 1-23 | 3-Py | Et | Et | (CH$_2$)$_3$ | 2 | 4-FPh | 4-FPh |
| 1-24 | 3-Py | Me | Me | (CH$_2$)$_3$ | 2 | Ph | Ph |
| 1-25 | 3-Py | Me | Me | (CH$_2$)$_2$ | 2 | Ph | Ph |
| 1-26 | 3-Py | Me | Me | (CH$_2$)$_3$ | 3 | Ph | Ph |
| 1-27 | 4-Py | Me | Me | (CH$_2$)$_3$ | 3 | Ph | 2-FPh |
| 1-28 | 3-Py | Me | Me | (CH$_2$)$_3$ | 3 | 4-FPh | 4-FPh |
| 1-29 | 2-Py | Me | Me | (CH$_2$)$_4$ | 3 | 4-FPh | 4-FPh |
| 1-30 | 3-Py | Me | Me | (CH$_2$)$_5$ | 3 | Ph | 4-ClPh |
| 1-31 | 4-Py | Me | Me | (CH$_2$)$_2$ | 3 | Ph | 3-ClPh |
| 1-32 | 3-Py | Et | Et | (CH$_2$)$_2$ | 3 | 4-FPh | 4-FPh |
| 1-33 | 3-Py | Et | Et | (CH$_2$)$_3$ | 3 | 4-FPh | 4-FPh |
| 1-34 | 3-Py | Me | Me | (CH$_2$)$_2$ | 3 | Ph | Ph |
| 1-35 | 3-Py | Me | Me | (CH$_2$)$_4$ | 3 | Ph | Ph |
| 1-36 | 3-Py | Me | Me | (CH$_2$)$_3$ | 2 | Ph | Ph |
| 1-37 | 3-Py | Me | Me | (CH$_2$)$_3$ | 2 | Ph | 2-FPh |
| 1-38 | 3-Py | Me | Me | (CH$_2$)$_3$ | 2 | Ph | 3-ClPh |
| 1-39 | 3-Py | Me | Me | (CH$_2$)$_3$ | 2 | 4-FPh | 3-MePh |
| 1-40 | 3-Py | Me | Me | (CH$_2$)$_3$ | 2 | 4-FPh | 2-MeOPh |
| 1-41 | 3-Py | Me | Me | 2-MeTm | 2 | Ph | Ph |
| 1-42 | 3-Py | Me | Me | 2-MeTm | 2 | Ph | 4-ClPh |
| 1-43 | 3-Py | Et | Et | 2-MeTm | 2 | Ph | 4-FPh |
| 1-44 | 3-Py | Me | Me | 2-MeTm | 2 | 4-FPh | 4-FPh |
| 1-45 | 3-Py | Me | Me | 2-MeTm | 3 | Ph | Ph |
| 1-46 | 3-Py | Me | Me | (CH$_2$)$_3$ | 3 | Ph | Ph |
| 1-47 | 3-Py | Me | Me | (CH$_2$)$_3$ | 3 | 4-FPh | 4-FPh |
| 1-48 | 3-Py | Et | Et | (CH$_2$)$_3$ | 3 | Ph | Ph |
| 1-49 | 3-Py | Me | Me | (CH$_2$)$_2$ | 3 | Ph | 2-Py |
| 1-50 | 3-Py | Me | Me | (CH$_2$)$_3$ | 3 | Ph | 2-Py |
| 1-51 | 3-Py | Me | Me | (CH$_2$)$_4$ | 3 | Ph | 2-Py |
| 1-52 | 3-Py | Me | Me | (CH$_2$)$_5$ | 3 | Ph | 2-Py |
| 1-53 | 3-Py | Me | Me | (CH$_2$)$_3$ | 3 | Ph | 2-Py |
| 1-54 | 3-Py | Me | Me | (CH$_2$)$_3$ | 3 | Ph | 2-Py |
| 1-55 | 3-Py | Me | Me | (CH$_2$)$_2$ | 3 | 4-FPh | 2-Py |
| 1-56 | 3-Py | Et | Et | (CH$_2$)$_3$ | 2 | 4-FPh | 2-Py |
| 1-57 | 3-Py | Me | Me | (CH$_2$)$_2$ | 2 | 4-ClPh | 2-Py |
| 1-58 | 3-Py | Me | Me | (CH$_2$)$_4$ | 2 | 4-ClPh | 2-Py |
| 1-59 | 3-Py | Me | Me | (CH$_2$)$_3$ | 2 | 4-MePh | 2-Py |
| 1-60 | 3-Py | Me | Me | (CH$_2$)$_2$ | 2 | 4-TfmPh | 2-Py |
| 1-61 | 3-Py | Me | Me | (CH$_2$)$_2$ | 3 | Ph | 2-Py |
| 1-62 | 3-Py | Me | Me | (CH$_2$)$_4$ | 3 | Ph | 2-Py |
| 1-63 | 3-Py | Me | Me | (CH$_2$)$_2$ | 2 | Ph | 2-Py |
| 1-64 | 3-Py | Me | Me | (CH$_2$)$_2$ | 2 | Ph | 3-Py |
| 1-65 | 3-Py | Me | Me | (CH$_2$)$_3$ | 2 | 4-ClPh | 3-Py |
| 1-66 | 3-Py | Me | Me | (CH$_2$)$_4$ | 2 | 4-FPh | 3-Py |
| 1-67 | 4-Py | Me | Me | (CH$_2$)$_2$ | 2 | Ph | 3-Py |
| 1-68 | 3-Py | Me | Me | (CH$_2$)$_2$ | 3 | Ph | 3-Py |
| 1-69 | 3-Py | Me | Me | (CH$_2$)$_2$ | 2 | Ph | 4-Py |
| 1-70 | 3-Py | Me | Me | (CH$_2$)$_4$ | 2 | Ph | 4-Py |
| 1-71 | 4-Py | Me | Me | (CH$_2$)$_2$ | 2 | Ph | Ph |
| 1-72 | 2-Me-3-Py | Me | Me | (CH$_2$)$_2$ | 2 | Ph | Ph |
| 1-73 | 3-Py | Me | Me | (CH$_2$)$_3$ | 2 | Ph | 4-ClPh |
| 1-74 | 3-Py | Me | Me | (CH$_2$)$_2$ | 2 | Ph | 4-ClPh |
| 1-75 | 3-Py | Me | Me | (CH$_2$)$_4$ | 2 | Ph | Ph |
| 1-76 | 3-Py | Me | Me | (CH$_2$)$_2$ | 2 | 4-FPh | 4-FPh |

TABLE 2

| Cpd. No. | R¹ | R¹⁰ | R¹¹ | D | m | R⁶ | R⁷ |
|---|---|---|---|---|---|---|---|
| 2-1 | 3-Py | Me | Me | (CH$_2$)$_3$ | 2 | 4-FPh | 4-FPh |
| 2-2 | 3-Py | Me | Me | (CH$_2$)$_3$ | 2 | 4-FPh | 4-FPh |
| 2-3 | 3-Py | Me | Me | (CH$_2$)$_4$ | 2 | 4-FPh | 3-FPh |
| 2-4 | 2-Py | Me | Me | (CH$_2$)$_3$ | 2 | Ph | 4-FPh |
| 2-5 | 3-Py | Me | Me | (CH$_2$)$_3$ | 2 | 4-FPh | 4-ClPh |
| 2-6 | 3-Py | Me | Me | (CH$_2$)$_2$ | 2 | 4-FPh | 4-MePh |
| 2-7 | 3-Py | Me | Me | (CH$_2$)$_3$ | 2 | 4-FPh | 3-MeOPh |
| 2-8 | 4-Py | Me | Me | (CH$_2$)$_4$ | 2 | 4-ClPh | 3-ClPh |
| 2-9 | 3-Py | Me | Me | (CH$_2$)$_3$ | 2 | 4-ClPh | 4-MeOPh |
| 2-10 | 3-Py | Me | Me | (CH$_2$)$_3$ | 2 | Ph | 4-MeOPh |

TABLE 2-continued

| Cpd. No. | R¹ | R¹⁰ | R¹¹ | D | $m$ | R⁶ | R⁷ |
|---|---|---|---|---|---|---|---|
| 2-11 | 2-Py | Me | Me | (CH₂)₂ | 2 | 4-MeOPh | 4-MeOPh |
| 2-12 | 4-Py | Me | Me | (CH₂)₃ | 2 | Ph | 4-MePh |
| 2-13 | 3-Py | Me | Me | (CH₂)₂ | 2 | 4-MePh | 4-MePh |
| 2-14 | Dme-3-Py | Me | Me | (CH₂)₄ | 2 | 4-FPh | 4-FPh |
| 2-15 | 2-Me-3-Py | Me | Me | (CH₂)₃ | 2 | Ph | Ph |
| 2-16 | 2-Py | Me | Me | (CH₂)₂ | 2 | 4-FPh | 4-FPh |
| 2-17 | 2-Py | Me | Me | (CH₂)₃ | 2 | Ph | Ph |
| 2-18 | 3-Py | Me | Me | (CH₂)₃ | 2 | Ph | 3-ClPh |
| 2-19 | 3-Py | Me | Me | (CH₂)₃ | 2 | Ph | Ph |
| 2-20 | 3-Py | Me | Me | (CH₂)₂ | 2 | Ph | Ph |
| 2-21 | 3-Py | Me | Me | (CH₂)₃ | 3 | Ph | Ph |
| 2-22 | 4-Py | Me | Me | (CH₂)₃ | 3 | Ph | 2-FPh |
| 2-23 | 3-Py | Me | Me | (CH₂)₃ | 3 | 4-FPh | 4-FPh |
| 2-24 | 2-Py | Me | Me | (CH₂)₄ | 3 | 4-FPh | 4-FPh |
| 2-25 | 4-Py | Me | Me | (CH₂)₂ | 3 | Ph | 3-ClPh |
| 2-26 | 3-Py | Me | Me | (CH₂)₂ | 3 | Ph | Ph |
| 2-27 | 3-Py | Me | Me | (CH₂)₄ | 3 | Ph | Ph |
| 2-28 | 3-Py | Me | Me | (CH₂)₃ | 2 | Ph | Ph |
| 2-29 | 3-Py | Me | Me | (CH₂)₃ | 2 | Ph | 2-FPh |
| 2-30 | 3-Py | Me | Me | (CH₂)₃ | 2 | Ph | 3-ClPh |
| 2-31 | 3-Py | Me | Me | (CH₂)₂ | 2 | 4-FPh | 3-MePh |
| 2-32 | 3-Py | Me | Me | (CH₂)₃ | 2 | 4-FPh | 2-MeOPh |
| 2-33 | 3-Py | Me | Me | (CH₂)₃ | 3 | Ph | Ph |
| 2-34 | 3-Py | Me | Me | (CH₂)₂ | 3 | 4-FPh | 4-FPh |
| 2-35 | 3-Py | Me | Me | (CH₂)₃ | 3 | Ph | 4-FPh |
| 2-36 | 3-Py | Me | Me | (CH₂)₂ | 2 | Ph | Ph |
| 2-37 | 3-Py | Me | Me | (CH₂)₃ | 3 | Ph | 2-Py |
| 2-38 | 3-Py | Me | Me | (CH₂)₄ | 3 | Ph | 2-Py |
| 2-39 | 3-Py | Me | Me | (CH₂)₂ | 3 | Ph | 2-Py |
| 2-40 | 3-Py | Me | Me | (CH₂)₃ | 3 | Ph | 2-Py |
| 2-41 | 3-Py | Me | Me | (CH₂)₃ | 3 | 4-FPh | 2-Py |
| 2-42 | 3-Py | Me | Me | (CH₂)₂ | 2 | 4-ClPh | 2-Py |
| 2-43 | 3-Py | Me | Me | (CH₂)₄ | 2 | 4-ClPh | 2-Py |
| 2-44 | 3-Py | Me | Me | (CH₂)₃ | 2 | 4-MePh | 2-Py |
| 2-45 | 3-Py | Me | Me | (CH₂)₂ | 2 | 4-TfmPh | 2-Py |
| 2-46 | 3-Py | Me | Me | (CH₂)₂ | 3 | Ph | 2-Py |
| 2-47 | 3-Py | Me | Me | (CH₂)₄ | 3 | Ph | 2-Py |
| 2-48 | 3-Py | Me | Me | (CH₂)₂ | 2 | Ph | 2-Py |
| 2-49 | 3-Py | Me | Me | (CH₂)₂ | 2 | Ph | 3-Py |
| 2-50 | 3-Py | Me | Me | (CH₂)₃ | 2 | 4-ClPh | 3-Py |
| 2-51 | 3-Py | Me | Me | (CH₂)₄ | 2 | 4-FPh | 3-Py |
| 2-52 | 3-Py | Me | Me | (CH₂)₂ | 2 | Ph | 3-Py |
| 2-53 | 3-Py | Me | Me | (CH₂)₂ | 3 | Ph | 3-Py |
| 2-54 | 3-Py | Me | Me | (CH₂)₂ | 2 | Ph | 4-Py |
| 2-55 | 3-Py | Me | Me | (CH₂)₄ | 2 | Ph | 4-Py |
| 2-56 | 3-Py | Me | Me | (CH₂)₂ | 2 | Ph | Ph |
| 2-57 | 3-Py | Me | Et | (CH₂)₂ | 2 | Ph | Ph |
| 2-58 | 3-Py | Me | Me | (CH₂)₃ | 2 | Ph | 4-ClPh |
| 2-59 | 3-Py | Me | Me | (CH₂)₂ | 2 | Ph | 4-ClPh |
| 2-60 | 3-Py | Me | Me | (CH₂)₄ | 2 | Ph | Ph |
| 2-61 | 3-Py | Me | Me | (CH₂)₂ | 2 | 4-FPh | 4-FPh |

TABLE 3

| Cpd. No. | R¹ | R² | R³ | $n$ | B | R⁶ | R⁷ |
|---|---|---|---|---|---|---|---|
| 3-1 | 3-Py | H | H | 2 | (CH₂)₂ | 4-FPh | 4-FPh |
| 3-2 | 3-Py | H | H | 2 | (CH₂)₃ | 4-FPh | 4-FPh |
| 3-3 | 3-Py | H | H | 2 | (CH₂)₄ | 4-FPh | 4-FPh |
| 3-4 | 3-Py | H | H | 2 | (CH₂)₃ | Ph | 4-FPh |
| 3-5 | 2-Py | H | H | 2 | (CH₂)₂ | 4-FPh | 4-ClPh |
| 3-6 | 3-Py | H | H | 2 | (CH₂)₃ | 4-FPh | 4-MePh |
| 3-7 | 3-Py | H | H | 2 | (CH₂)₄ | 4-FPh | 4-MeOPh |
| 3-8 | 4-Py | H | H | 2 | (CH₂)₃ | 4-ClPh | 3-ClPh |
| 3-9 | 3-Py | H | H | 2 | (CH₂)₂ | 4-ClPh | 4-MeOPh |
| 3-10 | 3-Py | H | H | 2 | (CH₂)₂ | Ph | 4-MeOPh |
| 3-11 | 3-Py | H | H | 2 | (CH₂)₃ | 4-MeOPh | 4-MeOPh |
| 3-12 | 4-Py | H | H | 2 | (CH₂)₂ | Ph | 4-MePh |
| 3-13 | 3-Py | H | H | 2 | (CH₂)₄ | 4-MePh | 4-MePh |
| 3-14 | Dme-3-Py | H | H | 2 | (CH₂)₃ | 4-FPh | 4-FPh |
| 3-15 | 3-Py | H | H | 2 | (CH₂)₃ | 4-FPh | 2-FPh |
| 3-16 | 2-Me-3-Py | H | H | 2 | (CH₂)₂ | Ph | Ph |
| 3-17 | 2-Py | H | H | 2 | (CH₂)₃ | 4-FPh | 4-FPh |
| 3-18 | 2-Py | H | H | 2 | (CH₂)₃ | Ph | Ph |
| 3-19 | 3-Py | H | H | 2 | (CH₂)₃ | Ph | 3-ClPh |
| 3-20 | 2-Me-3-Py | H | H | 2 | (CH₂)₃ | 4-FPh | 4-FPh |
| 3-21 | 3-Py | H | Me | 2 | (CH₂)₃ | 4-FPh | 4-FPh |
| 3-22 | 3-Py | H | H | 2 | (CH₂)₃ | Ph | Ph |
| 3-23 | 3-Py | H | H | 2 | (CH₂)₂ | Ph | Ph |
| 3-24 | 4-Py | H | H | 2 | (CH₂)₃ | Ph | Ph |
| 3-25 | 3-Py | H | H | 2 | (CH₂)₂ | 4-FPh | 4-FPh |
| 3-26 | 2-Py | H | H | 2 | (CH₂)₄ | 4-FPh | 4-FPh |
| 3-27 | 4-Py | H | H | 2 | (CH₂)₂ | 4-ClPh | 4-ClPh |
| 3-28 | 3-Py | H | H | 2 | (CH₂)₃ | 4-FPh | 4-ClPh |
| 3-29 | 3-Py | H | H | 2 | (CH₂)₂ | Ph | 4-MePh |
| 3-30 | 3-Py | H | H | 3 | (CH₂)₃ | Ph | 4-MePh |
| 3-31 | 3-Py | H | H | 3 | (CH₂)₂ | 4-MePh | 4-MePh |
| 3-32 | 3-Py | H | H | 3 | (CH₂)₄ | 4-MeOPh | 4-MeOPh |
| 3-33 | 3-Py | H | H | 2 | (CH₂)₃ | 4-FPh | 3-FPh |
| 3-34 | 3-Py | H | H | 2 | (CH₂)₃ | Ph | 2-FPh |
| 3-35 | 3-Py | H | H | 2 | (CH₂)₃ | Ph | 2-MePh |
| 3-36 | 3-Py | H | H | 2 | (CH₂)₃ | 4-FPh | 2-MeOPh |
| 3-37 | 3-Py | H | H | 2 | (CH₂)₃ | 4-FPh | Ph |
| 3-38 | 3-Py | H | H | 2 | 2-MeTm | Ph | 4-ClPh |
| 3-39 | 3-Py | H | H | 2 | 2-MeTm | Ph | 4-FPh |
| 3-40 | 3-Py | H | H | 2 | 2-MeTm | Ph | 4-FPh |
| 3-41 | 3-Py | H | H | 2 | 2-MeTm | 4-FPh | cHx |
| 3-42 | 3-Py | H | H | 2 | (CH₂)₂ | Ph | cHx |
| 3-43 | 3-Py | H | H | 3 | (CH₂)₂ | Ph | cHx |
| 3-44 | 3-Py | H | H | 2 | (CH₂)₄ | Ph | Ph |
| 3-45 | 3-Py | H | H | 3 | 2-MeTm | Ph | Ph |
| 3-46 | 3-Py | H | Me | 2 | (CH₂)₃ | Ph | 4-FPh |
| 3-47 | 3-Py | H | Me | 2 | (CH₂)₃ | 4-FPh | 4-FPh |
| 3-48 | 3-Py | 3-Py | H | 2 | (CH₂)₃ | 4-FPh | 2-Py |
| 3-49 | 3-Py | H | H | 2 | (CH₂)₂ | Ph | 2-Py |
| 3-50 | 3-Py | H | H | 2 | (CH₂)₃ | Ph | 2-Py |
| 3-51 | 3-Py | H | H | 2 | (CH₂)₄ | Ph | 2-Py |
| 3-52 | 3-Py | H | Me | 2 | (CH₂)₂ | Ph | 2-Py |
| 3-53 | 3-Py | H | Me | 2 | (CH₂)₂ | Ph | 2-Py |
| 3-54 | 3-Py | H | H | 2 | (CH₂)₂ | 4-FPh | 2-Py |
| 3-55 | 3-Py | H | H | 2 | (CH₂)₃ | 4-FPh | 2-Py |
| 3-56 | 3-Py | H | H | 2 | (CH₂)₂ | 4-ClPh | 2-Py |
| 3-57 | 3-Py | H | H | 2 | (CH₂)₄ | 4-ClPh | 2-Py |
| 3-58 | 3-Py | H | H | 2 | (CH₂)₂ | 4-MePh | 2-Py |
| 3-59 | 3-Py | H | H | 2 | (CH₂)₂ | 4-TfmPh | 2-Py |
| 3-60 | 3-Py | H | H | 3 | (CH₂)₂ | Ph | 2-Py |
| 3-61 | 3-Py | H | H | 3 | (CH₂)₄ | Ph | 2-Py |
| 3-62 | 4-Py | H | H | 2 | (CH₂)₂ | Ph | 2-Py |
| 3-63 | 3-Py | H | H | 2 | (CH₂)₂ | Ph | 3-Py |
| 3-64 | 3-Py | H | H | 2 | (CH₂)₃ | 4-ClPh | 3-Py |
| 3-65 | 3-Py | H | H | 2 | (CH₂)₄ | 4-FPh | 3-Py |
| 3-66 | 4-Py | H | H | 2 | (CH₂)₂ | Ph | 3-Py |
| 3-67 | 3-Py | H | H | 3 | (CH₂)₂ | Ph | 3-Py |
| 3-68 | 3-Py | H | H | 2 | (CH₂)₂ | Ph | 4-Py |
| 3-69 | 3-Py | H | H | 2 | (CH₂)₄ | Ph | 4-Py |
| 3-70 | 3-Py | H | H | 2 | (CH₂)₂ | 4-MePh | 4-FPh |
| 3-71 | 3-Py | H | H | 2 | (CH₂)₂ | Ph | 4-FPh |
| 3-72 | 3-Py | H | H | 2 | (CH₂)₃ | Ph | 4-FPh |
| 3-73 | 3-Py | H | H | 2 | (CH₂)₂ | Ph | 4-FPh |
| 3-74 | 3-Py | H | H | 2 | (CH₂)₄ | Ph | 4-FPh |

TABLE 4

| Cpd. No. | R¹ | R² | R³ | $n$ | $m$ | R⁶ | R⁷ |
|---|---|---|---|---|---|---|---|
| 4-1 | 3-Py | H | H | 2 | 3 | 4-FPh | 4-FPh |
| 4-2 | 3-Py | H | H | 2 | 4 | 4-FPh | 4-FPh |
| 4-3 | 3-Py | H | H | 3 | 3 | 4-FPh | 4-FPh |
| 4-4 | 3-Py | H | H | 2 | 3 | Ph | 4-FPh |
| 4-5 | 2-Py | H | H | 2 | 2 | 4-FPh | 4-ClPh |
| 4-6 | 3-Py | H | H | 2 | 3 | 4-FPh | 4-MePh |
| 4-7 | 4-Py | H | H | 2 | 3 | 4-ClPh | 3-ClPh |
| 4-8 | 3-Py | H | H | 2 | 3 | 4-ClPh | 4-MeOPh |

TABLE 4-continued

| Cpd. No. | R¹ | R² | R³ | $n$ | $m$ | R⁶ | R⁷ |
|---|---|---|---|---|---|---|---|
| 4-9 | 3-Py | H | H | 2 | 2 | Ph | 4-MeOPh |
| 4-10 | 3-Py | H | H | 2 | 3 | 4-MeOPh | 4-MeOPh |
| 4-11 | 4-Py | H | H | 2 | 2 | Ph | 4-MePh |
| 4-12 | Dme-3-Py | H | H | 2 | 3 | 4-FPh | 4-FPh |
| 4-13 | 3-Py | H | H | 2 | 3 | 4-FPh | 2-FPh |
| 4-14 | 2-Me-3-Py | H | H | 2 | 2 | Ph | Ph |
| 4-15 | 2-Py | H | H | 2 | 3 | 4-FPh | 4-FPh |
| 4-16 | 2-Py | H | H | 2 | 3 | Ph | Ph |
| 4-17 | 3-Py | H | H | 2 | 3 | Ph | 3-ClPh |
| 4-18 | 2-Py | H | H | 2 | 3 | 4-FPh | 4-FPh |
| 4-19 | 2-Me-3-Py | H | Me | 2 | 3 | 4-FPh | 4-FPh |
| 4-20 | 3-Py | H | H | 2 | 3 | Ph | Ph |
| 4-21 | 3-Py | H | H | 3 | 2 | Ph | Ph |
| 4-22 | 4-Py | H | H | 3 | 3 | Ph | Ph |
| 4-23 | 3-Py | H | H | 3 | 2 | 4-FPh | 4-FPh |
| 4-24 | 3-Py | H | H | 3 | 2 | 4-ClPh | 4-ClPh |
| 4-25 | 3-Py | H | H | 3 | 2 | 4-FPh | 4-ClPh |
| 4-26 | 3-Py | H | H | 2 | 2 | Ph | 4-MePh |
| 4-27 | 3-Py | H | H | 3 | 3 | Ph | 4-MePh |
| 4-28 | 3-Py | H | H | 3 | 2 | 4-MePh | 4-MePh |
| 4-29 | 3-Py | H | H | 3 | 4 | 4-MeOPh | 4-MeOPh |
| 4-30 | 3-Py | H | H | 2 | 3 | 4-FPh | 3-FPh |
| 4-31 | 3-Py | H | H | 2 | 3 | Ph | 2-FPh |
| 4-32 | 3-Py | H | H | 2 | 3 | Ph | 3-ClPh |
| 4-33 | 3-Py | H | H | 2 | 3 | 4-FPh | 3-MePh |
| 4-34 | 3-Py | H | H | 2 | 3 | 4-FPh | 2-MeOPh |
| 4-35 | 3-Py | H | H | 2 | 2 | Ph | cHx |
| 4-36 | 3-Py | H | H | 3 | 2 | Ph | cHx |
| 4-37 | 3-Py | H | Me | 2 | 2 | Ph | Ph |
| 4-38 | 3-Py | H | Me | 2 | 3 | 4-FPh | 4-FPh |
| 4-39 | 3-Py | 3-Py | H | 2 | 3 | 4-FPh | 2-FPh |
| 4-40 | 3-Py | H | H | 2 | 2 | Ph | 2-Py |
| 4-41 | 3-Py | H | H | 2 | 3 | Ph | 2-Py |
| 4-42 | 3-Py | H | Me | 2 | 2 | Ph | 2-Py |
| 4-43 | 3-Py | H | Me | 2 | 3 | Ph | 2-Py |
| 4-44 | 3-Py | H | H | 2 | 2 | 4-FPh | 2-Py |
| 4-45 | 3-Py | H | H | 2 | 3 | 4-FPh | 2-Py |
| 4-46 | 3-Py | H | H | 2 | 2 | 4-ClPh | 2-Py |
| 4-47 | 3-Py | H | H | 2 | 3 | 4-MePh | 2-Py |
| 4-48 | 3-Py | H | H | 2 | 2 | 4-TfmPh | 2-Py |
| 4-49 | 3-Py | H | H | 3 | 2 | Ph | 2-Py |
| 4-50 | 4-Py | H | H | 2 | 2 | Ph | 2-Py |
| 4-51 | 3-Py | H | H | 2 | 2 | Ph | 3-Py |
| 4-52 | 3-Py | H | H | 2 | 3 | 4-ClPh | 3-Py |
| 4-53 | 4-Py | H | H | 2 | 2 | Ph | 3-Py |
| 4-54 | 3-Py | H | H | 3 | 2 | Ph | 3-Py |
| 4-55 | 3-Py | H | H | 2 | 2 | Ph | 4-Py |
| 4-56 | 3-Py | H | H | 2 | 2 | Ph | Ph |
| 4-57 | 3-Py | H | H | 2 | 3 | Ph | Ph |
| 4-58 | 3-Py | H | H | 2 | 3 | Ph | 4-ClPh |
| 4-59 | 3-Py | H | H | 2 | 2 | Ph | 4-ClPh |
| 4-60 | 3-Py | H | H | 2 | 2 | 4-FPh | 4-FPh |

TABLE 5

| Cpd. No. | R¹ | R¹⁰ | R¹¹ | D | $m$ | R⁶ | R⁷ |
|---|---|---|---|---|---|---|---|
| 5-1 | 3-Py | Me | Me | (CH₂)₃ | 2 | 4-FPh | 4-FPh |
| 5-2 | 3-Py | Me | Me | (CH₂)₄ | 2 | 4-FPh | 4-FPh |
| 5-3 | 3-Py | Me | Me | (CH₂)₃ | 2 | 4-FPh | 3-FPh |
| 5-4 | 2-Py | Me | Me | (CH₂)₃ | 2 | Ph | 4-FPh |
| 5-5 | 3-Py | Me | Me | (CH₂)₂ | 2 | 4-FPh | 4-ClPh |
| 5-6 | 3-Py | Me | Me | (CH₂)₃ | 2 | 4-FPh | 4-MePh |
| 5-7 | 3-Py | Me | Me | (CH₂)₄ | 2 | 4-FPh | 3-MeOPh |
| 5-8 | 4-Py | Me | Me | (CH₂)₃ | 2 | 4-ClPh | 3-ClPh |
| 5-9 | 3-Py | Me | Me | (CH₂)₃ | 2 | 4-ClPh | 4-MeOPh |
| 5-10 | 3-Py | Me | Me | (CH₂)₂ | 2 | Ph | 4-MeOPh |
| 5-11 | 2-Py | Me | Me | (CH₂)₃ | 2 | 4-MeOPh | 4-MeOPh |
| 5-12 | 4-Py | Me | Me | (CH₂)₂ | 2 | Ph | 4-MePh |
| 5-13 | 3-Py | Me | Me | (CH₂)₄ | 2 | 4-MePh | 4-MePh |
| 5-14 | Dme-3-Py | Me | Me | (CH₂)₃ | 2 | 4-FPh | 4-FPh |
| 5-15 | 2-Me-3-Py | Me | Me | (CH₂)₂ | 2 | Ph | Ph |
| 5-16 | 2-Py | Me | Me | (CH₂)₃ | 2 | 4-FPh | 4-FPh |
| 5-17 | 2-Py | Me | Me | (CH₂)₃ | 2 | Ph | Ph |
| 5-18 | 2-Py | Me | Me | (CH₂)₃ | 2 | Ph | 3-ClPh |
| 5-19 | 3-Py | Me | Me | (CH₂)₃ | 2 | Ph | Ph |
| 5-20 | 3-Py | Me | Me | (CH₂)₂ | 2 | Ph | Ph |
| 5-21 | 3-Py | Me | Me | (CH₂)₃ | 3 | Ph | Ph |
| 5-22 | 4-Py | Me | Me | (CH₂)₃ | 3 | Ph | 2-FPh |
| 5-23 | 3-Py | Me | Me | (CH₂)₃ | 3 | 4-FPh | 4-FPh |
| 5-24 | 2-Py | Me | Me | (CH₂)₄ | 3 | 4-FPh | 4-FPh |
| 5-25 | 4-Py | Me | Me | (CH₂)₃ | 3 | Ph | 3-ClPh |
| 5-26 | 3-Py | Me | Me | (CH₂)₂ | 3 | Ph | Ph |
| 5-27 | 3-Py | Me | Me | (CH₂)₄ | 3 | Ph | Ph |
| 5-28 | 3-Py | Me | Me | (CH₂)₃ | 2 | Ph | Ph |
| 5-29 | 3-Py | Me | Me | (CH₂)₃ | 2 | Ph | 2-FPh |
| 5-30 | 3-Py | Me | Me | (CH₂)₃ | 2 | Ph | 3-ClPh |
| 5-31 | 3-Py | Me | Me | (CH₂)₃ | 2 | 4-FPh | 3-MePh |
| 5-32 | 3-Py | Me | Me | (CH₂)₃ | 2 | 4-FPh | 2-MeOPh |
| 5-33 | 3-Py | Me | Me | (CH₂)₃ | 3 | Ph | Ph |
| 5-34 | 3-Py | Me | Me | (CH₂)₂ | 3 | 4-FPh | 4-FPh |
| 5-35 | 3-Py | Et | Et | (CH₂)₃ | 3 | Ph | Ph |
| 5-36 | 3-Py | Me | Me | (CH₂)₂ | 2 | Ph | 2-Py |
| 5-37 | 3-Py | Me | Me | (CH₂)₃ | 3 | Ph | 2-Py |
| 5-38 | 3-Py | Me | Me | (CH₂)₄ | 3 | Ph | 2-Py |
| 5-39 | 3-Py | Me | Me | (CH₂)₂ | 3 | Ph | 2-Py |
| 5-40 | 3-Py | Me | Me | (CH₂)₃ | 3 | Ph | 2-Py |
| 5-41 | 3-Py | Me | Me | (CH₂)₂ | 3 | 4-FPh | 2-Py |
| 5-42 | 3-Py | Me | Me | (CH₂)₃ | 2 | 4-ClPh | 2-Py |
| 5-43 | 3-Py | Me | Me | (CH₂)₄ | 2 | 4-ClPh | 2-Py |
| 5-44 | 3-Py | Me | Me | (CH₂)₃ | 2 | 4-MePh | 2-Py |
| 5-45 | 3-Py | Me | Me | (CH₂)₂ | 2 | 4-TfmPh | 2-Py |
| 5-46 | 3-Py | Me | Me | (CH₂)₂ | 3 | Ph | 2-Py |
| 5-47 | 3-Py | Me | Me | (CH₂)₄ | 3 | Ph | 2-Py |
| 5-48 | 3-Py | Me | Me | (CH₂)₂ | 2 | Ph | 2-Py |
| 5-49 | 3-Py | Me | Me | (CH₂)₂ | 2 | Ph | 3-Py |
| 5-50 | 3-Py | Me | Me | (CH₂)₃ | 2 | 4-ClPh | 3-Py |
| 5-51 | 3-Py | Me | Me | (CH₂)₄ | 2 | 4-FPh | 3-Py |
| 5-52 | 4-Py | Me | Me | (CH₂)₂ | 2 | Ph | 3-Py |
| 5-53 | 3-Py | Me | Me | (CH₂)₂ | 3 | Ph | 3-Py |
| 5-54 | 3-Py | Me | Me | (CH₂)₂ | 2 | Ph | 4-Py |
| 5-55 | 3-Py | Me | Me | (CH₂)₄ | 2 | Ph | 4-Py |
| 5-56 | 3-Py | Me | Me | (CH₂)₂ | 2 | Ph | Ph |
| 5-57 | 3-Py | Me | Et | (CH₂)₂ | 2 | Ph | 4-FPh |
| 5-58 | 3-Py | Me | Me | (CH₂)₃ | 2 | Ph | 4-ClPh |
| 5-59 | 3-Py | Me | Me | (CH₂)₂ | 2 | Ph | 4-ClPh |
| 5-60 | 3-Py | Me | Me | (CH₂)₄ | 2 | Ph | Ph |
| 5-61 | 3-Py | Me | Me | (CH₂)₂ | 2 | 4-FPh | 4-FPh |

TABLE 6

| Cpd. No. | R¹ | R² | R³ | $n$ | B | R⁶ | R⁷ |
|---|---|---|---|---|---|---|---|
| 6-1 | 3-Py | H | H | 2 | (CH₂)₂ | Ph | Ph |
| 6-2 | 3-Py | H | H | 2 | (CH₂)₃ | Ph | Ph |
| 6-3 | 3-Py | H | H | 2 | (CH₂)₄ | Ph | Ph |
| 6-4 | 3-Py | H | H | 2 | (CH₂)₃ | Ph | 4-FPh |
| 6-5 | 3-Py | H | H | 3 | (CH₂)₄ | 4-FPh | 4-FPh |
| 6-6 | 3-Py | H | H | 2 | (CH₂)₃ | Ph | 4-ClPh |
| 6-7 | 3-Py | H | H | 2 | (CH₂)₃ | 4-ClPh | 4-ClPh |
| 6-8 | 4-Py | H | H | 3 | (CH₂)₂ | Ph | 4-MePh |
| 6-9 | 3-Py | H | H | 2 | (CH₂)₃ | 4-MeOPh | 4-MeOPh |
| 6-10 | 4-Py | H | H | 3 | (CH₂)₄ | 4-MeOPh | 4-MeOPh |
| 6-11 | 2-Py | H | H | 2 | (CH₂)₂ | Ph | 4-MeOPh |
| 6-12 | 4-Py | H | Me | 3 | (CH₂)₃ | Ph | Ph |
| 6-13 | 3-Py | H | Me | 3 | (CH₂)₃ | Ph | Ph |
| 6-14 | 2-Me-6-Py | H | H | 2 | (CH₂)₃ | Ph | Ph |
| 6-15 | 2-Py | H | H | 2 | (CH₂)₃ | Ph | Ph |
| 6-16 | 3-Py | H | H | 2 | (CH₂)₃ | 4-FPh | 3-FPh |
| 6-17 | 3-Py | H | H | 3 | (CH₂)₃ | Ph | 3-FPh |
| 6-18 | 3-Py | H | H | 2 | (CH₂)₃ | Ph | 3-ClPh |
| 6-19 | 3-Py | H | H | 2 | (CH₂)₃ | 4-ClPh | 2-ClPh |
| 6-20 | 3-Py | H | H | 2 | (CH₂)₃ | Ph | 3-MePh |
| 6-21 | 3-Py | H | H | 2 | (CH₂)₃ | 4-MePh | 3-MeOPh |
| 6-22 | 3-Py | H | H | 2 | 2-MeTm | Ph | Ph |

TABLE 6-continued

| Cpd. No. | R¹ | R² | R³ | n | B | R⁶ | R⁷ |
|---|---|---|---|---|---|---|---|
| 6-23 | 3-Py | H | H | 2 | 2-MeTm | Ph | 4-FPh |
| 6-24 | 3-Py | H | H | 2 | 2-MeTm | 4-FPh | 4-FPh |
| 6-25 | 3-Py | 3-Py | H | 2 | (CH₂)₃ | Ph | Ph |
| 6-26 | 3-Py | H | Me | 2 | (CH₂)₃ | Ph | Ph |
| 6-27 | 3-Py | H | Me | 2 | (CH₂)₃ | 4-FPh | 4-FPh |
| 6-28 | 3-Py | H | H | 2 | (CH₂)₂ | 4-FPh | 4-FPh |
| 6-29 | 3-Py | H | H | 2 | (CH₂)₃ | 4-FPh | 4-FPh |
| 6-30 | 3-Py | H | Me | 2 | (CH₂)₂ | 4-FPh | 4-FPh |
| 6-31 | 3-Py | H | Me | 2 | (CH₂)₃ | 4-FPh | 4-FPh |
| 6-32 | 3-Py | H | H | 2 | (CH₂)₂ | Ph | 3-Thi |
| 6-33 | 3-Py | H | H | 2 | (CH₂)₃ | Ph | 3-Thi |
| 6-34 | 2-Me-5-Py | H | H | 2 | (CH₂)₂ | 4-FPh | 4-FPh |
| 6-35 | 2-Me-5-Py | H | H | 2 | (CH₂)₃ | 4-FPh | 4-FPh |
| 6-36 | 2-Me-5-Py | H | H | 2 | (CH₂)₂ | Ph | Ph |
| 6-37 | 2-Me-5-Py | H | H | 2 | (CH₂)₃ | Ph | Ph |
| 6-38 | 4-Py | H | H | 2 | (CH₂)₃ | Ph | Ph |
| 6-39 | 2-Py | H | H | 2 | (CH₂)₂ | Ph | Ph |
| 6-40 | 2-Py | H | H | 2 | (CH₂)₄ | 4-FPh | 4-FPh |
| 6-41 | 2-Py | H | H | 3 | (CH₂)₂ | Ph | Ph |
| 6-42 | 3-Py | H | H | 3 | (CH₂)₂ | Ph | Ph |
| 6-43 | 2-Py | H | H | 2 | (CH₂)₃ | Ph | Ph |
| 6-44 | 3-Py | H | H | 2 | (CH₂)₃ | Ph | 4-MePh |

TABLE 7

| Cpd. No. | R¹ | R² | R³ | A²-B | R⁸ | R⁹ |
|---|---|---|---|---|---|---|
| 7-1 | 3-Py | H | H | NH—(CH₂)₂ | H | H |
| 7-2 | 2-Py | H | H | NH—(CH₂)₂ | H | H |
| 7-3 | 4-Py | H | H | NH—(CH₂)₂ | H | H |
| 7-4 | 2-Me-3-Py | H | H | NH—(CH₂)₂ | H | H |
| 7-5 | Dme-3-Py | H | H | NH—(CH₂)₂ | H | H |
| 7-6 | 3-Py | H | H | N(Me)—(CH₂)₂ | H | H |
| 7-7 | 2-Py | H | H | N(Me)—(CH₂)₂ | H | H |
| 7-8 | 4-Py | H | H | N(Me)—(CH₂)₂ | H | H |
| 7-9 | 3-Py | H | H | N(Et)—(CH₂)₂ | H | H |
| 7-10 | 3-Py | Me | H | NH—(CH₂)₂ | H | H |
| 7-11 | 3-Py | Et | H | NH—(CH₂)₂ | H | H |
| 7-12 | 3-Py | 3-Py | H | NH—(CH₂)₂ | H | H |
| 7-13 | 3-Py | Me | H | N(Me)—(CH₂)₂ | H | H |
| 7-14 | 3-Py | H | Me | N(Me)—(CH₂)₂ | H | H |
| 7-15 | 2-Py | H | Me | N(Me)—(CH₂)₂ | H | H |
| 7-16 | 4-Py | H | Me | N(Me)—(CH₂)₂ | H | H |
| 7-17 | 2-Me-3-Py | H | Me | N(Me)—(CH₂)₂ | H | H |
| 7-18 | Dme-3-Py | H | Me | N(Me)—(CH₂)₂ | H | H |
| 7-19 | 3-Py | H | Et | N(Me)—(CH₂)₂ | H | H |
| 7-20 | 3-Py | H | H | NH—(CH₂)₂ | 8-F | H |
| 7-21 | 2-Py | H | H | NH—(CH₂)₂ | 8-F | H |
| 7-22 | 4-Py | H | H | NH—(CH₂)₂ | 8-F | H |
| 7-23 | 2-Me-3-Py | H | H | NH—(CH₂)₂ | 8-F | H |
| 7-24 | Dme-3-Py | H | H | NH—(CH₂)₂ | 8-F | H |
| 7-25 | 3-Py | H | H | N(Me)—(CH₂)₂ | 8-F | H |
| 7-26 | 2-Py | H | H | N(Me)—(CH₂)₂ | 8-F | H |
| 7-27 | 4-Py | H | H | N(Me)—(CH₂)₂ | 8-F | H |
| 7-28 | 3-Py | H | H | N(Et)—(CH₂)₂ | 8-F | H |
| 7-29 | 3-Py | Me | H | NH—(CH₂)₂ | 8-F | H |
| 7-30 | 3-Py | 3-Py | H | NH—(CH₂)₂ | 8-F | H |
| 7-31 | 3-Py | Me | H | N(Me)—(CH₂)₂ | 8-F | H |
| 7-32 | 3-Py | H | Me | N(Me)—(CH₂)₂ | 8-F | H |
| 7-33 | 2-Py | H | Me | N(Me)—(CH₂)₂ | 8-F | H |
| 7-34 | 4-Py | H | Me | N(Me)—(CH₂)₂ | 8-F | H |
| 7-35 | 2-Me-3-Py | H | Me | N(Me)—(CH₂)₂ | 8-F | H |
| 7-36 | Dme-3-Py | H | Me | N(Me)—(CH₂)₂ | 8-F | H |
| 7-37 | 3-Py | H | H | NH—(CH₂)₂ | 8-Cl | H |
| 7-38 | 2-Py | H | H | NH—(CH₂)₂ | 8-Cl | H |
| 7-39 | 4-Py | H | H | NH—(CH₂)₂ | 8-Cl | H |
| 7-40 | 2-Me-3-Py | H | H | NH—(CH₂)₂ | 8-Cl | H |
| 7-41 | Dme-3-Py | H | H | NH—(CH₂)₂ | 8-Cl | H |
| 7-42 | 3-Py | H | H | N(Me)—(CH₂)₂ | 8-Cl | H |
| 7-43 | 2-Py | H | H | N(Me)—(CH₂)₂ | 8-Cl | H |
| 7-44 | 4-Py | H | H | N(Me)—(CH₂)₂ | 8-Cl | H |
| 7-45 | 3-Py | H | H | N(Et)—(CH₂)₂ | 8-Cl | H |
| 7-46 | 3-Py | Me | H | NH—(CH₂)₂ | 8-Cl | H |
| 7-47 | 3-Py | 3-Py | H | NH—(CH₂)₂ | 8-Cl | H |
| 7-48 | 3-Py | Me | H | N(Me)—(CH₂)₂ | 8-Cl | H |
| 7-49 | 3-Py | H | Me | N(Me)—(CH₂)₂ | 8-Cl | H |
| 7-50 | 2-Py | H | Me | N(Me)—(CH₂)₂ | 8-Cl | H |
| 7-51 | 4-Py | H | Me | N(Me)—(CH₂)₂ | 8-Cl | H |
| 7-52 | 2-Me-3-Py | H | Me | N(Me)—(CH₂)₂ | 8-Cl | H |
| 7-53 | Dme-3-Py | H | Me | N(Me)—(CH₂)₂ | 8-Cl | H |
| 7-54 | 3-Py | H | H | NH—(CH₂)₂ | 8-Br | H |

TABLE 7-continued

| Cpd. No. | R¹ | R² | R³ | A²-B | R⁸ | R⁹ |
|---|---|---|---|---|---|---|
| 7-55 | 3-Py | H | H | N(Me)—(CH₂)₂ | 8-Br | H |
| 7-56 | 3-Py | H | H | NH—(CH₂)₂ | 8-Me | H |
| 7-57 | 3-Py | H | H | N(Me)—(CH₂)₂ | 8-Me | H |
| 7-58 | 3-Py | H | H | NH—(CH₂)₂ | 8-OMe | H |
| 7-59 | 3-Py | H | H | N(Me)—(CH₂)₂ | 8-OMe | H |
| 7-60 | 3-Py | H | H | NH—(CH₂)₂ | 8-Tfm | H |
| 7-61 | 2-Py | H | H | NH—(CH₂)₂ | 8-Tfm | H |
| 7-62 | 3-Py | H | H | NH—(CH₂)₂ | 8-Tfm | H |
| 7-63 | 3-Py | H | Me | NH—(CH₂)₂ | 8-Tfm | H |
| 7-64 | 3-Py | H | H | N(Me)—(CH₂)₂ | 8-Tfm | H |
| 7-65 | 3-Py | H | H | NH—(CH₂)₂ | 8-OH | H |
| 7-66 | 3-Py | H | H | N(Me)—(CH₂)₂ | 8-OH | H |
| 7-67 | 3-Py | H | H | NH—(CH₂)₂ | H | 13-F |
| 7-68 | 2-Py | H | H | NH—(CH₂)₂ | H | 13-F |
| 7-69 | 3-Py | H | H | N(Me)—(CH₂)₂ | H | 13-F |
| 7-70 | 3-Py | H | Me | NH—(CH₂)₂ | H | 13-F |
| 7-71 | 3-Py | H | H | NH—(CH₂)₂ | 8-F | 13-F |
| 7-72 | 3-Py | H | H | NH—(CH₂)₂ | H | 13-Cl |
| 7-73 | 3-Py | H | Me | NH—(CH₂)₂ | H | 13-Cl |
| 7-74 | 3-Py | H | H | N(Me)—(CH₂)₂ | H | 13-Cl |
| 7-75 | 3-Py | H | H | NH—(CH₂)₂ | 8-Cl | 13-Cl |
| 7-76 | 3-Py | H | H | NH—(CH₂)₂ | H | 13-Me |
| 7-77 | 3-Py | H | H | NH—(CH₂)₂ | H | 13-OMe |
| 7-78 | 3-Py | H | H | NH—(CH₂)₃ | H | H |
| 7-79 | 2-Me-3-Py | H | H | NH—(CH₂)₃ | H | H |
| 7-80 | Dme-3-Py | H | H | NH—(CH₂)₃ | H | H |
| 7-81 | 2-Py | H | H | NH—(CH₂)₃ | H | H |
| 7-82 | 4-Py | H | H | NH—(CH₂)₃ | H | H |
| 7-83 | 3-Py | Me | H | NH—(CH₂)₃ | H | H |
| 7-84 | 3-Py | H | Me | NH—(CH₂)₂ | H | H |
| 7-85 | 3-Py | H | H | N(Me)—(CH₂)₃ | H | H |
| 7-86 | 2-Me-3-Py | H | H | N(Me)—(CH₂)₃ | H | H |
| 7-87 | Dme-3-Py | H | H | N(Me)—(CH₂)₃ | H | H |
| 7-88 | 2-Py | H | H | N(Me)—(CH₂)₃ | H | H |
| 7-89 | 4-Py | H | H | N(Me)—(CH₂)₃ | H | H |
| 7-90 | 3-Py | H | Me | N(Me)—(CH₂)₃ | H | H |
| 7-91 | 3-Py | H | H | NH—(CH₂)₃ | 8-F | H |
| 7-92 | 2-Py | H | H | NH—(CH₂)₃ | 8-F | H |
| 7-93 | 4-Py | H | H | NH—(CH₂)₃ | 8-F | H |
| 7-94 | 3-Py | H | Me | NH—(CH₂)₃ | 8-F | H |
| 7-95 | 3-Py | H | H | N(Me)—(CH₂)₃ | 8-F | H |
| 7-96 | 3-Py | H | H | NH—(CH₂)₃ | 8-Cl | H |
| 7-97 | 2-Py | H | H | NH—(CH₂)₃ | 8-Cl | H |
| 7-98 | 4-Py | H | H | NH—(CH₂)₃ | 8-Cl | H |
| 7-99 | 3-Py | H | Me | NH—(CH₂)₃ | 8-Cl | H |
| 7-100 | 3-Py | H | H | N(Me)—(CH₂)₃ | 8-Cl | H |
| 7-101 | 3-Py | H | H | NH—(CH₂)₃ | 8-Me | H |
| 7-102 | 3-Py | H | Me | NH—(CH₂)₃ | 8-Me | H |
| 7-103 | 3-Py | H | H | N(Me)—(CH₂)₃ | 8-Me | H |
| 7-104 | 3-Py | H | H | NH—(CH₂)₃ | 8-OMe | H |
| 7-105 | 3-Py | H | Me | NH—(CH₂)₃ | 8-OMe | H |
| 7-106 | 3-Py | H | H | N(Me)—(CH₂)₃ | 8-OMe | H |
| 7-107 | 3-Py | H | H | NH—(CH₂)₃ | 8-Tfm | H |
| 7-108 | 3-Py | H | Me | NH—(CH₂)₃ | 8-Tfm | H |
| 7-109 | 3-Py | H | H | N(Me)—(CH₂)₃ | 8-Tfm | H |
| 7-110 | 3-Py | H | H | NH—(CH₂)₃ | 8-OH | H |
| 7-111 | 3-Py | H | Me | NH—(CH₂)₃ | 8-OH | H |
| 7-112 | 3-Py | H | H | NH—(CH₂)₂ | 8-OH | H |
| 7-113 | 3-Py | H | H | NH—(CH₂)₂ | H | 13-F |
| 7-114 | 3-Py | H | Me | NH—(CH₂)₂ | H | 13-F |
| 7-115 | 3-Py | H | H | NH—(CH₂)₂ | H | 13-F |
| 7-116 | 3-Py | H | H | NH—(CH₂)₂ | H | 13-Cl |
| 7-117 | 3-Py | H | Me | NH—(CH₂)₂ | H | 13-Cl |
| 7-118 | 3-Py | H | H | NH—(CH₂)₂ | H | 13-Cl |
| 7-119 | 3-Py | H | H | NH—(CH₂)₂ | H | 13-Me |
| 7-120 | 3-Py | H | Me | NH—(CH₂)₂ | H | 13-Me |
| 7-121 | 3-Py | H | H | NH—(CH₂)₂ | H | 13-Me |
| 7-122 | 3-Py | H | H | NH—(CH₂)₂ | H | 13-OMe |
| 7-123 | 3-Py | H | Me | NH—(CH₂)₂ | H | 13-OMe |
| 7-124 | 3-Py | H | H | NH—(CH₂)₂ | H | 13-OMe |
| 7-125 | 3-Py | H | H | NH—(CH₂)₂ | H | H |
| 7-126 | 3-Py | H | Me | NH—(CH₂)₂ | H | H |
| 7-127 | 3-Py | H | H | NH—(CH₂)₂ | H | H |
| 7-128 | 3-Py | H | H | NH—(CH₂)₂ | 8-F | H |
| 7-129 | 3-Py | H | Me | NH—(CH₂)₂ | 8-F | H |
| 7-130 | 3-Py | H | H | NH—(CH₂)₂ | 8-F | H |

TABLE 7-continued

| Cpd. No. | R¹ | R² | R³ | A²-B | R⁸ | R⁹ |
|---|---|---|---|---|---|---|
| 7-131 | 3-Py | H | H | NH—(CH₂)₂ | 8-Cl | H |
| 7-132 | 3-Py | H | Me | NH—(CH₂)₂ | 8-Cl | H |
| 7-133 | 3-Py | H | H | NH—(CH₂)₂ | 8-Cl | H |
| 7-134 | 3-Py | H | H | NH—(CH₂)₂ | 8-Tfm | H |
| 7-135 | 3-Py | H | Me | NH—(CH₂)₂ | 8-Tfm | H |
| 7-136 | 3-Py | H | H | NH—(CH₂)₂ | 8-Tfm | H |
| 7-137 | 3-Py | H | H | NH—(CH₂)₂ | H | 13-F |
| 7-138 | 3-Py | H | Me | NH—(CH₂)₂ | H | 13-F |
| 7-139 | 3-Py | H | H | NH—(CH₂)₂ | H | 13-F |
| 7-140 | 3-Py | H | H | NH—(CH₂)₂ | H | 13-Cl |
| 7-141 | 3-Py | H | Me | NH—(CH₂)₂ | H | 13-Cl |
| 7-142 | 3-Py | H | H | N(Me)—(CH₂)₂ | H | 13-Cl |
| 7-143 | 3-Py | H | H | NH—(CH₂)₂ | H | H |
| 7-144 | 3-Py | Me | H | NH—(CH₂)₂ | H | H |
| 7-145 | 3-Py | H | Me | NH—(CH₂)₂ | H | H |
| 7-146 | 3-Py | H | H | N(Me)—(CH₂)₂ | H | H |
| 7-147 | 3-Py | H | H | NH—(CH₂)₂ | 8-F | H |
| 7-148 | 3-Py | H | H | N(Me)—(CH₂)₂ | 8-F | H |
| 7-149 | 3-Py | H | H | NH—(CH₂)₂ | 8-Cl | H |
| 7-150 | 3-Py | H | H | N(Me)—(CH₂)₂ | 8-Cl | H |
| 7-151 | 3-Py | H | H | NH—(CH₂)₂ | 8-Me | H |
| 7-152 | 3-Py | H | H | NH—(CH₂)₂ | 8-OMe | H |
| 7-153 | 3-Py | H | H | NH—(CH₂)₂ | H | 13-F |
| 7-154 | 3-Py | H | H | NH—(CH₂)₂ | H | 13-Cl |
| 7-155 | 3-Py | H | H | NH—CH₂CH(Me)₂ | H | H |
| 7-156 | 3-Py | H | Me | NH—CH₂CH(Me)₂ | H | H |
| 7-157 | 3-Py | H | H | N(Me)—CH₂CH(Me)₂ | H | H |
| 7-158 | 3-Py | H | H | NH—CH₂CH(Me)₂ | 8-F | H |
| 7-159 | 3-Py | H | H | NH—CH₂CH(Me)₂ | 8-Cl | H |
| 7-160 | 3-Py | H | H | NH—CH₂CH(Me)₂ | H | 13-F |
| 7-161 | 3-Py | H | H | NH—CH₂CH(Me)₂ | H | 13-Cl |
| 7-162 | 3-Py | H | H | — | H | H |
| 7-163 | 2-Py | H | H | — | H | H |
| 7-164 | 4-Py | H | H | — | H | H |
| 7-165 | 2-Me-3-Py | H | H | — | H | H |
| 7-166 | Dme-3-Py | H | H | — | H | H |
| 7-167 | 3-Py | Me | H | — | H | H |
| 7-168 | 3-Py | H | Me | — | H | H |
| 7-169 | 3-Py | H | H | — | 8-F | H |
| 7-170 | 2-Py | H | H | — | 8-F | H |
| 7-171 | 4-Py | H | H | — | 8-F | H |
| 7-172 | 3-Py | Me | H | — | 8-F | H |
| 7-173 | 3-Py | H | Me | — | 8-F | H |
| 7-174 | 3-Py | H | H | — | 8-Cl | H |
| 7-175 | 2-Py | H | H | — | 8-Cl | H |
| 7-176 | 4-Py | H | H | — | 8-Cl | H |
| 7-177 | 3-Py | Me | H | — | 8-Cl | H |
| 7-178 | 3-Py | H | Me | — | 8-Cl | H |
| 7-179 | 3-Py | H | H | — | 8-Br | H |
| 7-180 | 3-Py | H | H | — | 8-Me | H |
| 7-181 | 3-Py | H | H | — | 8-OMe | H |
| 7-182 | 3-Py | H | H | — | 8-Tfm | H |
| 7-183 | 3-Py | H | H | — | 8-OH | H |
| 7-184 | 3-Py | H | H | — | H | 13-F |
| 7-185 | 3-Py | H | H | — | H | 13-Cl |

TABLE 8

| Cpd. No. | R¹ | R² | R³ | A²-B | R⁹ |
|---|---|---|---|---|---|
| 8-1 | 3-Py | H | H | NH—(CH₂)₂ | H |
| 8-2 | 2-Py | H | H | NH—(CH₂)₂ | H |
| 8-3 | 4-Py | H | H | NH—(CH₂)₂ | H |
| 8-4 | 2-Me-3-Py | H | H | NH—(CH₂)₂ | H |
| 8-5 | Dme-3-Py | H | H | NH—(CH₂)₂ | H |
| 8-6 | 3-Py | H | H | N(Me)—(CH₂)₂ | H |
| 8-7 | 2-Py | H | H | N(Me)—(CH₂)₂ | H |
| 8-8 | 4-Py | H | H | N(Me)—(CH₂)₂ | H |
| 8-9 | 3-Py | Me | H | NH—(CH₂)₂ | H |
| 8-10 | 3-Py | Me | H | N(Me)—(CH₂)₂ | H |
| 8-11 | 3-Py | H | H | NH—(CH₂)₂ | 13-F |
| 8-12 | 3-Py | H | H | N(Me)—(CH₂)₂ | 13-F |
| 8-13 | 3-Py | H | Me | NH—(CH₂)₂ | 13-F |
| 8-14 | 3-Py | H | H | NH—(CH₂)₂ | 13-Cl |
| 8-15 | 3-Py | H | Me | NH—(CH₂)₂ | 13-Cl |
| 8-16 | 3-Py | H | H | NH—(CH₂)₂ | H |
| 8-17 | 2-Py | H | H | NH—(CH₂)₂ | H |
| 8-18 | 4-Py | H | H | NH—(CH₂)₂ | H |
| 8-19 | 3-Py | Me | H | NH—(CH₂)₂ | H |
| 8-20 | 3-Py | H | Me | NH—(CH₂)₂ | H |
| 8-21 | 3-Py | H | H | N(Me)—(CH₂)₂ | H |
| 8-22 | 3-Py | H | H | NH—(CH₂)₂ | 13-F |

TABLE 8-continued

| Cpd. No. | $R^1$ | $R^2$ | $R^3$ | $A^2$-B | $R^9$ |
|---|---|---|---|---|---|
| 8-23 | 3-Py | H | Me | NH—(CH$_2$)$_2$ | 13-F |
| 8-24 | 3-Py | H | H | N(Me)—(CH$_2$)$_2$ | 13-F |
| 8-25 | 3-Py | H | H | NH—(CH$_2$)$_2$ | 13-Cl |
| 8-26 | 3-Py | H | Me | NH—(CH$_2$)$_2$ | 13-Cl |
| 8-27 | 3-Py | H | H | N(Me)—(CH$_2$)$_2$ | 13-Cl |
| 8-28 | 3-Py | H | H | NH—CH(Me)CH$_2$ | H |
| 8-29 | 3-Py | H | Me | NH—CH(Me)CH$_2$ | H |
| 8-30 | 3-Py | H | H | N(Me)—CH(Me)CH$_2$ | H |
| 8-31 | 3-Py | H | H | NH—CH(Me)CH$_2$ | 13-F |
| 8-32 | 3-Py | H | H | NH—CH(Me)CH$_2$ | 13-Cl |
| 8-33 | 3-Py | H | H | NH—(CH$_2$)$_4$ | H |
| 8-34 | 3-Py | Me | H | NH—(CH$_2$)$_4$ | H |
| 8-35 | 3-Py | H | Me | NH—(CH$_2$)$_4$ | H |
| 8-36 | 3-Py | H | H | N(Me)—(CH$_2$)$_4$ | H |
| 8-37 | 3-Py | H | H | NH—(CH$_2$)$_2$ | 13-F |
| 8-38 | 3-Py | H | H | NH—(CH$_2$)$_2$ | 13-Cl |
| 8-39 | 3-Py | H | H | NH—CH$_2$CH(Me)CH$_2$ | H |
| 8-40 | 3-Py | H | H | NH—CH$_2$CH(Me)CH$_2$ | 13-F |
| 8-41 | 3-Py | H | H | NH—CH$_2$CH(Me)CH$_2$ | 13-Cl |
| 8-42 | 3-Py | H | H | NH—(CH$_2$)$_2$ | H |
| 8-43 | 2-Py | H | H | NH—(CH$_2$)$_2$ | H |
| 8-44 | 4-Py | H | H | NH—(CH$_2$)$_2$ | H |
| 8-45 | 2-Me-3-Py | H | H | NH—(CH$_2$)$_2$ | H |
| 8-46 | Dme-3-Py | H | H | NH—(CH$_2$)$_2$ | H |
| 8-47 | 3-Py | Me | H | NH—(CH$_2$)$_2$ | H |
| 8-48 | 3-Py | H | H | NH—(CH$_2$)$_2$ | 13-F |
| 8-49 | 3-Py | H | Me | NH—(CH$_2$)$_2$ | 13-F |
| 8-50 | 3-Py | H | H | NH—(CH$_2$)$_2$ | 13-Cl |
| 8-51 | 3-Py | H | Me | NH—(CH$_2$)$_2$ | 13-Cl |

TABLE 9

| Cpd. No. | $R^1$ | $R^2$ | $R^3$ | $A^2$-B | $R^8$ |
|---|---|---|---|---|---|
| 9-1 | 3-Py | H | H | NH—(CH$_2$)$_2$ | H |
| 9-2 | 2-Py | H | H | NH—(CH$_2$)$_2$ | H |
| 9-3 | 4-Py | H | H | NH—(CH$_2$)$_2$ | H |
| 9-4 | 2-Me-3-Py | H | H | NH—(CH$_2$)$_2$ | H |
| 9-5 | Dme-3-Py | H | H | NH—(CH$_2$)$_2$ | H |
| 9-6 | 3-Py | H | H | N(Me)—(CH$_2$)$_2$ | H |
| 9-7 | 2-Py | H | H | N(Me)—(CH$_2$)$_2$ | H |
| 9-8 | 4-Py | H | H | N(Me)—(CH$_2$)$_2$ | H |
| 9-9 | 3-Py | H | H | N(Et)—(CH$_2$)$_2$ | H |
| 9-10 | 3-Py | Me | H | NH—(CH$_2$)$_2$ | H |
| 9-11 | 3-Py | Et | H | NH—(CH$_2$)$_2$ | H |
| 9-12 | 3-Py | 3-Py | H | NH—(CH$_2$)$_2$ | H |
| 9-13 | 3-Py | Me | H | N(Me)—(CH$_2$)$_2$ | H |
| 9-14 | 3-Py | H | Me | N(Me)—(CH$_2$)$_2$ | H |
| 9-15 | 2-Py | H | Me | N(Me)—(CH$_2$)$_2$ | H |
| 9-16 | 4-Py | H | Me | N(Me)—(CH$_2$)$_2$ | H |
| 9-17 | 2-Me-3-Py | H | Me | N(Me)—(CH$_2$)$_2$ | H |
| 9-18 | Dme-3-Py | H | Me | N(Me)—(CH$_2$)$_2$ | H |
| 9-19 | 3-Py | H | Et | N(Me)—(CH$_2$)$_2$ | H |
| 9-20 | 3-Py | H | H | NH—(CH$_2$)$_2$ | 8-F |
| 9-21 | 2-Py | H | H | NH—(CH$_2$)$_2$ | 8-F |
| 9-22 | 4-Py | H | H | NH—(CH$_2$)$_2$ | 8-F |
| 9-23 | 2-Me-3-Py | H | H | NH—(CH$_2$)$_2$ | 8-F |
| 9-24 | Dme-3-Py | H | H | NH—(CH$_2$)$_2$ | 8-F |
| 9-25 | 3-Py | H | H | N(Me)—(CH$_2$)$_2$ | 8-F |
| 9-26 | 2-Py | H | H | N(Me)—(CH$_2$)$_2$ | 8-F |
| 9-27 | 4-Py | H | H | N(Me)—(CH$_2$)$_2$ | 8-F |
| 9-28 | 3-Py | H | H | N(Et)—(CH$_2$)$_2$ | 8-F |
| 9-29 | 3-Py | Me | H | NH—(CH$_2$)$_2$ | 8-F |
| 9-30 | 3-Py | 3-Py | H | NH—(CH$_2$)$_2$ | 8-F |
| 9-31 | 3-Py | Me | H | N(Me)—(CH$_2$)$_2$ | 8-F |

TABLE 9-continued

| Cpd. No. | $R^1$ | $R^2$ | $R^3$ | $A^2$-B | $R^8$ |
|---|---|---|---|---|---|
| 9-32 | 3-Py | H | Me | N(Me)—(CH$_2$)$_2$ | 8-F |
| 9-33 | 2-Py | H | Me | N(Me)—(CH$_2$)$_2$ | 8-F |
| 9-34 | 4-Py | H | Me | N(Me)—(CH$_2$)$_2$ | 8-F |
| 9-35 | 2-Me-3-Py | H | Me | N(Me)—(CH$_2$)$_2$ | 8-F |
| 9-36 | Dme-3-Py | H | Me | N(Me)—(CH$_2$)$_2$ | 8-F |
| 9-37 | 3-Py | H | H | NH—(CH$_2$)$_2$ | 8-Cl |
| 9-38 | 2-Py | H | H | NH—(CH$_2$)$_2$ | 8-Cl |
| 9-39 | 4-Py | H | H | NH—(CH$_2$)$_2$ | 8-Cl |
| 9-40 | 2-Me-3-Py | H | H | NH—(CH$_2$)$_2$ | 8-Cl |
| 9-41 | Dme-3-Py | H | H | NH—(CH$_2$)$_2$ | 8-Cl |
| 9-42 | 3-Py | H | H | N(Me)—(CH$_2$)$_2$ | 8-Cl |
| 9-43 | 2-Py | H | H | N(Me)—(CH$_2$)$_2$ | 8-Cl |
| 9-44 | 4-Py | H | H | N(Me)—(CH$_2$)$_2$ | 8-Cl |
| 9-45 | 3-Py | H | H | N(Et)—(CH$_2$)$_2$ | 8-Cl |
| 9-46 | 3-Py | Me | H | NH—(CH$_2$)$_2$ | 8-Cl |
| 9-47 | 3-Py | 3-Py | H | NH—(CH$_2$)$_2$ | 8-Cl |
| 9-48 | 3-Py | Me | H | N(Me)—(CH$_2$)$_2$ | 8-Cl |
| 9-49 | 3-Py | H | Me | N(Me)—(CH$_2$)$_2$ | 8-Cl |
| 9-50 | 2-Py | H | Me | N(Me)—(CH$_2$)$_2$ | 8-Cl |
| 9-51 | 4-Py | H | Me | N(Me)—(CH$_2$)$_2$ | 8-Cl |
| 9-52 | 2-Me-3-Py | H | Me | N(Me)—(CH$_2$)$_2$ | 8-Cl |
| 9-53 | Dme-3-Py | H | Me | N(Me)—(CH$_2$)$_2$ | 8-Cl |
| 9-54 | 3-Py | H | H | NH—(CH$_2$)$_2$ | 8-Cl |
| 9-55 | 3-Py | H | H | N(Me)—(CH$_2$)$_2$ | 8-Cl |
| 9-56 | 3-Py | H | H | NH—(CH$_2$)$_2$ | 8-Br |
| 9-57 | 3-Py | H | H | N(Me)—(CH$_2$)$_2$ | 8-Me |
| 9-58 | 3-Py | H | H | NH—(CH$_2$)$_2$ | 8-OMe |
| 9-59 | 3-Py | H | H | N(Me)—(CH$_2$)$_2$ | 8-OMe |
| 9-60 | 3-Py | H | H | NH—(CH$_2$)$_2$ | 8-Tfm |
| 9-61 | 2-Py | H | H | NH—(CH$_2$)$_2$ | 8-Tfm |
| 9-62 | 4-Py | H | H | NH—(CH$_2$)$_2$ | 8-Tfm |
| 9-63 | 3-Py | H | Me | NH—(CH$_2$)$_2$ | 8-Tfm |
| 9-64 | 3-Py | H | H | N(Me)—(CH$_2$)$_2$ | 8-Tfm |
| 9-65 | 3-Py | H | H | NH—(CH$_2$)$_2$ | 8-OH |
| 9-66 | 3-Py | H | H | N(Me)—(CH$_2$)$_2$ | 8-OH |
| 9-67 | 3-Py | H | H | NH—(CH$_2$)$_3$ | H |
| 9-68 | 2-Me-3-Py | H | H | NH—(CH$_2$)$_3$ | H |
| 9-69 | Dme-3-Py | H | H | NH—(CH$_2$)$_3$ | H |
| 9-70 | 2-Py | H | H | NH—(CH$_2$)$_3$ | H |
| 9-71 | 4-Py | H | H | NH—(CH$_2$)$_3$ | H |
| 9-72 | 3-Py | Me | H | NH—(CH$_2$)$_3$ | H |
| 9-73 | 3-Py | H | Me | NH—(CH$_2$)$_3$ | H |
| 9-74 | 3-Py | H | H | N(Me)—(CH$_2$)$_3$ | H |
| 9-75 | 2-Me-3-Py | H | H | N(Me)—(CH$_2$)$_3$ | H |
| 9-77 | Dme-3-Py | H | H | N(Me)—(CH$_2$)$_3$ | H |
| 9-78 | 2-Py | H | H | N(Me)—(CH$_2$)$_3$ | H |
| 9-79 | 4-Py | H | Me | N(Me)—(CH$_2$)$_3$ | H |
| 9-80 | 3-Py | H | H | NH—(CH$_2$)$_3$ | 8-F |
| 9-81 | 3-Py | H | H | NH—(CH$_2$)$_3$ | 8-F |
| 9-82 | 4-Py | H | H | NH—(CH$_2$)$_3$ | 8-F |
| 9-83 | 3-Py | H | Me | NH—(CH$_2$)$_3$ | 8-F |
| 9-84 | 3-Py | H | H | N(Me)—(CH$_2$)$_3$ | 8-F |
| 9-85 | 3-Py | H | H | NH—(CH$_2$)$_2$ | 8-Cl |
| 9-86 | 2-Py | H | H | NH—(CH$_2$)$_2$ | 8-Cl |
| 9-87 | 4-Py | H | H | NH—(CH$_2$)$_2$ | 8-Cl |
| 9-88 | 3-Py | H | Me | NH—(CH$_2$)$_2$ | 8-Cl |
| 9-89 | 3-Py | H | H | N(Me)H—(CH$_2$)$_2$ | 8-Cl |
| 9-90 | 3-Py | H | H | NH—(CH$_2$)$_2$ | 8-Me |
| 9-91 | 3-Py | H | Me | NH—(CH$_2$)$_2$ | 8-Me |
| 9-92 | 3-Py | H | H | N(Me)H—(CH$_2$)$_2$ | 8-Me |
| 9-93 | 3-Py | H | H | NH—(CH$_2$)$_2$ | 8-OMe |
| 9-94 | 3-Py | H | Me | NH—(CH$_2$)$_2$ | 8-OMe |
| 9-95 | 3-Py | H | H | N(Me)H—(CH$_2$)$_2$ | 8-OMe |
| 9-96 | 3-Py | H | H | NH—(CH$_2$)$_2$ | 8-Tfm |
| 9-97 | 3-Py | H | Me | NH—(CH$_2$)$_2$ | 8-Tfm |
| 9-98 | 3-Py | H | H | N(Me)H—(CH$_2$)$_2$ | 8-Tfm |

TABLE 9-continued

| Cpd. No. | R¹ | R² | R³ | A²-B | R⁸ |
|---|---|---|---|---|---|
| 9-99 | 3-Py | H | H | NH—(CH₂)₂ | 8-OH |
| 9-100 | 3-Py | H | Me | NH—(CH₂)₂ | 8-OH |
| 9-101 | 3-Py | H | H | N(Me)H—(CH₂)₂ | 8-OH |
| 9-102 | 3-Py | H | H | NH—CH(Me)CH₂ | H |
| 9-103 | 3-Py | H | H | N(Me)—CH(Me)CH₂ | H |
| 9-104 | 3-Py | H | H | NH—CH(Me)CH₂ | 8-F |
| 9-105 | 3-Py | H | H | N(Me)—CH(Me)CH₂ | 8-F |
| 9-106 | 3-Py | H | Me | N(Me)—CH(Me)CH₂ | 8-F |
| 9-107 | 3-Py | H | H | NH—CH(Me)CH₂ | 8-Cl |
| 9-108 | 3-Py | H | H | N(Me)—CH(Me)CH₂ | 8-Cl |
| 9-109 | 3-Py | H | Me | N(Me)—CH(Me)CH₂ | 8-Cl |
| 9-110 | 3-Py | H | H | NH—CH(Me)CH₂ | 8-Tfm |
| 9-111 | 3-Py | H | Me | NH—CH(Me)CH₂ | 8-Tfm |
| 9-112 | 3-Py | H | Me | N(Me)—CH(Me)CH₂ | 8-Tfm |
| 9-113 | 3-Py | H | H | NH—(CH₂)₂ | H |
| 9-114 | 3-Py | Me | H | NH—(CH₂)₂ | H |
| 9-115 | 3-Py | H | Me | NH—(CH₂)₂ | H |
| 9-116 | 3-Py | H | H | NH—(CH₂)₂ | H |
| 9-117 | 3-Py | H | H | NH—(CH₂)₂ | 8-F |
| 9-118 | 3-Py | H | H | NH—(CH₂)₂ | 8-F |
| 9-119 | 3-Py | H | H | NH—(CH₂)₂ | 8-Cl |
| 9-120 | 3-Py | H | H | NH—(CH₂)₂ | 8-Cl |
| 9-121 | 3-Py | H | H | NH—(CH₂)₂ | 8-Me |
| 9-122 | 3-Py | H | H | NH—(CH₂)₂ | 8-OMe |
| 9-123 | 3-Py | H | H | NH—(CH₂)₂ | H |
| 9-124 | 3-Py | H | Me | NH—(CH₂)₂ | H |
| 9-125 | 3-Py | H | H | NH—(CH₂)₂ | H |
| 9-126 | 3-Py | H | H | NH—(CH₂)₂ | 8-F |
| 9-127 | 3-Py | H | H | NH—(CH₂)₂ | 8-Cl |
| 9-128 | 3-Py | H | H | — | H |
| 9-129 | 2-Py | H | H | — | H |
| 9-130 | 4-Py | H | H | — | H |
| 9-131 | 2-Me-3-Py | H | H | — | H |
| 9-132 | Dme-3-Py | H | H | — | H |
| 9-133 | 3-Py | Me | H | — | H |
| 9-134 | 3-Py | Et | H | — | H |
| 9-135 | 3-Py | 3-Py | H | — | H |
| 9-136 | 3-Py | H | Me | — | H |
| 9-137 | 3-Py | H | Et | — | H |
| 9-138 | 3-Py | H | H | — | 8-F |
| 9-139 | 2-Py | H | H | — | 8-F |
| 9-140 | 4-Py | H | H | — | 8-F |
| 9-141 | 3-Py | Me | H | — | 8-F |
| 9-142 | 3-Py | H | Me | — | 8-F |
| 9-143 | 3-Py | H | H | — | 8-Cl |
| 9-144 | 2-Py | H | H | — | 8-Cl |
| 9-145 | 4-Py | H | H | — | 8-Cl |
| 9-146 | 3-Py | Me | H | — | 8-Cl |
| 9-147 | 3-Py | H | Me | — | 8-Cl |
| 9-148 | 3-Py | H | H | — | 8-Me |
| 9-149 | 3-Py | H | H | — | 8-OMe |
| 9-150 | 3-Py | H | H | — | 8-Tfm |
| 9-151 | 3-Py | H | Me | — | 8-Tfm |
| 9-152 | 3-Py | H | H | — | 8-OH |

TABLE 10

| Cpd. No. | R¹ | R² | R³ | n | B | R⁸ | R⁹ |
|---|---|---|---|---|---|---|---|
| 10-1 | 3-Py | H | H | 2 | (CH₂)₂ | H | H |
| 10-2 | 2-Py | H | H | 2 | (CH₂)₂ | H | H |
| 10-3 | 4-Py | H | H | 2 | (CH₂)₂ | H | H |
| 10-4 | 2-Me-3-Py | H | H | 2 | (CH₂)₂ | H | H |
| 10-5 | Dme-3-Py | H | H | 2 | (CH₂)₂ | H | H |
| 10-6 | 3-Py | Me | H | 2 | (CH₂)₂ | H | H |
| 10-7 | 3-Py | H | Me | 2 | (CH₂)₂ | H | H |
| 10-8 | 3-Py | H | H | 2 | (CH₂)₂ | 8-F | H |
| 10-9 | 2-Py | H | H | 2 | (CH₂)₂ | 8-F | H |
| 10-10 | 4-Py | H | H | 2 | (CH₂)₂ | 8-F | H |
| 10-11 | 3-Py | Me | H | 2 | (CH₂)₂ | 8-F | H |
| 10-12 | 3-Py | H | Me | 2 | (CH₂)₂ | 8-F | H |
| 10-13 | 3-Py | H | H | 2 | (CH₂)₂ | 7-F | H |
| 10-14 | 3-Py | H | H | 2 | (CH₂)₂ | 8-Cl | H |
| 10-15 | 3-Py | Me | H | 2 | (CH₂)₂ | 8-Cl | H |
| 10-16 | 3-Py | H | Me | 2 | (CH₂)₂ | 8-Cl | H |
| 10-17 | 3-Py | H | H | 2 | (CH₂)₂ | 8-Me | H |
| 10-18 | 3-Py | H | H | 2 | (CH₂)₂ | 8-OMe | H |
| 10-19 | 3-Py | H | H | 2 | (CH₂)₂ | 8-Tfm | H |
| 10-20 | 3-Py | H | H | 2 | (CH₂)₂ | 8-OH | H |
| 10-21 | 3-Py | H | H | 2 | (CH₂)₂ | H | 13-F |
| 10-22 | 3-Py | H | Me | 2 | (CH₂)₂ | H | 13-F |
| 10-23 | 3-Py | H | H | 2 | (CH₂)₂ | H | 12-F |
| 10-24 | 3-Py | H | H | 2 | (CH₂)₂ | H | 13-Cl |
| 10-25 | 3-Py | H | Me | 2 | (CH₂)₂ | H | 13-Cl |
| 10-26 | 3-Py | H | H | 2 | (CH₂)₃ | H | H |
| 10-27 | 2-Py | H | H | 2 | (CH₂)₃ | H | H |
| 10-28 | 4-Py | H | H | 2 | (CH₂)₃ | H | H |
| 10-29 | 3-Py | H | Me | 2 | (CH₂)₃ | H | H |
| 10-30 | 3-Py | H | H | 2 | (CH₂)₃ | 8-F | H |
| 10-31 | 3-Py | H | Me | 2 | (CH₂)₃ | 8-F | H |
| 10-32 | 3-Py | H | H | 2 | (CH₂)₃ | 8-Cl | H |
| 10-33 | 3-Py | H | Me | 2 | (CH₂)₃ | 8-Cl | H |
| 10-34 | 3-Py | H | H | 2 | (CH₂)₃ | 8-Tfm | H |
| 10-35 | 3-Py | H | H | 2 | (CH₂)₃ | H | 13-F |
| 10-36 | 3-Py | H | H | 2 | (CH₂)₃ | H | 13-Cl |
| 10-37 | 3-Py | H | H | 2 | CH(Me)CH₂ | H | H |

TABLE 10-continued

| Cpd. No. | R¹ | R² | R³ | $n$ | B | R⁸ | R⁹ |
|---|---|---|---|---|---|---|---|
| 10-38 | 3-Py | H | H | 2 | CH(Me)CH₂ | 8-F | H |
| 10-39 | 3-Py | H | H | 2 | CH(Me)CH₂ | 8-Cl | H |
| 10-40 | 3-Py | H | H | 2 | CH(Me)CH₂ | 8-Tfm | H |
| 10-41 | 3-Py | H | H | 2 | CH(Me)CH₂ | H | 13-F |
| 10-42 | 3-Py | H | H | 2 | CH(Me)CH₂ | H | 13-Cl |
| 10-43 | 3-Py | H | H | 2 | (CH₂)₄ | H | H |
| 10-44 | 3-Py | H | H | 2 | (CH₂)₄ | 8-F | H |
| 10-45 | 3-Py | H | H | 2 | (CH₂)₄ | 8-Cl | H |
| 10-46 | 3-Py | H | H | 2 | (CH₂)₄ | H | 13-F |
| 10-47 | 3-Py | H | H | 2 | (CH₂)₄ | H | 13-Cl |
| 10-48 | 3-Py | H | H | 2 | CH₂CH(Me)CH₂ | H | H |
| 10-49 | 3-Py | H | H | 3 | (CH₂)₂ | H | H |
| 10-50 | 2-Py | H | H | 3 | (CH₂)₂ | H | H |
| 10-51 | 4-Py | H | H | 3 | (CH₂)₂ | H | H |
| 10-52 | 2-Me-3-Py | H | H | 3 | (CH₂)₂ | H | H |
| 10-53 | Dme-3-Py | H | H | 3 | (CH₂)₂ | H | H |
| 10-54 | 3-Py | Me | H | 3 | (CH₂)₂ | H | H |
| 10-55 | 3-Py | H | Me | 3 | (CH₂)₂ | H | H |
| 10-56 | 3-Py | H | H | 3 | (CH₂)₂ | 8-F | H |
| 10-57 | 3-Py | H | H | 3 | (CH₂)₂ | 8-Cl | H |
| 10-58 | 3-Py | H | H | 3 | (CH₂)₂ | 8-Me | H |
| 10-59 | 3-Py | H | H | 3 | (CH₂)₂ | 8-OMe | H |
| 10-60 | 3-Py | H | H | 3 | (CH₂)₂ | 8-Tfm | H |
| 10-61 | 3-Py | H | H | 3 | (CH₂)₂ | 8-OH | H |
| 10-62 | 3-Py | H | H | 3 | (CH₂)₂ | H | 13-F |
| 10-63 | 3-Py | H | H | 3 | (CH₂)₂ | H | 13-Cl |
| 10-64 | 3-Py | H | H | 3 | (CH₂)₃ | H | H |
| 10-65 | 2-Py | H | H | 3 | (CH₂)₃ | H | H |
| 10-66 | 4-Py | H | H | 3 | (CH₂)₃ | H | H |
| 10-67 | 3-Py | H | H | 3 | (CH₂)₃ | 8-F | H |
| 10-68 | 3-Py | H | H | 3 | (CH₂)₃ | 8-Cl | H |
| 10-69 | 3-Py | H | H | 3 | (CH₂)₃ | 8-Tfm | H |
| 10-70 | 3-Py | H | H | 3 | (CH₂)₃ | H | 13-F |
| 10-71 | 3-Py | H | H | 3 | (CH₂)₃ | H | 13-Cl |
| 10-72 | 3-Py | H | H | 3 | CH(Me)CH₂ | H | H |
| 10-73 | 3-Py | H | H | 3 | (CH₂)₄ | H | H |
| 10-74 | 3-Py | H | H | 3 | (CH₂)₄ | 8-F | H |
| 10-75 | 3-Py | H | H | 3 | (CH₂)₄ | 8-Cl | H |
| 10-76 | 3-Py | H | H | 3 | (CH₂)₄ | H | 13-F |
| 10-77 | 3-Py | H | H | 3 | (CH₂)₄ | H | 13-Cl |
| 10-78 | 3-Py | H | H | 3 | CH₂CH(Me)CH₂ | H | H |

TABLE 11

| Cpd. No. | R¹ | R² | R³ | $n$ | 3 | R⁹ |
|---|---|---|---|---|---|---|
| 11-1 | 3-Py | H | H | 2 | (CH₂)₂ | H |
| 11-2 | 2-Py | H | H | 2 | (CH₂)₂ | H |
| 11-3 | 4-Py | H | H | 2 | (CH₂)₂ | H |
| 11-4 | 2-Me-3-Py | H | H | 3 | (CH₂)₂ | H |
| 11-5 | Dme-3-Py | H | H | 3 | (CH₂)₂ | H |
| 11-6 | 3-Py | Me | H | 2 | (CH₂)₂ | H |
| 11-7 | 3-Py | H | Me | 2 | (CH₂)₂ | H |
| 11-8 | 3-Py | H | H | 2 | (CH₂)₂ | 13-F |
| 11-9 | 3-Py | H | H | 2 | (CH₂)₂ | 12-F |
| 11-10 | 3-Py | H | H | 2 | (CH₂)₂ | 13-Cl |
| 11-11 | 3-Py | H | H | 2 | (CH₂)₃ | H |
| 11-12 | 3-Py | H | H | 2 | (CH₂)₃ | H |
| 11-13 | 3-Py | H | H | 2 | (CH₂)₃ | H |
| 11-14 | 3-Py | H | H | 2 | (CH₂)₃ | 13-F |
| 11-15 | 3-Py | H | H | 2 | (CH₂)₃ | 13-Cl |
| 11-16 | 3-Py | H | H | 2 | CH(Me)CH₂ | H |
| 11-17 | 3-Py | H | H | 2 | (CH₂)₄ | H |
| 11-18 | 3-Py | H | H | 2 | (CH₂)₄ | 13-F |
| 11-19 | 3-Py | H | H | 2 | (CH₂)₄ | 13-Cl |
| 11-20 | 3-Py | H | H | 2 | CH₂CH(Me)CH₂ | H |
| 11-21 | 3-Py | H | H | 2 | (CH₂)₂ | H |
| 11-2 | 2-Py | H | H | 2 | (CH₂)₂ | H |
| 11-23 | 4-Py | H | H | 2 | (CH₂)₂ | H |
| 11-24 | 2-Me-3-Py | H | H | 3 | (CH₂)₂ | H |
| 11-25 | Dme-3-Py | H | H | 3 | (CH₂)₂ | H |
| 11-26 | 3-Py | H | H | 2 | (CH₂)₂ | 13-Cl |
| 11-27 | 3-Py | H | H | 2 | (CH₂)₃ | H |
| 11-28 | 2-Py | H | H | 2 | (CH₂)₃ | H |
| 11-29 | 4-Py | H | H | 3 | (CH₂)₃ | H |
| 11-30 | 3-Py | H | H | 3 | (CH₂)₃ | 13-F |
| 11-31 | 3-Py | H | H | 3 | (CH₂)₃ | 13-Cl |
| 11-32 | 3-Py | H | H | 3 | CH(Me)CH₂ | H |
| 11-33 | 3-Py | H | H | 3 | (CH₂)₄ | H |
| 11-34 | 3-Py | H | H | 3 | (CH₂)₄ | 13-F |
| 11-35 | 3-Py | H | H | 3 | (CH₂)₄ | 13-Cl |
| 11-36 | 3-Py | H | H | 3 | CH₂CH(Me)CH₂ | H |

TABLE 12

| Cpd. No. | R¹ | R² | R³ | n | B | R⁸ |
|---|---|---|---|---|---|---|
| 12-1 | 3-Py | H | H | 2 | (CH₂)₂ | H |
| 12-2 | 2-Py | H | H | 2 | (CH₂)₂ | H |
| 12-3 | 4-Py | H | H | 2 | (CH₂)₂ | H |
| 12-4 | 2-Me-3-Py | H | H | 2 | (CH₂)₂ | H |
| 12-5 | Dme-3-Py | H | H | 2 | (CH₂)₂ | H |
| 12-6 | 3-Py | Me | H | 2 | (CH₂)₂ | H |
| 12-7 | 3-Py | H | Me | 2 | (CH₂)₂ | H |
| 12-8 | 3-Py | H | H | 2 | (CH₂)₂ | 8-F |
| 12-9 | 2-Py | H | H | 2 | (CH₂)₂ | 8-F |
| 12-10 | 4-Py | H | H | 2 | (CH₂)₂ | 8-F |
| 12-11 | 3-Py | Me | H | 2 | (CH₂)₂ | 8-F |
| 12-12 | 3-Py | H | Me | 2 | (CH₂)₂ | 8-F |
| 12-13 | 3-Py | H | H | 2 | (CH₂)₂ | 7-F |
| 12-14 | 3-Py | H | H | 2 | (CH₂)₂ | 8-Cl |
| 12-15 | 3-Py | Me | H | 2 | (CH₂)₂ | 8-Cl |
| 12-16 | 3-Py | H | Me | 2 | (CH₂)₂ | 8-Cl |
| 12-17 | 3-Py | H | H | 2 | (CH₂)₂ | 8-Me |
| 12-18 | 3-Py | H | H | 2 | (CH₂)₂ | 8-OMe |
| 12-19 | 3-Py | H | H | 2 | (CH₂)₂ | 8-Tfm |
| 12-20 | 3-Py | H | H | 2 | (CH₂)₂ | 8-OH |
| 12-21 | 3-Py | H | H | 2 | (CH₂)₃ | H |
| 12-22 | 2-Py | H | H | 2 | (CH₂)₃ | H |
| 12-23 | 4-Py | H | H | 2 | (CH₂)₃ | H |
| 12-24 | 3-Py | H | Me | 2 | (CH₂)₃ | H |
| 12-25 | 3-Py | H | H | 2 | (CH₂)₃ | 8-F |
| 12-26 | 3-Py | H | H | 2 | (CH₂)₃ | 8-Cl |
| 12-27 | 3-Py | H | H | 2 | (CH₂)₃ | 8-Tfm |
| 12-28 | 3-Py | H | H | 2 | CH(Me)CH₂ | H |
| 12-29 | 3-Py | H | H | 2 | (CH₂)₄ | H |
| 12-30 | 3-Py | H | H | 2 | (CH₂)₄ | 8-F |
| 12-31 | 3-Py | H | H | 2 | (CH₂)₄ | 8-Cl |
| 12-32 | 3-Py | H | H | 2 | CH₂CH(Me)CH₂ | H |
| 12-33 | 3-Py | H | H | 3 | (CH₂)₂ | H |
| 12-34 | 2-Py | H | H | 3 | (CH₂)₂ | H |
| 12-35 | 4-Py | H | H | 3 | (CH₂)₂ | H |
| 12-36 | 2-Me-3-Py | H | H | 3 | (CH₂)₂ | H |
| 12-37 | Dme-3-Py | H | H | 3 | (CH₂)₂ | H |
| 12-38 | 3-Py | H | H | 3 | (CH₂)₂ | 8-F |
| 12-39 | 3-Py | H | H | 3 | (CH₂)₂ | 8-Cl |
| 12-40 | 3-Py | H | H | 3 | (CH₂)₂ | 8-Me |
| 12-41 | 3-Py | H | H | 3 | (CH₂)₂ | 8-OMe |
| 12-42 | 3-Py | H | H | 3 | (CH₂)₂ | 8-Tfm |
| 12-43 | 3-Py | H | H | 3 | (CH₂)₂ | 8-OH |
| 12-44 | 3-Py | H | H | 3 | (CH₂)₃ | H |
| 12-45 | 2-Py | H | H | 3 | (CH₂)₃ | H |
| 12-46 | 4-Py | H | H | 3 | (CH₂)₃ | H |
| 12-47 | 3-Py | H | H | 3 | (CH₂)₃ | 8-F |
| 12-48 | 3-Py | H | H | 3 | (CH₂)₃ | 8-Cl |
| 12-49 | 3-Py | H | H | 3 | (CH₂)₃ | 8-Tfm |
| 12-50 | 3-Py | H | H | 3 | CH(Me)CH₂ | H |
| 12-51 | 3-Py | H | H | 3 | (CH₂)₄ | H |
| 12-52 | 3-Py | H | H | 3 | (CH₂)₄ | 8-F |
| 12-53 | 3-Py | H | H | 3 | (CH₂)₄ | 8-Cl |
| 12-54 | 3-Py | H | H | 3 | CH₂CH(Me)CH₂ | H |

Of the compounds listed above, preferred compounds are Compounds No.: 1-1, 1-2, 1-3, 1-6, 1-12, 1-17, 1-23, 1-24, 1-25, 1-26, 1-27, 1-28, 1-32, 1-33, 1-34, 1-36, 1-37, 1-46, 1-47, 1-48, 1-73, 1-74, 1-76, 2-1, 2-2, 2-4, 2-15, 2-17, 2-19, 2-20, 2-21, 2-23, 2-26, 2-27, 2-28, 2-33, 2-34, 2-35, 2-56, 2-57, 2-61, 3-1, 3-10, 3-23, 3-25, 3-27, 3-29, 3-31, 3-42, 3-43, 3-49, 3-52, 3-54, 3-56, 3-60, 3-70, 3-71, 3-73, 4-9, 4-14, 4-21, 4-23, 4-26, 4-28, 4-35, 4-36, 4-51, 4-56, 4-59, 4-60, 5-1, 5-2, 5-3, 5-15, 5-17, 5-19, 5-20, 5-21, 5-23, 5-24, 5-26, 5-27, 5-28, 5-33, 5-34, 5-56, 5-57, 5-60, 5-61, 6-1, 6-2, 6-3, 6-5, 6-13, 6-24, 6-26, 6-28, 6-29, 6-42, 7-1, 7-6, 7-9, 7-14, 7-20, 7-25, 7-28, 7-32, 7-37, 7-42, 7-45, 7-54, 7-56, 7-57, 7-58, 7-65, 7-67, 7-69, 7-71, 7-72, 7-75, 7-76, 7-77, 7-78, 7-84, 7-85, 7-91, 7-94, 7-95, 7-96, 7-100, 7-101, 7-104, 7-107, 7-110, 7-112, 7-113, 7-116, 7-118, 7-119, 7-122, 7-124, 7-125, 7-143, 7-146, 7-147, 7-149, 7-151, 7-152, 7-153, 7-154, 7-162, 7-169, 7-174, 7-180, 7-181, 7-184, 8-1, 8-6, 8-11, 8-12, 8-14, 8-16, 8-21, 8-22, 8-24, 8-25, 8-27, 8-28, 8-33, 8-42, 8-48, 9-1, 9-6, 9-9, 9-20, 9-25, 9-28, 9-37, 9-42, 9-45, 9-54, 9-56, 9-57, 9-58, 9-59, 9-60, 9-65, 9-67, 9-74, 9-80, 9-83, 9-84, 9-85, 9-89, 9-90, 9-92, 9-93, 9-95, 9-96, 9-99, 9-102, 9-113, 9-117, 9-119, 9-121, 9-122, 9-128, 9-138, 9-143, 9-148, 9-149, 10-1, 10-8, 10-13, 10-14, 10-17, 10-18, 10-19, 10-20, 10-21, 10-23, 10-24, 10-26, 10-30, 10-32, 10-35, 10-36, 10-43, 10-44, 10-45, 10-46, 10-47, 10-49, 10-56, 10-57, 10-58, 10-62, 10-64, 10-67, 10-68, 10-70, 10-73, 10-74, 10-76, 11-1, 11-8, 11-9, 11-10, 11-11, 11-14, 11-15, 11-17, 11-18, 11-21, 11-27, 11-29, 11-33, 12-1, 12-8, 12-13, 12-14, 12-17, 12-18, 12-19, 12-20, 12-21, 12-25, 12-28, 12-29, 12-30, 12-38, 12-44, 12-47, 12-50, 12-51 and 12-52.

More preferred specific compounds from this list are Compounds No.: 1-1, 1-2, 1-17, 1-23, 1-24, 1-25, 1-26, 1-28, 1-32, 1-33, 1-34, 1-36, 1-46, 1-47, 1-48, 1-76, 2-1, 2-2, 2-19, 2-20, 2-21, 2-23, 2-28, 2-56, 2-57, 2-61, 3-1, 3-23, 3-25, 3-29, 3-42, 3-43, 3-70, 3-71, 3-73, 4-21, 4-23, 4-26, 4-29, 4-35, 4-36, 4-56, 4-59, 4-60, 5-1, 5-17, 5-19, 5-20, 5-23, 5-26, 5-28, 5-33, 5-34, 5-56, 5-61, 6-1, 6-2, 6-3, 6-13, 6-26, 6-28, 6-29, 6-42, 7-1, 7-6, 7-9, 7-14, 7-20, 7-25, 7-28, 7-37, 7-42, 7-56, 7-57, 7-58, 7-69, 7-71, 7-76, 7-77, 7-78, 7-84, 7-85, 7-91, 7-95, 7-96, 7-101, 7-104, 7-107, 7-110, 7-113, 7-116, 7-118, 7-119, 7-122, 7-143, 7-146, 7-147, 7-153, 7-162, 7-169, 7-174, 8-1, 8-6, 8-16, 8-21, 8-33, 8-42, 9-1, 9-6, 9-67, 9-74, 9-102, 9-113, 9-128, 10-1, 10-8, 10-14, 10-17, 10-18, 10-20, 10-26, 10-30, 10-32, 10-43, 10-44, 10-45, 10-49, 10-56, 10-57, 10-67, 10-68, 10-73, 10-74, 11-1, 11-11, 11-17, 11-21, 11-27, 11-29, 11-33, 12-1, 12-21, 12-29, 12-30, 12-44, 12-50 and 12-51.

Still more preferred specific compounds are Compounds No.: 1-1, 1-2, 1-17, 1-24, 1-25, 1-34, 1-36, 1-46, 1-47, 1-76, 2-1, 2-19, 2-20, 2-28, 2-56, 2-61, 3-1, 3-23, 3-25, 3-29, 3-42, 3-71, 3-73, 4-21, 4-23, 4-35, 4-56, 4-59, 4-60, 5-1, 5-17, 5-20, 5-28, 5-33, 5-56, 5-61, 6-1, 6-2, 6-29, 6-42, 7-1, 7-6, 7-14, 7-20, 7-25, 7-37, 7-42, 7-56, 7-78, 7-85, 7-91, 7-95, 7-104, 7-110, 7-142, 7-143, 7-162, 7-169, 7-174, 8-1, 8-16, 8-42, 9-1, 9-6, 9-67, 9-113, 9-128, 10-1, 10-8, 10-18, 10-26, 10-30, 10-43, 10-49, 10-56, 10-73, 11-1, 11-11, 11-17, 12-1, 12-21, 12-29, 12-44 and 12-51.

Of these, the most preferred are Compounds No.:

1-1. N-Methyl-N-{3-{N-[2-bis(4-fluorophenyl)-methoxyethyl]-N-methylamino}propyl}-2-(3-pyridyl)-thiazolidine-4-carboxamide;

1-24. N-Methyl-N-{3-[N-(2-diphenylmethoxyethyl)-N-methylamino]propyl}-2-(3-pyridyl)thiazolidine-4-carboxamide;

1-25. N-Methyl-N-{2-[N-(2; -diphenylmethoxyethyl)-N-methylamino]ethyl}-2-(3-pyridyl)thiazolidine-4-carboxamide;

3-1. 1-[2-Bis(4-fluorophenyl)methoxyethyl]-4-[2-(3-pyridyl)thiazolidin-4-ylcarbonyl]piperazine;

3-23. 1-(2-Diphenylmethoxyethyl)-4-[2-(3-pyridyl)-thiazolidin-4-ylcarbonyl]homopiperazine;

3-25. 1-{2-[Bis(4-fluorophenyl)methoxy]ethyl}-4-[2-(3-pyridyl)thiazolidin-4-ylcarbonyl]homopiperazine;

3-29. 1-{2-[α-(4-Methylphenyl)benzyloxy]ethyl}-4-[2-(3-pyridyl)thiazolidin-4-ylcarbonyl]piperazine;

3-42. 1-[2-(α-Cyclohexylbenzyloxy)ethyl]-4-[2-(3-pyridyl)thiazolidin-4-ylcarbonyl]piperazine;

3-71. 1-(2-Diphenylmethoxyethyl)-4-[2-(3-pyridyl)-thiazolidin-4-ylcarbonyl]piperazine;

3-73. 1-{2-[α-(4-Chlorophenyl)benzyloxy]ethyl}-4-[2-(3-pyridyl)thiazolidin-4-ylcarbonyl]piperazine;

4-21. 1-[2-(1,1-Diphenylethoxy)ethyl]-4-[2-(3-pyridyl)-thiazolidin-4-ylcarbonyl]homopiperazine;

4-23. 1-{2-[1,1-bis(4-Fluorophenyl)ethoxy]ethyl}-4-[2-(3-pyridyl)thiazolidin-4-ylcarbonyl]homopiperazine;

4-56. 1-[2-(1,1-Diphenylethoxy)ethyl]-4-[2-(3-pyridyl)-thiazolidin-4-ylcarbonyl]piperazine;

4-59. 1-{2-[1-(4-Chlorophenyl)-1-phenylethoxy]ethyl}-4-[2-(3-pyridyl)thiazolidin-4-ylcarbonyl]-piperazine;

4-60. 1-{2-[1,1-Bis(4-fluorophenyl)ethoxy]ethyl}-4-[2-(3-pyridyl)thiazolidin-4-ylcarbonyl]piperazine;

6-1. 1-{2-[4-(Diphenylmethylene)-1-piperidinyl]-ethyl}-4-[2-(3-pyridyl)thiazolidin-4-ylcarbonyl]-piperazine;

7-1. N-{2-(1,2,3,4,10,14b-Hexahydrodibenzo[c,f]-pyrazino[1,2-a]azepin-2-yl)ethyl}-2-(3-pyridyl)-thiazolidine-4-carboxamide;

7-6. N-{2-(1,2,3,4,10,14b-Hexahydrodibenzo[c,f]-pyrazino[1,2-a]azepin-2-yl)ethyl}-N-methyl-2-(3-pyridyl)thiazolidine-4-carboxamide;

7-20. N-{2-(8-Fluoro-1,2,3,4,10,14b-hexahydrodibenzo[c,f]pyrazino[1,2-a]azepin-2-yl)ethyl}-2(3-pyridyl)-thiazolidine-4-carboxamide;

7-37. N-{2-(9-Chloro-1,2,3,4,10,14b-hexahydrodibenzo[c,f]pyrazino[1,2-a]azepin-2-yl)ethyl}-2-(3-pyridyl)-thiazolidine-4-carboxamide;

7-78. N-{3-(1,2,3,4,10,14b-Hexahydrodibenzo[c,f]-pyrazino[1,2-a]azepin-2-yl)propyl}-2-(3-pyridyl)-thiazolidine-4-carboxamide;

7-143. N-{4-(1,2,3,4,10,14b-Hexahydrodibenzo[c,f]-pyrazino[1,2-a]azepin-2-yl)butyl}-2-(3-pyridyl)-thiazolidine-4-carboxamide;

7-162. 2-[2-(3-Pyridyl)thiazolidin-4-ylcarbonyl]-1,2,3,4,10,14b-hexahydrodibenzo[c,f]pyrazino[1,2-a]-azepine;

8-1. N-{2-[1,2,3,4,10,14b-Hexahydropyrazine[2,1-a]-pyrido[2,3-c][2]benzoazepin-2-yl]ethyl}-2-(3-pyridyl)-thiazolidine-4-carboxamide;

9-1. N-{2-[1,2,3,4,10,14b-Hexahydropyrazino[1,2-a]-pyrrolo[2,1-c][1,4]benzodiazepin-2-yl[ethyl}-2-(3-pyridyl)thiazolidine-4-carboxamide;

10-1. 1-{2-[1,2,3,4,10,14b-Hexahydrodibenzo[c,f]-pyrazino[1,2-a]azepin-2-yl]ethyl}-4-[2-(3-pyridyl)-thiazolidin-4-ylcarbonyl]piperazine;

and salts thereof.

The compounds of the present invention may be prepared by a variety of processes known for the preparation of this type of compound. For example, in general terms, they may be prepared by reacting a carboxylic acid compound of formula (XII):

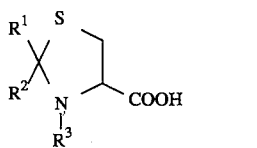

(XII)

(wherein $R^1$, $R^2$ and $R^3$ are as defined above) or a reactive derivative thereof with an amine compound of formula (XIII):

(XIII)

(wherein $R^4$ is as defined above).

The reaction of the carboxylic acid of formula (XII) itself and the amine derivative of formula (XIII) may be carried out in the presence or absence of a base; it is also preferably carried out in the presence of an inert solvent and preferably in the presence of a condensing agent.

There is no particular restriction on the nature of the condensing agents employed, and any such agent commonly used in reations of this type may equally be employed here, provided that it can form an amide bond from the carboxylic acid and the amine. Preferred examples include: dicyclohexylcarbodiimide (DCC), diethyl cyanophosphonate (DEPC), carbonyldiimidazole, diphenylphosphorylazide (DPPA), dicyclohexylcarbodiimide plus 1-hydroxybenzotriazole and diethylazodicarboxylate plus triphenylphospine, more preferably dicyclohexylcarbodiimide plus 1-hydroxybenzotriazole or diethyl cyanophosphonate.

There is equally no particular restriction on the nature of the base, when employed, provided that it has no adverse effect on other parts of the molecule. Examples of suitable bases include organic amines, such as trimethylamine, triethylamine, pyridine, dimethylaniline, N-methylmorpholine and 4-dimethylaminopyridine, most preferably triethylamine or N-methylmorpholine.

The reaction is normally and preferably carried out in the presence of an inert solvent, the nature of which is not critical, provided that it has no adverse effect upon the reaction and that it can dissolve the reagents, at least to some extent. Examples of suitable solvents include: aromatic hydrocarbons, such as benzene, toluene and xylene; halogenated hydrocarbons, especially halogenated aliphatic hydrocarbons, such as methylene chloride, dichloroethane and chloroform; esters, such as ethyl acetate and propyl acetate; ethers, such as diethyl ether, tetrahydrofuran and dioxane; amides, such as dimethylformamide, dimethylacetamide and hexamethylphosphoric triamide; and nitrides, such as acetonitrile. Of these, we prefer the ethers (particularly tetrahydroduran), halogenated hydrocarbons (particularly methylene chloride), amides (particularly dimethylformamide) and esters (particularly ethyl acetate).

The reaction will take place over a wide range of temperatures, and the precise reaction temperature chosen is not critical to the invention. In general, we find it convenient to carry out the reaction at a temperature in the range of from −10° C. to 50° C. (more preferably from 0° C. to 30° C.). The time required for the reaction may likewise vary widely, depending on many factors, notably the reaction temperature and the nature of the reagents. However, in most cases, a period of from 30 minutes to 24 hours will normally suffice.

Instead of using the carboxylic acid of formula (XII) itself, a reactive derivative can be employed in this reaction, as is well known in the art for reactions of this type. Examples of reactive derivatives of carboxylic acids include: acid halides, such as the acid chlorides and acid bromides; acid azides; active esters with 1-hydroxybenzotriazole, N-hydroxysuccinimide, etc.; acid anhydrides of the carboxylic acid of formula (XII); or mixed acid anhydrides with a monoalkyl carbonate in which the alkyl group has from 1 to 4 carbon atoms, such as monomethyl carbonate, monoethyl carbonate or monoisobutyl carbonate, or with a monoaryl carbonate, such as monophenyl carbonate of monotolyl (especially mono-o- tolyl carbonate; of these, we prefer the mixed acid anhydrides with alkyl carbonates.

Reactive derivatives of carboxylic acids, such as the acid halides and the acid anhydrides, can be obtained by conventional methods, for example, by reacting a carboxylic acid of formula (XII) with a halogenating agent (for example thionyl chloride or thionyl bromide), with an acid chloride or acid bromide of a desired carboxylic acid, or with methyl chlorocarbonate, ethyl chlorocarbonate, isobutyl chlorocarbonate, phenyl chlorocarbonate or tolyl chlorocarbonate. This reaction normally and preferably takes place in an inert solvent (for example methylene chloride, benzene or tetrahydrofuran) at a suitable temperature, for example from 20° C. to 100° C., for the required time, which is generally from 1 to 20 hours. If necessary, the reaction may be carried out in the presence of a base (for example pyridine, triethylamine and dimethylaniline).

Reactive derivatives, such as the acid azides and active esters, can be prepared by reacting a carboxylic acid of formula (XII) with an azidating or esterifying agent, for example hydrogen azide, 1-hydroxybenzo-triazole or N-hydroxysuccinimide); the reaction conditions employed are preferably the same as those employed for the reaction between the carboxylic acid of formula (XII) and the amine of formula (XIII).

The reaction between a reactive derivative of the carboxylic acid of formula (XII) and the amine of formula (XIII) is normally and preferably carried out in an inert solvent, the nature of which is not critical, provided that it has no adverse effect upon the reaction and that it can dissolve the reagents, at least to some extent. Examples of suitable solvents include: halogenated hydrocarbons, especially halogenated aliphatic hydrocarbons, such as methylene chloride, dichloroethane and chloroform; ethers, such as diethyl ether, tetrahydrofuran and dioxane; esters, such as ethyl acetate; and aromatic hydrocarbons, such as benzene, toluene and xylene. Of these, we prefer the aromatic hydrocarbons and the ethers, such as tetrahydrofuran.

Alternatively, a large excess of the compound of formula (XIII) may be used and will also serve as the solvent.

The reaction will take place over a wide range of temperatures, and the precise reaction temperature chosen is not critical to the invention. In general, we find it convenient to carry out the reaction at a temperature in the range of from −10° C. to 50° C. (more preferably from 0° C. to 25° C.). The time required for the reaction may likewise vary widely, depending on many factors, notably the reaction temperature and the nature of the reagents. However, in most cases, a period of from 5 minutes to 20 hours (more preferably from 30 minutes to 10 hours) will normally suffice.

The desired product of this reaction can be recovered from the reaction mixture by conventional methods. For example, one suitable recovery procedure comprises: suitably neutralizing the reaction mixture; and then distilling the solvent from the reaction mixture. If necessary, after the solvent is distilled off from the reaction mixture, the residue may be poured into water and the resulting mixture extracted with a water-immiscible organic solvent. The solvent is then removed from the extract by evaporation, optionally under reduced pressure, to obtain the desired compound. If desired, the resulting compound can be further purified by conventional techniques, such as recrystallization, reprecipitation or the various chromatography techniques, notably column chromatography.

Those compounds of formula (I) wherein $R^3$ represents an alkyl group can be prepared by acylating the corresponding compound of formula (I) wherein $R^3$ represents a hydrogen atom to give a compound in which $R^3$ is replaced by an acyl group and then reducing this acyl group to the corresponding alkyl group. The first step of acylation may be carried out by formylating the starting material by a known method [for example, as described in J. Org. Chem., 27, 4058 (1962), the disclosure of which is incorporated herein by reference] or by reacting the starting material with a fatty acid halide having from 2 to 4 carbon atoms (for example acetyl chloride, propionyl chloride or butyryl chloride) in an inert solvent (for example, methylene chloride) at a suitable temperature, for example around room temperature, for a suitable period, for example from 30 minutes to 2 hours, in the presence of a base (for example triethylamine or pyridine) to provide an acyl compound. This acyl compound may then be reacted with a reducing agent (for example an aluminum hydride, such as lithium aluminum hydride) in an inert solvent (for example an ether, such as diethyl ether or tetrahydofuran) at a suitable temperature, for example from −10° C. to 80° C., for a suitable period, for example from 30 minutes to 5 hours.

The starting compound of formula (XII) is known or may easily be produced by known methods (for example as described in French Patent No. 2267089 or Japanese Unexamined Patent Publication No. 2-179) or by analogous methods. A compound of formula (XII) in which $R^3$ represents an alkyl group may easily be prepared from the corresponding compound in which $R^3$ represents a hydrogen atom by a reaction analogous to that described above for converting a compound of formula (I) in which $R^3$ represents a hydrogen atom to a corresponding compound in which $R^3$ represents an alkyl group.

The following preparations are described in the Japanese Unexamined Patent Publication No. 2-179:

REFERENECE EXAMPLE 1

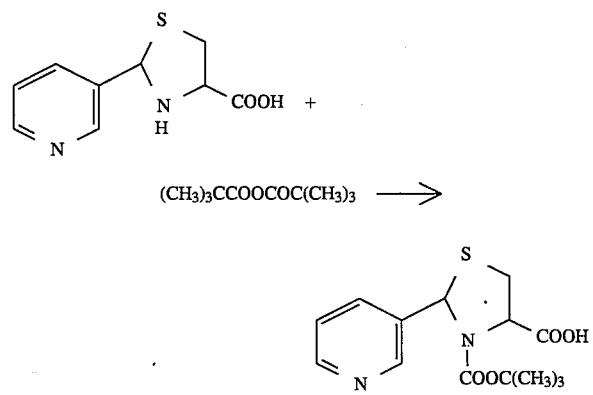

Di-tert-butyl discarbonate (2.4 g) and 10 ml of 1N aqueous sodium hydroxide were added to a mixture of 2.1 g of 2-(3-pyridyl)thiazolidine-4-carboxylic acid (prepared from L-cysteine and pyridine-3-carbaldehyde), 20 ml of water and 40 ml of dioxane at a temperatue not higher than 4° C., and the mixture was stirred at room temperature for 30 minutes. The reaction mixture was concentrated under reduced pressure, 30 ml of water was added, the pH was adjusted to 2 to 3 by addition of 0.5M aqueous citric acid, and the mixture was extracted with ethyl acetate. The extract was washed with water, dried over anhydrous sodium sulfate and concentrated under reduced pressure, and the residue was recrystallized from ethyl acetate to give 1 g of N-tert-butoxycarbonyl-2-(3-pyridyl)thiazolidine-4-carboxylic acid. Melting point 167°–169° C.

REFERENCE EXAMPLE 2

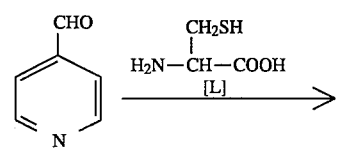

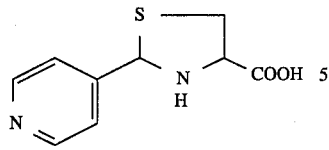

Pyridine-4-carbaldehyde (1.07 g) and 1.21 g of L-cysteine were heated in 60% ethanol at a refluxing temperature for 4 hours. Activated charcoal (100 mg) was added to the reaction mixture while it was warm. The mixture was filtered. After cooling, the resultant crystalline precipitate was collected by filtration and washed with ethanol to give 1.2 g of 2-(4-pyridyl)-thiazolidine-4-carboxylic acid. Melting point 171°–173° C.

NMR (DMSO-d$_6$) δ: 3.0–3.5 (2H), 3.9–4.2 (1H), 5.56 and 5.78 (s, respectively 1H), 7.4–7.6 (2H), 8.5–8.6(2H).

REFERENCE EXAMPLE 3

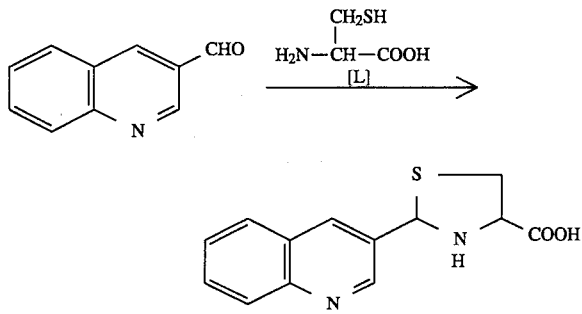

Quinoline-3-carbaldehyde (1.57 g) and 1.21 g of L-cysteine were dissolved in 50 ml of 50% ethanol, and the solution was stirred at room temperature for 1 hour. The resultant crystalline precipitate was collected by suction filtrating, washed with 50% ethanol and dried to give 1.95 g of 2-(3-quinolyl)thiazolidine-4-carboxylic acid. Melting point 173°–175° C. (decomposition).

REFERENCE EXAMPLE 53

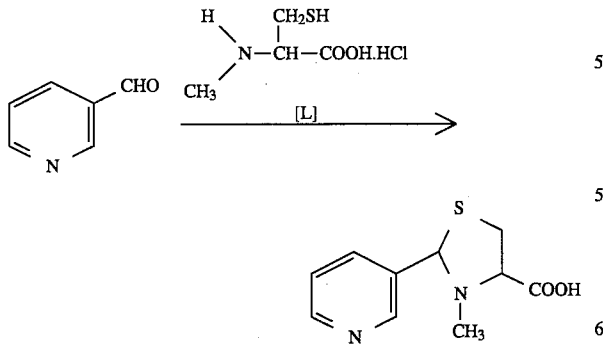

A mixture of 1.72 g of L-N-methylcysteine, 1.07 g of nicotinaldehyde and 2 ml of water was stirred at room temperature for 24 hours. Pyridine (0.8 ml) and 1 ml of ethanol were added to the reaction mixture, and the resultant crystalline precipitate was collected by filtration, washed with ethanol and dried to give 0.74 g of 3-methyl-2-(3-pyridyl)thiazolidine-4-carboxylic acid.

NMR (DMSO-d$_6$) δ: 2.24, 2.32 (3H/$_2$X2, s, N—CH$_3$), 3.0–3.64 (5/2H, m), 4.16–4.32 (H/$_2$, m), 4.92, 5.36 (H/$_2$X2, s), 7.10–7.32 (1H, m), 7.80–8.00 (1H, m), 8.44–8.72 (2H, m)

MS (FAB): m/z 225 (M+H)+

REFERENCE EXAMPLE 54

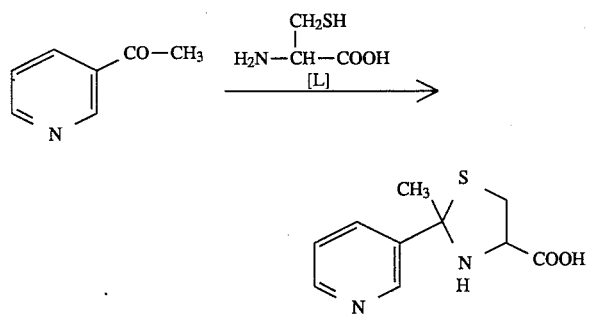

A mixture of 3.63 g of 3-acetylpyridine, 3.63 g of L-cysteine, 25 ml of water and 25 ml of ethanol was refluxed for 24 hours. The reaction mixture was concentrated under reduced pressure, isopropanol was added to the residue, and the resultant powder was collected by filtration. Ethanol was added to the powder, the insoluble matter was filtered off, and the filtrate was concentrated to dryness. The residue was dissolved in water and adjusted to pH 6 by addition of diluted hydrochloric acid under ice cooling and stirring, and the resultant powder was collected by filtration, washed with ethanol and dried to give 2.54 g of 2-methyl-2-(3-pyridyl)thiazolidine-4- carboxylic acid.

NMR (DMSO-d6) δ: 1.78 and 1.88 (s, respectively 3H), 2.92–3.56 (2H, m), 3.56–4.38 (1H, m), 7.20–7.44 (1H, m), 7.80–9.08 (1H, m), 9.32–9.52 (1H, m), 9.68–9.86 (1H, m)

MS (FAB): m/z 225 (M+H)+

REFERENCE EXAMPLE 55

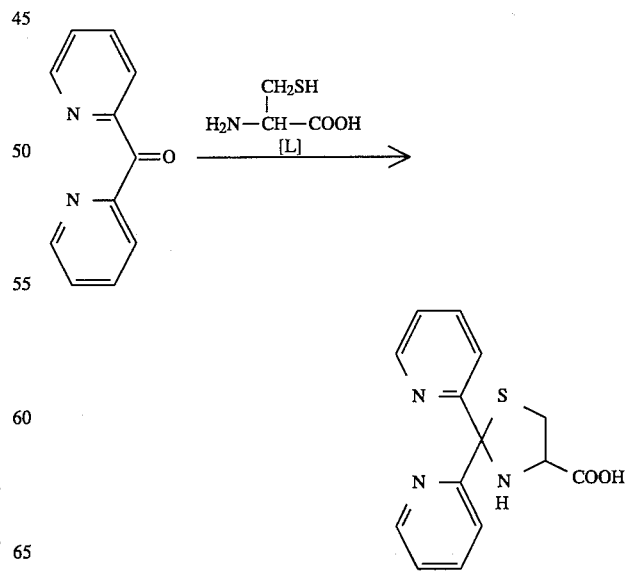

A mixture of 3.68 g of di-2-pyridyl ketone, 2.42 g of L-cysteine, 25 ml of ethanol was refluxed for 3.5 hours. After allowing the mixture to cool, the insoluble matter was filtered off, and the filtrate was concentrated to dryness under reduced pressure. The residue was washed in sequence with ethyl acetate and ether to give 0.63 g of 2,2-di(2-pyridyl)-thiazolidine-4-carboxylic acid.

NMR (DMSO-d6) δ: 2.85~4.15 (3H, m), 7.20~8.90 (8H, m)

| Desired Product | |
|---|---|
| Chemical Structure and Chemical Name | Physiochemical Properties |

Ref. Ex. 58

2-[3-(4-Dimethylamino-pyridyl)]thiazolidine-4-carboxylic acid.

NMR (DMSO-$d_6$)
δ: 2.85(6H, s), 2.98–3.56 (2H, m), 3.72–4.44(1H, m), 5.68, 5.92(1H, s), 6.80–7.00(1H, m), 8.16–8.34(1H, m), 8.60–8.75(1H, m)
MS (FAB): m/z 254 (M + H)$^+$

Ref. Ex. 59

2-]3-(5,6-Dimethoxy-pyridyl)]thiazolidine-4-carboxylic acid

Melting point: 154–155° C. (decomposition)
Ms (FAB): m/z 271 (M + H)$^+$

Ref. Ex. 60

2-[3-(2-Methylpyridyl)]-thiazolidine-4-carboxylic acid

NMR (DMSO-$d_6$)
δ: 2.60(3H, s), 2.80–4.60 (3H, m), 5.70, 6.00 (1H, s), 7.00–8.50(3H, m)

Ref. Ex. 61

2-(1-tert-Butoxycarbonyl-4-piperidinyl)thiazolidine-4-carboxylic acid

Melting point: 169–171° C. (decomposition)
NMR (CDCl$_3$ + DMSO-$d_6$)
δ: 1.48(9H, s), 1.4–2.1 (5H), 2.6–3.0(1H), 2.95(1H, dd, J=7 and 10Hz), 3.22(1H, dd, J=7 and 10Hz), 3.6–4.0 (1H), 3.96(1H, t, J=7Hz), 4.49(1H, d, J=8Hz), 6.3(2H, br, exchange with D$_2$O)

Ref. Ex. 62

2-(2-Pyrazyl)thiazolidine-4-carboxylic acid

Melting point: 144–146° C. (decomposition)
Elemental analysis (for C$_8$H$_9$N$_3$O$_2$S):

|  | C (%) | H (%) | N (%) | S (%) |
|---|---|---|---|---|
| Calcd: | 45.49 | 4.29 | 19.89 | 15.18 |
| Found: | 45.20 | 4.18 | 19.76 | 15.43 |

Ref. Ex. 63

-continued

| Desired Product | |
|---|---|
| Chemical Structure and Chemical Name | Physiochemical Properties |
| 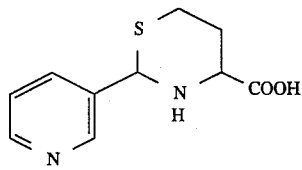<br>2-[3-Pyridyl]-3,4,5,6-tetrahydro-2H-thiazine-4-carboxylic acid<br>Ref. Ex. 64 | Melting point: 204–207° C.<br>MS: m/z 225 (M$^+$ + 1) |
| 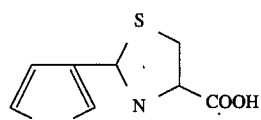<br>2-(3-Thienyl)thiazolidine-4-carboxylic acid<br>Ref. Ex. 65 | Melting point: 165–167° C.<br>Elemental analysis<br>(for $C_8H_9NO_2S_2$):<br>        C (%)  H (%)  N (%)  S (%)<br>Calcd:  44.63    4.21    6.51    29.79<br>Found:  44.57    4.23    6.49    29.99 |
| 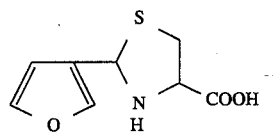<br>2-(3-Furyl)thiazolidine-4-carboxylic acid<br>Ref. Ex. 66 | Melting point: 169–170° C.<br>(decomposition)<br>Elemental analysis<br>(for $C_8H_9NO_3S$):<br>        C (%)  H (%)  N (%)  S (%)<br>Calcd:  48.23    4.55    7.03    16.09<br>Found:  48.03    4.51    7.00    16.28 |
| 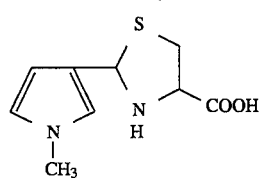<br>2-[3-(1-Methylpyrrolyl)]-thiazolidine-4-carboxylic acid<br>Ref. Ex. 67 | Melting point: 148–147° C.<br>(decomposition)<br>MS (FAB): m/z 213 (M$^+$+1) |
| 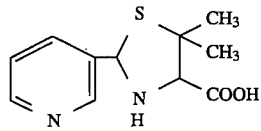<br>5,5-Dimethyl-2-(3-pyridyl)-thiazolidine-4-carboxylic acid | Melting point: 143–144° C.<br>MS (FAB): m/z 1239 (M$^+$+1) |

The starting compound of formula (XIII) is known or may easily be produced by known methods [for example as described in Chem. Pharm. Bull., 37, 100 (1989) or J. Med. Chem., 32, 583 (1989)], for example as shown below in Reaction Schemes A and B, or by analogous methods.

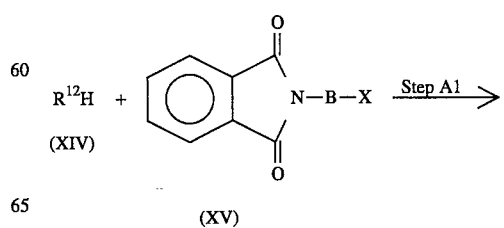

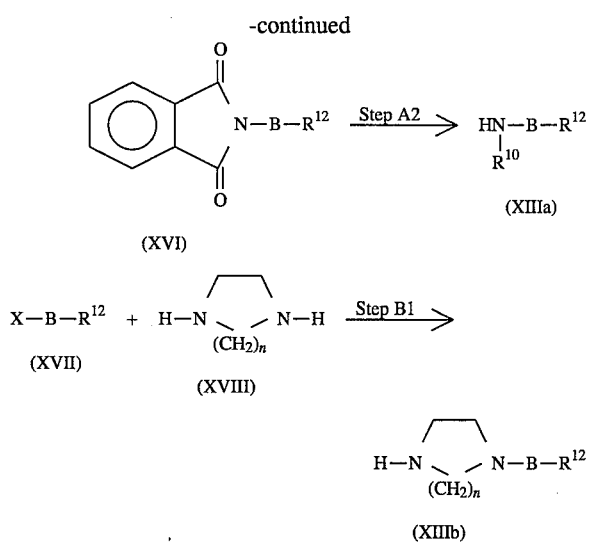

In the above formulae, $R^{10}$, B and $n$ are as defined above; X represents a halogen atom (preferably a chlorine, bromine or iodine atom) and $R^{12}$ represents a group of formula (XIX), (XX) or (XXI):

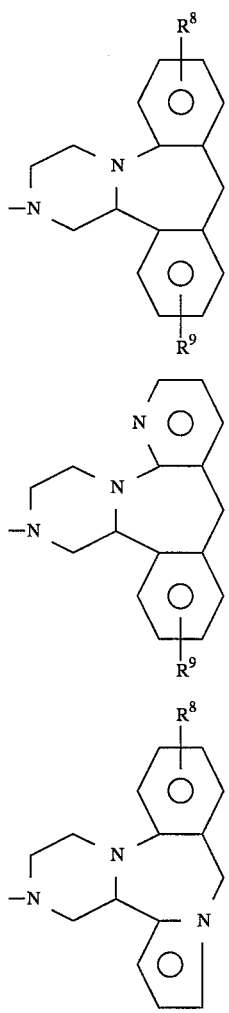

In the above formulae, $R^8$ and $R^9$ are as defined above.

In Reaction Scheme A, a compound of formula (XIIIa), which corresponds to a compound of formula (XIII) wherein $A^2$ represents a group of the formula $N(R^{10})$-B (wherein $R^{10}$ and B are as defined above) is prepared in two steps.

In Step A1, a compound of formula (XVI) is prepared by reaching a compound of formula (XIV) with a compound of formula (XV). This reaction is normally and preferably carried out in an inert solvent and in the presence of a base.

There is no particluar limitation on the nature of the base which may be employed, and any base commonly used in reactions of this type may equally be used here. Preferred examples include: alkali metal carbonates, such as sodium carbonate and potassium carbonate; and alkali metal hydrogencarbonates, such as sodium hydrogencarbonate and potassium hydrogen-carbonate. Of these, we particularly prefer sodium carbonate or potassium carbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ketones, such as acetone, methyl ethyl ketone and methyl isobutyl ketone; and amides, such as dimethylformamide, dimethylacetamide and hexamethyl-phosphoric triamide. Of these, we prefer the ketones, particularly methyl isobutyl ketone.

The reaction can take place over a wide range of temperatures, and the precise reaction temperature is not critical to the invention. In general, we find it convenient to carry out the reaction at a temperature of from −10° C. to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours will usually suffice.

This reaction may also be carried out, if necessary, in the presence of a catalytic amount of an alkali metal iodide, such as sodium iodide or potassium iodide.

In Step A2 of this Reaction Scheme, a compound of formula (XIIIa) is prepared by reacting a compound of formula (XVI), which may have been prepared as described in Step A1, with an amine, followed by alkylation of the amino group, if desired. Examples of amines which may be employed in this reaction include hydrazine and butylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include alcohols, such as methanol, ethanol and propyl alcohol.

The reaction can take place over a wide range of temperatures, and the precise reaction temperature is not critical to the invention. In general, we find it convenient to carry out the reaction at a temperature of from −10° C. to 90° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours will usually suffice.

The optional alkylation reaction may be carried out by reacting a compound of formula (XIIIa) wherein $R^{10}$ represents a hydrogen atom with an acylating agent and then a reducing agent, in the same manner as in the alkylation of $R^3$ in the preparation of the compounds of formula (I).

In Reaction Scheme B, a compound of formula (XIIIb), which corresponds to the compound of formula (XIII) wherein A represents a piperazine or homopiperazine group, is prepared.

In this reaction, a compound of formula (XVII) is allowed to react with a compound of formula (XVIII), normally and preferably in an inert solvent and in the presence of a base, to give a compound of formula (XIIIb).

There is no particluar limitation on the nature of the base which may be employed, and any base commonly used in reactions of this type may equally be used here. Preferred examples include organic amines such as triethylamine or pyridine; alternatively, an excess of the compound of formula (XVIII) can be used and will serve also as the base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include aromatic hydrocarbons, such as benzene, toluene and xylene.

The reaction can take place over a wide range of temperatures, and the precise reaction temperature is not critical to the invention. In general, we find it convenient to carry out the reaction at a temperature of from 20° C. to 130° C. The time required for the reaction may also vary widely, depending on many factors, notably the reaction temperature and the nature of the reagents and solvent employed. However, provided that the reaction is effected unde3r the preferred conditions outlined above, a period of from 30 minutes to 24 hours will usually suffice.

The desired product of each step can be recovered from the reaction mixture by conventional methods. For example, one suitable recovery procedure comprises: suitably neutralizing the reaction mixture; and then distilling the solvent from the reaction mixture. If necessary, after the solvent has been distilled from the reaction mixture, the residue may be poured into water and the resulting mixture extracted with a water-immiscible organic solvent, followed by evaporation of the solvent from the extract to obtain the desired compound. If desired, the resulting compound can be further purified by conventional techniques, such as recrystallization, reprecipitation or the various chromatography techniques, notably column chromatography.

The pyridylthiazolinecarboxylic acid amide derivatives of the present invention have excellent anti-allergic and anti-asthmatic activities. In addition, since they are antagonists to the manifestation of inflammation caused by PAF and can thus inhibit the accumulation of eosinophiles, they are effective for the treatment not only of early allergic reactions but also of late allergic reactions. They are thus useful as therapeutic agents for the treatment or prophylaxis of allergic diseases and asthma.

The compounds of the present invention may therefore be used in the treatment and prophylaxis of disorders such as those referred to above, and, for this purpose, may be formulated as conventional pharmaceutical preparations, as is well known in the art. Thus, the compounds may be administered orally, e.g. in the form of tablets, capsules, granules, powders, syrups, or other such well known forms, parenterally, e.g. by injections, suppositories, or by other means, for example, as patches, inhalation or opthalmic solutions.

These pharmaceutical preparations can be prepared by conventional means and may contain known adjuvants of a type commonly used in this field, for example vehicles, binders, disintegrators, lubricants, stabilizers, corrigents, etc. depending upon the intended use and form of the preparation. The dose will depend upon the condition, age, and body weight of the patient as well as upon the nature and severity of the disorder to be treated, but, in the case of oral administration to an adult human patient, we would normally suggest a total daily dose of from 10 mg to 1000 mg, more preferably from 10 mg to 500 mg, which may be administered in a single dose or in divided doses, e.g. from one to three times a day.

BIOLOGICAL ACTIVITY

The biological activity of the compounds of the present invention is shown in the following Experiments. In these Experiments, the compounds of the invention are identified by reference to the number of one of the subsequent Examples which illustrates their preparation.

EXPERIMENT 1

Inhibitory Effect on Passive Cutaneous Anaphylaxis (PCA) in Rats

According to Mota's method [I. Mota, Immunology, 7, 681–699 (1964)], antiserum (256 times the PCA titer) of rat against egg albumin was prepared and diluted four times with physiological saline. Male SD rats (5 weeks old) were used as the test animals in groups, each containing 4 animals. The rats were sensitized by intradermal injection of 0.05 ml of the diluted antiserum solution in the dorsal position. 48 hours after this injection, a suspension of the test compound in an aqeous 0.5% w/v tragacanth solution was orally administered to the rats, which had been fasted for one day, and 60 minutes later they were injected in the caudal vein with 5 ml/kg body weight of physiological saline containing 0.4% w/v egg albumin and 1.0% w/v Evans Blue. 30 minutes after this last injection, the rats were sacrificed with carbon dioxide and the Evans Blued exuded in the dorsal intradermal portion was determined according to Harada's method (Harada et al., J. Pharm. Pharmac., 23, 218–219 (1971)].

The results achieved from the test groups which were treated with a test compound were evaluated to determine the inhibitory rate by comparison with the average amount of exuded dye in a control group, which was not given the test compound. The inhibitory rate was calculated by the following equation.

$$Inhibitory\ rate(\%) = (1 - B/A) \times 100$$

A: amount of exuded dye in the control group
B: amount of exuded dye in the test group.

The results are shown in Table 13.

TABLE 13

| Compound of Example No. | Salt | Dose (p.o., mg/kg) | Inhibitory rate (%) |
|---|---|---|---|
| 1 | hydrochloride | 6.4 | 33 |
| 5 | hydrochloride | 6.4 | 42 |
| 6 | hydrochloride | 6.4 | 45 |
| 16 | hydrochloride | 6.4 | 62 |
| 17 | hydrochloride | 6.4 | 73 |
| 25 | hydrochloride | 6.4 | 55 |

EXPERIMENT 2

Inhibitory Effect in Vitro Against PAF-induced blood platelet aggregation

Blood samples were obtained by cardiac puncture from a rabbit and one part by volume of each sample was immediately mixed with 0.1 part of a 3.8% w/v aqueous solution of sodium citrate. A platelet rich plasma (PRP) fraction was prepared by centrifuging the samples at 150×G for 15 minutes at room temperature, and a platelet poor plasma (PPP) fraction was then prepared by further centrifugation at 1,000×G for 15 minutes. The platelet count in the PRP was adjusted to $6 \times 10^5$ per μl by the addition of an appropriate amount of the PPP fraction. According to the method reported by Born et al. [G. V. R. Born et al.: J. Physiol. 52, 67–68 (1962)], blood platelet aggregation was determined turbidimetrically in a 6-channel aggregometer (Hemetracer, NKB, Tokyo, Japan). Aliquots of the PRP (272 μl) were preincubated with 3 μl of a solution of the test compound in dimethyl sulfoxide for 1 minute, and then stimulated with l-$C_{16:0}$ PAF (at a final concentration of $10^{-8}$–$3 \times 10^{-8}$M) at 37° C. with stirring (100 rpm). Changes in light transmission were monitored for 5 minutes. Vehicle (dimethyl sulfoxide) controls were tested simultaneously, and the inhibitory effects of the test compounds were assed on the maximal aggregation. The $IC_{50}$ values were calculated by the method of least squares.

Table 14 below shows the results.

TABLE 14

| Compound of Example No. | Salt | Platelet aggregation inhibition, $IC_{50}$ (g/ml) |
|---|---|---|
| 1 | hydrochloride | $6.3 \times 10^{-8}$ |
| 4 | hydrochloride | $8.5 \times 10^{-8}$ |
| 6 | hydrochloride | $5.5 \times 10^{-8}$ |
| 7 | hydrochloride | $9.5 \times 10^{-8}$ |
| 9 | hydrochloride | $2.8 \times 10^{-7}$ |
| 11 | hydrochloride | $7.2 \times 10^{-8}$ |
| 12 | hydrochloride | $1.9 \times 10^{-7}$ |
| 13 | hydrochloride | $2.2 \times 10^{-7}$ |
| 14 | oxalate | $1.4 \times 10^{-7}$ |

EXPERIMENT 3

Inhibitory Effect on PAF-Receptor Binding

Blood samples were drawn from the heart of a rabbit. 1 part by volume of each sample was mixed immediately with ⅑ part of 0.077M solution of disodium ethylenediaminetetraacetate. After a similar procedure to that described in Experiment 2, a precipitated blood platelet sample was obtained. This blood platelet sample was washed, and, after repeated freezing and thawing to rupture the cells, it was placed on top of two layers consisting of 0.25M and 1.5 M sucrose solutions. By centrifugation at 63,500×G, for 2 hours at 4° C., the fraction obtained from the interface between the 0.25M and 1.5M sucrose solutions was collected and is regarded as a PAF-receptor membrane fraction. A receptor binding experiment was then conducted according to a method very similar to that reported by Hwang et al. [San-Bao Hwang et al.: J. Biol. Chem. 260, 15639–15645 (1985)]. The specific binding of $^3$H-PAF was measured using a Wattman GF/C filter. A test compound was dissolved in dimethyl sulfoxide and diluted 100 fold with a buffer solution containing 0.5% bovine serum albumin. Nine parts by volume of the solution, for a receptor binding experiment, was mixed with one part of the test compound solution prepared above. The percent inhibition of the specific binding was plotted against the log of the concentration of the test compound, and the 50% inhibitory concentration ($IC_{50}$) was calculated from the linear line connecting all the plotted points.

The results are shown in Table 15.

| Compound of Example No. | Salt | Receptor binding inhibition, $IC_{50}$ (g/ml) |
|---|---|---|
| 4 | hydrochloride | $2.7 \times 10^{-8}$ |
| 6 | hydrochloride | $2.1 \times 10^{-8}$ |
| 7 | free base | $2.5 \times 10^{-8}$ |
| 9 | hydrochloride | $2.1 \times 10^{-7}$ |
| 11 | hydrochloride | $2.2 \times 10^{-7}$ |
| 12 | hydrochloride | $2.1 \times 10^{-7}$ |
| 13 | hydrochloride | $1.4 \times 10^{-7}$ |
| 14 | oxalate | $0.1 \times 10^{-7}$ |

EXPERIMENT 4

Inhibitory effect on intracutaneous reaction in rats by PAF

Male SD rats (5 weeks old) were used as the test animals in groups, each containing 4 animals. Each rat was administered orally with a suspension of the test compound in a 0.5% w/v aqueous tragacanth solution. Sixty minutes after the administration, aqueous physiological saline containing 1.0% w/v Evans blue was injected into the tail vein in an amount of 5 ml/kg of the body weight. Immediately after the injection, 0.05 ml of a solution containing 2 μg/ml of PAF was intradermally injected into the back of the rat to induce a cutanous reaction. After 30 minutes, the rats were sacrificed using carbon dioxide, and the quantity of Evans blue which had leaked into the skin of the back was determined by the method of Harada et al. (J. Pharm. Pharmac., 23, 218–219 (1971)]. The inhibition rate of the compound was calculated by comparing the average amount of colorant which had leaked in the group treated with the test compound with that of control group to which no test compound was administered.

The inhibition rate was calculated according to the following equation:

$$\text{Inhibition rate (\%)} = (1 - B/A) \times 100$$

were:
A: Amount of colorant leaked in the control group
B: Amount of colorant leaked in the group to which the test compound was administered.

The results are shown in Table 16.

TABLE 16

| Compound of Example No. | Salt | Dose (p.o., mg/kg) | Inhibitory rate (%) |
|---|---|---|---|
| 1 | hydrochloride | 6.4 | 57 |
| 4 | hydrochloride | 6.4 | 64 |
| 7 | hydrochloride | 6.4 | 70 |
| 14 | hydrochloride | 6.4 | 47 |
| 16 | hydrochloride | 6.4 | 62 |

The invention is further illustrated by the following non-limiting Examples. Preparation of certain of the starting materials employed in these Examples is illustrated by the subsequent Preparations.

EXAMPLE 1

(4R)-N-Methyl-N-{2-[N-(2-diphenylmethoxyethyl)-N-methylamino]ethyl}-2-(3-pyridyl)thiazolidine-4-carboxamide and its hydrochloride A mixture of 500 mg (2.4 mmole) of (4R)-2-(3-pyridyl)thiazolidine-4-carboxylic acid, 710 mg (2.4 mmole) of N-[2-(diphenylmethoxy)ethyl]-N-methyl-N'-methylethylenediamine (prepared as described in Preparation 2), 490 mg (2.4 mmole) of dicyclohexylcarbodiimide, 320 mg (2.4 mmol) of 1-hydroxybenzotriazole and 10 ml of dimethylformamide was stirred overnight at room temperature. At the end of this time, the reaction mixture was diluted with ethyl acetate, and the insolubles were filtered off. The filtrate was washed with water, and then the solvent was removed by distillation under reduced pressure. The residue was subjected to column chromatography through silica gel, using a 20:1 by volume mixture of chloroform and methanol as the eluent, to obtain 540 mg (yield 60%) of the title compound as an oil.

Infrared Absorption Spectrum $(CHCl_3)$ $v_{max}cm^{-1}$: 3280, 2980, 2830 1640, 1400.

Mass spectrum, M/z (%): 490 ($M^+$, 5), 254 (34), 167 (100).

The oil thus obtained was dissolved in ethyl acetate, and a 4N solution of hydrogen chloride in ethyl acetate was added thereto. The crystals which precipitated were collected by filtration, to obtain the hydrochloride of the title compound, melting at 64°–67° C., in a quantitative yield.

EXAMPLE 2

(4R)-N-Methyl-N-{3-[N-(2-diphenylmethoxyethyl)-N-methylamino]propyl}-2-(3-pyridyl)thiazolidine-4-carboxamide and its hydrochloride Following a procedure similar to that described in Example 1, but using (4R)-2-(3-pyridyl)thiazolidine-4-carboxylic acid and N-[2-(diphenylmethoxy)ethyl]-N-methyl-N'-methylpropanediamine (prepared as described in Preparation 1), the title compund was obtained in a yield of 42%.

Infrared Absorption Spectrum $(CHCl_3)v_{max}cm^{-1}$: 3280, 2930, 1640, 1400.

Mass spectrum, m/z (%): 503 ($M^+$, 4), 307 (63), 167 (100).

The hydrochloride of the title compound, melting at 80°–83° C., was obtained in a quantitative yield by following a procedure similar to that described in the second step of Example 1.

EXAMPLE 3

(4R)-N-Methyl-N-{3-{N-[2-bis(4-fluorophenyl)methoxyethyl]-N-methylamino}propyl}-2-(3-pyridyl)thiazolidine-4-carboxamide Following a procedure similar to that described in Example 1, but using (4R)-2-(3-pyridyl)thiazolidine-4-carboxylic acid and N-{2-[bis(4-fluorophenyl)methoxy]ethyl}-N-methyl-N'-methylpropanediamine (prepared as described in Preparation 3), the title compound was obtained in a yield of 52%.

Infrared Absorption Spectrum $(CHCl_3)v_{max}cm^{-1}$: 3180, 2930, 1640, 1505, 1400.

Mass spectrum, m/z (%): 540 ($M^+$, 6), 307 (50), 203 (100).

EXAMPLE 4

(4R)-1-{2-[α-(4-Chlorophenyl)benzyloxylethyl}-4-[2-(3-pyridyl)thiazolidine-4-ylcarbonyl]piperazine and its hydrochloride A mixture of 500 mg (2.4 mmole) of (4R)-2-(3-pyridyl)thiazolidine-4-carboxylic acid, 800 mg (2.4 mmole) of 1-{2-[α-(4-chlorophenyl)benzyloxylethyl)piperazine (prepared as described in Preparation 4), 490 mg (2.4 mmole) of dicyclohexylcarbodiimide, 320 mg (2.4 mmole) of 1-hydroxybenzotriazole and 10 ml of dimethylformamide was stirred overnight at room temperature. At the end of this time, the reaction mixture was diluted with ethyl acetate, and the insolubles were filtered off. The filtrate was washed with water, and then the solvent was removed by distillation under reduced pressure. The resulting residue was subjected to column chromatography through silica gel, using a 10:1 by volume mixture of ethylacetate and ethanol as the eluent, to obtain 1.1·g (yield 85%) of the title compound as an oil.

Infrared Absorption Spectrum $(CHCl_3)v_{max}cm^{-1}$: 3280, 2980, 1640, 1415.

Mass spectrum, m/z (%): 522 ($M^+$, 4), 201 (69), 168 (100).

The oil thus obtained was dissolved in ethyl acetate, and then a 4N solution of hydrogen chloride in ethyl acetate was added to the resulting solution. The crystals which precipitated were collected by filtration to obtain the hydrochloride of the title compound, melting at 125°–127° C. (with decomposition), in a quantitative yield.

EXAMPLE 5

(4R)-1-{2-[4-(Diphenylmethylene)1-piperidinyl]ethyl}-4-[2-(3-pyridyl)thiazolidine-4-ylcarbonyl]piperazine and its hydrochloride Following a procedure similar to that described in Example 1, but using (4R)-2-(3-pyridyl)thiazolidine-4-carboxylic acid and 1-[2-(4-diphenylmethylene-1-piperidinyl)ethyl]piperazine (prepared as described in Preparation 5), the title compound was obtained in a yield of 46%.

Infrared Absorption Spectrum $(CHCl_3)v_{max}cm^{-1}$: 3300, 2940, 2820, 1645, 1435, 1415.

Mass spectrum, m/x (%): 533 ($M^+$, 2), 384 (22), 262 (100).

This compound was treated with a 4N solution of hydrogen chloride in ethyl acetate in the same manner as described in the second step of Example 1, to obtain the hydrochloride of the title compound, melting at 183°–186° C. (with decomposition), in a quantitative yield.

EXAMPLE 6

(4R)-1-{2-[α-(4-Methylphenyl)benzyloxylethyl}-4-[2-(3-pyridyl)thiazolidin-4-ylcarbonyl]piperazine and its hydrochloride Following a procedure similar to that described in Example 1, but using (4R)-2-(3-pyridyl)thiazolidine-4-carboxylic acid and 1-{2-[α-(4-methylphenyl)benzyloxyethyl)piperazine (prepared as described in Preparation 6), the title compound was obtained in a yield of 92%.

Infrared Absorption Spectrum $(CHCl_3)\nu_{max}cm^{-1}$: 3280, 2980, 2640, 1415.

Mass spectrum m/z (%): 502 ($M^+$, 6), 168 (55), 181 (100).

This compound was treated with a 4N solution of hydrogen chloride in ethyl acetate in the same manner as described in the second step of Example 1, to obtain the hydrochloride of the title compound, melting at 135°–137° C. (with decomposition).

EXAMPLE 7

(4R)-1-(2-Diphenylmethylene)-4-[2-(3-pyridyl)thiazolidin-4-ylcarbonyl]piperazine and its hydrochloride Following a procedure similar to that described in Example 1, but using (4R)-2-(3--pyridyl)thiazolidine-4-carboxylic acid and 1-[2-(diphenylmethoxy)ethyl]piperazine (prepared as described in Preparation 7), the title compound was obtain in a yield of 98%.

Infrared Absorption Spectrum $(CHCl_3)\nu_{max}cm^{-1}$: 3300, 2900, 1640, 1420.

Mass spectrum, m/z (%): 488 ($M^+$, 23), 291 (46), 167 (100).

This compound was treated with a 4N solution of hydrogen chloride in ethyl acetate in the same manner as described in the second step of Example 1, to obtain the hydrochloride of the title compound, melting at 108°–120° C.

EXAMPLE 8

(4R)-1-{2-(1,1-Diphenylmethylene)ethyl]-4-[2-(3-pyridyl)thiazolidin-4-ylcarbonyl]piperazine and its hydrochloride A mixture of 500 mg (2.4 mmole) of (4R)-2-(3-pyridyl)thiazolidine-4-carboxylic acid, 740 mg (2.4 mmole) of 1-[2-(1,1-diphenylethoxy)ethyl]-piperazine (prepared as described in Preparation 8), 490 mg (2.4 mmole) of dicyclohexylcarbodiimide, 320 mg (2.4 mmole) of 1-hydroxybenzotriazole and 10 ml of dimethylformamide was stirred overnight at room temperature. At the end of this time, the reaction mixture was diluted with ethyl acetate, and the insolubles were filtered off. The filtrate was washed with water, and the solvent was removed by distillation under reduced pressure. The resulting residue was subjected to column chromatography through silica gel, using a 20:1 by volume mixture of chloroform and methanol as the eluent, to obtain 1.1 g (yield 92%) of the title compound as an oil.

Infrared Absorption Spectrum $(CHCl_3)\nu_{max}cm^{-1}$: 3280, 2975, 2920, 1640, 1440, 1415.

Mass spectrum, m/z (%): 502 ($M^+$, 40), 29 (80), 181 (100).

The oil thus obtained was treated with a 4N solution of hydrogen chloride in ethyl acetate in the same manner as described in the second step of Example 1, to obtain the hydrochloride of the title compound, melting at 121°–123° C.

EXAMPLE 9

(4R)-1-{2-[1-(4-Chlorophenyl)-1phenylethoxylethyl}-4-[2-(3-pyridyl)thiazolidine-4-ylcarbonyl]piperazine and its hydrochloride Following a procedure similar to that described in Example 1, but using (4R)-2-(3-pyridyl)thiazolidine-4-carboxylic acid and 1-{2-[1-(4-chlorophenyl)-1-phenylethoxyl]ethyl)piperazine (prepared as described in Preparation 9), the title compound was obtained in a yield of 98%.

Infrared Absorption Spectrum $(CHCl_3)\nu_{max}cm^{-1}$: 3280, 2930, 1640, 1440.

Mass spectrum, m/z (%): 503 ($M^+$, 4) 307 (63), 167 (100).

This compound was treated with a 4N solution of hydrogen chloride in ethyl acetate in the same manner as described in the second step of Example 1, to obtain the hydrochloride of the title compound, melting at 113°–115° C.

EXAMPLE 10

(4)-1-{2-[1,1-Bis(4-fluorophenyl)ethoxylethyl}-4-[2-(3-pyridyl)thiazolidin-4-ylcarbonyl]piperazine and its hydrochloride Following a procedure similar to that described in Example 1, but using (4R)-2-(3-pyridyl)thiazolidine-4-carboxylic acid and 1-{2-[1,1-bis(4-fluorophenyl)ethoxy]ethyl}piperazine (prepared as described in Preparation 10), the title compound was obtained in a yield of 91%.

Infrared Absorption Spectrum $(CHCl_3)\nu_{max}cm^{-1}$: 3280, 2970, 2920, 1640, 1505, 1415.

Mass spectrum m/z (%): 538 ($M^+$, 36), 257 (54), 217 (100).

This compound was treated with a 4N solution of hydrogen chloride in ethyl acetate in the same manner as described in the second step of Example 1, to obtain the hydrochloride of the title compound, melting at 116°–118° C. (with decomposition).

EXAMPLE 11

(4R)-1-[2-(α-Chlorophenylbenzyloxy)ethyl]-4-[2-(3-pyridyl)thiazolidin-4-ylcarbonyl]piperazine and its hydrochloride Following a procedure similar to that described in Example 1, but using (4R)-2-(3-pyridyl)thiazolidin-4-carboxylic acid and 1-[2-(α-cyclohexylbenzyloxy)ethyl]piperazine (prepared as described in Preparation 11), the title compound was obtained in a yield of 82%.

Infrared Absorption Spectrum $(CHCl_1)\nu_{max}cm^{-1}$: 3380, 2820, 2840, 1640, 1415.

Mass spectrum, m/z (%): 494 ($M^+$, 59), 300(64), 291 (100).

This compound was treated with a 4N solution of hydrogen chloride in ethyl acetate in the same manner as described in the second step of Example 1, to obtain the hydrochloride of the title compound, melting at 140°–142° C. (with decomposition).

EXAMPLE 12

(4)-1-[2-Bis(4-fluorophenyl)methoxyethyl]-4-[2-(3-pyridyl)thiazolidin-4-ylcarbonyl]piperazine and its hydrochloride Following a procedure similar to that described in Example 1, but using (4R)-2-(3-pyridyl)thiazolidin-4-carboxylic acid and 1-{2-[bis(4-fluorophenyl)methoxy]ethyl}homopiperazine (prepared as described in Preparation 12), the title compound was obtained in a yield of 70%.

Infrared Absorption Spectrum $(CHCl_3)\nu_{max}cm^{-1}$: 3310, 2960, 1645, 1510, 1415.

Mass spectrum m/z (%): 538 (M$^+$, 5), 305 (61), 203 (100).

This compound was treated with a 4N solution of hydrogen chloride in ethyl acetate in the same manner as hydrochloride of the title compound, melting at 124°14 126° C. (with decomposition).

EXAMPLE 13

(4R)-1-(2-Diphenylmethoxyethyl)-4-[2-(3-pyridyl)thiazolidin-4-ylcarbonyl]homopiperazine and its hydrochloride Following a procedure similar to that described in Example 1, but using (4R)-2-(3-pyridyl)thiazolidin-4-carboxylic acid and 1-[2-(diphenylmethoxy)ethyl]homopiperazine (prepared as described in Preparation 13), the title compound was obtained in a yield of 63.

Infrared Absorption Spectrum (CHCl$_3$)$\nu_{max}$cm$^{-1}$: 3300, 3000, 2930, 1640, 1410.

Mass spectrum, m/z (%): 503 (M$^+$, 4), 305 (50), 167 (100).

This compound was treated with a 4N solution of hydrogen chloride in ethyl acetate in the same manner as described in the second step of Example 1, to obtain the hydrochloride of the title compound, melting at 56°–58° C. (with decomposition).

EXAMPLE 14

(4)-1-[2-Bis(4-fluorophenyl)methoxyethyl]-4-[2-(3-pyridyl)thiazolidin-4-ylcarbonyl]piperazine and its oxalate Following a procedure similar to that described in Example 1, but using (4R)-2-(3-pyridyl)thiazolidin-4-carboxylic acid and 1-[2-bis(4-fluorophenyl)methoxyethyl]piperazine (prepared in a similar manner to that described in Preparation 8), the title compound was obtained in a yield of 96%.

Infrared Absorption Spectrum (CHCl$_3$)$\nu_{max}$cm$^{-1}$: 3200, 3000, 2930, 1670, 1645, 1605, 1510.

Mass spectrum, m/z (%): 524 (M$^+$, 21), 291 (34), 203 (100).

This compound was dissolved in ethanol, and a solution of oxalic acid in ethanol was added to the resulting solution. The crystals which precipitated were collected by filtraton, to obtain the oxalate of the title compound, melting at 60°–62° C.

EXAMPLE 15

(4R)-N-{2-(1,2,3,4,10,14b-Hexahydrodibenzo[c,f]pyrazino[1,2,-a]azepin-2-yl)ethyl}ethyl}-2-(3-pyridyl)thiazolidin-4-carboxamide and its hydrochloride A mixture of 0.72 g (3.42 mmole) of (4R)-2-(3-pyridyl)thiazolidin-4-carboxylic acid, 1.0 g (3.40 mmole) of 2-(2-aminoethyl)-1,2,3,4,10,14b-hexahydrodibenzo [c,f]-pyrazino[1,2-a]azepine (prepared as described in Preparation 14), 0.7 g (3.42 mmole) of dicyclohexylcarbodiimide, 0.46 g (3.4 mmole) of 1-hydrocybenzotriazole and 15 ml of dimethylformamide was stirred overnight at toom temperature. At the end of this time, the mixture was diluted with ethyl acetate, and insolubles were filtered off. The filtrate was washed with water and concentrated by evaporation under reduced pressure. The resulting residue was subjected to column chromatography through silica gel, using a 20:1 by volume mixture of chloroform and methanol as the eluent, to obtain 1.30 g (yield 79%) of the title compound as an oil.

Infrared Absorption Spectrum (CHCl$_3$)$\nu_{max}$cm$^{-1}$: 3380, 3000, 2940, 2810, 1670, 1515, 1490.

Mass spectrum, m/z (%): 485 (M$^+$, 11), 263 (90), 73 (100).

The oil thus obtained was dissolved in ethyl acetate, and a 4N solution of hydrogen chloride in ethyl acetate was added to the resulting solution. The crystals which precipitated were collected by filtration, to obtain the hydrochloride of the title compound, melting at 164°–167° C. (with decomposition).

EXAMPLE 16

(4R)-N-{2[(14bR)-1,2,3,4,10,14b-Hexahydrodibenzo[c,f]pyrazino[1,2,-a]azepin-2-yl[ethyl}ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-2-(2-aminoethyl)-1,2,3,4,10,14b-hexahydrodibenzo[c,f]pyrazino[1,2-a]azepine (prepared as described in Preparation 15), the title compound was obtained in a yield of 78%.

Infrared Absorption Spectrum (CHCl$_3$)$\nu_{max}$cm$^{-1}$: 3380, 3010, 2950, 2820, 1675, 1525, 1495.

Mass spectrum m/z (%): 485 (M$^+$, 27), 263 (100), 208 (88).

This compound was treated with a 4N solution of hydrogen chloride in ethyl acetate in the same manner as described in the second step of Example 1, to obtain the hydrochloride of the title compound, melting at 175°–178° C. (with decomposition).

EXAMPLE 17

(4R)-N-{2[(14bR)-1,2,3,4,10,14b-Hexahydrodibenzo[c,f]pyrazino[1,2,-a]azepin-2-yl]ethyl}ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bS)-2-(2-aminoethyl)1,2,3,4,10,14b-hexahydrodibenzo[c,f]pyrazino[1,2-a]azepine (prepared as described in Preparation 16), the title compound was obtained in a yield of 83%.

Infrared Absorption Spectrum (CHCl$_1$)$\nu_{max}$cm$^{-1}$: 3380, 3010, 2950, 2820, 1675, 1515, 1495.

Mass spectrum m/z (%): 485 (M$^+$, 18), 263 (100), 208 (73).

This compound was treated with a 4N solution of hydrogen chloride in ethyl acetate in the same manner as described in the second step of Example 1, to obtain the hydrochloride of the title compound, melting at 188°–190° C. (with decomposition).

EXAMPLE 18

(4R)-N-{2[(14bR)-1,2,3,4,10,14b-Hexahydrodibenzo[c,f]pyrazino[1,2,a]alazepin-2-yl[ethyl}-N-methyl-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-2-(2-(N-methylamino)ethyl]-1,2,3,4,10,14b-hexahydrodibenzo[c,f]pyrazino[1,2-a]azepine (prepared as described in Preparation 17), the title compound was obtained in a yield of 83%.

Infrared Absorption Spectrum (CHCl$_3$)$\nu_{max}$cm$^{-1}$: 3320, 3000, 2950, 2820, 1645, 1495.

Mass spectrum m/z (%): 499 (M$^+$, 9), 263 (100), 208 (85).

This compound was treated with a 4N solution of hydrogen chloride in ethyl acetate in the same manner as described in the second step of Example 1, to obtain the hydrochloride of the title compound, melting at 192°–194° C. (with decomposition).

EXAMPLE 19

(4R)-N-{2[(14bS)-1,2,3,4,10,14b-Hexahydrodibenzo[c,f]pyrazino[1,2-a]azepin-2-yl)ethyl]-N-methyl-2-(3-pyridyl)thiazolidin-4-carboxamide and its hydrochloride Following a procedure similar to that described in Example 15, but using (4R)-2-(3-pyridyl)thiazolidin-4-carboxylic acid and (14bS)-2-[2-(N-methylamino)ethyl]-1,2,3,4,10,14b-hexahydrodibenzo[c,f]pyrazino[1,2-a]azepine (prepared as described in Preparation 18), the title compound was obtained in a yield of 84%.

Infrared Absorption Spectrum (CHCl$_1$)$\nu_{max}$cm$^{-1}$: 3320, 3020, 2950, 2820, 1675, 1650, 1500.

Mass spectrum m/z (%): 499 (M$^+$, 16), 263 (100), 208 (90).

This compound was treated with a 4N solution of hydrogen chloride in ethyl acetate in the same manner as described in the second step of Example 1, to obtain the hydrochloride of the title compound, melting at 191°–194° C. (with decomposition).

EXAMPLE 20

(4R)-N-{3[(14bR)-1,2,3,4,10,14b-Hexahydrodibenzo[c,f]pyrazino[1,2,-a]azepin-2-yl]propyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-2-(3-aminopropyl)-1,2,3,4,10,14b-hexahydrodibenzo[c,f]pyrazino[1,2-a]azepine (prepared as described in Preparation 19), the title compound was obtained in a yield of 59%.

Infrared Absorption Spectrum (CHCl$_3$)$\nu_{max}$cm$^{-1}$: 3350, 3010, 2950, 2820, 1680, 1520, 1495.

Mass spectrum m/z (%): 499 (M$^+$, 4), 208 (84), 193 (71), 92 (74).

This compound was treated with a 4N solution of hydrogen chloride in ethyl acetate in the same manner as described in the second step of Example 1, to obtain the hydrochloride of the title compound, melting at 143°–145° C. (with decomposition).

EXAMPLE 21

(4R)-N-{4[(14bR)-1,2,3,4,10,14b-Hexahydrodibenzo[c,f]pyrazino[1,2-a]azepin-2-yl]butyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-4-(2-aminobutyl)-1,2,3,4,10,14b-hexahydrodibenzo[c,f]pyrazino[1,2-a]azepine (prepared as described in Preparation 20), the title compound was obtained in a yield of 66%.

Infrared Absorption Spectrum (CHCl$_3$)$\nu_{max}$cm$^{-1}$: 3400, 3010, 2950, 2820, 1680, 1525, 1495.

Mass spectrum m/z (%): 513 (M$^+$, 0.1), 208 (49), 193 (100).

This compound was treated with a 4N solution of hydrogen chloride in ethyl acetate in the same manner as described in the second step of Example 1, to obtain the hydrochloride of the title compound, melting at 181°–183° C. (with decomposition).

EXAMPLE 22

(4R)-N-{2-[(14bR)-8-Chloro-1,2,3,4,10,14b-hexahydrodibenzo[c,f]pyrazino[1,2,-a]azepin-2-yl]ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-2-(2-aminoethyl)-8-chloro-1,2,3,4,10,14b-hexahydrodibenzo[c,f]pyrazino[1,2-a]azepine (prepared as described in Preparation 21), the title compound was obtained in a yield of 63%.

Infrared Absorption Spectrum (CHCl$_3$)$\nu_{max}$cm$^{-1}$: 3350, 2950, 2850, 1670, 1550, 1480.

Mass spectrum m/z (%): 519 (M$^+$, 15), 485 (15), 325 (14), 297 (100).

This compound was treated with a 4N solution of hydrogen chloride in ethyl acetate in the same manner as described in the second step of Example 1, to obtain the hydrochloride of the title compound, melting at 80°–85° C.

EXAMPLE 23

(4R)-N-{2[(14bS)-8-Chloro-1,2,3,4,10,14b-hexahydrodibenzo[c,f]pyrazino[1,2-a]azepin-2-yl]ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bS)-2-(2-aminoethyl)-8-chloro-1,2,3,4,10,14b-hexahydrodibenzo[c,f]pyrazino[1,2-a]azepine (prepared as described in Preparation 22), the title compound was obtained in a yield of 57%.

Infrared Absorption Spectrum (CHCl$_3$)$\nu_{max}$cm$^{-1}$: 3350, 2950, 2850, 1670, 1550, 1480.

Mass spectrum m/z (%): 519 (M$^+$, 18), 485 (18), 325 (16), 297 (100).

This compound was treated with a 4N solution of hydrogen chloride in ethyl acetate in the same manner as described in the second step of Example 1, to obtain the hydrochloride of the title compound, melting at 78°–80° C.

EXAMPLE 24

(4R)-N-{2-[(14bR)-8-Fluoro-1,2,3,4,10,14b-hexahydrodibenzo[c,f]pyrazino[1,2-a]azepin-2-yl]ethyl}-2-(3-pyridyl) thiazolidin-4-carboxamide and its hydrochloride Following a procedure similar to that described in Example 15, but using (4R)-2-(3-pyridyl)thiazolidin-4-carboxylic acid and (14bR)-2-(2-aminoethyl)-8-fluoro-1,2,3,4,10,14b-hexahydrodibenzo [c,f]pyrazino[1,2-a]-azepine (prepared as described in Preparation 25), the title compound was obtained in a yield of 62%.

Infrared Absorption Spectrum (CHCl$_3$) $v_{max}$ cm$^{-1}$: 3380, 2990, 2940, 2810, 1670, 1495, 1445.

Mass spectrum, m/z (%): 503 (M$^+$, 15), 281 (100), 211 (50).

This compound was treated with a 4 N solution of hydrogen chloride in ethyl acetate in the same manner as described in the second step of Example 1, to obtain the hydrochloride of the title compound, melting at 60°–70° C.

EXAMPLE 25

(4R)-N-{2-[(14bS)-8-Fluoro-1,2,3,4,10,14b-hexahydrodibenzo[c,f]pyrazino[1,2-a]azepin-2-yl]ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bS)-2-(2-aminoethyl)-8fluoro-1,2,3,4,10,14b-hexahydrodibenzo[c,f]pyrazino[1,2-a] azepine (prepared as described in Preparation 26), the title compound was obtained in a yield of 67%.

Infrared Absorption Spectrum (CHCl$_3$) $v_{max}$ cm$^{-1}$: 3380, 2990, 2940, 2810, 1670, 1495, 1445.

Mass spectrum, m/z (%): 503 (M$^+$, 16), 281 (100), 211 (43).

This compound was treated with a 4N solution of hydrogen chloride in ethyl acetate in the same manner as described in the second step of Example 1, to obtain the hydrochloride of the title compound, melting at 75°–80° C.

EXAMPLE 26

2-[2-(3-Pyridyl)thiazolidin-4-ylcarbonyl]-1,2,3,4,10,14b-hexahydrodibenzo[c,f]pyrazino[1,2-a]azepine and its hydrochloride Following a procedure similar to that described in Example 15, but using (4R)-2-(3-pyridyl)thiazolidin-4-carboxylic acid and 1,2,3,4,10,14b-hexahydrodibenzo-[c,f]pyrazino[1,2-a]azepine, the title compound was obtained in a yield of 50%.

Infrared Absorption Spectrum (CHCl$_3$) $v_{max}$ cm$^{-1}$: 3300, 3000, 2940, 2820, 1645, 1490.

Mass spectrum, m/z (%). 442 (M$^+$, 56), 248 (98), 208 (100).

This compound was treated with a 4N solution of hydrogen chloride in ethyl acetate in the same manner as described in the second step of Example 1, to obtain the hydrochloride of the title compound, melting at 165°–167° C. (with decomposition).

EXAMPLE 27

(4R)-N-{2-[(14bR)-1,2,3,4,10,14b-Hexahydropyrazino-[2,1-a]pyrido[2,3c][2]benzoazepin-2-yl]ethyl}-2-(3-pyridyl)thiazolidin-4-carboxamide and its hydrochloride Following a procedure similar to that described in Example 15, but using (4R)-2-(3-pyridyl)thiazolidin-4-carboxylic acid and (14bR)-2-(2-aminoethyl)-1,2,3,4,10,14b-hexahydropyrazino[2,1-a]pyrido[2,3-c][2]benzoazepine (prepared as described in Preparation 27), the title compound was obtained in a yield of 77%.

Infrared Absorption Spectrum (CHCl$_3$) $v_{max}$ cm$^{-1}$: 3350, 2950, 2850, 1670, 1590, 1510, 1440.

Mass spectrum, m/z (%): 486 (M$^+$, 9), 368 (15), 264 (38), 195 (100).

This compound was treated with a 4N solution of hydrogen chloride in ethyl acetate in the same manner as described in the second step of Example 1, to obtain the hydrochloride of the title compound, metling at 164°–178° C.

EXAMPLE 28

(4R)-N-{2-[(14bS)-1,2,3,4,10,14b-Hexahydropyrazino-[2,1-a]pyrido[2,3-c][2]benzoazepin-2-yl]ethyl}-2-(3-pyridyl)thiazolidin-4-carboxamide and its hydrochloride Following a procedure similar to that described in Example 15, but using (4R)-2-(3-pyridyl)thiazolidin- 4-carboxylic acid and (14bS)-2-(2-aminoethyl)-1,2,3,4,10,14b-hexahydropyrazino[2,1-a]pyrido[2,3-c][2]benzoazepine (prepared as described in Preparation 28), the title compound was obtained in a yield of 82%.

Infrared Absorption Spectrum (CHCl$_3$) $v_{max}$ cm$^{-}$: 3350, 2950, 2850, 1670, 1590, 1510, 1440.

Mass spectrum, m/z (%): 486 (M$^+$, 1), 264 (38), 195 (100).

This compound was treated with a 4N solution of hydrogen chloride in ethyl acetate in the same manner as described in the second step of Example 1, to obtain the hydrochloride of the title compound, melting at 117°–121° C. (with decomposition).

EXAMPLE 29

(4R)-N-{2-[(14bR)-1,2,3,4,10,14b-Hexahydropyrazino-[1,2a]pyrrolo[2,1c][1,4]benzodiazepin-2-yl]ethyl}-2-(3pyridyl)thiazolidin-4-carboxamide and its hydrochloride Following a procedure similar to that described in Example 15, but using (4R)-2-(3-pyridyl)thiazolidin-4-carboxylic acid and (14bR)-2-(2-aminoethyl)-1,2,3,4,10,14b-hexahydropyrazino[1,2-a]pyrrolo[2,1-c][1,4]benzodiazepine (prepared as described in Preparation 24), the title compound was obtained in a yield of 76%.

Infrared Absorption Spectrum (CHCl$_3$) $v_{max}$ cm$^{-1}$: 3380, 2990, 2820, 1665, 1515, 1495

Mass spectrum, m/z (%): 474 (M$^+$, 10), 252 (100), 197 (65).

This compound was treated with a 4N solution of hydrogen chloride in ethyl acetate in the same manner as described in the second step of Example 1, to obtain the hydrochloride of the title compound, melting at 143°–145° C. (with decomposition).

EXAMPLE 30

(4R)-N-{2-[(14bS)-1,2,3,4,10,14b-Hexahydropyrazino-[1,2-a]pyrrolo[2,1-c][1,4]benzodiazepin-2-yl]ethyl}-2-(3-pyridyl)thiazolidin-4-carboxamide and its hydrochloride Following a procedure similar to that described in Example 15, but using (4R)-2-(3-pyridyl)thiazolidine-4-carboxylic acid and (14bS)-2-(2aminoethyl)-1,2,3,4,10,14b- hexahydropyrazino[1,2-a]pyrrolo[2,1-c][1,4]benzodiazepine (prepared as described in Preparation 23), the title compound was obtained in a yield of 42%.

Infrared Absorption Spectrum (CHCl$_3$) $\nu_{max}$ cm$^{-1}$: 3380, 2990, 2820, 1670, 1515, 1495.

Mass spectrum, m/z (%): 474 (M$^+$, 28), 252 (100), 197 (95).

This compound was treated with a 4N solution of hydrogen chloride in ethyl acetate in the same manner as described in the second step of Example 1, to obtain the hydrochloride of the title compound, melting at 145°–147° C. (with decomposition).

EXAMPLE 31

1-{2-[(14bR)-1,2,3,4,10,14b-Hexahydrodibenzo[c,f]-pyrazino[1,2-a]azepin-2-yl]ethyl}-4-[(4R)-2-(3-pyridyl)thiazolidin-4-ylcarbocnyl]piperazine and its hydrochloride Following a procedure similar to that described in Example 15, but using (4R)-2-(3-pyridyl)thiazolidin-4-carboxylic acid and 1-{2-[(14bR)-1,2,3,4,10,14b-hexahydrodibenzo[c,f]pyrazino[1,2-a]azepin-2-yl]ethyl}-piperazine (prepared as described in Preparation 29), the title compound was obtained in a yield of 85%.

Infrared Absorption Spectrum (CHCl$_3$) $\nu_{max}$ cm$^{-1}$: 3000, 2950, 2820, 1745, 1595, 1490.

Mass spectrum, m/z (%): 263 (100), 431 (3), 554 (1.6).

This compound was treated with a 4N solution of hydrogen chloride in ethyl acetate in the same manner as described in the second step of Example 1, to obtain the hydrochloride of the title compound, melting at 208°–210° C. (with decomposition).

PREPARATION 1

N-[2-(diphenylmethoxy)ethyl-N-methyl-N'-methylpropanediamine

A mixture of 3 g (12.2 mmole) of 2- (diphenyl-methoxy)ethyl chloride, 5 g (49 mmole) of N,N' -dimethyl-propanediamine and 40 ml of toluene was heated under reflux overnight. At the end of this time, the toluene layer was separated and washed with water; 25 ml of a 10% w/v aqueous solution of acetic acid was then added thereto. The aqueous layer was separated, and a 10% w/v aqueous solution of sodium hydroxide was added to make it alkaline. The mixture was then extracted with diethyl ether, and the solvent was removed by distillation under reuced pressure, to obtain 2.4 g (yield 63%) of the title compound as an oil.

Infrared Absorption Spectrum (CHCl$_3$) $\nu_{max}$ cm$^{-1}$: 2920, 2820, 2780, 1490, 1450.

PREPARATION 2

N-[2-(Diphenylmethocy)ethyl]-N-methyl-N'-methylethylenediamine

Following a procedure similar to that described in Preparation 1, but using 2-using 2-(diphenylmethoxy)ethyl cloride and N,N'-dimethylethylenediamine, the title compound was obtained in a yield of 66%.

Infrared Absorption Spectrum (CHCl$_3$) $\nu_{max}$ cm$^{-1}$: 3300, 2930, 2840, 1490, 1450.

PREPARATION 3

N-{2-[bis(4-Fluorophenyl)methoxy]ethyl}-N-methyl-N'-methylpropanediamine

Following a procedure similar to that described in Preparation 1, but using 2-[bis(4-fluorophenyl)methoxy]ethyl chloride and N,N'-dimethylprppanediamine, the title compound was obtained in a yield of 97%.

Infrared Absroption Spectrum (CHCl$_3$) $\nu_{max}$ cm$^{-1}$: 3270, 3130, 1600, 1505.

PREPARATION 4

1-{2-[α-(4-Chlorophenyl)benzyloxy]ethyl}piperazine

Following a procedure similar to that described in Preparation 1, but using 2-[α-(4-chlorophenyl)benzyloxy]ethyl chloride and anhydrous piperazine, the title compound was obtained in a yield of 73%.

Infrared Absorption Spectrum (CHCl$_3$) $\nu_{max}$ cm$^{-1}$: 3340, 3150, 2930, 2810, 1490, 1450.

PREPARATION 5

1-[2-(4-Diphenylmethylene-1-piperidinyl)ethyl]piperazine

5(a)
4-Diphenylmethylene)-1-(2-hydroxyethyl)piperidine

A mixture of 2.0 g (8 mmole) of 4-(diphenylmethylene)piperidine, 0.8 g (9.9 mmole) of 2-chloroethanol, 4.8 g (45.7 mmole) of sodium carbonate, 0.05 g of sodium iodide and 40 ml of methyl isobutyl ketone was heated under reflux overnight. At the end of this time, the reaction mixture was filtered. The filtrate was concentrated by evaporaton under reduced pressure, and the resulting residue was subjected to column chromatography through silica gel, using a 20:1 by volume mixture of ethyl acetate and triethylamine as the eluent, to obtain the title compound as crystals, melting at 58°–59° C., in a yield of 61%.

Infrared Absorption Spectrum (CHCl$_3$) $\nu_{max}$ cm$^{-1}$: 3430, 2940, 1600, 1490, 1440.

5(b)
4-(Diphenylmethylene)-1-(2-chloroethyl)piperidine

A solution of 2.2 g (7.5 mmole) of 4-(diphenylmethlene)-1-(2-hyfroxethyl)piperidine [prepared as described in step (a) above] and 1.6 ml (22 mmole) of thionyl chloride in 20 ml of chloroform was heated under reflux for 1 hour. At the end of this time, the reaction mixture was poured into ice water, and the mixture was made alkaline by the addition of a 10% w/v aqueous solution of sodium hydroxide. The chloroform layer was distilled off, and the residue was subjected to column chromatography through silica gel, using a 5:1 by volume mixture of hexane and ethyl acetate as the eluent, to obtain the title compound as crystals, melting at 85°–86° C., in a yield of 86%.

Infrared Absorption Spectrum (CHCl$_3$) $\nu_{max}$ cm$^{-1}$: 2940, 2800, 1595, 1490, 1440.

5(c) 1-[2-(4-(Diphenylmethylene)-1-piperidinyl)ethyl]piperazine

A mixture of 2.2 g (7 mmole) of 4-(diphenylmethylene)-1-(2-chloroethyl)piperidine [prepared as described in step (b) above], 4.8 g (55.7 mmole) of anhydrous piperazine and 60 ml of toluene was heated under reflux overnight. At the end of this time, water was added to the reaction mixture, the toluene layer was separated, and a 10% w/v aqueous solution of acetic acid was added to the toluene layer to extract the desired compound. The aqueous layer was separated and made alkaline by the addition of a 10% w/v aqueous solution of sodium hydroxide, after which it was extracted with diethyl ether. The diethyl ether was removed by distillation under reduced pressure, to obtain the title compound as crystals, melting at 73°–75° C., in a yield of 86%.

Infrared Absorption Spectrum (CHCl$_3$) $v_{max}$ cm$^{-1}$: 3200, 2930, 2810, 1595, 1490, 1440.

PREPARATION 6

1-{2-[α-(4-Methylphenyl)benzyloxy]ethyl}piperazine

Following a procedure similar to that described in Preparation 5(c), but using 2-[α-(4-methylphenyl)-benzyloxy]ethyl chloride and anhydrous piperazine, the title compound was obtained in a yield of 65%.

Infrared Absorption Spectrum (CHCl$_3$) $v_{max}$ cm$^{-1}$: 3330, 3150, 2950, 2820, 1490, 1440.

PREPARATION 7

1-[2-(Diphenylmethoxy)ethyl]piperazine

Following a procedure similar to that described in Preparation 5(c), but using 2-(diphenylmethoxy)ethyl chloride and anhydrous piperazine, the title compound was obtained in a yield of 75%.

Infrared Absorption Spectrum (CHCl$_3$) $v_{max}$ cm$^{-1}$: 2875, 1630, 1490, 1450, 1320.

PREPARATION 8

1-[2-(1,1-Diphenylethoxy)ethyl]piperazine

8(a) 1-Ethoxycarbonyl-4-[2-(1,1-diphenylethoxy)ethyl]piperazine

A mixture of 1.8 g (9.1 mmole) of α-methylbenzhydrol, 2.0 g (9.1 mmole) of 1-(2-chloroethyl)-4-(ethoxycarbonyl)piperazine, 0.36 g (9.2 mmole) of sodium amide and 20 ml of benzene was heated under reflux overnight. At the end of this time, water was poured onto the reation mixture, and the mixture was extracted with ethyl acetate. The solvent was then removed from the mixture by distillation under reduced pressure, and the residue was subjected to column chromatography through silica gel, using a 1:1 by volume mixture of ethyl acetate and hexane as the eluent, to obtain 2.5 g (yield 75%) of the title compound as an oil.

Infrared Absorption Spectrum (CHCl$_3$) $v_{max}$ cm$^{-1}$: 3450, 2979, 1680, 1435.

8(b) 1-[2-(1,1-Diphenylethoxy)ethyl]piperazine

A mixture of 2.6 g (6.8 mmole) of 4-ethoxycarbonyl-1-[2-(1,1-diphenylethoxy)ethyl]piperazine [prepared as described in step (a) above], 3.0 g (5.3 mmole) of potassium hydroxide, 9 ml of water and 30 ml of ethylene glycol was stirred at 160° C. for 2 hours while the water formed was removed by evaporation. The reaction mixture was then poured into ice water, and the mixture was extracted with chloroform, after which it was washed with water. The solvent was then removed by evaporation under reduced pressure, to obtain 1.5 g (yield 71%) of the title compound as an oil.

Infrared Absorption Spectrum (CHCl$_3$) $v_{max}$ cm$^{-1}$: 3430, 2930, 1600, 1445.

PREPARATION 9

1-{2-[1-(4-Chlorophenyl)-1-phenylethoxy]ethyl}piperazine

9(a)
4-{2-[1-(4-Chlorophenyl)-1-phenylethoxy]ethyl}-1-(ethoxycarbonyl)piperazine Following a procedure similar to that described in Preparation 8(a), but using 1-(4-chlorophenyl)-1-phenylethanol and 1-(2-chloroethyl)-4-(ethoxycarbonyl)piperazine, the title compound was obtained in a yield of 89%.

Infrared Absorption Spectrum (CHCl$_3$) $v_{max}$ cm$^{-1}$: 2970, 2920, 1680, 1480, 1450, 1430.

9(b) 1-{2-[1-(4-Chlorophenyl)-1-phenylethoxylethyl}piperazine

Following a procedure similar to that described in Preparation 8(b), but using 4-{2-[1-(4-chlorophenyl)-1-phenylethoxy]ethyl}-1-(ethoxycarbonyl)piperazine [prepared as described in step (a) above], potassium hydroxide and ethylene glycol, the title compound was obtained in a yield of 77%.

Infrared Absorption Spectrum (CHCl$_3$) $v_{max}$ cm$^{-1}$: 3330, 3150, 2920, 2820, 1490, 1445.

PREPARATION 10

1-{2-[1,1-Bis(4-fluorophenyl)ethoxy]ethyl}piperazine

Following a procedure similar to that described in Preparation 8(b), but using 4-{2-[1,1-bis(4-fluorophenyl)ethoxy]ethyl}-1-ethoxycarbonylpiperazine [prepared in a similar manner to that described in Preparation 8(a)], potassium hydroxide and ethylene glycol, the title compound was obtained in a yield of 83%.

Infrared Absorption Spectrum (CHCl$_3$) $v_{max}$ cm$^{-1}$: 3280, 2970, 2920, 1640, 1510.

PREPARATION 11

1-[2-(α-Cyclohexylbenzyloxy)ethyl]piperazine

Following a procedure similar to that described in Preparation 5(c), but using 2-(α-cyclohexylbenzyl)ethyl chloride and anhydrous piperazine, the title compound was obtained in a yield of 72%.

Infrared Absorption Spectrum (CHCl$_3$) $v_{max}$ cm$^{-1}$: 3330, 3150, 2920, 2840, 1410.

PREPARATION 12

1-{2-[Bis(4-fluorophenyl)methoxy]ethyl}homopiperazine

Following a procedure similar to that described in Preparation 1, but using 2-[bis(4-fluorophenyl)methoxy]ethyl chloride and homopiperazine, the title compound was obtained in a yield of 88%.

Infrared Absorption Spectrum (CHCl$_3$) $v_{max}$ cm$^{-1}$: 3280, 3200, 2970, 1610, 1515.

PREPARATION 13

1-[2-(Diphenylmethoxy)ethyl]homopiperazine

Following a procedure similar to that described in Preparation 1, but using 2-(diphenylmethoxy)ethyl chloride and homopiperazine, the title compound was obtained ina yield of 68%.

Infrared Absorption Spectrum (CHCl$_3$) $v_{max}$ cm$^{-1}$: 3360, 3170, 3080, 2930, 1495, 1450.

PREPARATION 14

2-(2-Aminoethyl)-1,2,3,4,10,14b-hexahydrodibenzo[c,f]pyrazino[1,2-alazepine

14(a) 2-(2-Phthalimidoethyl)-1,2,3,4,10,14b-hexahydrodibenzo[c,f]pyrazino[[1,2-alazepine A mixture of 1.5 g (5.99 mmole) of 1,2,3,4,10,14b-hexahydrodibenzo[c,f]pyrazino[1,2-a]azepine, 1.68 g (6.61 mmole) of N-(2-bromoethyl)phthalimide, 2.55 g (24 mmole) of sodium carbonate and 30 mg of sodium iodide in 50 ml of methyl isobutyl ketone was heated under reflux overnight. At the end of this time, the reacton mixture was filtered, and the solvent was removed by distillation under reduced pressure. The resulting residue was subjected to column chromatography through silica gel, using a 1:1 by volume mixture of ethyl acetate and hexane as the eluent, to obtain 2.18 g (yield 86%) of the title compound, melting at 130°–132° C.

Infrared Absorption Spectrum (CHCl$_3$) $v_{max}$ $^{-1}$: 2950, 2920, 1770, 1710, 1490, 1395.

14(b) 2-(2-Aminoethyl)-1,2,3,4,10,14b-hexahydrodibenzo[c,f]pyrazino[1,2-a]azepine A mixtue of 1.7 g (4.01 mmole) of 2-phthalimidoethyl)-1,2,3,4,10,14b-hexahyfrodibenzo[c,f]pyrazino[1,2-a] azepine [prepared as described in step (a) above], 0.6 g of hydrazine hydrate and 100 ml of ethanol was heated under reflux for 2 hours. At the end of this time, the crystals which had precipitated were filtered off, and the solvent was removed by distillation under reduced pressure, to obtain 1.00 g (yield 89%) of the title compound as an oil.

Infrared Absorption Spectrum (CHCl$_3$) $v_{max}$ cm$^{-1}$: 2950, 2810, 1595, 1490, 1450.

PREPARATION 15

(14bR)-2-(2-Aminoethyl)-1,2,3,4,10,14b-hexahydrodibenzo[c,f]pyranzino[1,2-a]azepine 15(a) (14bR)-2-(2Phthalimidoethyl)-1,2,3,4,10,14b-hexahydrodibenzo[c,f]pyrazino[1,2-a]azepine Following a procedure similar to that described in Preparation 14(a), but using (14bR)-1,2,3,4,10,14b-hexahydrodibenzo[c,f]pyrazino[1,2-a]azepine, the title compound was obtained in a yield of 97%.

Infrared Absorption Spectrum (CHCl$_3$) $v_{max}$ cm$^{-1}$: 2820, 1775, 1710, 1495, 1445, 1400.

15(b) (14bR)-2-(2-Aminoethyl)-1,2,3,4,10,14b-hexahydrodibenzo[c,f]pyranzino[1,2-a]azepine Following a procedure similar to that described in Preparation 14(b), but using (14bR)-2-(2-phthalimidoethyl)-1,2, 3,4,10, 14b-hexahydrodibenzo[c,f]pyrazono[1,2-]azepine [prepared as described in step (a) above], the title compound was obtained in a quantitative yield.

Infrared Absorption Spectrum (CHCl$_3$) $v_{max}$ cm$^{-1}$: 2950, 2820, 1600, 1490, 1450.

PREPARATION 16

(14bS)-2-(2-Aminoethyl)-1,2,3,4,10,14b-hexahydrodibenzo[c,f]pyrazino[1,2-a]azepine 16(a) (14bS)-2-(2-Phthalimidoethyl)-1,2,3,4,10,14b-hexahydrodibenzo[c,f]pyrazino[1,2-]azepine Following a procedure similar to that described in Preparation 14(a), but using (14bS)-1,2,3,4,10, 14b-hexahydrodibenzo[c,f]pyrazino[1,2-a]azepine, the title compound was obtained in a yield of 52%.

Infrared Absorption Spectrum (CHCl$_3$) $v_{max}$ $^{-1}$: 2950, 2800, 1770, 1710, 1440, 1395.

16(b) (14bS)-2-(2-Aminoethyl)-1,2,3,4,10,14b-hexahydrodibenzo[c,f]pyrazino[1,2-a]azepine Following a procedure similar to that described in Preparaton 14(b), but using (14bS)-2-(2-phthalimidoethyl)-1,2, 3,4,10,14b-hexahydrodibenzo[c,f]pyrazino[1,2-a]azepine [prepared as described in step (a) above], the title compound was obtained in a yield of 94%.

Infrared Absorption Spectrum (CHCl$_3$) $v_{max}$ cm$^{-1}$: 2950, 1590, 1440, 1330.

PREPARATION 17

(14bR)-2-[3-(N-Methylamono)ethyl-1,2,3,4,10,14b-hexahydrodibenzo[c,f]pyrazino[1,2-a]azepine 17(a)
(14bR)-2-[2-(N-Formylamino)ethyl-1,2,3,4,10,14b-hexahydrodibenzo[c,f]pyrazino[1,2a]azepine A mixture of 1.0 g (3.4 mmole) of (14bR)-2-(2-aminoethyl)-1,2,3,4,10,14b-hexahydrodibenzo[c,f]pyrazino[1,2-a] azepine [prepared as described in Preparation 15(b)], and 10 ml of ethyl formate was heated under reflux for 8 hours. At the end of this time, the reaction mixture was concentrated by evaporation under reduced pressure, and the crystals which precipitated were subjected tocolumn chromatography through silica gel, using a 1:4 by volume mixture of ethanol and ethyl acetate as the eluent, toobtain 1.10 g (a quantitative yield) of the title compund as crystals, melting at 137°–138° C.

Infrared Absorption Spectrum (CHCl$_3$) $v_{max}$ cm$^{-1}$: 3420, 3020, 2960, 2830, 1685, 1495.

17(b)
(14bR)-2-[2-(N-Methylamino)ethyl-1,2,3,4,10,14b-hexahydrodibenzo[c,f]pyrazono[1,2-a]azepine A mixture of 0.6 g (1.87 mmole) of (14bR)-2-[2-(N-formylamino)ethyl]-1,2,3,4,10,14b-hexahydrodibenzo[c,f] pyrazono[1,2-a]azepine [prepared as described in step (a) above, 0.12 g (3.17 mmole) of lithium aluminum hydride and 11 ml of tetrtahydrofuran was stirred at room temperature for 1 hour, after which it was heated under reflux for 3 hours. At the end of this time, 0.6 g of sodium sulfate decahydrate was added to the reaction mixture, after which water was added, and the crystals which precipitated were filtered off. The filtrate was concentrated by evaporation under reduced pressure, to obtain 0.52 g (yield 87%) of the title compound as an oil.

Infrared Absorption Spectrum (CHCl$_3$) $v_{max}$ cm$^{-1}$: 2950, 2820, 1600, 1495, 1450.

PREPARATION 18

(14bS)-2-[2-(N-Methylamino)ethyl]-1,2,3,4,10,14b-hexahydrodibenso[c,f]pyrazino[1,2-a]azepine

18(a)
(14bS)-2-[2-N-Formylamino)ethyl]-1,2,3,4,10,14b-hexahydrodibenzo[c,f]pyrazino[1,2-a]azepine Following a procedure similar to that described in Preparation 17(a), but using 2-aminoethyl-(14bS)-1,2,3,4,10,14b-hexahydrodibenzo[c,f]pyrazino[1,2-a]azepine, the title compound was obtained in a yield of 87%.

Infrared Absorption Spectrum (CHCl$_3$) $v_{max}$ cm$^{-1}$: 3400, 3000, 2940, 2820, 1680, 1490, 1450.

18(b)
(14bS)-2-[2-(N-Methylamino)ethyl]-1,2,3,4,10,14b-hexahydrodibenzo[c,f]pyrazino[1,2-a]azepine Following a procedure similar to that described in Preparation 17(b), but using (14bS)-2-[2-(N-formylamino)ethyl]-1,2,3,4,10,14b-hexahydrodibenzo]c,f]pyrazino[1,2-a]azepine [prepared as described in step (a) above], the title compound was obtained in a yield of 83%.

Infrared Absorption Spectrum (CHCl$_3$) $v_{max}$ cm$^{-1}$: 2940, 2820, 1730, 1600, 1490, 1450.

PREPARATION 19

(14bR)-2-(3-Aminopropyl)-1,2,3,4,10,14b-hexahydrodibenzo[c,f]pyrazono[1,2-a]azepine

19(a)
(14bR)-2-(3-Phthalimidopropyl)-1,2,3,4,10,14b-hexahydrodibenzo[c,f]pyrazino[1,2-a]azepine Following a procedure similar to that described in Preparation 14(a), but using (14bR)-1,2,3,4,10,14b-hexahydrodibenzo[c,f]pyrazino[1,2-a]azepine and N-(3-bromopropyl)phthalimide, the title compound was obtained in a quantitative yield.

Infrared Absorption Spectrum (CHCl$_3$) $v_{max}$ cm$^{-1}$: 2950, 2820, 1770, 1710, 1490, 1395.

19(b) (14bR)-2-(3-Aminopropyl)-1,2,3,4,10,14b-hexahydrodibenzo[c,f]pyrazino[1,2-a]azepine Following a procedure similar to that described in Preparation 14(b), but using (14bR)-2-(3-phthalimidoprpyl)-1,2,3,4,10,14b-hexahyrdodibenzo[c,f]pyrazino[1,2-a]azepine [prepared as described in step (a) above], the title compound was obtained in a quantitative yield.

Infrared Absorption Spectrum (CHCl$_3$) $v_{max}$ cm$^{-1}$: 2950, 2810, 1595, 1495.

PREPARATION 20

(14bR)-2-(4-Aminobutyl)-1,2,3,4,10,14b-hexahydrodibenzo[c,f]pyrazino[1,2-a]azepine

20(a) (14bR)-2-(4-Phthalimidobutyl)-1,2,3,4,10,14b-hexahydrodibenzo[c,f]pyrazino[1,2-a]azepine Following a procedure similar to that described in Preparation 14(a), but using (14bR)-1,2,3,4,10,14b-hexahydrodibenzo[c,f]pyrazino[1,2-a]azepine and N-(4-bromobutyl)phthalimide, the title compound was obtained in a quantitative yield.

Infrared Absorption Spectrum (CHCl$_3$) $v_{max}$ cm$^{-1}$: 2950, 2820, 1770, 1710, 1490, 1395.

20(b) (14bR)-2-(4-Aminobutyl)-1,2,3,4,10,14b-hexahydrodibenzo[c,f]pyrazino[1,2-a]azepine Following a procedure similar to that described in Preparation 14(b), but using (14bR)-2-(4-phthalimidobutyl)-1,2,3,4,10,14b-hexahydrodibenzo[c,f]pyrazino[1,2-a]azepine [prepared as described in step (a) above], the title compound was obtained in a yield of 97%.

Infrared Absorption Spectrum (CHCl$_3$) $v_{max}$ cm$^{-1}$: 2930, 2820, 1595, 1490.

PREPARATION 21

(14bR)-2-(2-Aminoethyl)-8-chloro-1,2,3,4,10,14b-hexahydrodibenzo[c,f]pyrazino[1,2-a]azepine

21(a) (14bR)-8-Chloro-2-(2-phthalimidoethyl)-1,2,3,4,10,14b-hexahydrodibenzo[c,f]pyrazino[1,2-a]azepine Following a procedure similar to that described in Preparation 14(a), but using (14bR)-8-chloro-1,2,3,4,10,14b-hexahydrodibenzo[c,f]pyrazino[1,2-a]azepine and N-(2-bromoethyl)phthalimide, the title compound was obtained in a yield of 47%.

Infrared Absorption Spectrum (CHCl$_3$) $v_{max}$ cm$^{-1}$: 2810, 1775, 1710, 1485, 1395.

21(b)
(14bR)-2-(2-Aminoethyl)-8chloro-1,2,3,4,10,14b-hexahydrodibenzo[c,f]pyrazino[1,2-a]azepine Following a procedure similar to that described in Preparation 14(b), but using (14bR)-8-chloro-2-(2-phthalimidoethyl)-1,2,3,4,10,14b-hexahydrodibenzo[c,f]pyrazino[1,2-a]azepine [prepared as described in step (a) above], the title compound was obtained in a quantitative yield.

Infrared Absorption Spectrum (CHCl$_3$) $v_{max}$ cm$^{-1}$: 2950, 2820, 1485, 1450.

PREPARATION 22

(14bS)-2-(2-Aminoethyl)-8-chloro-1,2,3,4,10,14b-hexahydrodibenzo[c,f]pyrazino[1,2-a]azepine

22(a)
(14b,S)-8-Chloro-2-phthalimidoethyl)-1,2,3,4,10,14b-hexahydrodibenzo[c,f]pyrazino[1,2-a]azepine Following a procedure similar to that described in Preparation 14(a), but using (14bS)-8-chloro-1,2,3,4,10,14b-hexahydrodibenao[c,f]pyrazino[1,2-a]azepine and N-(2-bromoethyl)phthalimide, the title compound was obtained in a yield of 58%.

Infrared Absorption Spectrum (CHCl$_3$) $v_{max}$ cm$^{-1}$: 2810, 1775, 1710, 1485, 1395.

22(b)
(14bS)-2-(2-Aminoethyl)-8-chloro-1,2,3,4,10,14b-hexahydrodibenzo[c,f]pyrazino[1,2-a]azepine Following a procedure similar to that described in Preparation 14(b), but using (14bS)-8-chloro-2-(2-phthalimidoethyl)-1,2,3,4,10,14b-hexahydrodibenzo[c,f]pyrazino[1,2-a]azepine [prepared as described in step (a) above], the title compound was obtained in a yield of 41%.

Infrared Absorption Spectrum (CHCl$_3$) $v_{max}$ cm$^{-1}$: 2950, 2820, 1485, 1450.

PREPARATION 23

(14bS)-2-(2-Aminoethyl)-1,2,3,4,10,14b-hexahydropyrazino[1,2-a]pyrrolo[2,1-c][1,4]benzodiazepine

23(a) (14bS)-2-(2-Phthalimidoethyl)-1,2,3,4,10,14b-hexahydropyrazino[1,2-a]pyrrolo[2,1-c][1,4]benzodiazepine Following a procedure similar to that described in Preparation 14(a), but using (14bS)-1,2,3,4,10,14b-hexahydropyrazino[1,2-a]pyrrolo[2,1-c][1,4]benzodiazepine and N-(2-bromoethyl)phthalimide, the title compound was obtained in a quantitative yield.

Infrared Absorption Spectrum (CHCl$_3$) $v_{max}$ cm$^{-1}$: 3000, 2820, 1770, 1710, 1600, 1490, 1395.

23(b) (14bS)-2-(2-Aminoethyl)-1,2,3,4,10,14b-hexahydropyrazino[1,2-a]pyrrolo[2,1-c][1,4]benzodiazepine Following a procedure similar to that described in Preparation 14(b), but using (14Bs)-2-(2-phthalimidoethyl)-1,2,3,4,10,14b-hexahydropyrazino[1,2-a]pyrrolo[2,1-c][1,4]benzodiazepine [prepared as described in step (a) above], the title compound was obtained in a quantitative yield.

Infrared Absorption Spectrum (CHCl$_3$) $v_{max}$ cm$^{-1}$: 2980, 2930, 2800, 1600, 1490.

PREPARATION 24

(14bR)-2-(2-Aminoethyl)-1,2,3,4,10,14b-hexahydropyrazino[1,2-a]pyrrolo[2,1-c][1,4benzodiazepine

24(a) (14bR)-2-(2-Phthalimidoethyl)-1,2,3,4,10,14b-hexahydropyrazino[1,2-a]pyrrolo[2,1c][1,4]benaodiazepine Following a procedure similar to that described in Preparation 14(a), but using (14bR)-1,2,3,4,10,14b-hexahydropyrazino[1,2-a]pyrrolo[2,1-c][1,4]benzodiazepine and N-(2-bromoethyl)phthalimide, the ttitle compound was obtained in a quantitative yield.

Infrared Absorption Spectrum (CHCl$_3$) $v_{max}$ cm$^{-1}$: 3000, 2820, 1770, 1690, 1490, 1395.

24(b) (14bR)-2-(2-Aminoethyl)-1,2,3,4,10,14b-hexahydropyrazino[1,2-a]pyrrole[2,1-c][1,4]benzodiazepine Following a procedure similar to that described in Preparation 14(b), but using (14bR)-2-(2-phthalimidoethyl)-1,2,3,4,10,14b-hexahydropyrazino[1,2-a]pyrrolo[2,1c][1,4-benzodiazepine [prepared as described in step (a) above], the title compound was obtained in a yield of 94%.

Infrared Absorption Spectrum (CHCl$_3$) $v_{max}$ cm$^{-1}$: 2980, 2930, 2800, 1600, 1490.

PREPARATION 25

(14bR)-2-(2-Aminoethyl)-8-fluoro-1,2,3,4,10,14b-hexahydrodibenzo[c,f]pyrazino[1,2-a]azepine

25(a)
(14bR)-2-(2-Phthalimidoethyl)-8-fluoro-1,2,3,4,10,14b-hexahydrodibenzo[c,f]pyrazino[1,2-a]azepine Following a procedure similar to that described in Preparation 14(a), but using (14bR)-8-fluoro-1,2,3,4,10,14b-hexahydrodibenzo[c,f]pyrazino[1,2-a]azepine and N-(2-bromoethyl)phthalimide, the title compound was obtained in a yield of 93%.

Infrared Absorption Apectrum (CHCl$_3$) $v_{max}$ cm$^{-1}$: 2800, 1770, 1705, 1490, 1395.

25(b)
(14bR)-2-(2-Aminoethyl)-8-fluoro-1,2,3,4,10,14b-hexahydrodibenao[c,f]pyrazino[1,2-a]azepine Following a procedure similar to that described in Preparation 14(b), but using (14bR)-2-(2-phthalimidoethyl)-8-fluoro-1,2,3,4,10,14b-hexahydrodibenzo[1,2-a]azepine [prepared as described in step (a) above], the title compound was obtained in a quantitative yield.

Infrared Absorption Spectrum (CHCl$_3$) $v_{max}$ cm$^{-1}$: 2940, 2800, 1595, 1495, 1445.

PREPARATION 26

(14bS)-2-(2-Aminoethyl)-8-fluoro-1,2,3,4,10,14b-hexahydrodibenzo[c,f]pyrazino[1,2-a]azepine

26(a)
(14bS)-2-(2-Phthalimidoethyl)-8-fluoro-1,2,3,4,10,14b-hexahydrodibenzo[c,f]pyrazino[1,2-a]azepine Following a procedure similar to that described in Preparation 14(a), but using (14bS)-8-fluoro-1,2,3,4,10,14b-hexahydrodibenzo[c,f]pyrazino[1,2-a]azepine and N-(2-bromoethyl)phthalimide, the title compound was obtained in a yield of 91%.

Infrared Absorption Spectrum (CHCl$_3$) $v_{max}$ cm$^{-1}$: 2805, 1770, 1705, 1490, 1395.

26(b)
(14bS)-2-(2-Aminoethyl)-8-fluoro-1,2,3,4,10,14b-hexahydrodibenzo[c,f]pyrazino[1,2-a]azepine Following a procedure similar to that described in Preparation 14(b), but using (14bS)-2-(2-phthalimidoethyl)-8-fluoro-1,2,3,4,10,14b-hexahydrodibenzo[c,f]pyranzino[1,2-a]azepine [prepared as described in step (a) above], the title compound was obtained in a yield of 98%.

Infrared Absorption Spectrum (CHCl$_3$) $v_{max}$ cm$^{-1}$: 2940, 2805, 1595, 1490, 1445.

PREPARATION 27

(14bR)-2-(2-Aminoethyl)-1,2,3,4,10,14b-hexahydropyrazino [2,1-a]pyrido[2,3-c][2]benzoazepine

27(a) (14bR)-2-(2-Phthalimidoethyl)-1,2,3,4,10,14b-hexahydropyrazino [2,1-a]pyrido[2,3-c][2]benzoazepine Following a procedure similar to that described in Preparation 14(a), but using (14bR)-1,2,3,4,10,14b-hexahydropyrazino [2,1-a]pyrido[2,3-c][2]benzoazepine and N-(2-bromoethyl)phthalimide, the title compound was obtained in a yield of 47%.

Infrared Absorption Spectrum (CHCl$_3$) $v_{max}$ cm$^{-1}$: 2800, 1770, 1710, 1590, 1440, 1395.

27(b) (14bR)-2-(2-Aminoethyl)-1,2,3,4,10,14b-hexahydropyrazino [2,1-a]pyrido[2,3-c]benzoazepine Following a procedure similar to that described in Preparation 14(b), but using (14bR)-2-(2-phthalimidoethyl)-1,2,3,4,10,14b-hexahydropyrazino[2,1-a]pyrido-[2,3-c][2]benzoazepine [prepared as described in step (a) above], the title compound was obtained in a quantitative yield.

Infrared Absorption Spectrum (CHCl$_3$), $v_{max}$ cm$^{-1}$: 2950, 2810, 1590, 1495, 1460, 1440.

PREPARATION 28

(14bS)-2-(2-Aminoethyl)-1,2,3,4,10,14b-hexahydropyrazino [2,1-a]pyrido [2,3-c][2]benzoazepine

28(a) (14bS)-2-(2-Phthalimidoethyl)-1,2,3,4,10,14b-hexahydropyrazino [2,1-a]pyrido [2,3-c][2]benzoazepine Following a procedure similar to that described in Preparation 14(a), but using (14bS)-1,2,3,4,10,14b-hexahydropyrazino [2,1-a]pyrido [2,3-c]benzoazepine and N-(2-bromoethyl) phthalimide, the title compound was obtained in a yield of 48%.

Infrared Absorption Spectrum (CHCl$_3$), $v_{max}$ cm$^{-1}$: 2805, 1770, 1710, 1590, 1440, 1395.

28(b) (14bS)-2-(2-Aminoethyl)-1,2,3,4,10,14b-hexahydropyrazino [2,1-a]pyrido [2,3-c][2]benzoazepine Following a procedure similar to that described in Preparation 14(b), but using (14bS)-2-(2-phthalimidoethyl)-1,2,3, 4,10,14b-hexahydropyrazino[2,1-a]pyrido [2,3-c][2]benzoazepine [prepared as described in step (a) above], the title compound was obtained in a yield of 82%.

Infrared Absorption Spectrum (CHCl$_3$) $v_{max}$ cm$^{-1}$: 2950, 2805, 1590, 1490, 1460, 1440.

PREPARATION 29

1-{2-[(14bR)-1,2,3,4,10,14b-Hexahydrodibenzo[c,f]-pyrazino [1,2-a]azepin-2-yl]ethyl}piperazine

29(a) (14bR)-2-(2-Chloroethyl)-1,2,3,4,10,14-b-hexahydrodibenzo [c,f]pyrazino [1,2a]azepine A mixture of 3.1 g (10.5 mmole) of (14bR)-2-(2-hydroxyethyl)-1,2,3,4,10,14b-hexahydrodibenzo[c,f]-pyrazino [1,2-a]azepine, 1.5 ml of thionyl chloride and 50 ml of chloroform was heated under reflux for 2 hours. At the end of this time, the reaction mixture was poured into ice water, and sufficient sodium carbonate was added to the mixture to make it alkaline. The resulting mixture was extracted with chloroform, and then the solvent was removed from the extract by evaporation under reduced pressure. The resulting residue was subjected to column chromatography through silica gel, using a 1:5 by volume mixture of ethyl acetate and hexane as the eluent, to obtain 2.30 g (yield 70%) of the title compound.

Infrared Absorption Spectrum (CHCl$_3$) $v_{max}$ cm$^{-1}$: 3010, 2960, 2820, 1600, 1495, 1450.

Mass spectrum, m/z (%): 312 (46), 220 (31), 193 (100).

29(b) 1-{2-[(14bR)-1,2,3,4,10,14b-Hexahydrodibenzo[c,f]pyrazino[1,2-a]azepin-2-yl]ethyl}piperazine A mixture of 1.3 g (15.5 mmole) of (14bR)-2-(2-chloroethyl)-1,2,3,4,10,14b-hexahydrodibenzo[c,f]-pyrazino [1,2-a]azepine [prepared as described in step (a) above], 3.6 g of piperazine and 30 ml of toluene was header under reflux for 16 hours. At the end of this time, the mixture was cooled and water was added. Sufficient of a 10% w/v aqueous solution of acetic acid was then added to make it acidic. The aqueous layer was separated, neutralized with a 10% w/v aqueous solution of sodium hydroxide, and extracted with diethyl ether. The solvent was then removed by evaporation under reduced pressure, to give 1.38 g (yield 92%) of the title compound.

Infrared Absorption Spectrum (CHCl$_3$) $v_{max}$ cm$^{-1}$: 2960, 2830, 1600, 1490, 1450.

Mass spectrum, m/z (%): 362 (20), 263 (73), 99 (100).

In a second embodiment wherein R$^4$ is VI'.

In the compounds of the present invention, where the substituent on the pyridyl group represented by R$^1$ or R$^2$ is an alkyl group or where R$^2$, R$^3$, R$^{4'}$, R$^{5'}$, R$^{6'}$, substituents (a) or the substituent on aryl groups or said groups of formulae (II)', (III)', (IV)' or (V)' is an alkyl group, this may be a straight or branched chain alkyl group having from 1 to 4 carbon atoms. Examples of such groups include the methyl, ethyl, propyl, isopropyl, butyl, isobutyl, sec-butyl and t-butyl groups, of which the methyl, ethyl, propyl, isopropyl, butyl and sec-butyl groups are preferred, the methyl and ethyl groups being more preferred, and the methyl group being most preferred.

Where the substituent on the pyridyl group represented by R$^1$ or R$^2$ is an alkoxy group or where substituents (a) or the substituent on aryl groups is an alkoxy group, this may be a straight or branched chain alkoxy group having from 1 to 4 carbon atoms. Examples of such groups include the methoxy, ethoxy, propoxy, isopropoxy, butoxy, isobutoxy, sec-butoxy and t-butoxy groups, of which the methoxy, ethoxy, propoxy. isopropoxy, butoxy and isobutoxy groups are preferred, the methoxy and ethoxy groups being more preferred, and the methoxy group being most preferred.

$R^1$ is preferably as unsubstituted pyridyl group or a substituted pyridyl group having at least one substituent selected from the group consisting of alkyl groups which have from 1 to 4 carbon atoms, and more preferably having 0 to 1 such substituent, and is most preferably an unsubstituted pyridyl group.

$R^2$ is preferably a hydrogen atom.

Where $R^3$ represents an alkoxycarbonyl group, the alkoxy part of this may be a straight or branched chain alkoxy group having from 1 to 4 carbon atoms, i.e. the alkoxycarbonyl group itself has from 2 to 5 carbon atoms. Examples of such groups include the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, of which the methoxycarbonyl, ethoxycarbonyl, propoxycarbonyl, isopropoxycarbonyl, butoxycarbonyl, isobutoxycarbonyl and t-butoxycarbonyl groups are preferred, the methoxycarbonyl and t-butoxycarbonyl groups being most preferred.

Where $R^3$ represents an aralkyloxycarbonyl group, the alkyl part has from 1 to 4 carbon atoms and may be any of the alkyl groups exemplified above. The aryl part is as defined above, and is preferably a phenyl or naphthyl (1- or 2- naphthyl) group, especially a phenyl group, which may be substituted or unsubstituted. If substituted, the group has one or more substituents selected from the group consisting of alkyl and alkoxy groups each having from 1 to 4 carbon atoms (e.g. as exemplified above) and halogen atoms (e.g. fluorine, chlorine, bromine or iodine atoms, preferably fluorine or chlorine atoms). Where the group is substituted, there is, in principle, no restriction on the number of substituents, except such as may be imposed by the number of substitutable positions or possibly be steric constraints. Hence, for a phenyl group, the maximum number of substituents is 5, whilst the maximum number of substituents on a naphthyl group is 7. However, in general, we prefer from 1 to 3 substituents. Similar considerations apply herein wherever substituted groups are referred to and the number of substituents is not otherwise specified. Examples of such aralkyloxy, carbonyl groups include the benzyloxycarbonyl, phenethyloxycarbonyl, 1-, 2- and 3-phenylpropoxycarbonyl, 4-phenylbutoxycarbonyl and 1- and 2-naphthylmethoxycarbonyl groups and substituted analogs thereof, such as the 4-chlorobenzyloxycarbonyl, 4-fluorobenzyloxycarbonyl, 3-chlorobenzylooxycarbonyl, 3-fluorobenzykoxycarbonyl, 4-methylbenzyloxycarbonyl, 4-methoxybenzyloxycarbonyl, 3-methylbenzyloxyycarbonyl, 3-methoxybenzyloxycarbonyl, 4-ethylbenzyloxycarbonyl, 4-ethoxybenzyloxycarbonyl, 3-ethylbenzyloxycarbonyl, 3-ethoxybenzyloxycarbonyl, 4-propylbenzyloxycarbonyl, 4-propoxybenzyloxycarbonyl, 3-propylbenzyloxycarbonyl, 3-propoxybenzyloxycarbonyl, 4-butylbenzyloxycarbonyl, 4-butoxybenzylkoxycarbonyl, 3-butylbenzyloxycarbonyl and 3-butoxybenzyloxycarbonyl groups.

Where $R^3$ represents an aryloxycarbonyl group, the aryl part is as defined above and examples of such groups include the phenoxycarbonyl, 1- and 2- naphthyloxycarbonyl, o-, m- and p-tolyloxycarbonyl, o-, m- and p-methoxyphenoxycarbonyl, o-, m- and p-chlorophenoxycarbonyl and o-, m- and p-fluorophenoxycarbonyl groups, of which the phenoxycarbonyl group is preferred.

Where $R^3$ represents an aliphatic carboxylic acyl group, this may be a straight or branched chain group having from 1 to 5 carbon atoms, and, in the case of those groups which have from 2 to 5 carbon atoms, it may be unsubstituted or substituted by at least one halogen atom, and preferably 0 or from 1 to 3 halogen atoms. The group is preferably an alkanoyl group having from 1 to 5 carbon atoms or a haloalkanoyl group having from 2 to 5 carbon atoms, but it may also be an alkenoyl or alkynoyl group having from 3 to 5 carbon atoms. Examples of the unsubstituted groups include the formyl, acetyl, propionyl, butyryl, isobutyryl, valeryl, isovaleryl, pivaloyl, acryloyl, methacryloyl, propioloyl, crotonoyl and isocrotonoyl groups, of which the formyl, acetyl, propionyl, butyryl, valeryl, isovaleryl and pivaloyl groups are preferred. Examples of the substituted groups include the trifluoroacetyl, chloroacetyl, fluoroacetyl, 3,3,3-trichloropropionyl, 4-chlorobutyryl and 5-fluorovaleryl groups, of which the trifluoroacetyl and chloroacetyl groups are preferred. The acetyl group is most preferred.

Where $R^3$ represents an arylcarbonyl group, the aryl part is as defined above, and examples of such groups include the benzoyl, 1- and 2-naphthoyl, o-, m- and p-toluoyl, o-, m- and p-anisoyl and veratroyl groups, of which the benzoyl group is preferred.

Where $R^3$ represents an alkylsulfonyl group, this may be a straight or branched chain alkylsulfonyl group having from 1 to 4 carbon atoms. Examples of such groups include the methanesulfonyl, ethanesulfonyl, propanesulfonyl, isopropanesulfonyl, butanesulfonyl, isobutanesulfonyl, sec-butanesulfonyl and t-butanesulfonyl groups, of which the methanesulfonyl, ethanesulfonyl, propanesulfonyl, isopropanesulfonyl, butanesulfonyl and sec-butanesulfonyl groups are preferred, the methanesulfonyl and ethanesulfonyl groups being most preferred.

Where $R^3$ represents an arylsulfonyl group, the aryl part is as defined above, the examples of such groups include the benzenesulfonyl, 1- and 2-naphthalenesulfonyl, and o-, m- and p-toluenesulfonyl groups, of which the benzenesulfonyl and p-toluenesulfonyl groups are preferred.

B' represents an alkylene or alkylidene group having from 2 to 4 carbon atoms, which may be a straight or branched chain group. Examples of such groups include the ethylene, ethylidene, trimethylene, propylene, isopropylidene, tetramethylene and 2-methyltrimethylene groups, preferably the ethylene group.

$R^3$ is preferably a hydrogen atom, an alkyl group having from 1 to 4 carbon atoms, an alkoxycarbonyl group having from 2 to 5 carbon atoms or an unsubstituted alkanoyl group, most preferably a hydrogen atom.

$R^{4'}$ is most preferably a hydrogen atom.

A' represents an alkylene or alkylidene group having from 2 to 7, preferably from 2 to 6, carbon atoms, which may be a straight or branched chain group. Examples of such groups include the ethylene, ethylidene, trimethylene, propylene, isopropylidene, tetramethylene, 2-methyltrimethylene, pentamethylene, hexamethylene and heptamethylene groups, preferably the ethylene, trimethylene and tetramethylene groups, and more preferably the ethylene and trimethylene groups.

Examples of the groups and atoms which may be included in substituents (a) are:

alkyl groups having from 1 to 4 carbon atoms, such as the methyl, ethyl, propyl, isopropyl, butyl, isobutyl, sec-butyl and t-butyl groups, the methyl and ethyl groups being more preferred, and the methyl group being most preferred:

alkoxy groups having from 1 to 4 carbon atoms, such as the methoxy, ethoxy, propoxy, isopropoxy, butoxy, isobutoxy, sec-butoxy and t-butoxy groups, the methoxy and ethoxy groups being more preferred, and the methoxy group being most preferred;

halogen atoms, such as the fluorine, chlorine, bromine and iodine atoms, the fluorine and chlorine atoms being most preferred; and haloalkyl groups having from 1 to 4 carbon atoms, such as the chloromethyl, fluoromethyl, bromomethyl, iodomethyl, 2-chloroethyl, 2-fluoroethyl, 2-bromoethyl, 2-iodoethyl, 2-chloropropyl, 3-fluoropropyl, 3-bromopropyl, 3-iodopropyl 4-chlorobutyl, 4-fluorobutyl, 4-bromobutyl, 4-iodobutyl, dichloromethyl, difluoromethyl, dibromomethyl, diiodomethyl, trichloromethyl, trifluoromethyl, tribromomethyl, triiodomethyl, 2,2,2-trichloroethyl and 2,2,2-trifluoroethyl groups, of which the trifluoromethyl group is preferred.

$R^{7'}$ and $R^{8'}$ may represent unsubstituted phenyl groups or substituted phenyl groups which are substituted by at least one of these substituents (a). In the case of the substituted groups, there may be one or more substituents, preferably from 1 to 3 substituents, and more preferably 1 substituent. Where there is one substituents, it is preferably at the 4-position of the phenyl groups, and, where there is more than one substituent, one of these is preferably at the 4-position of the phenyl group. Preferred examples of such substituted phenyl groups include the chlorophenyl, fluorophenyl, bromophenyl, iodophenyl, 2,4-dichlorophenyl, 2,4-difluorophenyl, tolyl, ethylphenyl, propylphenyl, butylphenyl, methoxyphenyl, ethoxyphenyl, propoxyphenyl, butoxyphenyl and trifluoromethylphenyl groups, the chlorophenyl, fluorophenyl, tolyl, methoxyphenyl and trifluoromethylphenyl groups being more preferred, and the chlorophenyl, fluorophenyl and tolyl groups being most preferred, and, in the case of the mono-substituted groups, these may be o, m- or p-, preferably p-, substituted.

Where $R^{7'}$ or $R^{8'}$ represents an aromatic heterocyclic groups, this has 5 or 6 ring atoms. Of these atoms, 1 or 2 are hetero-atoms selected from the group consisting of nitrogen, oxygen and sulfur hetero-atoms. Where there are two heteroatoms, these may be the same or different and they are selected from nitrogen, oxygen and sulfur atoms; however, more preferably one is a nitrogen atom and the other is a nitrogen, oxygen or sulfur atom. Most preferably, there is a single hetero-atom, and still more preferably this is a nitrogen or sulfur atom. Such groups may be unsubstituted or they may be substituted by at least one (preferably from 1 to 3) of substituents (a), defined and exemplified above, preferably an alkyl group having from 1 to 4 carbon atoms. Examples of such unsubstituted groups include the furyl, thienyl, pyrrolyl, pyridyl, thiazolyl, isothiazolyl, oxoazolyl, isoxazolyl, imidazolyl, pyrazolyl, pyranyl, pyrazinyl, pyridazinyl, pyrimidinyl, H-pyrrolyl and furazanyl groups, preferably the furyl, thienyl and pyridyl groups, and more preferably the thienyl and pyridyl groups. Such groups may be unsubstituted or they may have at least one substituent selected from the group consisting of substituents (a), defined and exemplified above.

More preferably either both of $R^{7'}$ and $R_{8'}$ represents an optionally substituted phenyl group or one of them represents an optionally substituted phenyl group and the other represents one of these heterocyclic groups, more preferably a thienyl or pyridyl group.

Examples of groups which may be represented by Z' include the 4-(diphenylmethyl)-1-piperazinyl, 4-[α-(fluorophenyl)benzyl]-1-piperazinyl, 4-[α-(chlorophenyl)benzyl]-1-piperazinyl, 4-[bis(fluorophenyl)methyl]-1-piperazinyl, 4-[α-(chlorophenyl)-o-, m- or p-fluorobenzyl]-1-piperazinyl, 4-[α-(fluorophenyl)-o-, m- or p-methylbenzyl]-1-piperazinyl, 4-[α-(fluorophenyl)-o-, m- or p-methoxybenzyl]-1-piperazinyl, 4-[bis(chlorophenyl)methyl]-1-piperazinyl, 4-[α-(chlorophenyl)-o-, m- or p-methylbenzyl]-1-piperazinyl, 4-[α-(chlorophenyl) -o-, m- or p-methoxybenzyl]-1-piperazinyl, 4-[α-(methoxyphenyl)benzyl]-1-piperazinyl, 4-[bis(methoxyphenyl)methyl]-1-piperazinyl, 4-[α-(methylphenyl)benzyl]-1-piperazinyl, 4-[bis(methylphenyl)methyl]-1-piperazinyl, 4-(diphenylmethyl)-2,5-dimethyl-1-piperazinyl, 4-[α-(fluorophenyl)benzyl]-2,5-dimethyl-1-piperazinyl, 4-[bis(fluorophenyl)methyl]-2,5-dimethyl-1-piperazinyl, 4-(diphenylmethyl)-1-homopiperazinyl, 4-[α-(fluorophenyl)benzyl]-1-homopiperazinyl, 4-[bis(fluorophenyl)methyl]-1-homopiperazinyl, 4-[α-(chlorophenyl)benzyl]-1-homopiperazinyl, 4-[bis(chlorophenyl)methyl]-1-homopiperazinyl, 4-[α-(chlorophenyl) -o-, m- or p-fluorobenzyl]-1-homopiperazinyl, 4-[α-(methylphenyl)benzyl]-1-homopiperazinyl, 4-[bis(methylphenyl)methyl]-1-homopiperazinyl, 4-[α-(methoxyphenyl)benzyl]-1-homopiperazinyl, 4-[α-(methoxyphenyl) -o-, m- or p-methylbenzyl]-1-homopiperazinyl, 4-[α-(methoxyphenyl) -o-, m- or p-methylbenzyl]-1-piperazinyl, 4-(diphenylmethyl)-1-piperidyl, 4-[α-(fluorophenyl)benzyl]-1-piperidyl, 4-bis(fluorophenyl)methyl]-1-piperidyl, 4-[α(chlorophenyl)benzyl]-1-piperidyl, 4-[bis(chlorophenyl)methyl]-1-piperidyl, 4-α-(methylphenyl)benzyl]-1-piperidyl, 4-[bis(methylphenyl)methyl]-1-piperidyl, 4-[α-(methoxyphenyl)-o-, m- or p-methylbenzyl]-1-piperidyl, 4-[α-(methoxyphenyl)benzyl]-1-piperidyl, 4-[bis(methoxyphenyl)methyl]-1-piperidyl, 4-(diphenylmethoxy)-1-piperidyl, 4-[α-(fluorophenyl)benzyloxy]-1-piperidyl, 4-[bis(fluorophenyl)methoxy]-1-piperidyl, 4-[α-(chlorophenyl)benzyloxy]-1-piperidyl, 4-[bis(chlorophenyl)methoxy]-1-piperidyl, 4-[α-(chlorophenyl)-o-, m- or p-fluorobenzyloxy]-1-piperidyl, 4-[α-(methylphenyl)benzyloxy]-1-piperidyl, 4-[bis(methylphenyl)methoxy]-1-piperidyl, 4-[α-(methoxyphenyl)-o-, m- or p-methylbenzyloxy]-1-piperidyl, 4-[α-(methoxyphenyl)benzyloxy]-1-piperidyl, 4-(diphenylmethylene)-1-piperidyl, 4-[α-(fluorophenyl)benzylidene]-1-piperidyl, 4-[bis(fluorophenyl)methylene]-1-piperidyl, 4-[α-(chlorophenyl)benzylidene]-1-piperidyl, 4-[bis(chlorophenyl)methylene]-1-piperidyl, 4-[α-(methylphenyl)benzylidene]-1-piperidyl, 4-[bis(methylphenyl)methylene]-1-piperidyl, 4-[α-(methoxyphenyl) -o-, m- or p-methylbenzlidene]-1-piperidyl, 4-[α-(methoxyphenyl)benzylidene]-1-piperidyl, 4-[bis(methoxyphenyl)methylene]-1-piperidyl, 4-(α-hydroxydiphenylmethyl)-1-piperidyl, 4-[α-(fluorophenyl)-α-hydroxybenzyl]-1-piperidyl, 4-[bis(fluorophenyl)-α-hydroxymethyl]-1-piperidyl, 4-[α-(chlorophenyl)-α-hydroxybenzyl]-1-piperidyl, 4-[bis(chlorophenyl)-α-hydroxymethyl]-1-piperidyl, 4-[α-hydroxy-α-(methylphenyl)benzyl]-1-piperidyl, 4-[α-hydroxy-bus(methylphenyl)methyl]-1-piperidyl and 4-[α-hydroxy-α-(methoxyphenyl)benzyl]-1-piperidyl groups.

More preferred examples of the groups which may be represented by Z' include the 4-(diphenylmethyl)-1-piperazinyl, 4-[α-(chlorophenyl)benzyl]-1-piperazinyl, 4-[bis(fluorophenyl)methyl]-1-piperazinyl, 4-[α-(chlorophenyl)-o-, m- or p-fluorobenzyl]-1-piperazinyl, 4-[bis(chlorophenyl)methyl]-1-piperazinyl, 4-(diphenylmethyl)-1-piperidyl, 4-[bis(fluorophenyl)methyl]-1-piperidyl, 4-[α-(chlorophenyl)benzyl]-1-piperidyl, 4-(diphenylmethoxy)-1-piperidyl, 4-[α-(fluorophenyl)-benzyloxy]-1-piperidyl, 4-[bis(fluorophenyl)methoxy]-1-piperidyl, 4-[α-(chlorophenyl)benzyloxy]-1-piperidyl, 4-(diphenylmethylene)-1-piperidyl, 4-[α-(fluorophenyl- )benzylidene]-1-piperidyl, 4-[bis(fluorophenyl)methylene]-1-piperidyl, 4-[α-(chlorophenyl)benzylidene]-1-piperidyl, 4-(α-hydroxydiphenylmethyl)-1-piperidyl, 4-[α-(fluorophenyl)-α-hydroxybenzyl]-1-piperidyl, 4-[bis(fluorophenyl)-α-hydroxymethyl]-1-piperidyl and 4-[α-(chlorophenyl)-α-hydroxybenzyl]-1-piperidyl groups.

In all of the mono-substituted phenyl groups above which are included among the preferred and more preferred meanings of Z', the substituent may be at the o-, m- or p- position, but is preferably at the p-position.

The compounds of the present invention can form acid addition salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesfulonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. The preferred configuration at the 4-position of the thiazolidine ring is the R configuration. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

A preferred class of compounds of the present invention are those compounds of formula (I) and salts thereof in which:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 7 carbon atoms; and Z' represents a group of formula (II)', (III)', (IV)' or (V)', in which:

$R^{7'}$ and $R^{8'}$ are independently selected from the group consisting of unsubstituted phenyl groups, substituted phenyl groups which are substituted by at least one substituent selected from the group consisting of substituents (a'), defined below, and aromatic heterocyclic groups which have 5 or 6 ring atoms of which 1 is a hetero-atom selected from the group consisting of nitrogen, oxygen and sulfur hetero-atoms, said aromatic heterocyclic groups being unsubstituted or being substituted by at least one substituent selected from the group consisting of alkyl groups having from 1 to 4 carbon atoms;

said substituents (a') are selected from the group consisting of alkyl groups having from 1 to 4 carbon atoms, halogen atoms and trifluoromethyl groups;

E' represents an oxygen atom; and m is 2.

Still more preferred compounds of the present invention are those compounds of formula (I) and salts thereof in which:

$R^1$ represents an unsubstituted pyridyl group;

$R^2$ represents a hydrogen atom;

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a group of formula (II)', (III)', (IV)' or (V)', in which:

$R^7$ and $R^8$ are independently selected from the group consisting of unsubstituted phenyl groups, substituted phenyl groups which are substituted by at least one substituent selected from the group consisting of substituents (a'), defined below, pyridyl groups and thienyl groups;

said substituents (a'') are selected from the group consisting of methyl groups, fluorine atoms and chlorine atoms;

E' represents an oxygen atom; and m is 2.

Another preferred class of compounds of the present invention are those compounds of formula (I) and salts thereof in which:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 6 carbon atoms; and Z' represents a group of formula (II)', (III)', (IV)' or (V)', in which:

$R^{7'}$ and $R^{8'}$ are independently selected from the group consisting of unsubstituted phenyl groups and substituted phenyl groups which are substituted by at least one substituents selected from the group consisting of substituents (a'''), defined below;

said substituents (a''') are selected from the group consisting of alkyl groups having from 1 to 4 carbon atoms and halogen atoms;

E' represents a direct carbon-carbon single bond or an oxygen atom; and m is 2 or 3.

Another still more preferred class of compounds of the present invention are those compounds of formula (I) and salts thereof in which:

$R^1$ represents an unsubstituted pyridyl group;

$R^2$ represents a hydrogen atom;

$R^3$ represents a hydrogen atom;
$R^{4'}$ represents a hydrogen atom or a methyl or ethyl group;
A' represents an alkylene or alkylidene group having from 2 to 4 carbon atoms; and
Z' represents a group of formula (II)', (III)', (IV)' or (V)', in which:
  $R^{7'}$ and $R^{8'}$ are independently selected from the group consisting of unsubstituted phenyl groups and substituted phenyl groups which are substituted by at least one substituent selected from the group consisting of substituents (a''), defined above;
  E' represents an oxygen atom; and
  m is 2.

Most preferred are those compounds of formula (I) and salts thereof in which:
$R^1$ represents an unsubstituents pyridyl group;
$R^2$ represents a hydrogen atom;
$R^3$ represents a hydrogen atom;
$R^{4'}$ represents a hydrogen atom or a methyl or ethyl group;
A' represents an alkylene or alkylidene group having from 2 to 4 carbon atoms; and
Z' represents a 4-[α-(chlorophenyl)benzyl]-1-piperazinyl, 4-[bis(fluorophenyl)methyl]-1-piperazinyl, 4-(diphenylmethylene)-1-piperidyl, 4-[bis(fluorophenyl)methoxy]-1-piperidyl or 4-(α-hydroxydiphenylmethyl)-1-piperidyl group.

Examples of certain of the compounds of the present invention are shown by the following formulae (I–1) to (I–4), in which the symbols used in the formulae are as defined in the respective one of Tables 1 to 4, that is Table 1 relates to formula (I–1), Table 2 relates to formula (I–2), and so on. In the Tables, the following abbreviations are used:

| | |
|---|---|
| Ac | acetyl |
| tBoc | t-butoxycarbonyl |
| DMA | 2-(dimethylamino)ethyl |
| Fo | formyl |
| Me | methyl |
| Mec | methoxycarbonyl |
| Ph | phenyl |
| Py | pyridyl |
| Tfm | trifluoromethyl |
| Thi | thienyl |

In Table 2, in the column for E', a dash (–) means a direct carbon-carbon single bond and "O" means an oxygen atom.

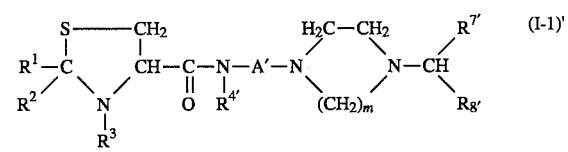 (I-1)'

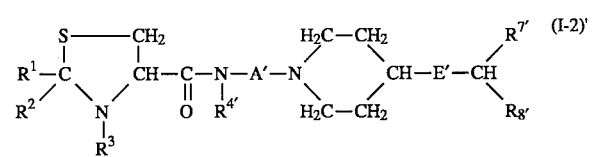 (I-2)'

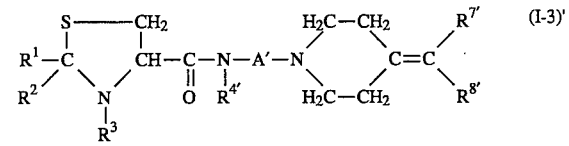 (I-3)'

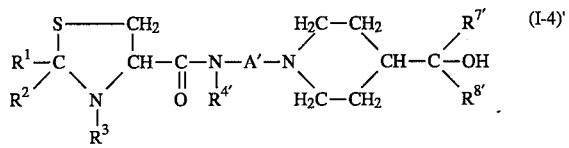 (I-4)'

TABLE 1'

| Cpd. | $R^1$ | $R^2$ | $R^3$ | $R^{4'}$ | m | $R^{7'}$ | $R^{8'}$ | A' |
|---|---|---|---|---|---|---|---|---|
| 1-1' | 3-Py | H | H | tBoc | 2 | Ph | Ph | —(CH$_2$)$_2$— |
| 1-2' | 3-Py | H | H | tBoc | 2 | Ph | Ph | —(CH$_2$)$_3$— |
| 1-3' | 3-Py | H | H | tBoc | 2 | Ph | Ph | —(CH$_2$)$_4$— |
| 1-4' | 3-Py | H | H | tBoc | 2 | 4-FPh | 4-FPh | —(CH$_2$)$_2$— |
| 1-5' | 3-Py | H | H | tBoc | 2 | 4-FPh | 4-FPh | —(CH$_2$)$_3$— |
| 1-6' | 3-Py | H | H | tBoc | 2 | 4-FPh | 4-FPh | —(CH$_2$)$_4$— |
| 1-7' | 3-Py | H | H | tBoc | 2 | Ph | 4-ClPh | —(CH$_2$)$_3$— |
| 1-8' | 3-Py | H | H | Mec | 2 | Ph | Ph | —(CH$_2$)$_2$— |
| 1-9' | 3-Py | H | H | Mec | 2 | Ph | Ph | —(CH$_2$)$_3$— |
| 1-10' | 3-Py | H | H | Mec | 2 | Ph | Ph | —(CH$_2$)$_4$— |
| 1-11' | 3-Py | H | H | Mec | 2 | 4-FPh | 4-FPh | —(CH$_2$)$_2$— |
| 1-12' | 3-Py | H | H | H | 2 | 4-FPh | 4-FPh | —(CH$_2$)$_3$— |
| 1-13' | 3-Py | H | H | H | 2 | 4-FPh | 4-FPh | —(CH$_2$)$_4$— |
| 1-14' | 3-Py | H | H | H | 2 | 4-FPh | 4-FPh | —(CH$_2$)$_5$— |
| 1-15' | 3-Py | H | H | H | 2 | 4-FPh | 3-FPh | —(CH$_2$)$_3$— |
| 1-16' | 3-Py | H | H | H | 2 | Ph | 4-FPh | —(CH$_2$)$_3$— |
| 1-17' | 3-Py | H | H | H | 2 | 4-FPh | 4-ClPh | —(CH$_2$)$_2$— |
| 1-18' | 3-Py | H | H | H | 2 | 4-FPh | 4-MePh | —(CH$_2$)$_3$— |
| 1-19' | 3-Py | H | H | H | 2 | 4-FPh | 4-MeOPh | —(CH$_2$)$_4$— |
| 1-20' | 4-Py | H | H | H | 2 | 4-ClPh | 4-ClPh | —(CH$_2$)$_3$— |
| 1-21' | 3-Py | H | H | H | 2 | 3-ClPh | 4-MePh | —(CH$_2$)$_5$— |
| 1-22' | 3-Py | H | H | H | 2 | 4-ClPh | 4-MeOPh | —(CH$_2$)$_3$— |
| 1-23' | 3-Py | H | H | H | 2 | Ph | 4-MeOPh | —(CH$_2$)$_2$— |
| 1-24' | 3-Py | H | H | H | 2 | 4-MeOPh | 4-MeOPh | —(CH$_2$)$_3$— |
| 1-25' | 4-Py | H | H | H | 2 | Ph | 4-MePh | —(CH$_2$)$_2$— |
| 1-26' | 3-Py | H | H | H | 2 | 4-MePh | 4-MePh | —(CH$_2$)$_4$— |
| 1-27' | 5,6-diMe-3-Py | H | H | H | 2 | 4-FPh | 4-FPh | —(CH$_2$)$_3$— |

TABLE 1'-continued

| Cpd. | R¹ | R² | R³ | R⁴' | $m$ | R⁷' | R⁸' | A' |
|---|---|---|---|---|---|---|---|---|
| 1-28' | 3-Py | H | H | H | 2 | Ph | 2-FPh | —(CH$_2$)$_3$— |
| 1-29' | 2-Me-3-Py | H | H | H | 2 | Ph | Ph | —(CH$_2$)$_2$— |
| 1-30' | 2-Py | H | H | H | 2 | 4-FPh | 4-FPh | —(CH$_2$)$_3$— |
| 1-31' | 2-Py | H | H | H | 2 | Ph | Ph | —(CH$_2$)$_3$— |
| 1-32' | 3-Py | H | H | H | 2 | Ph | 3-ClPh | —(CH$_2$)$_3$— |
| 1-33' | 2-Me-6-Py | H | H | H | 2 | 4-FPh | 4-FPh | —(CH$_2$)$_3$— |
| 1-34' | 3-Py | H | Me | H | 2 | 4-FPh | 4-FPh | —(CH$_2$)$_3$— |
| 1-35' | 3-Py | H | Fo | H | 2 | 4-FPh | 4-FPh | —(CH$_2$)$_4$— |
| 1-36' | 3-Py | H | Ac | H | 2 | Ph | Ph | —(CH$_2$)$_2$— |
| 1-37' | 3-Py | H | H | H | 2 | Ph | Ph | —(CH$_2$)$_3$— |
| 1-38' | 3-Py | H | DMA | H | 2 | 4-FPh | 4-FPh | —(CH$_2$)$_3$— |
| 1-39' | 3-Py | H | H | H | 3 | Ph | Ph | —(CH$_2$)$_2$— |
| 1-40' | 4-Py | H | H | H | 3 | Ph | Ph | —(CH$_2$)$_3$— |
| 1-41' | 3-Py | H | H | H | 3 | 4-FPh | 4-FPh | —(CH$_2$)$_3$— |
| 1-42' | 2-Py | H | H | H | 3 | 4-FPh | 4-FPh | —(CH$_2$)$_4$— |
| 1-43' | 3-Py | H | H | H | 3 | Ph | 4-ClPh | —(CH$_2$)$_5$— |
| 1-44' | 4-Py | H | H | H | 3 | 4-ClPh | 4-ClPh | —(CH$_2$)$_2$— |
| 1-45' | 3-Py | H | H | H | 3 | 4-FPh | 4-ClPh | —(CH$_2$)$_3$— |
| 1-46' | 3-Py | H | H | H | 3 | Ph | 4-MePh | —(CH$_2$)$_3$— |
| 1-47' | 3-Py | H | H | H | 3 | 4-MePh | 4-MePh | —(CH$_2$)$_2$— |
| 1-48' | 3-Py | H | H | H | 3 | 4-MeOPh | 4-MeOPh | —(CH$_2$)$_4$— |
| 1-49' | 3-Py | H | H | H | 2 | 4-FPh | 3-FPh | —(CH$_2$)$_3$— |
| 1-50' | 3-Py | H | H | H | 2 | Ph | 2-FPh | —(CH$_2$)$_3$— |
| 1-51' | 3-Py | H | H | H | 2 | Ph | 3-ClPh | —(CH$_2$)$_3$— |
| 1-52' | 3-Py | H | H | H | 2 | 4-FPh | 3-MePh | —(CH$_2$)$_3$— |
| 1-53' | 3-Py | H | H | H | 2 | 4-FPh | 2-MeOPh | —(CH$_2$)$_3$— |
| 1-54' | 3-Py | H | H | H | 2 | Ph | Ph | —CH$_2$CH(Me)CH$_2$— |
| 1-55' | 3-Py | H | H | H | 2 | Ph | 4-ClPh | —CH$_2$CH(Me)CH$_2$— |
| 1-56' | 3-Py | H | H | H | 2 | Ph | 4-FPh | —CH$_2$CH(Me)CH$_2$— |
| 1-57' | 3-Py | H | H | H | 2 | 4-FPh | 4-FPh | —CH$_2$CH(Me)CH$_2$— |
| 1-58' | 3-Py | H | H | H | 3 | Ph | Ph | —CH$_2$CH(Me)CH$_2$— |
| 1-59' | 3-Py | H | tBoc | H | 2 | Ph | Ph | —CH$_2$CH(Me)CH$_2$— |
| 1-60' | 3-Py | H | Me | Me | 2 | Ph | Ph | —(CH$_2$)$_3$— |
| 1-61' | 3-Py | H | Me | Me | 2 | 4-FPh | 4-FPh | —(CH$_2$)$_3$— |
| 1-62' | 3-Py | 3-Py | H | H | 2 | 4-FPh | 4-FPh | —(CH$_2$)$_3$— |
| 1-63'* | 3-Py | H | H | H | 2 | Ph | Ph | —(CH$_2$)$_3$— |
| 1-64' | 3-Py | H | H | H | 2 | Ph | 2-Py | —(CH$_2$)$_2$— |
| 1-65' | 3-Py | H | H | H | 2 | Ph | 2-Py | —(CH$_2$)$_3$— |
| 1-66' | 3-Py | H | H | H | 2 | Ph | 2-Py | —(CH$_2$)$_4$— |
| 1-67' | 3-Py | H | H | H | 2 | Ph | 2-Py | —(CH$_2$)$_5$— |
| 1-68' | 3-Py | H | Me | H | 2 | Ph | 2-Py | —(CH$_2$)$_2$— |
| 1-69' | 3-Py | H | Me | H | 2 | Ph | 2-Py | —(CH$_2$)$_3$— |
| 1-70' | 3-Py | H | H | H | 2 | 4-FPh | 2-Py | —(CH$_2$)$_2$— |
| 1-71' | 3-Py | H | H | H | 2 | 4-FPh | 2-Py | —(CH$_2$)$_3$— |
| 1-72' | 3-Py | H | H | H | 2 | 4-ClPh | 2-Py | —(CH$_2$)$_2$— |
| 1-73' | 3-Py | H | H | H | 2 | 4-ClPh | 2-Py | —(CH$_2$)$_4$— |
| 1-74' | 3-Py | H | H | H | 2 | 4-MePh | 2-Py | —(CH$_2$)$_2$— |
| 1-75' | 3-Py | H | H | H | 2 | 4-TfmPh | 2-Py | —(CH$_2$)$_2$— |
| 1-76' | 3-Py | H | H | H | 3 | Ph | 2-Py | —(CH$_2$)$_2$— |
| 1-77' | 3-Py | H | H | H | 3 | Ph | 2-Py | —(CH$_2$)$_4$— |
| 1-78' | 4-Py | H | H | H | 2 | Ph | 2-Py | —(CH$_2$)$_2$— |
| 1-79' | 3-Py | H | H | H | 2 | Ph | 3-Py | —(CH$_2$)$_2$— |
| 1-80' | 3-Py | H | H | H | 2 | 4-ClPh | 3-Py | —(CH$_2$)$_3$— |
| 1-81' | 3-Py | H | H | H | 2 | 4-FPh | 3-Py | —(CH$_2$)$_4$— |
| 1-82' | 4-Py | H | H | H | 2 | Ph | 3-Py | —(CH$_2$)$_2$— |
| 1-83' | 3-Py | H | H | H | 3 | Ph | 3-Py | —(CH$_2$)$_2$— |
| 1-84' | 3-Py | H | H | H | 2 | Ph | 4-Py | —(CH$_2$)$_2$— |
| 1-85' | 3-Py | H | H | H | 2 | Ph | 4-Py | —(CH$_2$)$_4$— |
| 1-86' | 3-Py | H | H | Me | 2 | Ph | Ph | —(CH$_2$)$_2$— |
| 1-87' | 3-Py | H | H | H | 2 | Ph | Ph | —(CH$_2$)$_2$— |
| 1-88' | 3-Py | H | H | H | 2 | Ph | 4-ClPh | —(CH$_2$)$_3$— |
| 1-89' | 3-Py | H | H | H | 2 | Ph | 4-ClPh | —(CH$_2$)$_2$— |
| 1-90' | 3-Py | H | H | H | 2 | Ph | Ph | —(CH$_2$)$_4$— |
| 1-91' | 3-Py | H | H | H | 2 | 4-FPh | 4-FPh | —(CH$_2$)$_2$— |

*In Compound No. 63', the piperazinyl group has methyl substituents at the 2- and 5- positions.

TABLE 2'

| Cpd. | R¹ | R² | R³ | R⁴' | E' | R⁷' | R⁸' | A' |
|---|---|---|---|---|---|---|---|---|
| 2-1' | 3-Py | H | H | H | — | Ph | Ph | —(CH$_2$)$_2$— |
| 2-2' | 3-Py | H | H | H | — | Ph | 4-FPh | —(CH$_2$)$_4$— |
| 2-3' | 3-Py | H | H | H | — | 4-FPh | 3-FPh | —(CH$_2$)$_3$— |

TABLE 2'-continued

| Cpd. | R¹ | R² | R³ | R⁴' | E' | R⁷ | R⁸' | A' |
|---|---|---|---|---|---|---|---|---|
| 2-4' | 3-Py | H | H | H | — | Ph | 4-ClPh | —(CH$_2$)$_2$— |
| 2-5' | 3-Py | H | H | H | — | Ph | 4-ClPh | —(CH$_2$)$_3$— |
| 2-6' | 3-Py | H | H | H | — | 4-ClPh | 4-ClPh | —(CH$_2$)$_4$— |
| 2-7' | 3-Py | H | H | H | — | Ph | 4-MePh | —(CH$_2$)$_3$— |
| 2-8' | 3-Py | H | H | H | — | 4-MePh | 4-MePh | —(CH$_2$)$_2$— |
| 2-9' | 3-Py | H | H | H | — | 4-MePh | 4-MeOPh | —(CH$_2$)$_3$— |
| 2-10' | 3-Py | H | H | H | — | 4-MeOPh | 4-MeOPh | —(CH$_2$)$_4$— |
| 2-11' | 2-Py | H | H | H | — | Ph | 4-MeOPh | —(CH$_2$)$_5$— |
| 2-12' | 3-Py | H | H | H | O | 4-FPh | 4-FPh | —(CH$_2$)$_2$— |
| 2-13' | 3-Py | H | H | H | O | 4-FPh | 4-FPh | —(CH$_2$)$_3$— |
| 2-14' | 3-Py | H | H | H | O | Ph | Ph | —(CH$_2$)$_4$— |
| 2-15' | 3-Py | H | H | H | O | Ph | 4-FPh | —(CH$_2$)$_3$— |
| 2-16' | 3-Py | H | H | H | O | 4-FPh | 4-FPh | —(CH$_2$)$_2$— |
| 2-17' | 3-Py | H | H | H | O | 4-FPh | 4-ClPh | —(CH$_2$)$_3$— |
| 2-18' | 3-Py | H | H | H | O | 4-ClPh | 4-ClPh | —(CH$_2$)$_4$— |
| 2-19' | 3-Py | H | H | H | O | Ph | 4-ClPh | —(CH$_2$)$_2$— |
| 2-20' | 2-Py | H | H | H | O | Ph | Ph | —(CH$_2$)$_3$— |
| 2-21' | 4-Py | H | H | H | O | Ph | Ph | —(CH$_2$)$_2$— |
| 2-22' | 3-Py | H | H | H | O | Ph | 4-MePh | —(CH$_2$)$_3$— |
| 2-23' | 3-Py | H | H | H | O | 4-MePh | 4-MePh | —(CH$_2$)$_2$— |
| 2-24' | 2-Py | H | H | H | O | Ph | 4-MeOPh | —(CH$_2$)$_4$— |
| 2-25' | 2-Py | H | H | H | O | 4-MeOPh | 4-MeOPh | —(CH$_2$)$_5$— |
| 2-26' | 3-Py | H | H | H | O | Ph | 2-FPh | —(CH$_2$)$_3$— |
| 2-27' | 3-Py | H | H | H | O | 4-FPh | 3-FPh | —(CH$_2$)$_3$— |
| 2-28' | 3-Py | H | H | H | O | 2-FPh | 4-ClPh | —(CH$_2$)$_3$— |
| 2-29' | 3-Py | H | H | H | O | 4-ClPh | 2-ClPh | —(CH$_2$)$_3$— |
| 2-30' | 3-Py | H | H | H | O | Ph | 3-MePh | —(CH$_2$)$_3$— |
| 2-31' | 3-Py | H | H | H | O | 4-MePh | 3-MeOPh | —(CH$_2$)$_3$— |
| 2-32' | 3-Py | H | H | H | O | Ph | Ph | —CH$_2$CH(Me)CH$_2$— |
| 2-33' | 3-Py | H | H | H | O | Ph | 4-ClPh | —CH$_2$CH(Me)CH$_2$— |
| 2-34' | 3-Py | H | H | H | O | Ph | 4-FPh | —CH$_2$CH(Me)CH$_2$— |
| 2-35' | 3-Py | H | H | H | O | 4-FPh | 4-FPh | —CH$_2$CH(Me)CH$_2$— |
| 2-36' | 3-Py | H | H | H | — | Ph | Ph | —CH$_2$CH(Me)CH$_2$— |
| 2-37' | 3-Py | 3-Py | H | H | O | 4-FPh | 4-FPh | —(CH$_2$)$_3$— |
| 2-38' | 3-Py | H | H | H | — | Ph | Ph | —(CH$_2$)$_3$— |
| 2-39' | 4-Py | H | H | H | — | Ph | Ph | —(CH$_2$)$_3$— |
| 2-40' | 2-Me-5-Py | H | H | H | — | Ph | Ph | —(CH$_2$)$_2$— |
| 2-41' | 2-Me-5-Py | H | H | H | — | Ph | Ph | —(CH$_2$)$_3$— |

TABLE 3'

| Cpd. | R¹ | R² | R³ | R⁴' | R⁷ | R⁸' | A' |
|---|---|---|---|---|---|---|---|
| 3-1' | 3-Py | H | tBoc | H | Ph | Ph | —(CH$_2$)$_2$— |
| 3-2' | 3-Py | H | tBoc | H | Ph | Ph | —(CH$_2$)$_3$— |
| 3-3' | 3-Py | H | H | H | Ph | Ph | —(CH$_2$)$_2$— |
| 3-4' | 3-Py | H | H | H | Ph | Ph | —(CH$_2$)$_3$— |
| 3-5' | 3-Py | H | H | H | Ph | Ph | —(CH$_2$)$_4$— |
| 3-6' | 3-Py | H | H | H | Ph | Ph | —(CH$_2$)$_5$— |
| 3-7' | 3-Py | H | H | H | Ph | 4-FPh | —(CH$_2$)$_3$— |
| 3-8' | 3-Py | H | H | H | 4-FPh | 4-FPh | —(CH$_2$)$_4$— |
| 3-9' | 3-Py | H | H | H | Ph | 4-ClPh | —(CH$_2$)$_3$— |
| 3-10' | 3-Py | H | H | H | 4-ClPh | 4-ClPh | —(CH$_2$)$_3$— |
| 3-11' | 4-Py | H | H | H | Ph | 4-MePh | —(CH$_2$)$_2$— |
| 3-12' | 2-Py | H | H | H | 4-MePh | 4-MePh | —(CH$_2$)$_5$— |
| 3-13' | 3-Py | H | H | H | 4-MeOPh | 4-MeOPh | —(CH$_2$)$_3$— |
| 3-14' | 4-Py | H | H | H | 4-MeOPh | 4-MeOPh | —(CH$_2$)$_4$— |
| 3-15' | 2-Py | H | H | H | Ph | 4-MeOPh | —(CH$_2$)$_2$— |
| 3-16' | 3-Py | H | Me | H | Ph | Ph | —(CH$_2$)$_2$— |
| 3-17' | 3-Py | H | DMA | H | Ph | Ph | —(CH$_2$)$_3$— |
| 3-18' | 3-Py | H | Me | H | Ph | Ph | —(CH$_2$)$_3$— |
| 3-19' | 2-Me-6-Py | H | H | H | Ph | Ph | —(CH$_2$)$_3$— |
| 3-20' | 2-Py | H | H | H | Ph | Ph | —(CH$_2$)$_3$— |
| 3-21' | 3-Py | H | H | H | Ph | Ph | —(CH$_2$)$_6$— |
| 3-22' | 3-Py | H | H | H | 4-FPh | 3-FPh | —(CH$_2$)$_3$— |
| 3-23' | 3-Py | H | H | H | Ph | 3-FPh | —(CH$_2$)$_3$— |
| 3-24' | 3-Py | H | H | H | Ph | 3-ClPh | —(CH$_2$)$_3$— |
| 3-25' | 3-Py | H | H | H | 4-ClPh | 3-ClPh | —(CH$_2$)$_3$— |
| 3-26' | 3-Py | H | H | H | Ph | 3-MePh | —(CH$_2$)$_3$— |
| 3-27' | 3-Py | H | H | H | 4-MePh | 3-MeOPh | —(CH$_2$)$_3$— |

TABLE 3'-continued

| Cpd. | R¹ | R² | R³ | R⁴' | R⁷' | R⁸' | A' |
|---|---|---|---|---|---|---|---|
| 3-28' | 3-Py | H | H | H | Ph | Ph | —CH₂CH(Me)CH₂— |
| 3-29' | 3-Py | H | H | H | Ph | 4-FPh | —CH₂CH(Me)CH₂— |
| 3-30' | 3-Py | H | H | H | 4-FPh | 4-FPh | —CH₂CH(Me)CH₂— |
| 3-31' | 3-Py | 3-Py | H | H | Ph | Ph | —(CH₂)₃— |
| 3-32' | 3-Py | H | Me | Me | Ph | Ph | —(CH₂)₃— |
| 3-33' | 3-Py | H | Me | Me | 4-FPh | 4-FPh | —(CH₂)₃— |
| 3-34' | 3-Py | H | H | H | 4-FPh | 4-FPh | —(CH₂)₂— |
| 3-35' | 3-Py | H | H | H | 4-FPh | 4-FPh | —(CH₂)₃— |
| 3-36' | 3-Py | H | H | H | Ph | Ph | —(CH₂)₇— |
| 3-37' | 3-Py | H | H | H | 4-FPh | 4-FPh | —(CH₂)₇— |
| 3-38' | 3-Py | H | Me | H | 4-FPh | 4-FPh | —(CH₂)₂— |
| 3-39' | 3-Py | H | Me | H | 4-FPh | 4-FPh | —(CH₂)₃— |
| 3-40' | 3-Py | H | H | H | Ph | 3-Thi | —(CH₂)₂— |
| 3-41' | 3-Py | H | H | H | Ph | 2-Thi | —(CH₂)₃— |
| 3-42' | 2-Me-5-Py | H | H | H | 4-FPh | 4-FPh | —(CH₂)₂— |
| 3-43' | 2-Me-5-Py | H | H | H | 4-FPh | 4-FPh | —(CH₂)₃— |
| 3-44' | 2-Me-5-Py | H | H | H | Ph | Ph | —(CH₂)₂— |
| 3-45' | 2-Me-5-Py | H | H | H | Ph | Ph | —(CH₂)₃— |
| 3-46' | 4-Py | H | H | H | Ph | Ph | —(CH₂)₃— |
| 3-47' | 2-Py | H | H | Me | Ph | Ph | —(CH₂)₂— |
| 3-48' | 2-Py | H | H | Me | Ph | Ph | —(CH₂)₄— |
| 3-49' | 2-Py | H | H | Me | 4-FPh | 4-FPh | —(CH₂)₂— |
| 3-50' | 2-Py | H | H | Et | Ph | Ph | —(CH₂)₂— |
| 3-51' | 2-Py | H | H | Et | Ph | Ph | —(CH₂)₃— |
| 3-52' | 3-Py | H | H | Et | Ph | Ph | —(CH₂)₃— |
| 3-53' | 3-Py | H | H | Me | Ph | Ph | —(CH₂)₂— |

TABLE 4'

| Cpd | R¹ | R² | R³ | R⁴' | R⁷' | R⁸' | A' |
|---|---|---|---|---|---|---|---|
| 4-1' | 3-Py | H | H | H | Ph | Ph | —(CH₂)₂— |
| 4-2' | 3-Py | H | H | H | Ph | Ph | —(CH₂)₃— |
| 4-3' | 3-Py | H | H | H | Ph | Ph | —(CH₂)₅— |
| 4-4' | 3-Py | H | H | H | 4-FPh | 4-FPh | —(CH₂)₂— |
| 4-5' | 3-Py | H | H | H | 4-FPh | 4-FPh | —(CH₂)₄— |
| 4-6' | 4-Py | H | H | H | 4-FPh | 4-FPh | —(CH₂)₃— |
| 4-7' | 3-Py | H | H | H | Ph | 4-FPh | —(CH₂)₃— |
| 4-8' | 3-Py | H | H | H | Ph | 4-ClPh | —(CH₂)₅— |
| 4-9' | 3-Py | H | H | H | 4-ClPh | 4-ClPh | —(CH₂)₃— |
| 4-10' | 3-Py | H | H | H | Ph | 4-MePh | —(CH₂)₄— |
| 4-11' | 3-Py | H | H | H | Ph | 4-MeOPh | —(CH₂)₂— |
| 4-12' | 4-Py | H | H | H | Ph | Ph | —(CH₂)₃— |
| 4-13' | 3-Py | H | H | H | Ph | 3-FPh | —(CH₂)₃— |
| 4-14' | 3-Py | H | H | H | 2-FPh | 4-ClPh | —(CH₂)₃— |
| 4-15' | 3-Py | H | H | H | Ph | 3-ClPh | —(CH₂)₃— |
| 4-16' | 3-Py | H | H | H | 4-ClPh | 2-ClPh | —(CH₂)₃— |
| 4-17' | 3-Py | H | H | H | Ph | Ph | —CH₂CH(Me)CH₂— |
| 4-18' | 3-Py | H | H | H | Ph | 4-FPh | —CH₂CH(Me)CH₂— |
| 4-19' | 3-Py | H | H | H | Ph | 4-ClPh | —CH₂CH(Me)CH₂— |
| 4-20' | 3-Py | H | H | H | 4-FPh | 4-FPh | —CH₂CH(Me)CH₂— |
| 4-21' | 3-Py | H | Me | H | 4-FPh | 4-FPh | —(CH₂)₂— |
| 4-22' | 3-Py | H | Me | H | 4-FPh | 4-FPh | —(CH₂)₄— |
| 4-23' | 4-Py | H | H | H | Ph | Ph | —(CH₂)₄— |
| 4-24' | 3-Py | H | H | Me | 4-FPh | 4-FPh | —(CH₂)₂— |

Of these compounds, the following are preferred, that is to say Compounds No. 1–1', 1–2', 1–3', 1–4', 1–5', 1–6', 1–7', 1–12', 1–13', 1–14', 1–15', 1–16', 1–37', 1–54', 1–58', 1–64', 1–65', 1–68', 1–70', 1–71', 1–72', 1–75', 1–79', 1–83', 1–84', 1–86', 1–87', 1–88', 1–89', 1–90', 1–91', 2–12', 2–13', 2–14', 2–26', 2–32', 2–38', 2–40', 3–1', 3–2', 3–3', 3–4', 3–5', 3–6', 3–8', 3–19', 3–28', 3–30', 3–34', 3–35', 3–36', 3–38', 3–40', 3–41', 3–42', 3–43', 3–45', 3–46', 3–47', 3–48', 3–49', 3–52', 3–53', 4–1', 4–2', 4–4', 4–21' and 4–24', of which Compounds No. 1–12', 1–13', 1–65', 1–86', 1–87', 1–88', 1–89', 1-91', 2-12', 2-13', 2-32', 2-38', 3-3', 3-4', 3-5', 3-6', 3-34', 3-35', 3-36', 3-41', 3-47', 3-52', 3-53', 4-1', 4-2' and 4-4' are more preferred.

The most preferred compounds are Compounds No.:

1-12'. {3-[4-bis(4-fluorophenyl)methyl-1-piperazinyl]-propylcarbamoyl}-2-(3-pyridyl)thiazolidine;
1-65'. {3-[4-(α-2-pyridylbenzyl)-1-piperazinyl]-propylcarbamoyl}-2-(3-pyridyl)thiazolidine;
1-87'. [2-(4-diphenylmethyl-1-piperazinyl)ethylcarbamoyl]-2-(3-pyridyl)thiazolidine;
1-88'. [3-{4-[α-(4-chlorophenyl)benzyl]-1-piperazinly}propylcarbamoyl]-2-(3-pyridyl)thiazolidine;
1-89'. [2-{4-[α-(4-chlorophenyl)benzyl]-1-piperazinyl}ethylcarbamoyl]-2-(3-pyridyl)thiazolidine;
2-13'. {3-[4-bis(4-fluorophenyl)methoxy-1-piperidyl]-propylcarbamoyl}-2-(3-pyridyl)thiazolidine;
3-3'. {2-[4-(diphenylmethylene)-1-piperidyl]ethylcarbamoyl}-2-(3-pyridyl)thiazolidine;
3-4'. {3-[4-(diphenylmethylene)-1-piperidyl]propylcarbamoyl}-2-(3-pyridyl)thiazolidine;
3-5'. {4-[4-(diphenylmethylene)-1-piperidyl]butylcarbamoyl}-2-(3-pyridyl)thiazolidine;
3-35'. [3-{4-[bis(4-fluorophenyl)methylene]-1-piperidyl}propylcarbamoyl]-2-(3-pyridyl)thiazolidine;
3-41'. {3-[4-(α-2-thienyl)benzylidene-1-piperidyl]-propylcarbamoyl}-2-(3-pyridyl)thiazolidine;
3-52'. [N-{3-[4-diphenylmethylene-1-piperidyl]-propyl}-N-ethylcarbamoyl]-2-(3-pyridyl)thiazolidine;
3-53'. [N-{2-[4-diphenylmethylene-1-piperidyl]-ethyl}-N-methylcarbamoyl]-2-(3-pyridyl)thiazolidine; and
4-1'. {2-[4-(α-hydroxydiphenylmethyl)-1-piperidyl]-ethylcarbamoyl}-2-(3-pyridyl)thiazolidine;

and salts, especially hydrochlorides, thereof.

The compounds of the present invention may be prepared by a variety of methods well known in the art for the preparation of compounds of this type. For example, they may be prepared by reacting a compound of formula (VI):

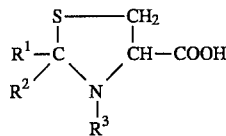

(in which $R^1$, $R^2$ and $R^3$ are as defined above) or a reactive derivative thereof with a compound of formula (VII'):

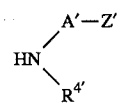

(in which A', Z' and $R^{4'}$ are as defined above). Where either compound contains a reactive group in one of the substituents Z', $R^1$, $R^2$, $R^3$ and $R^{4'}$, this may be protected prior to the reaction and the protecting group may then be removed after the reaction using methods well known in the art. If desired, the resulting compound of formula (I) may be salified.

The carboxylic acid of formula (VI)' may be employed as such or a reactive derivative of the carboxylic acid of formula (VI)' may be employed. Examples of suitable reactive derivatives include: acid halides, such as the acid chloride or acid bromide; the acid azide; active esters with, for example, N-hydroxybenzotriazole or N-hydroxysuccinimide; acid anhydrides of the carboxylic acid to be used; and mixed acid anhydrides with, for example, a mono($C_1$-$C_4$ alkyl) carbonic acid ester, such as monomethyl carbonate, monoethyl carbonate or monoisobutyl carbonate, or a monoaryl carbonic acid ester, such as monophenyl carbonate or monotolyl carbonate, preferably a mixed acid anhydride with a monoalkyl carbonate.

The reaction between the carboxylic acid of formula (VI)' itself and the amine of formula (VII)' can be preferably carried out in the presence or absence of a base, in the presence of a condensing agent and in an inert solvent.

There is no particular restriction on the nature of the condensing agent to be used, provided that it can assist the formation of an amide bond from a carboxylic acid and an amine, and preferred examples include dicyclohexylcarbodiimide (DCC), diethylphosphoryl cyanide (DEPC), carbonyldiimidazole, diphenylphosphoryl azide (DPPA) and diethylazodicarboxylate/triphenylphosphine, more preferably dicyclohexylcarbodiimide or diethylphosphoryl cyanide.

There is likewise no particular limitation on the nature of the base to be used provided that it does not have any adverse effect on the reagents, and preferred examples include organic amines, such as trimethylamine, triethylamine, pyridine, dimethylaniline, N-methylmorpholine and N,N-dimethylpyridine, more preferably triethylamine or N-methylmorpholine.

There is no particular restriction on the nature of the solvent to be employed, provided that it has no adverse effect on the reaction or on the regents involved and that it can dissolve the regents, at least to some extent. Examples of suitable solvents include: aromatic hydrocarbons, such as benzene, toluene and xylene; halogenated hydrocarbons, especially halogenated aliphatic hydrocarbons, such as methylene chloride, dichloroethane and chloroform; esters, such as ethyl acetate and propyl acetate; ethers, such as diethyl ether, tetrahydrofuran and dioxane; amides, especially fatty acid amides, such as dimethylformamide, dimethylacetamide and hexamethylphosphoric triamide; and nitriles, such as acetonitrile. Of these, we most prefer the ethers (particularly tetrahydrofuran), the halogenated hydrocarbons (particularly methylene chloride), the amides (particularly dimethylformamide) and the esters (particularly ethyl acetate).

The reaction can take place over a wide range of temperatures, and the precise reaction temperature is not critical to the invention. In general, we find it convenient to carry out the reaction at a temperature of from −10° to 50° C., more preferably from 0° to 30° C. The time required for the reaction may also vary widely, depending on many factors, notably the reaction temperature and the nature of the regents. However, provided that the reaction is effected under the preferred conditions outlined above, a period of from 30 minutes to 20 hours will usually suffice.

Alternatively, the desired compound of formula (I) can be prepared by converting the carboxylic acid of formula (VI)' into a reactive derivative, and then reacting the reactive derivative with the amine of formula (VII)'.

The reactive derivative of the carboxylic acid, such as the acid halide or acid anhydride, can be prepared by conventional methods, for example by reacting the carboxylic acid of formula (VI)' with a corresponding active halide (e.g. thionyl chloride, thionyl bromide, an acid chloride or acid bromide of the desired carboxylic acid to form a mixed anhydride, methyl chlorocarbonate, ethyl chlorocarbonate, isobutyl chlorocarbonate, phenyl chlorocarbonate or tolyl chlorocarbonate) at a suitable temperature, e.g. from 20° to 100° C., for a suitable time, e.g. from 1 to 20 hours, in an inert solvent (e.g. methylene chloride, benzene or tetrahydrofuran) and in the presence of a base (e.g. pyridine, triethylamine or dimethylaniline) as necessary. Where the reactive derivative is an acid amide or an active ester, this can be prepared by reacting the carboxylic acid of formula (VI)' with the corresponding compound (e.g. hydrogen azide, N-hydroxybenzotriazole or N-hydroxysuccinimide); the conditions employed are similar to those employed to prepare an amide bond by reacting a carboxylic acid of formula (VI)' with an amine of formula (VII)' as described above.

The reaction of the reactive derivative of the carboxylic acid of formula (VI)' with the amine of formula (VII)' is preferably carried out in an inert solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride, dichloroethane and chloroform; ethers, such as diethyl ether, tetrahydrofuran and dioxane; esters, such as ethyl acetate; and aromatic hydrocarbons, such as benzene, toluene and xylene. Of these, we especially prefer the aromatic hydrocarbons and the ethers, such as tetrahydrofuran.

Alternatively, in some cases, the compound of formula (VII)' can be used in a great excess, in which case it may serve also as a solvent.

The reaction can take place over a wide range of temperatures, and the precise reaction temperature is not critical to the invention. In general, we find it convenient to carry out the reaction at a temperature of from −10° to 50° C. (more preferably from 0° to 25° C.). The time required for the reaction may also vary widely, depending on many factors, notably the reaction temperature and the nature of the reagents. However, provided that the reaction is effected under the preferred conditions outlined above, a period of from 5 minutes to 20 hours (more preferably from 30 minutes to 10 hours) will usually suffice.

Further, the compound of formula (I) wherein $R^3$ represents a t-butoxycarbonyl group can, if desired, be reacted with an acid in an inert solvent to convert it into a corresponding compound where $R^3$ represents a hydrogen atom.

There is no particular restriction on the nature of the acid to be used here, and examples include: mineral acids, such as hydrochloric acid, hydrobromic acid, sulfuric acid and nitric acid; carboxylic acids, such as acetic acid, trifluoroacetic acid and benzoic acid; and sulfonic acids, such as methanesulfonic acid, benzenesulfonic acid and p-toluenesulfonic acid. Of these, we prefer hydrochloric acid, hydrobromic acid and trifluoroacetic acid.

There is likewise no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; ketones, such as acetone, methyl ethyl ketone and methyl isobutyl ketone; nitriles, such as acetonitrile; and water. Of these, we prefer the ethers and water.

The reaction can take place over a wide range of temperatures, and the precise reaction temperature is not critical to the invention. In general, we find it convenient to carry out the reaction at a temperature of from 0° to 50° C. (preferably around room temperature). The time required for the reaction may also vary widely, depending on many factors, notably the reaction temperature and the nature of the reagents. However, provided that the reaction is effected under the preferred conditions outlined above, a period of from 1 to 20 hours will usually suffice.

The compound prepared in the reactions described above can be collected from the reaction mixture by conventional means. For example, one suitable recovery procedure comprises neutralizing the reaction mixture and then evaporating the solvent from the neutralized mixture, or simply evaporating the solvent from the reaction mixture, as necessary; after this, the reaction mixture may be poured into water, and then extracted with a water-insoluble organic solvent; the desired compound can then be obtained by evaporation of the solvent from the extract, normally under reduced pressure. The product thus obtained can, if desired, be further purified by conventional methods, such as recrystallization, reprecipitation or the various chromatography techniques, notably column chromatography or preparative thin layer chromatography.

The starting compound of formula (VI)' may be known per se or it may easily be prepared by known methods (e.g. FR 2 267 089; Japanese Kokai Hei 2–179) or similar methods.

The starting compound of formula (VII)' may be known per se or it may easily be prepared by conventional methods [e.g. Chem. Pharm. Bull., 37, 100 (1989); J. Med. Chem., 32, 583 (1989)] or by similar methods. Alternatively, a compound of formula (VII)' in which $F^{4'}$ represents an alkyl group having from 1 to 4 carbon atoms can also be prepared by reacting the corresponding N-($C_1$–$D_4$ aliphatic acyl) compounds {which can be prepared by conventional methods [e.g. J. Org. Chem., 27, 4058 (1962)] or by a similar reaction so that between the reactive derivative of the carboxylic acid of formula (VI)', but using a derivative of the acid forming the aliphatic acyl group, and the compound of formula (VII)'} with lithium aluminum hydride in a suitable solvent (e.g. an ether, such as diethyl ether or tetrahydrofuran) at from room temperature to 80° C. for a period of from 30 minutes to 5 hours.

The thiazolidinecarboxylic acid amide derivatives of the present invention have excellent anti-allergic and anti-asthmatic activities, as well as PAF antagonism, and are thus useful as therapeutic agents for the treatment or prophylaxis of allergic diseases and asthma.

The compounds of the present invention may therefore be used in the treatment and prophylaxis of disorders such as those referred to above, and, for this purpose, may be formulated as conventional pharmaceutical preparations, as is well known in the art. Thus, the compounds may be administered orally, e.g. in the form of tablets, capsules, granules, powders, syrups, or other such well known forms, parenterally, e.g. by injections, suppositories, or by other means, for example, as patches, inhalation or ophthalmic solutions.

These pharmaceutical preparations can be prepared by conventional means and may contain known adjuvants of a type commonly used in this field, for example vehicles, binders, disintegrators, lubricants, stabilizers, corrigents, etc. depending upon the intended use and form of the preparation. The dose will depend upon the condition, age, and body weight of the patient as well as upon the nature and severity of the disorder to be treated, but, in the case of oral administration to an adult human patient, we would normally suggest a total daily dose of from 10 mg to 1000 mg, more preferably from 10 mg to 500 mg, which may be administered in a single dose or in divided doses, e.g. from one to three times a day.

BIOLOGICAL ACTIVITY the biological activity of the compounds of the present invention is shown in the following Experiments. In these Experiments, the compounds of the invention are identified by reference to the number of one of the subsequent Examples which illustrates their preparation.

EXPERIMENT 1

Inhibitory effect on passive cutaneous anaphylaxis (PCA) in rats

According to Mota's method [I. Mota, Immunology, 7, 681–699 (1964)], antiserum (256 times the PCA titer) of rat against egg albumin was prepared and diluted four times with physiological saline. Male SD rats (5 weeks old) were used as the test animals in groups, each containing 4 animals. The rats were sensitized by intradermal injection of 0.05 ml of the diluted antiserum solution in the dorsal position. 48 hours after this injection, a suspension of the test compound in an aqueous 0.5% w/v tragacanth solution was orally administered to the rats, which had been fasted for one day, and 60 minutes later they were injected in the caudal vein with 5 ml/kg body weight of physiological saline containing 0.4% w/v egg albumin and 1.0% w/v Evans Blue. 30 minutes after this last injection, the rats were sacrificed with carbon dioxide and the Evans Blue exuded in the dorsal intradermal portion was determined according to Harada' method (Harada et al., J. Pharm. Pharmac., 23, 218–219 (1971)).

The results achieved from the test groups which were treated with a test compound were evaluated to determine the inhibitory rate by comparison with the average amount of exuded dye in a control group, which was not given the test compound.

The inhibitory rate was calculated by the following equation.

Inhibitory rate (%)=(1−$B/A$)×100

A. amount of exuded dye in the control group
B. amount of exuded dye in the test group.
The results are shown in Table 5'.

TABLE 5'

| Compound of Example | Salt | Dose (p.o., mg/kg) | Inhibitory rate (%) |
|---|---|---|---|
| 14' | hydrochloride | 25 | 72 |
|  |  | 6.4 | 42 |
| 16' | hydrochloride | 25 | 65 |
| 17' | hydrochloride | 25 | 79 |
|  |  | 6.4 | 48 |
| 20' | free base | 25 | 76 |
| 22' | hydrochloride | 25 | 88 |
|  |  | 6.4 | 56 |
| 30' | free base | 6.4 | 57 |
| 44' | hydrochloride | 6.4 | 51 |

EXPERIMENT 2'

Inhibitory effect in vitro against PAF-induced blood platelet aggregation

Blood samples were obtained by cardiac puncture from a rabbit and one part by volume of each sample was immediately mixed with 0.1 part of a 3.8% w/v aqueous solution of sodium citrate. A platelet rich plasma (PRP) fraction was prepared by centrifuging the samples at 150×G for 15 minutes at room temperature, and a platelet poor plasma (PPP) fraction was then prepared by further centrifugation at 1,000×G for 15 minutes. The platelet count in the PRP was adjusted to $6 \times 10^5$ per μl by the addition of an appropriate amount of the PPP fraction. According to the method reported by Born et al. [G. V. R. Born et al.: J. Physiol. 62, 67–68 (1962)], blood platelet aggregation was determined turbidimetrically in a 6-channel aggregometer (Hemetracer, NKB, Tokyo, Japan). Aliquots of the PRP (272 μl) were preincubated with 3 μl of a solution of the test compound in dimethyl sulfoxie for 1 minute, and then stimulated with 1-$C_{16:0}$ PAF (at a final concentration of $10^{-8}$–$3 \times 10^{-8}$ M) at 37° C. with stirring (100 rpm). Changes in light transmission were monitored for 5 minutes. Vehicle (dimethyl sulfoxide) controls were tested simultaneously, and the inhibitory effects of the test compounds were assessed on the maximal aggregation. The $IC_{50}$ values were calculated by the method of least squares.

Table 6' below shows the results.

TABLE 6'

| Compound of Example | Salt | Platelet aggregation inhibition, $IC_{50}$ (g/ml) |
|---|---|---|
| 17' | hydrochloride | $1.9 \times 10^{-6}$ |
| 20' | free base | $3.3 \times 10^{-6}$ |
| 22' | hydrochloride | $1.8 \times 10^{-6}$ |
| 28' | hydrochloride | $6.0 \times 10^{-7}$ |
| 38' | hydrochloride | $4.3 \times 10^{-7}$ |
| 43' | hydrochloride | $9.5 \times 10^{-7}$ |

EXPERIMENT 3'

Inhibitory effect on PAF-receptor binding

Blood samples were drawn from the heart of a rabbit. 1 part by volume of each sample was mixed immediately with ⅑ part of a 0.077 M solution of disodium ethylenediaminetetraacetate. After a similar procedure to that described in Experiment 2, a precipitated blood platelet sample was obtained. This blood platelet sample was washed, and, after repeated freezing and thawing to rupture the cells, it was placed on top of two layers consisting of 0.25 M and 1.5 M sucrose solutions. By centrifugation at 63, 500×G, for 2 hours at 4° C., the fraction obtained from the interface between the 0.25 M and 1.5 M sucrose solutions was collected and is regarded as a PAF-receptor membrane fraction. A receptor binding experiment was then conducted according to a method very similar to that reported by Hwang et al. [San-Bao Hwang et al.: J. Biol. Chem. 260, 15639–15645 (1985)]. The specific binding of $^3$H-PAF was measured using a Wattman GF/C filter. A test compound was dissolved in dimethyl sulfoxide and diluted 100 fold with a buffer solution containing 0.5% bovine serum albumin. Nine parts by volume of the solution, for a receptor binding experiment, was mixed with one part of the test compound solution prepared above. The percent inhibition of the specific binding was plotted against the log of the concentration of the test compound, and the 50% inhibitory concentration ($IC_{50}$) was calculated from the linear line connecting all the plotted points.

The results are shown in Table 7'.

TABLE 7'

| Compound of Example | Salt | Receptor binding inhibition, $IC_{50}$ (g/ml) |
|---|---|---|
| 16' | hydrochloride | $3.8 \times 10^{-7}$ |
| 17' | hydrochloride | $6.8 \times 10^{-7}$ |
| 20' | free base | $6.3 \times 10^{-7}$ |

91

TABLE 7'-continued

| Compound of Example | Salt | Receptor binding inhibition, $IC_{50}$ (g/ml) |
|---|---|---|
| 22' | hydrochloride | $6.7 \times 10^{-7}$ |
| 30' | hydrochloride | $2.5 \times 10^{-7}$ |
| 38' | hydrochloride | $3.8 \times 10^{-7}$ |
| 43' | hydrochloride | $5.4 \times 10^{-7}$ |

The invention is further illustrated by the following non-limiting Examples. Preparation of certain of the starting materials employed in these Examples is illustrated by the subsequent Preparations.

EXAMPLE 1'

3-t-Butoxycarbonyl-4(R)-[3-(4-diphenylmethyl-1-piperazinyl)propylcarbamoyl]-2-(3-pyridyl)thiazolidine

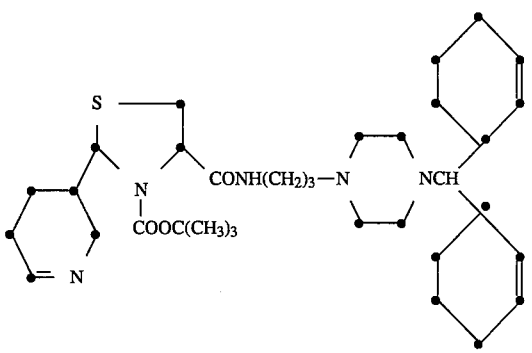

A mixture of 500 mg (1.61 mmole) of 3-t-butoxycarbonyl-2-(3-pyridyl)thiazolidine-4(R)-carboxylic acid, 500 mg (1.61 mmole) of 1-(3-aminopropyl)-4-(diphenylmethyl) piperazine (prepared as described in Preparation 16'), 263 mg (1.61 mmole) of diethylphosphoryl cyanide, 163 mg (1.61 mmole) of triethylamine and 10 ml of tetrahydrofuran was stirred at room temperature overnight. At the end of this time, the reaction mixture was concentrated by evaporation under reduced pressure, diluted with water and extracted with methylene chloride. The solvent was then removed by evaporation under reduced pressure, and the resulting residue was subjected to column chromatography through alumina, using ethyl acetate as the eluent, to afford 840 mg (yield 89%) of the title compound as an oil.

Infrared Absorption Spectrum (KBr), $\nu_{max}$ cm$^{-1}$: 3350, 2973, 2934, 2808, 1669, 1367, 1158.

Mass Spectrum, m/z (%): 601 (M$^+$, 0.2), 407 (16), 167 (100).

92

EXAMPLE 2'

4(R)-[3-(4-diphenylmethyl-1-piperazinyl)propylcarbamoyl]-2-(3-ovridyl)thiazolidine and its hydrochloride

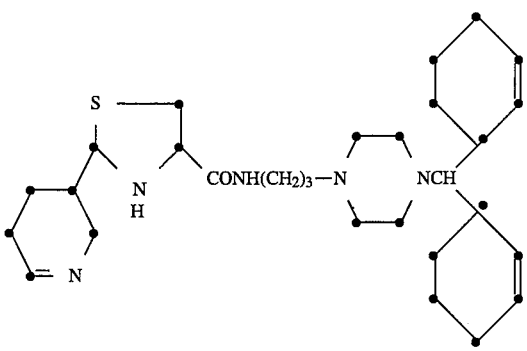

0.8 g (1.36 mmole) of 3-t-butoxycarbonyl-4(R)-[3-(4-diphenylmethyl-1-piperazinyl)propylcarbamoyl]-2-(3-pyridyl) thiazolidine (prepared as described in Example 1') were dissolved in 15 ml of 10% w/v aqueous hydrochloric acid, and the resulting solution was stirred at room temperature overnight. The reaction mixture was then neutralized and extracted with chloroform. The solvent was removed from the extract by evaporation under reduced pressure, and the resulting residue was subjected to column chromatography through silica gel, eluted with a 20:1 by volume mixture of methylene chloride and methanol, to afford 0.5 g (yield 74%) of the title compound as an oil.

Infrared Absorption Spectrum (CHCl$_3$), $\nu_{max}$ cm$^{-1}$: 3000, 2900, 2800, 1665, 1520, 1450.

Mass Spectrum, m/z (%): 501 (M$^+$, 4), 167 (100), 125 (48).

The oil thus obtained was dissolved in ethyl acetate, and a 4N solution of hydrogen chloride in ethyl acetate was added to the resulting solution. The crystals which precipitated were collected by filtration to afford the desired hydrochloride, melting at 193° to 195° C. (with decomposition).

EXAMPLES 3' to 10'

A procedure similar to that described in Example 1 was repeated using the same carboxylic acid, except that the cyclic aminoalkylamine specified in each Example was used in place of the 4-(3-aminopropyl)-1-(diphenylmethyl)piperazine used in Example 1', to afford the following compounds.

EXAMPLE 3'

3-t-Butoxycarbonyl-4(R)-[2-(4-diphenylmethyl-1-piperazinyl) ethylcarbamoyl]-2-(3-pyridyl)thiazolidine This compound was obtained in a yield of 69%, from 4-(2-aminoethyl)-1-(diphenylmethyl)piperazine (a known compound).

Infrared Absorption Spectrum (CHCl$_3$), $\nu_{max}$ cm$^{-1}$: 3375, 2970, 1685, 1510.

Mass Spectrum, m/z (%): 587 (M⁺, 4), 265 (48), 167 (100).

EXAMPLE 4'

3-t-Butoxycarbonyl-4(R)-[4-(4-diphenylmethyl-1-piperazinyl)
butylcarbamoyl]-2-(3-pyridyl)thiazolidine This compound was obtained in a yield of 61%, from 1-(4-aminobutyl)-4-(diphenylmethyl)piperazine (prepared as described in Preparation 17').

Infrared Absorption Spectrum (CHCl$_3$), $v_{max}$ cm$^{-1}$: 3350, 2940, 1685, 1530.

Mass Spectrum, m/z (%): 615 (M⁺, 5), 421 (72), 167 (100).

EXAMPLE 5'

3-t-Butoxycarbonyl-4(R)-{2-[4-bis(4-fluorophenyl)
methyl-1-piperazinyl]ethylcarbamoyl}-2-(3-ovridyl)-
thiazolidine This compound was obtained in a yield of 73%, from 1-(2-aminoethyl)-4-[bis(4-fluorophenyl)methyl]piperazine (prepared as described in Preparation 18').

Infrared Absorption Spectrum (CHCl$_3$), $v_{max}$ cm$^{-1}$: 3340, 2975, 2937, 2814, 1698, 1505.

Mass Spectrum, m/z (%): 624 (M⁺, 6), 393 (57), 203 (100).

EXAMPLE 6'

3-t-Butoxycarbonyl-4(R)-{3-[4-bis(4-fluorophenyl)-
methyl-1-piperazinyl]propylcarbamoyl}-2-(3-pyridyl)-
thiazolidine This compound was obtained in a yield of 87%, from 1-(3-aminopropyl)-4-[bis(4-fluorophenyl)methyl]piperazine (prepared as described in Preparation 19').

Infrared Absorption Spectrum (CHCl$_3$), $v_{max}$ cm$^{-1}$: 3350, 2973, 2938, 2811, 1698, 1505.

Mass Spectrum, m/z (%): 637 (M⁺, 3), 407 (34), 203 (100).

EXAMPLE 7'

3-t-Butoxycarbonyl-4(R)-{4-[4-bis(4-fluorophenyl)-
methyl-1-piperazinyl]butylcarbamoyl}-2-(3-ovridyl)-
thiazolidine This compound was obtained in a yield of 70%, from 1-(4-aminobutyl)-4-[bis(4-fluorophenyl)methyl]piperazine (prepared as described in Preparation 20').

Infrared Absorption Spectrum (CHCl$_3$), $v_{max}$ cm$^{-1}$: 2970, 2930, 1685, 1505.

Mass Spectrum, m/z (%): 651 (M⁺, 2), 421 (36), 203 (100).

EXAMPLE 8'

3-t-Butoxycarbonyl-4(R)-[3-[4-[z-(4-chlorophenyl)-
benzyl-1-piperazinyl)propylcarbamoyl]-2-(3-pyridyl)-
thiazolidine This compound was obtained in a yield of 76%, from 1-(3-aminopropyl)-4-[α-(4-chlorophenyl)benzyl]-piperazine (prepared as described in Preparation 23').

Infrared Absorption Spectrum (CHDl$_3$), $v_{max}$cm$^{-1}$: 3350, 2970, 2830, 1690, 1525.

Mass Spectrum, m/z (%): 635 (M⁺, 6), 407 (71), 201 (100).

EXAMPLE 9'

3-t-Butoxycarbonyl-4(R)-[2-(4-diphenylmethylene-1-piperidyl)ethylcarbamoyl]-2-(3-pyridyl)thiazolidine This compound was obtained in a yield of 70%, from 1-(2-aminoethyl)-4-(diphenylmethylene)piperidine (prepared as described in Preparation 24').

Infrared Absorption Spectrum (CHCl$_3$), $v_{max}$ cm$^{-1}$: 3330, 2974, 2930, 1700, 1544.

Mass Spectrum, m/z (%): 598 (M⁺, 34), 323 (45), 262 (100).

EXAMPLE 10'

3-t-Butoxycarbonyl-4(R)-[3-(4-diphenylmethylene-1-piperidyl)
propylcarbamoyl]-2-(3-pyridyl)thiazolidine This compound was obtained in a yield of 91%, from 1-(3-aminopropyl)-4-(diphenylmetyhlene)piperidine (prepared as described in Preparation 15).

Infrared Absorption Spectrum (CHCl$_3$), $v_{max}$ cm$^{-1}$. 3400, 2980, 1690, 1560.

Mass Spectrum, m/z (%): 584 (M⁺,18), 365 (12), 262 (100).

EXAMPLES 11' to 16'

The compounds obtained as described in Examples 3' to 8' were treated in the same manner as described in Example 2' to afford the compounds of Examples 11' to 16', respectively.

EXAMPLE 11'

4(R)-[2-(4-Diphenylmethyl-1-
piperazinyl)ethylcarbamoyl-2-(3-pyridyl)thiazolidine This compound, melting at 183° to 185° C., was obtained in a yield of 58%.

Infrared Absorption Spectrum (KBr), $v_{max}$ cm$^{-1}$: 3380, 3270, 1662, 1516.

Mass Spectrum, m/z (%): 487 (M⁺, 19), 265 (53), 167 (100).

EXAMPLE 12'

4(R)-[4-(4-Diphenylmethyl-1-
piperazinyl)butylcarbamoyl]-2-(3-pyridyl)thiazolidine This compound was obtained in a yield of 93%.

Infrared Absorption Spectrum (CHCl$_3$), $v_{max}$ cm$^{-1}$: 3380, 3270, 2950, 1670, 1520.

Mass Spectrum, m/z (%): 515 (M⁺, 7), 481 (14), 321 (28), 167 (100).

EXAMPLE 13'

4(R)-{2-[4-Bis(4-fluorophenyl)methyl-1-piperazinyl]-
ethylcarbamoyl}-2-(3-pyridyl)thiazolidine This compound, melting at 162° to 164° C., was obtained in a yield of 92%.

Infrared Absorption Spectrum (KBr), $v_{max}$ cm$^{-1}$: 3380, 3263, 2808, 1658, 1506.

Mass Spectrum, m/z (%): 523 (M$^+$, 11), 301 (28), 203 (100).

EXAMPLE 14'

4(R)-{3-[4-Bis(4-fluorophenyl)methyl-1-piperazinyl]-propylcarbamoyl}-2-(3-pyridyl)thiazolidine and its hydrochloride This compound was obtained in a yield of 92%.

Infrared Absorption Spectrum (CHCl$_3$), $v_{max}$ cm$^{-1}$: 3400, 2970, 1605, 1505.

Mass Spectrum, m/z (%): 537 (M$^+$, 19), 203 (100), 125 (41).

Treatment of the title compound with a 4N solution of hydrogen chloride in ethyl acetate, as described in Example 2', gave the hydrochloride, melting at 185° to 188° C. (with decomposition).

EXAMPLE 15'

4(R)-{4-[4-Bis(4-fluorophenyl)methyl-1-piperazinyl]-butylcarbamoyl}-2-(3-pyridyl)thiazolidine and its hydrochloride This compounds was obtained in a yield of 86%.

Infrared Absorption Spectrum (CHCl$_3$), $v_{max}$ cm$^{-1}$: 3400, 2950, 1670, 1510.

Mass Spectrum, m/z (%): 551 (M$^+$, 3) 293 (10), 203 (100).

Treatment of the title compound with a 4N solution of hydrogen chloride in ethyl acetate, as described in Example 2', gave the hydrochloride, melting at 188° to 190° C. (with decomposition).

EXAMPLE 16'

4(R)-[3-{4-[α-(4-Chlorophenyl)benzyl]-1-piperazinyl}-propylcarbamoyl]-2-(3-pyridyl)thiazolidine and its hydrochloride This compound was obtained in a yield of 75%.

Infrared Absorption Spectrum (KBr), $v_{max}$ cm$^{-1}$: 3290, 2940, 2810, 1666, 1520.

Mass Spectrum, m/z (%): 535 (M$^+$, 6), 201 (195), 165 (100).

Treatment of the title compound with a 4N solution of hydrogen chloride in ethyl acetate, as described in Example 2', gave the hydrochloride, melting at 188° to 190° C. (with decomposition).

EXAMPLE 17'

4(R)-(3-4-Bis(4-fluorophenyl)methoxy-1-piperidyl]-propylcarbamoyl}-2-(3-pyridyl)thiazolidine and its hydrochloride

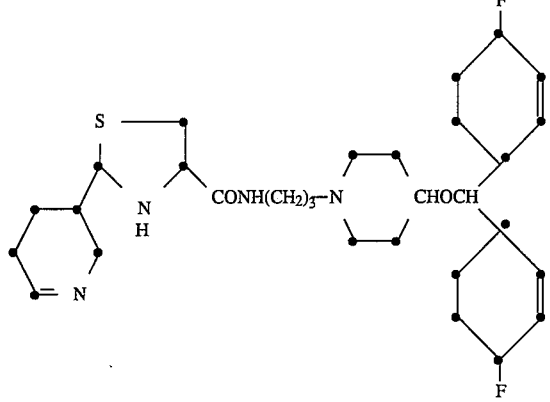

A mixture of 400 mg (1.90 mmole) of 2-(3-pyridyl)-thiazolidine-4(R)-carboxlyic acid, 686 mg (1.9 mmole) of 1-(3-aminopropyl)-4-[bis(4-fluorophenyl)methoxy]-piperidine (prepared as described in Preparation 27'), 392 mg (1.9 mmole) of dicyclohexylcarbodiimide, 257 mg (1.9 mmole) of 1-hydroxybenzotriazole and 6 ml of dimethylformamide was stirred overnight at room temperature. At the end of this time, the reaction mixture was diluted with ethyl acetate and insolubles were filtered off. A 0.5N aqueous solution of sodium hydroxide was added to the filtrate, and the mixture was extracted with ethyl acetate. A 1N aqueous solution of hydrochloric acid was added to the ethyl acetate extract, and the aqueous layer thus obtained was separated and made alkaline by the addition of a 2N aqueous solution of sodium hydroxide, after which it was extracted with ethyl acetate. The extract was concentrated by evaporation under reduced pressure, and the resulting residue was subjected to columm chromatography through alumina, using a 20 : 1 by volume mixture of ethyl acetate and ethanol as the eluent, to afford 710 mg (yield 68%) of the title compound as an oil.

Infrared Absorption Spectrum (CHCl$_3$), $v_{max}$ cm$^{-1}$: 3400, 3300, 2950, 1665, 1605, 1505.

Mass Spectrum, m/z (%): 552 (M$^+$, 1), 384 (12), 165 (100).

The oil obtained was dissolved in ethyl acetate and treatment of the resulting solution with a 4N solution of hydrogen chloride in ethyl acetate, as described in Example 2', gave the hydrochloride, melting at 114° to 117° C. (with decomposition).

EXAMPLES 18' to 19'

Following a procedure similar to that described in Example 17', but using the piperidinoalkylamine specified, the compounds shown were also obtained.

The hydrochlorides of these compounds were also obtained in quantitative yields by following the procedure described in Example 2'.

EXAMPLE 18'

4(R)-{2-[4-Bis(4-fluorophenyl)methoxy-1-piperidyl]-ethylcarbamoyl}-2-3-pyridyl)thiazolidine The title compound was obtained in a yield of 55% from 1-(2-aminoethyl)-4-[bis(4-fluorophenyl)methoxy]-piperidine (prepared as described in Preparation 26').

Infrared Absorption Spectrum (CHCl$_3$), $v_{max}$ cm$^-$: 3350, 2930, 1665, 1510.

Mass Spectrum, m/z (%): 538 (M$^+$, 0.3) 316 (39), 203 (100).

The hydrochloride was then obtained as a hygroscopic powder, melting at 75° to 77° C.

EXAMPLE 19'

4(R)-{3-[4-(α-Hydroxydiphenylmethyl)-1-piperidyl]-propylcarbamoyl}-2-(3-pyridyl)thiazolidine The title compound was obtained in a yield in 65% from 1-(3-aminopropyl)-4-(α-hydroxydiphenylmethyl)-piperidine (prepared as described in Preparation 28').

Infrared Absorption Spectrum (CHCl$_3$), $v_{max}$ cm$^{-1}$: 3289, 2942, 1660, 1524.

Mass Spectrum, m/z (%): 516 (M$^+$, 1), 280 (69) 28 (100).

The hydrochloride was then obtained, melting at 110° to 113° C.

EXAMPLE 20'

4(R)-[2-{4-[α-(4-Chlorophenyl)benzyl-1-piperazinyl]-ethylcarbamoyl]-2-(3-pyridyl)thiazolidine

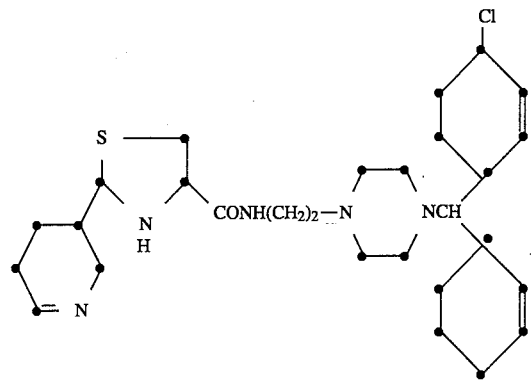

A mixture of 408 mg (1.94 mmole) of 2-(3-pyridyl)-thiazolidine-4(R)-carboxylic acid, 640 mg (1.94 mmole) of 1-(2-aminoethyl)-4-[α-(4-chlorophenyl)benzyl]-piperazine (prepared as described in Preparation 22'). 400 mg (1.94 mmole) of dicyclohexylcarbodiimide, 262 mg (1.94 mmole) of 1-hydroxybenzotriazole and 12 ml of dimethylformamide was stirred overnight at room temperature. At the end of this time, the reaction mixture was diluted with ethyl acetate and insolubles were filtered off. A 5% w/v aqueous solution of sodium hydrogencarbonate was added to the filtrate, and the ethyl acetate layer was separated and concentrated by evaporation under reduced pressure. The resulting residue was subjected to column chromatography through alumina, using ethyl acetate as the eluent, to afford 580 mg (yield 58%) of the title compound as crystals, melting at 157°–159° C. (after recrystallization from ethanol).

Mass Spectrum, m/z (%): 521 (M$^+$, 13), 295 (51), 201 (100).

EXAMPLE 21'

4(R)-{2-[4-(Diphenylmethylene)-1-piperidyl]ethyl-carbamoyl)-2-(3-pyridyl)thiazolidine and its hydrochloride

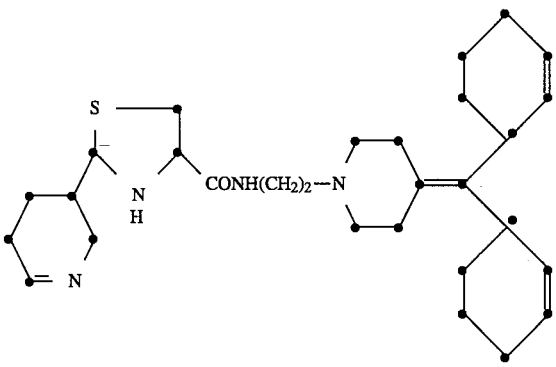

A mixture of 1.1 g (1.88 mmole) of 3-t-butoxy-carbonyl-4(R)-[2-(4-diphenylmethylene-1-piperidyl)-ethylcarbamoyl]-2-(3-pyridyl)thiazolidine (prepared as described in Example 9), 10 ml of a 4N solution of hydrogen chloride in dioxane and 10 ml of methylene chloride was stirred at room temperature for 3 hours. At the end of this time, the reaction mixture was poured into ice water, neutralized by the addition of a 2N aqueous solution of sodium hydroxide and extracted with chloroform. The extract was concentrated by distillation under reduced pressure, and the resulting residue was subjected to column chromatography through silica gel, using a 10 : 2 by volume mixture of chloroform and methanol as the eluent, to afford 1.0 g (a quantitative yield) of the title compound as an oil.

Infrared Absorptio Spectrum (CHCl$_3$), $v_{max}$ cm$^{-1}$: 3250, 2982, 1677, 1265.

Mass Spectrum, m/z (%): 484 (M$^+$, 13), 262 (100).

The oil obtained was dissolved in ethyl acetate and a 4N solution of hydrogen chloride in ethyl acetate was added to the resulting solution. The crystals which precipitated were collected by filtration to afford the hydrochloride of the title compound, melting at 102° to 105° C.

EXAMPLE 22'

4(R)-{3-[4-(Diphenylmethylene)-1-piperidyl]propylcarbamoyl}-2-(3-pyridyl)thiazolidine and its hydrochloride

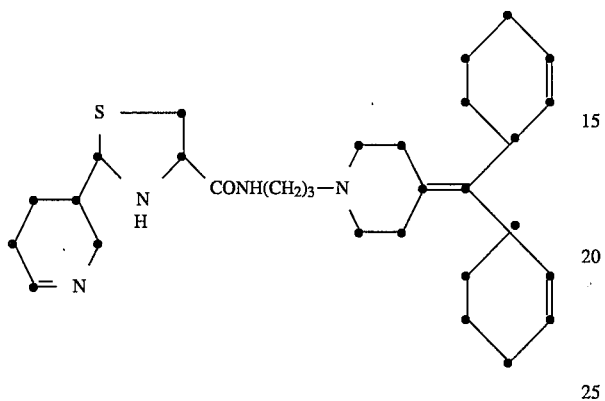

The title compound was obtained in a yield of 68% by following the procedure described in Example 20' and using the same carboxylic acid as was used in Example 20' and 1-(3-aminopropyl)-4-(diphenylmethylene)piperidine (prepared as described in Preparation 15').

Infrared Absorption Spectrum (KBr), $v_{max}$ cm$^{-1}$: 3300, 2942, 1979, 1661.

Mass Spectrum, m/z (%): 498 (M$^+$, 14), 359 (24), 262 (100).

The hydrochloride of the title compound, melting at 140°–142° C. (with decomposition), was obtained in the same manner as described in Example 2'.

EXAMPLE 23'

4(R)-{4-[4-(Diphenylmethylene)-1-piperidyl]butylcarbamoyl}-2-(3-pyridyl) thiazolidine and its hydrochloride

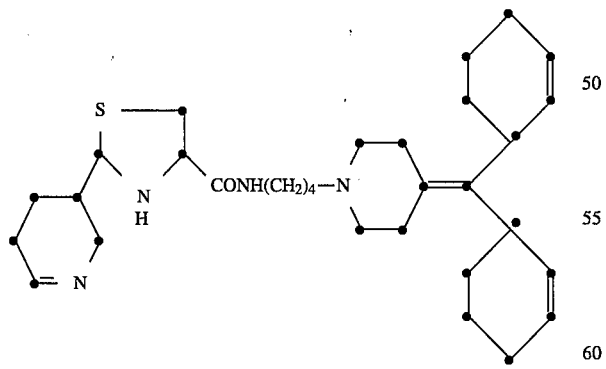

The title compound was obtained in a yield of 46% by following the procedure described in Example 20' and using the same carboxylic acid as was used in Example 20' and 1-(4-aminobutyl)-4-(diphenylmethylene) piperidine (prepared as described in Preparation 25').

Infrared Absorption Spectrum (CHCl$_3$), $v_{max}$ cm$^{-1}$: 3400, 3050, 2960, 1735, 1665, 1530.

Mass Spectrum, m/z (%): 512 (M$^+$, 1) 262 (100).

The hydrochloride of the title compound, melting at 122° to 124° C., was obtained in the same manner as described in Example 2'.

EXAMPLE 24'

4(R)-[5-{4-[Bis(4-fluorophenyl)methyl]-1-piperazinyl)pentylcarbamoyl]-2-(3-pyridinyl)thiazolidine and its hydrochloride

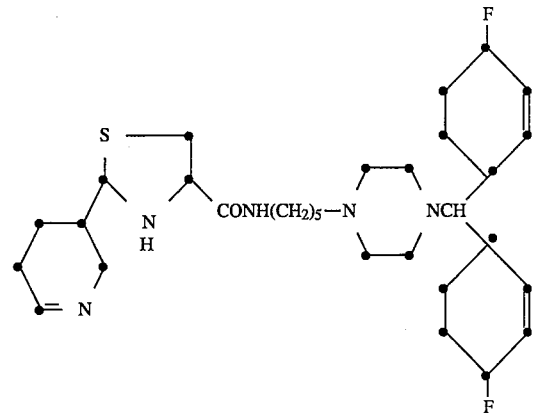

A mixture of 500 mg (2.4 mmole) of 2-(3-pyridyl)thiazolidine-4(R)-carboxylic acid, 900 mg (2.4 mmole) of 1-(5-aminopentyl)-4-[bis(4-fluorophenyl)methyl]piperazine (prepared as described in Preparation 21'), 497 mg (2.4 mmole) of dicyclohexylcarbodiimide, 326 mg (2.4 mmole) of 1-hydroxybenzotriazole and 8 ml of dimethylformamide was stirred overnight at room temperature. At the end of this time, the reaction mixture was diluted with ethyl acetate and insolubles were filtered off. A 0.5N aqueous solution of sodium hydroxide was added to the filtrate, after which the mixture was extracted with ethyl acetate. A 1N aqueous solution of hydrochloric acid was added to the ethyl acetate extract, and the aqueous layer thus obtained was separated and made alkaline by the addition of a 2N aqueous solution of sodium hydroxide. It was then extracted with ethyl acetate. The extract was concentrated by evaporation under reduced pressure, and the resulting residue was subjected to column chromatography through silica gel, using a 20 : 1 by volume mixture of chloroform and methanol as the eluent, to afford 800 mg (yield 60%) of the title compound as an oil.

Infrared Absorption Spectrum (CHCl$_3$), $v_{max}$ cm$^{-1}$: 3400, 2960, 2830, 1745, 1670, 1610, 1505.

Mass Spectrum, m/z (%): 565 (M$^+$, 0.3), 203 (100).

The oil thus obtained was dissolved in ethyl acetate and a 4N solution of hydrogen chloride in ethyl acetate was added to the resulting solution, to afford the hydrochloride of the title compound, melting at 174° to 176° C. (with decomposition).

EXAMPLE 25'

4(R)-[2-{4-[Bis(4-fluorophenyl)-α-hydroxymethyl]-1-piperidyl}ethylcarbamoyl]-2-(3-pyridyl) thiazolidine and its hydrochloride The title compound was prepared in a yield of 42% in a similar manner to that described in Example 17' by reacting 2-(3-pyridyl) thiazolidine-4(R)-carboxylic acid and 1-(2-aminoethyl)-4-[bis(4-fluorophenyl)-α-hydroxymethyl]piperidine (prepared as described in Preparation 55').

Infrared Absorption Spectrum (CHCl$_3$), $v_{max}$ cm$^{-1}$: 3350, 2935, 1660, 1505.

Mass spectrum, m/z (%): 538 (M$^+$, 1), 316 (100), 298 (19).

The hydrochloride of the title compound, melting at 143°–145° C., was prepared in a similar manner to that described in Example 2'.

EXAMPLE 26'

4(R)-[2{4-[Bis(4-fluorophenyl)methylene]-1-piperidyl}ethylcarbamoyl]-2-(3-pyridyl) thiazolidine The title compound, melting at 119°–121° C., was prepared in a yield of 91% in a similar manner to that described in Example 17' by reacting 2-(3-pyridyl)-thiazolidine-4(R)-carboxylic acid and 1-(2-aminoethyl)-4[bis-(4-fluorophenyl)methylene]piperidine (prepared as described in Preparation 56').

Infrared Absorption Spectrum (CHCl$_3$), $v_{max}$ cm$^{-1}$: 3400, 2960, 1675, 1510. Mass spectrum, m/z (%): 520 (M$^+$, 8), 298 (100)

EXAMPLE 27'

4(R)-[5-(4-Diphenylmethylene-1-piperidyl)pentylcarbamoyl]-2-(3-pyridyl) thiazolidine and its hydrochloride The title compound was prepared in a yield of 36% in a similar manner to that described in Example 17' by reacting 2-(3-pyridyl) thiazolidine-4(R)-carboxylic acid and 1-(5-aminopentyl)-4-(diphenylmethylene) piperidine (prepared as described in Preparation 42').

Infrared Absorption Spectrum (CHCl$_3$), $v_{max}$ cm$^{-1}$: 2950, 1670, 1530, 1450.

Mass spectrum, m/z (%): 526 (M$^+$, 4), 262 (100).

The hydrochloride of the title compound, melting at 74°–77° C., was prepared in a similar manner to that described in Example 2'.

EXAMPLE 28'

4(R)-[7-(4-Diphenylmethylene-1-piperidyl)heptylcarbamoyl]-2-(3-pyridyl) thiazolidine The title compound was prepared in a yield of 46% in a similar manner to that described in Example 17' by reacting 2-(3-pyridyl) thiazolidine-4(R)-carboxylic acid and 1-(7-aminoheptyl)-4-(diphenylmethylen) piperidine (prepared as described in Preparation 43').

Infrared Absorption Spectrum (CHCl$_3$), $v_{max}$ cm$^{-1}$: 3400, 2935, 1670, 1525.

Mass spectrum, m/z (%): 554 (M$^+$, 0.3), 262 (100).

EXAMPLE 29'

4(R)-[3-{4-[Bis(4-fluorophenyl) methylene]-1-piperidyl}propylcarbamoyl]-2-(3-pyridyl) thiazolidine and its hydrochloride The title compound was prepared in a yield of 15% in a similar manner to that described in Example 17' by reacting 2-(3-pyridyl) thiazolidine-4(R)-carboxylic acid and 1-(3-aminopropyl)-4-[bis(4-fluorophenyl)methylene]-piperidine (prepared as described in Preparation 57').

Infrared Absorption Spectrum (CHCl$_3$), vmax cm$^{-1}$: 3375, 3275, 2935, 2800, 1655, 1600, 1505.

Mass spectrum, m/z (%), 534 (M$^+$, 18), 395 (31), 298 (100).

The hydrochloride of the title compound, melting at 95°–98° C. (with decomposition), was prepared in a similar manner to that described in Example 2'.

EXAMPLE 30'

4(R)-{3-[4-(α-2-Pyridylbenzyl)-1-piperazinyl]propylcarbamoyl}-2-(3-pyridyl) thiazolidine The title compound was prepared in a yield of 16% in a similar manner to that described in Example 17 by reacting 2-(3-pyridyl) thiazolidine-4(R)-carboxylic acid and 4-[α-(2-pyridyl)benzyl]-1-(3-aminopropyl)piperazine (prepared as described in Preparation 41').

Infrared Absorption Spectrum (CHCl$_3$), $v_{max}$ cm$^{-1}$: 3300, 2960, 2830, 1670, 1590, 1520.

Mass spectrum, m/z (%): 502 (M$^+$, 6), 197 (52), 169 (100).

EXAMPLE 31'

4(R)-{2-[4-(α-3-Pyridylbenzyl)-1-piperazinyl]ethylcarbamoyl}-2-(3-pyridyl) thiazolidine The title compound, melting at 130°–131° C., was prepared in a yield of 56% in a similar manner to that described in Example 17' by reacting 2-(3-pyridyl)thiazolidine-4(R)-carboxylic acid and 1-(2-aminoethyl)-4-[α-(3-pyridyl)benzyl)piperazine (prepared as described in Preparation 58').

Infrared Absorption Spectrum (CHCl$_3$), $v_{max}$ cm$^{-1}$: 3380, 3010, 2970, 2830, 1670, 1580, 1520.

Mass spectrum, m/z (%): 486 (M$^+$–2, 30), 266 (52), 168 (100).

EXAMPLE 32'

4(R)-{2-[4-(α-4-Pyridylbenzyl)-1-piperazinyl]ethylcarbamoyl}-2-(3-pyridyl) thiazolidine The title compound, melting at 160°–162° C., was prepared in a yield of 60% in a similar manner to that described in Example 17' by reacting 2-(3-pyridyl)thiazolidine-4(R)-carboxylic acid and 1-(2-aminoethyl)-4-[α-(4-pyridyl)benzyl]piperazine (prepared as described in Preparation 59').

Infrared Absorption Spectrum (CHCl$_3$), $v_{max}$ cm$^{-1}$: 3400, 3000, 2950, 2830, 1670, 1600, 1520.

Mass spectrum, m/z (%): 488 (M$^+$, 13), 266 (100), 168 (98).

EXAMPLE 33'

4(R)-{2-[4-(α-2-Pyridyl-4-fluorobenzyl)-1-piperazinyl]ethylcarbamoyl}-2-(3-pyridyl) thiazolidine The title compound, melting at 144°–146° C., was prepared in a yield of 71% in a similar manner to that described in Example 17' by reacting 2-(3-pyridyl)thiazolidine-4(R)-carboxylic acid and 1-(2-aminoethyl)-4-[α-(2-pyridyl)-4-fluorobenzyl]piperazine (prepared as described in Preparation 60').

Infrared Absorption Spectrum (CHCl$_3$), $v_{max}$ cm$^{-1}$: 3380, 3000, 2950, 2820, 1670, 1605, 1590, 1505.

Mass spectrum, m/z (%): 506 (M$^+$, 10), 215 (46), 186 (100).

EXAMPLE 34'

4(R)-{2-[4-(α-2-Pyridyl-4-trifluoromethylbenzyl)-1-piperazinyl]ethylcarbamoyl}-2-(3-pyridyl)thiazolidine and its hydrochloride The title compound was prepared in a yield of 54% in a similar manner to that described in Example 17' by reacting 2-(3-pyridyl) thiazolidine-4(R)-carboxylic acid and 1-(2-aminoethyl)-4-[α-(2-pyridyl)-4-trifluoromethylbenzyl]piperazine (prepared as described in Preparation 61').

Infrared Absorption Spectrum (CHCl$_3$), $v_{max}$ cm$^{-1}$: 3380, 2960, 2825, 1670, 1590, 1520.

Mass Spectrum, m/z (%): 556 (M$^+$, 18), 265 (71), 236 (100).

The hydrochloride of the title compound, melting at 164°–167° C. (with decomposition), was prepared in a similar manner to that described in Example 2'.

EXAMPLE 35'

4(R)-{2-[4-Bis(4-fluorophenyl)methylene-1-piperidyl]ethylcarbamyol}-3-methyl-2-(3-pyridyl)thiazolidine and its hydrochloride The title compound was prepared in a yield of 82% in a similar manner to that described in Example 17' by reacting 3-methyl-2-(3-pyridyl)thiazolidine-4(R)-carboxylic acid and 1-(2-aminoethyl)-4-[bis(4-fluorophenyl) methylene]piperidine (prepared as described in Preparation 56').

Infrared Absorption Spectrum (CHCl$_3$), $v_{max}$ cm$^{-1}$: 3380, 3120, 3060, 2820, 1670, 1605, 1510.

Mass spectrum, m/z (%): 534 (M$^+$, 18), 298 (100), 179 (29).

The hydrochloride of the title compound, melting at 148°–150° C. (with decomposition), was prepared in a similar manner to that described in Example 2'.

EXAMPLE 36'

4(R)-{2-[4-Bis(4-fluorophenyl)-α-hydroxymethyl-1-piperidyl]ethylcarbamoyl}-3-methyl-2-(3-pyridyl)thiazolidine and its hydrochloride The title compound was prepared in a yield of 57% in a similar manner to that described in Example 17' by reacting 3-methyl-2-(3-pyridyl) thiazolidine-4(R)carboxylic acid and 1-(2-aminoethyl)-[4-bis(4-fluorophenyl)-α-hydroxymethyl] piperidine (prepared as described in Preparation 55').

Infrared Absorption Spectrum (CHCl$_3$), $v_{max}$ cm$^{-1}$: 3360, 2980, 2940, 1665, 1600, 1505.

Mass spectrum, m/z (%): 520 (M$^+$, 3), 316 (100), 123 (22).

The hydrochloride of the title compound, melting at 115°–117° C. (with decomposition), was prepared in a similar manner to that described in Example 2.

EXAMPLE 37'

4(R)-{2-[4-(α-2-Pyridyl)benzyl-1-piperazinyl]ethylcarbamoyl}-3-methyl-2-(3-pyridyl)thiazolidine and its hydrochloride The title compounds was prepared in a yield of 93% in a similar manner to that described in Example 17' by reacting 3-methyl-2-(3-pyridyl)thiazolidine-4(R)-carboxylic acid and 1-(2-aminoethyl)-[4-(α-2-pyridyl)benzyl]piperazine (prepared as described in Preparation 62).

Infrared Absorption Spectrum (CHCl$_3$), $v_{max}$ cm$^{-1}$: 3360, 2980, 2940, 1665, 1600, 1505.

Mass spectrum, m/z (%): 502 (M$^+$, 27), 334 (73), 169 (100).

The hydrochloride of the title compound, melting at 148°–150° C., was prepared in a similar manner to that described in Example 2'.

EXAMPLE 38'

4(R)-{3-[4-(α-2-Thienyl)benzylidene-1-piperidyl]propylcarbamoyl}-2-(3-pyridyl)thiazolidine and its hydrochloride The title compound was prepared in a yield of 47% in a similar manner to that described in Example 17' by reacting 2-(3-pyridyl)thiazolidine-4(R)-carboxylic acid and 1-(3-aminopropyl)-4-[α-(2-thienyl)benzylidene]-piperidine (prepared as described in Preparation 63').

Infrared Absorption Spectrum (CHCl$_3$), $v_{max}$ cm$^{-1}$: 3300, 3000, 2930, 1665, 1520.

Mass spectrum, m/z (%): 504 (M$^+$, 19) 268 (100), 129 (37).

The hydrochloride of the title compound, melting at 133°–135° C. (with decomposition), was prepared in a similar manner to that described in Example 2'.

EXAMPLE 39'

4(R)-{N-[2-(4-Diphenylmethyl-1-piperazinyl]ethyl)-N-methylcarbamoyl}-2-3-pyridyl)thiazolidine and its hydrochloride The title compound was prepared in a yield of 46% in a similar manner to that described in Example 17' by reacting 2-(3-pyridyl)thiazolidine-4(R)-carboxylic acid and 4-diphenylmethyl-1-[2-(N-methylamino)ethyl]-piperazine (prepared as described in Preparation 36').

Infrared Absorption Spectrum (CHCl$_3$), $v_{max}$ cm$^{-1}$: 3320, 3020, 2960, 1650, 1495.

Mass spectrum, m/z (%): 501 (M$^+$, 4), 265 (39), 167 (100).

The hydrochloride of the title compound, melting at 185°–188° C. (with decomposition), was prepared in a similar manner to that described in Example 2'.

EXAMPLE 40'

4(R)-{2-[4-Bis(4-fluorophenyl)methylene-1-piperidyl]ethylcarbamoyl}-2-[5-(2-methylpyridyl)]thiazolidine and its hydrochloride The title compounds was prepared in a yield of 50% in a similar manner to that described in Example 17' by reacting 2-[5-(2-methylpyridyl)]thiazolidine-4(R)-carboxylic acid and 1-(2-aminoethyl)-4-[bis(4-fluorophenyl) methylene]piperidine (prepared as described in Preparation 56').

Infrared Absorption Spectrum (CHCl$_3$), $v_{max}$ cm$^{-1}$: 3200, 2950, 1670, 1605, 1510, 1220.

Mass spectrum, m/z (%): 534 (M$^+$, 10), 298 (100).

The hydrochloride of the title compound, melting at 144°–146° C. (with decomposition), was prepared in a similar manner to that described in Example 2'.

EXAMPLE 41'

4(R)-{3-[4-Bis(4-fluorophenyl)methylene-1-piperidyl]propylcarbamoyl}-2-[5-(2-methylpyridyl)]thiazolidine and its hydrochloride The title compound was prepared in a yield of 33% in a similar manner to that described in Example 17' by reacting 2-[5-(2-methylpyridyl)]thiazolidine-4(R)-carboxylic acid and 1-(3-aminopropyl)-4-[bis(4-fluorophenyl) methylene] piperidine (prepared as described in Preparations 57').

Infrared Absorption Spectrum (CHCl$_3$), $v_{max}$ cm$^{-1}$: 3300, 2950, 1670, 1605, 1510, 1220.

Mass spectrum, m/z (%): 548 (M$^+$, 24), 395 (40) 298 (100).

The hydrochloride of the title compound, melting at 146°–148° C., was prepared in a similar manner to that described in Example 2'.

EXAMPLE 42'

4(R)-{3-(4-Diphenylmethylene-1-piperidyl]propylcarbamoyl}-2-[5-(2-methylpyridyl)]thiazolidine and its hydrochloride The title compound was prepared in a yield of 80% in a similar manner to that described in Example 17' by reacting 2-[5-(2-methylpyridyl)]thiazolidine-4(R)-carboxylic acid and 1-(3-aminopropyl)-4-(diphenylmethylene) piperidine (prepared as described in Preparation 15').

Infrared Absorption Spectrum (CHCl$_3$), $v_{max}$ cm$^{-1}$: 3300, 2950, 1670, 1605, 1525, 1495.

Mass spectrum, m/z (%): 512 (M$^+$, 41), 359 (53) 212 (100).

The hydrochloride of the title compound, melting at 98°–101° C., was prepared in a similar manner to that described in Example 2'.

EXAMPLE 43'

4(R)-[N-{3-[4-Diphenylmethylene-1-piperidyl]-propyl]-N-ethylcarbamyl]-2-(3-pyridyl)thiazolidine and its hydrochloride The title compound was prepared in a yield of 27% in a similar manner to that described in Example 17' by reacting 2-(3-pyridyl)thiazolidine-4(R)-carboxylic acid and 4-diphenylmethylene-1-[3-(N-ethylamino)propyl]-, piperidine (prepared as described in Preparation 32').

Infrared Absorption Spectrum (CHCl$_3$), $v_{max}$ cm$^{-1}$: 3000, 1680, 1640, 1380.

Mass spectrum, m/z (%): 526 (M$^+$, 47), 387 (52) 262 (100).

The hydrochloride of the title compound, melting at 92°–94° C., was prepared in a similar manner to that described in Example 2'.

EXAMPLE 44'

4(R)-[N-{2-[4-Diphenylmethylene-1-piperidyl]-ethyl}-N-methylcarbamoyl]-2-(3-pyridyl)thiazolidine and its hydrochloride The title compound was prepared in a yield of 82% in a similar manner to that described in Example 17' by reacting 2-(3-pyridyl)thiazolidine-4(R)-carboxylic acid and 4-diphenylmethylene-1-[2-(N-methylamino)ethyl]-piperidine (prepared as described in Preparation 30').

Infrared Absorption Spectrum (CHCl$_3$), $v_{max}$ cm$^{-1}$: 3000, 1740, 1640, 1500, 1400.

Mass spectrum, m/z (%): 498 (M$^+$, 8), 262 (100).

The hydrochloride of the title compound, melting at 135°–140° C., was prepared in a similar manner to that described in Example 2'.

EXAMPLE 45'

4(S)-{3-[4-Diphenylmethylene-1-piperidyl]-propylcarbamoyl}-2-(3-pyridyl)thiazolidine-4(S)-carboxylic acid and its hydrochloride The title compound was prepared in a yield of 27% in a similar manner to that described in Example 17' by reacting 2-(3-pyridyl)thiazolidine-4(S)-carboxylic acid (prepared as described in Preparation 29') and 1-(3-aminopropyl)-4-(diphenylmethylene) piperidine (prepared as described in Preparation 15').

Infrared Absorption Spectrum (CHCl$_3$), $v_{max}$ cm$^{-1}$: 3400, 2940, 2710, 1680.

Mass spectrum, m/z (%): 498 (M$^+$, 34) 359 (43), 262 (100).

The hydrochloride of the title compound, melting at 81°–83° C., was prepared in a similar manner to that described in Example 2'.

EXAMPLE 46'

4(R)-[3-(4-Diphenylmethylene-1-piperidyl)propyl-carbamoyl]-2-(4-pyridyl) thiazolidine and its hydrochloride The title compound was prepared in a yield of 15% in a similar manner to that described in Example 17' by reacting 2-(4-pyridyl)thiazolidine-4(R)-carboxylic acid and 1-(3-aminopropyl)-4-(diphenylmethylene) piperidine (prepared as described in Preparation 15').

Infrared Absorption Spectrum (CHCl$_3$), $v_{max}$ cm$^{-1}$: 3050, 2935, 2567, 1665.

Mass spectrum, m/z (%): 496 (M$^+$-2, 50), 359 (39), 262 (100).

The hydrochloride of the title compound, melting at 84°–85° C., was prepared in a similar manner to that described in Example 2'.

EXAMPLE 47'

4(R)-[3-(4-Diphenylmethyl-1-piperidyl)propylcarbamoyl]-2-(3-pyridyl)thiazolidine The title compound, melting at 166°–168° C., was prepared in a yield of 50% in a similar manner to that described in Example 17' by reacting 2-(3-pyridyl)-thiazolidine-4(R)-carboxylic acid and 1-(3-aminopropyl)-4-(diphenylmethyl)piperidine (prepared as described in Preparation 45').

Infrared Absorption Spectrum (CHCl$_3$), $v_{max}$ cm$^{-1}$: 3300, 2960, 1670, 1525.

Mass spectrum, m/z (%): 500 (M$^+$, 1) 264 (100).

PREPARATION 1'

4-(Diphenylmethyl)-1-(3-phthalimidopropyl)piperazine

A mixture of 500 mg (1.98 mmole) of 4-(diphenylmethyl)piperazine, 530 mg (1.98 mmole) of N-(3-bromopropyl)phthalimide, 840 mg (7.92 mmole) of sodium carbonate, 10 mg of sodium iodide and 12 ml of methyl isobutyl ketone was heated under reflux overnight. The reaction mixture was then filtered, and the solvent was removed from the filtrate by evaporation under reduced pressure. The resulting residue was subjected to column chromatography through silica gel, using a 1:1 by volume mixture of ethyl acetate and hexane as the eluent, to afford 830 mg (yield 96%) of the title compound as an oil.

Infrared Absorption Spectrum (CHCl$_3$), $v_{max}$ cm$^{-1}$: 1710, 1395.

PREPARATIONS 2' TO 14'

Using the corresponding cyclic amines, reactions were carried out in the same manner as described in Preparation 1' to obtain the following compounds.

PREPARATION 2'

4-(Diphenylmethyl)-1-(4-phthalimidobutyl)piperazine

The title compound, melting at 125°–129° C., was obtained in a yield of 90%.

Infrared Absorption Spectrum (CHCl$_3$), $v_{max}$ cm$^{-1}$: 1770, 1710, 1495, 1365.

PREPARATION 3'

4-[Bis(4-fluorophenyl)methyl]-1-(2-phthalimidoethyl)-piperazine

The title compound, melting at 125°–126° C., was obtained in a yield of 77%.

Infrared Absorption Spectrum (CHCl$_3$), $v_{max}$ cm$^{-1}$: 1766, 1710, 1507, 1396.

PREPARATION 4'

4-[Bis(4-fluorophenyl)methyl]-1-(3-phthalimidopropyl)-piperazine

The title compound was obtained in a yield of 96%.

Infrared Absorption Spectrum (KBr), $v_{max}$ cm$^{-1}$: 1780, 1710, 1505, 1367.

PREPARATION 5'

4-[Bis(4-fluorophenyl)methyl]-1-(4-phthalimidobutyl)-piperazine

The title compound was obtained in a yield of 85%.

Infrared Absorption Spectrum (CHCl$_3$), $v_{max}$ cm$^{-1}$: 1770, 1710, 1505, 1395.

PREPARATION 6'

4-[Bis(4-fluorophenyl)methyl]-1-(5-phthalimidopentyl)-piperazine

The title compound was obtained in a yield of 70%.

Infrared Absorption Spectrum (CHCl$_3$), $v_{max}$ cm$^{-1}$: 1770, 1710, 1505, 1395.

PREPARATION 7'

4-[α-(4-Chlorophenyl)benzyl]-1-(2-phthalimidoethyl)-piperazine

The title compound was obtained in a yield of 89%.

Infrared Absorption Spectrum (KBr), $v_{max}$ cm$^{-1}$: 1770, 1710, 1396.

PREPARATION 8'

4-[α-(4-Chlorophenyl)benzyl]-1-(3-phthalimidopropyl)-piperidine

The title compound was obtained in a yield of 90%.

Infrared Absorption Spectrum (CHCl$_3$), $v_{max}$ cm$^{-1}$: 1770, 1710, 1395.

PREPARATION 9'

4-(Diphenylmethylene)-1-(2-phthalimidoethyl)piperidine

The title compound, melting at 106°–108° C., was obtained in a yield of 79%.

Infrared Absorption Spectrum (KBr), $v_{max}$ cm$^{-1}$: 1768, 1710, 1397.

PREPARATION 10'

4-(Diphenylmethylene)-1-(3-phthalimidopropyl)piperidine

The title compound, melting at 108°–110° C., was obtained in a yield of 91%.

Infrared Absorption Spectrum (KBr), $v_{max}$ cm$^{-1}$: 1770, 1705, 1403.

PREPARATION 11'

4-(Diphenylmethylene)-1-(4-phthalimidobutyl)piperidine

The title compound, melting at 102°–103° C., was obtained in a yield of 91%.

Infrared Absorption Spectrum (KBr), $v_{max}$ cm$^{-1}$: 1770, 1704, 1393.

PREPARATION 12'

4-[Bis(4-fluorophenyl)methoxy]-1-(2-phthalimidoethyl)-piperidine

The title compound was obtained in a yield of 70%.

Infrared Absorption Spectrum (CHCl$_3$), $v_{max}$ cm$^{-1}$: 1780, 1715, 1610.

Preparation 13'

4-[Bis(4-fluorophenyl)methoxy]-1-(3-phthalimidopropyl)-piperidine

The title compound was obtained in a yield of 95%.

Infrared Absorption Spectrum (CHCl$_3$), $\nu_{max}$ cm$^{-1}$: 1770, 1710, 1510, 1395.

PREPARATION 14'

4-(α-Hydroxy-diphenylmethyl)-1-(3-phthalimidopropyl)-piperidine

The title compound was obtained in a yield of 83%.

Infrared Absorption Spectrum (KBr), $\nu_{max}$ cm$^{-1}$: 1770, 1709, 1396.

PREPARATION 15'

1-(3-Aminopropyl)-4-(diphenylmetylene)piperidine

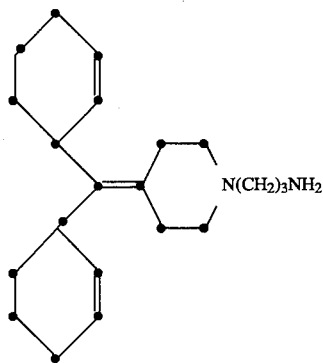

A mixture of 900 mg (2.06 mmole) of 4-(diphenylmethylene)-1-(3-phthalimidopropyl)piperidine (prepared as described in Preparation 10'), 350 mg (7 mmole) of hydrazine hydrate and 20 ml of ethanol was heated under reflux for 2 hours. At the end of this time, the crystals which precipitated were filtered off and the solvent was removed from the filtrate by distillation under reduced pressure, to afford 460 mg (yield 73%) of the title compound as an oil.

Infrared Absorption Spectrum (CHCl$_3$), $\nu_{max}$ cm$^{-1}$: 2950, 2800, 1595, 1490.

PREPARATIONS 16' TO 28'

Using the corresponding phthalimide derivatives and hydrazine hydrate, reactions were carried out in the same manner as described in Preparation 15' to obtain the following compounds.

PREPARATION 16'

1-(3-Aminopropyl)-4-(diphenylmethyl)piperazine

The title compound, melting at 62°–63° C., was obtained in a yield of 22%.

Infrared Absorption Spectrum (KBr), $\nu_{max}$ cm$^{-1}$: 3024, 2949, 2803, 1596, 1450.

PREPARATION 17'

1-(4-Aminobutyl)-4-(diphenylmethyl)piperazine

The title compound was obtained in a quantitative yield.

Infrared Absorption Spectrum (CHCl$_3$), $\nu_{max}$ cm$^{-1}$: 3400, 2950, 2830, 1670, 1600, 1500.

PREPARATION 18'

1-(2-Aminoethyl)-4-[bis(4-fluorophenyl)methyl]piperazine

The title compound was obtained in a yield of 45%.

Infrared Absorption Spectrum (CHCl$_3$), $\nu_{max}$ cm$^{-1}$: 3350, 2820, 1605, 1510.

PREPARATION 19'

1-(3-Aminopropyl)-4-[bis(4-fluorophenyl)methyl]piperazine

The title compound was obtained in a yield of 71%.

Infrared Absorption Spectrum (CHCl$_3$), $\nu_{max}$ cm$^{-1}$: 3350, 2820, 1605, 1510.

PREPARATION 20'

1-(4-Aminobutyl)-4-[bis(4-fluorophenyl)methyl]piperazine

The title compound was obtained in a quantitative yield.

Infrared Absorption Spectrum (CHCl$_3$), $\nu_{max}$ cm$^{-1}$: 3200 (broad), 2930, 2820, 1605, 1505.

PREPARATION 21'

1-(5-Aminopentyl)-4-[bis(4-fluorophenyl)methyl]piperazine

The title compound was obtained in a yield of 93%.

Infrared Absorption Spectrum (CHCl$_3$), $\nu_{max}$ cm$^{-1}$: 3500–3100 (broad), 2940, 2830, 1640, 1605, 1505.

PREPARATION 22'

1-(2-Aminoethyl)-4-[α-(4-chlorophenyl)benzyl]-piperazine

The title compound was obtained in a yield of 89%.

Infrared Absorption Spectrum (CHCl$_3$), $\nu_{max}$ cm$^{-1}$: 3200 (broad), 2950, 2830, 1490.

PREPARATION 23'

1-(3-Aminopropyl)-4-[α-(4-chlorophenyl)benzyl]-piperazine

The title compound was obtained in a yield of 68%.

Infrared Absorption Spectrum (CHCl$_3$), $\nu_{max}$ cm$^{-1}$: 3200, 2950, 2830, 1490.

PREPARATION 24'

1-(2-Aminoethyl)-4-(diphenylmethylene)piperidine

The title compound was obtained in a yield of 42%.

Infrared Absorption Spectrum (CHCl$_3$), $\nu_{max}$ cm$^{-1}$: 3600–3160 (broad), 2950, 2820, 1650, 1595, 1495.

PREPARATION 25'

1-(4-Aminobutyl)-4-(diphenylmethylene)piperidine

The title compound was obtained in a quantitative yield.

Infrared Absorption Spectrum (CHCl$_3$), $v_{max}$ cm$^{-1}$: 3500–3100 (broad), 2940, 1640, 1600, 1570, 1495.

PREPARATION 26'

1-(2-Aminoethyl)-4-[bis(4-fluorophenyl)methoxy]piperidine

The title compound was obtained in a quantitiative yield.

Infrared Absorption Spectrum (CHCl$_3$), $v_{max}$ cm$^{-1}$: 3400, 2970, 1610, 1515.

PREPARATION 27'

1-(3-Aminopropyl)-4-[Bis(4-fluorophenyl)methoxy]-piperidine

The title compound was obtained in a yield of 85%.

Infrared Absorption Spectrum (CHCl$_3$), $v_{max}$ cm$^{-1}$: 3200, 2950, 1610, 1510.

PREPARATION 28'

1-(3-Aminopropyl)-4-(α-hydroxydiphenylmethyl)piperidine

The title compound, melting at 102°–104° C., was obtained in a yield of 93%.

Infrared Absorption Spectrum (KBr), $v_{max}$ cm$^{-1}$: 3348, 3257, 2938, 2816, 1489, 1447.

PREPARATION 29'

2-(3-Pyridyl)thiazolidine-4(S)-carboxylic acid

A solution of 1.07 g of pyridine-3-aldehyde and 1.21 g of D-cysteine in 60% v/v aqueous ethanol was heated under reflux for 4 hours. The mixture was cooled to room temperature and the resulting solid material was removed by filtration. The filtrate was concentrated by evaporation under reduced pressure, and 5 ml of ethanol were added to the resulting residue. Collecting the precipitated crystals by filtration gave 1.13 g (yield 54%) of the title compound, melting at 138°–139° C.

Infrared Absorption Spectrum (KBr), $v_{max}$ cm$^{-1}$: 3260, 2920, 2400, 1720, 1200.

PREPARATION 30'

4-Diphenylmethylene-1-[2-(N-methylamino)-ethyl]piperidine

A solution of 1.13 g of 4-diphenylmethylene-1-(2-N-formamidoethyl)piperidine (prepared as described in Preparation 31') in tetrahydrofuran was added dropwise to a suspension of 140 mg of lithium aluminum hydride in 10 ml of tetrahydrofuran at room temperature under a nitrogen atmosphere, and the mixture was heated under reflux for 1 hour. At the end of this time, the mixture was cooled to room temperature and sodium sulfate decahydrate was added to the mixture to decompose the excess lithium aluminum hydride. The insoluble material was removed by filtration. Ethyl acetate was added to the filtrate, and the mixture was washed with water and with a saturated aqueous solution of sodium chloride, in that order, after which it was dried over anhydrous magnesium sulfate. Evaporation of solvent under reduced pressure gave 830 mg (yield 80%) of the title compound as an oil.

Infrared Absorption Spectrum (CHCl$_3$), $v_{max}$ cm$^{-1}$: 2875, 1500, 1440, 1100.

PREPARATION 31'

4-Diphenylmethylene-1-(2-N-formamidoethyl)piperidine

A solution of 1.0 g of 1-(2-aminoethyl)-4-(diphenylmethylene)piperidine (prepared as described in Preparation 24') in 10 ml of ethyl formate was heated under reflux overnight. At the end of this time, the mixture was cooled to room temperature and the solvent was removed by evaporation under reduced pressure. The residue was purified by column chromatography through silica gel, using a 40:1 by volume mixture of chloroform and methanol as the eluent, to give 1.13 g (a quantitative yield) of the title compound as an oil.

Infrared Absorption Spectrum (CHCl$_3$), $v_{max}$ cm$^{-1}$: 3400, 3000, 1680, 1490.

PREPARATION 32'

4-Diphenylmethylene-1-[3-(N-ethylamino)propyl]-piperidine

A solution of 1.14 g of 1-(3-acetamidopropyl)-4-(diphenylmethylene)piperidine (prepared as described in Preparation 33') in 7 ml of tetrahydrofuran was added dropwise to a suspension of 140 mg of lithium aluminum hydride in 10 ml of tetrahydrofuran at room temperature under a nitrogen atmosphere, and the mixture was heated under reflux for 4 hours. At the end of this time, the mixture was cooled to room temperature, and sodium sulfate decahydrate was added to the mixture to decompose excess lithium aluminum hydride. The insoluble material was removed by filtration. Ethyl acetate was added to the filtrate, and the mixture was washed with water and with a saturated aqueous solution of sodium chloride, in that order, after which it was dried over anhydrous magnesium sulfate. Evaporation of solvent under reduced pressure gave 710 mg (yield 65%) of the title compound as an oil.

Infrared Absorption Spectrum (CHCl$_3$), $v_{max}$ cm$^{-1}$: 2950, 2850, 1500, 1440, 1120.

PREPARATION 33'

1-(3-Acetamidopropyl)-4-(diphenylmethylene)piperidine 680 mg of triethylamine was added to a solution of 1.0 g of 1-(3-aminopropyl)-4-(diphenylmethylene)-piperidine (prepared as described in Preparation 15') in 10 ml of methylene chloride at room temperature; a solution of 680 mg of acetyl chloride in 2 ml of methylene chloride was then added dropwise to it at −10° C., after which the mixture was stirred at the same temperature for 5 minutes. Methylene chloride was then added to the mixturem, which was then washed with water and with a saturated aqueous solution of sodium chloride, in that order, after which it was dried over anhydrous sodium sulfate. Evaporation of the solvent under reduced pressure gave 1.14 g (a quantitative yield) of the title compound as an oil.

Infrared Absorption Spectrum (liquid film), $v_{max}$ cm$^{-1}$: 3350, 2815, 1650, 1537.

PREPARATION 34'

2-(N-Ethoxycarbonyl-N-methylamino)ethyl methanesulfonate 1.65 g of methanesulfonyl chloride was added dropwise, with stirring, to a solution of 1.66 g of 2-(N-ethoxycarbonyl-N-methylamino)ethanol and 1.65 g of triethylamine in 20 ml of methylene chloride, whilst ice-cooling, and the solution was then stirred at the same temperature for 30 minutes. At the end of this time, the mixture was poured into ice-water and extracted with methylene chloride. The extracts were combined and washed with water, after which they were dried over anhydrous sodium sulfate. Evaporation of the solvent under reduced pressure gave a residue which was purified by column chromatography through silica gel, using a 2:1 by volume mixture of ethyl acetate and hexane as the eluent, to give 2.62 g (yield 81%) of the title compound as an oil.

Infrared Absorption Spectrum (CHCl$_3$), $v_{max}$ cm$^{-1}$: 3000, 1750, 1590, 1485.

PREPARATION 35'

4-Diphenylmethyl-1-[2-(N-ethoxycarbonyl-N-methylamino)ethyl]piperazine

A mixture of 0.23 g of 2-(N-ethoxycarbonyl-N-methylamino)ethyl methanesulfonate (prepared as described in Preparation 34') and 0.26 g of 4-diphenylmethylpiperazine was stirred at 80° C. for 5 hours. At the end of this time, the mixture was purified by column chromatography through silica gel, using a 20:1 by volume mixture of ethyl acetate and ethanol as the eluent, to give 0.25 g (yield 64%) of the title compound as an oil.

Infrared Absorption Spectrum (CHCl$_3$), $v_{max}$ cm$^{-1}$: 3010, 2930, 2820, 1750, 1690, 1490.

PREPARATION 36'

4-Diphenylmethyl-1-[2-(N-methylamino)ethyl]piperazine

A solution of 1.6 g of 4-diphenylmethyl-1-[2-(N-ethoxycarbonyl-N-methylamino)ethyl]piperazine (prepared as described in Preparation 35') in 20 ml of a 10% w/v aqueous solution of potassium hydroxide and 20 ml of ethylene glycol was stirred at 140° C. for 20 hours. At the end of this time, the mixture was cooled to room temperature, poured into ice-water and extracted with methylene chloride. The extracts were combined, washed with water and dried over anhydrous sodium sulfate. Evaporation of the solvent under reduced pressure gave 1.14 g (yield 88%) of the title compound as an oil.

Infrared Absorption Spectrum (CHCl$_3$), $v_{max}$ cm$^{-1}$: 2970, 2830, 1610, 1495.

PREPARATION 37'

2-[5-(2-Methylpyridyl)]thiazolidine-4(R)-carboxylic acid

The title compound, melting at 147°–148° C., was prepared in a yield of 81% in a similar manner to that described in Preparation 29' by reacting 2-methyl-5-pyridinealdehyde and L-cysteine.

Infrared Absorption Spectrum (KBr), $v_{max}$ cm$^{-1}$: 3260, 2920, 2420, 1950, 1720, 1610.

PREPARATION 38'

4-[α-(2-Pyridyl)benzyl]-1-(2-cyanoethyl)piperazine 1.05 g of N,N-diisopropyl-N-ethylamine was added, with stirring, to a solution of 2.0 g of 4-[α-(2-pyridyl)benzyl]piperazine and 1.0 g of 3-bromopropionitrile in 20 ml of methylene chloride, whilst ice-cooling, and the mixture was stirred at room temperature for 16 hours. At the end of this time, the mixture was poured into ice-water and extracted with chloroform. The extracts were combined and dried over anhydrous sodium sulfate, after which the solvent as removed by evaporation under reduced pressure. The resulting residue was purified by column chromatography through silica gel, using a 20:1 by volume mixture of ethyl acetate and ethanol as the eluent, to give 2:1 g (yield 88%) of the title compound as crystals, melting at 114°–116° C.

Infrared Absorption Spectrum (CHCl$_3$), $v_{max}$ cm$^{-1}$: 2950, 2825, 2250, 1590, 1575, 1490, 1465, 1455, 1439.

PREPARATION 39'

4-(Diphenylmethylene)-1-(4-cyanobutyl)piperidine

The title compound was prepared in a yield of 50% in a similar manner to that described in Preparation 38' by reacting 4-(diphenylmethylene)piperidine and 4-bromobutylnitrile.

Infrared Absorption Spectrum (CHCl$_3$), $v_{max}$ cm$^{-1}$: 2950, 2850, 1500, 1450.

PREPARATION 40'

4-(Diphenylmethylene)-1-(6-cyanohexyl)piperidine

The title compound was prepared in a yield of 53% in a similar manner to that described in Preparation 38' by reacting 4-(diphenylmethylene)piperidine and 6-bromohexylnitrile.

Infrared Absorption Spectrum (CHCl$_3$), $v_{max}$ cm$^{-1}$: 2930, 2860, 2520, 2240, 1600, 1490.

PREPARATION 41'

4-α-(2-Pyridyl)benzyl]-1-(3-aminopropyl)piperazine

A solution of 2.0 g of 4-[α-(2-pyridyl)benzyl]-1-(2-cyanoethyl) piperazine (prepared as described in Preparation 38') in 30 ml of tetrahydrofuran was added dropwise to a suspension of 0.24 g of lithium aluminum hydride in 30 ml of tetrahydrofuran at 5°–7° C., and the mixture was stirred at room temperature for 30 minutes. At the end of this time, excess lithium aluminum hydride was decomposed by adding a 4% w/v aqueous solution of sodium hydroxide, and the insoluble material was removed by filtration. The filtrate was dried over anhydrous sodium sulfate, and then the solvent was removed by evaporation under reduced pressure, to give 1.8 g (yield 90%) of the title compound as an oil.

Infrared Absorption Spectrum (CHCl$_3$), $v_{max}$ cm$^{-1}$: 3250, 2950, 2825, 1660, 1590.

PREPARATION 42'

1-(5-Aminopentyl)-4-(diphenylmethylene)piperidine

The title compound was prepared in a yield of 36% in a similar manner to that described in Preparation 41' by reacting 4-(diphenylmethylene)-1-(4-cyanobutyl)-piperidine (prepared as described in Preparation 39') and lithium aluminum hydride.

Infrared Absorption Spectrum (CHCl$_3$), $v_{max}$ cm$^{-1}$: 3400, 2950, 1670, 1530, 1450.

PREPARATION 43'

1-(7-Aminoheptyl)-4-(diphenylmethylene)piperidine

The title compound was prepared in a yield of 91% in a similar manner to that described in Preparation 41' by reacting 4-(diphenylmethylene)-1-(6-cyanohexyl)-piperidine (prepared as described in Preparation 40') and lithium aluminum hydride.

Infrared Absorption Spectrum (CHCl$_3$), $v_{max}$ cm$^{-1}$: 3060, 2930, 2850, 2800, 1665, 1595.

PREPARATION 44'

4-Diphenylmethyl-1-(3-phthalimidopropyl)piperidine

A mixture of 1.8 g of 4-diphenylmethylpiperidine, 1.92 g of N-(3-bromopropyl)phthalimide, 3.0 g of sodium carbonate and 20 mg of sodium iodide in 70 ml of methyl isobutyl ketone was heated under reflux for 5 hours. At the end of this time, the mixture was cooled to room temperature and filtered. The filtrate was concentrated by evaporation under reduced pressure, and the resulting residue was purified by column chromatography through silica gel, using a 1:1 by volume mixture of hexane and ethyl acetate as the eluent, to give 3.0 g (yield 95%) of the title compound as crystals, melting at 104°–106° C.

Infrared Absorption Spectrum (CHCl$_3$), $v_{max}$ cm$^{-1}$: 2960, 1775, 1715, 1445, 1400.

PREPARATION 45'

1-(3-Aminopropyl)-4-diphenylmethylpiperidine

A mixture of 2.8 g of 4-diphenylmethyl-1-(3-phthalimidopropyl)piperidine (prepared as described in Preparation 44') and 0.90 g of hydrazine hydrate in 100 ml of ethanol was heated under reflux for 2 hours. At the end of this time, the mixture was cooled to room temperature and filtered. The mixture was concentrated by evaporation under reduced pressure, to give 0.93 g (yield 47%) of the title compound as an oil.

Infrared Absorption Spectrum (CHCl$_3$), $v_{max}$ cm$^{-1}$: 3400, 2970, 1670, 1600, 1495, 1455.

PREPARATION 46'

4-[Bis(4-fluorophenyl)-α-hydroxymethyl]-1-(2-phthalimidoethyl)piperidine

The title compound was prepared in a yield of 78% in a similar manner to that described in Preparation 1' by reacting N-(2-bromoethyl)phthalimide and 4-[bis(4-fluorophenyl)-α-hydroxymethyl]piperidine Infrared Absorption Spectrum (CHCl$_3$), $v_{max}$ cm$^{-1}$: 2940, 2800, 1770, 1710, 1600, 1505.

PREPARATION 47'

4-Diphenylmethylene-1-(2-phthalimidoethyl)piperidine

The title compound was prepared in a yield of 88% in a similar manner to that described in Preparation 1' by reacting N-(2-bromoethyl)phthalimide and 4-diphenylmethylenepiperidine.

Infrared Absorption Spectrum (CHCl$_3$), $v_{max}$ cm$^{-1}$: 2950, 2800, 1770, 1710, 1600, 1505.

PREPARATION 48'

4-[Bis(4-fluorophenyl)methylene]-1-(3-phthalimidopropyl)piperidine

The title compound was prepared in a yield of 97% in a similar manner to that described in Preparation 1' by reacting N-(3-bromopropyl)phthalimide and 4-[bis(4-fluorophenyl)methylene]piperidine.

Infrared Absorption Spectrum (CHCl$_3$), $v_{max}$ cm$^{-1}$: 2950, 2800, 1775, 1715, 1605, 1505.

PREPARATION 49'

4-[α-(3-Pyridyl)benzyl]-1-(2-phthalimidoethyl)piperazine

The title compound was prepared in a yield of 53% in a similar manner to that described in Preparation 1' by reacting N-(2-bromoethyl)phthalimide and 4-[α-(3-pyridyl)benzyl]piperazine.

Infrared Absorption Spectrum (CHCl$_3$), $v_{max}$ cm$^{-1}$: 2950, 2810, 1775, 1710, 1395.

PREPARATION 50'

4-[α-(4-Pyridyl)benzyl]-1-(2-phthalimidoethyl)piperazine

The title compound was prepared in a yield of 77% in a similar manner to that described in Preparation 1' by reacting N-(2-bromoethyl)phthalimide and 4-[α-(4-pyridyl)benzyl]piperazine.

Infrared Absorption Spectrum (CHCl$_3$), $v_{max}$ cm$^{-1}$: 2950, 2820, 1775, 1710, 1595, 1395.

PREPARATION 51'

4-[α-(2-Pyridyl)-4-fluorobenzyl]-1-(2-phthalimidoethyl)piperazine

The title compound was prepared in a yield of 80% in a similar manner to that described in Preparation 1' by reacting N-(2-bromoethyl)phthalimide and 4-[α-(2-pyridyl)-4-fluoronenzyl]piperazine.

Infrared Absorption Spectrum (CHCl$_3$), $v_{max}$ cm$^{-1}$: 2900, 1625, 1595, 1575.

PREPARATION 52'

4-[α-(2-Prydiyl)-4-trifluoromethylbenzyl]-1-(2-phthalimidoethyl)piperazine

The title compound was prepared in a yield of 87% in a similar manner to that described in Preparation 1' by reacting N-(2-bromoethyl)phthalimide and 4-[α-(2-pyridyl)-4-trifluoromethylbenzyl]piperazine.

Infrared Absorption Spectrum (CHCl$_3$), $v_{max}$ cm$^{-1}$: 2960, 2830, 1775, 1715, 1595, 1330.

PREPARATION 53'

4-[α-(2-Pyridyl)benzyl]-1-(2-phthalimidoethyl)piperazine

The title compound, melting at 114°–117° C., was prepared in a yield of 90% in a similar manner to that described in Preparation 1' by reacting N-(2-bromoethyl)-phthalimide and 4-[α-(2-pyridyl)benzyl]piperazine.

Infrared Absorption Spectrum (CHCl$_3$), $v_{max}$ cm$^{-1}$: 2950, 2800, 1780, 1710, 1590, 1400.

PREPARATION 54'

4-[α-(2-Thienyl)benzylidene]-1-(3-phthalimidopropyl)piperidine

The title compound was prepared in a yield of 84% in a similar manner to that described in Preparation 1' by reacting N-(3-bromopropyl)phthalimide and 4-[α-(2-thienyl)benzylidene]piperidine.

Infrared Absorption Spectrum (CHCl$_3$), $v_{max}$ cm$^{-1}$: 3000, 2940, 2900, 2805, 1595, 1490, 1440.

PREPARATION 55'

1-(2-Aminoethyl)-4-[bis(4-fluorophenyl)-α-hydroxymethyl]piperidine

The title compound was prepared in a yield of 98% in a similar manner to that described in Preparation 15 by reacting 4-[bis(4-fluorophenyl)-α-hydroxymethyl]-1-(2-phthalimidoethyl)piperidine (prepared as described in Preparation 46) and hydrazine hydrate.

Infrared Absorption Spectrum (CHCl$_3$), $v_{max}$ cm$^{-1}$: 2950, 2810, 1605, 1505.

PREPARATION 56'

1-(2-Aminoethyl)-4-[bis(4-fluorophenyl)-methylene]piperidine

The title compound was prepared in a yield of 97% in a similar manner to that described in Preparation 15 by reacting 4-[bis(4-fluorophenyl)methylene]-1-(2-phthalimidoethyl)piperidine and hydrazine hydrate.

Infrared Absorption Spectrum (CHCl$_3$), $v_{max}$ cm$^{-1}$: 2950, 2810, 1605, 1505.

PREPARATION 57'

1-(3-Aminopropyl)-4-[bis(4-fluorophenyl)-methylene]piperidine

The title compound was prepared in a yield of 20% in a similar manner to that described in Preparation 15' by reacting 4-[bis(4-fluorophenyl)methylene]-1-(3-phthalimidopropyl)piperidine (prepared as described in Preparation 48') and hydrazine hydrate.

Infrared Absorption Spectrum (CHCl$_3$), $v_{max}$ cm$^{-1}$: 3370, 3270, 3170, 2940, 2820, 1660, 1605, 1505.

PREPARATION 58'

1-(2-Aminoethyl)-4-[α-(3-pyridyl)benzyl]piperazine

The title compound was prepared in a yield of 98% in a similar manner to that described in Preparation 15' by reacting 4-[α-(3-pyridyl)benzyl]-1-(2-phthalimidoethyl)piperazine (prepared as described in Preparation 49') and hydrazine hydrate.

Infrared Absorption Spectrum (CHCl$_3$), $v_{max}$ cm$^{-1}$: 3380, 3300, 3200, 2970, 2830, 1670, 1605, 1590, 1580.

PREPARATION 59'

1-(2-Aminoethyl)-4-[α-(4-pyridyl)benzyl]piperazine

The title compound was prepared in a quantitative yield in a similar manner to that described in Preparation 15' by reacting 4-[α-(4-pyridyl)benzyl]-1-(2-phthalimidoethyl)piperazine (prepared as described in Preparation 50') and hydrazine hydrate.

Infrared Absorption Spectrum (CHCl$_3$), $v_{max}$ cm$^{-1}$: 3380, 3300, 3200, 2970, 2830, 1670, 1600.

PREPARATION 60'

1-(2-Aminoethyl)-4-[α-(2-pyridyl)-4-fluorobenzyl]piperazine

The title compound was prepared in a yield of 88% in a similar manner to that described in Preparation 15' by reacting 4-[α-(2-pyridyl)-4-fluorobenzyl]-1-(2-phthalimidoethyl)piperazine (prepared as described in Preparation 51') and hydrazine hydrate.

Infrared Absorption Spectrum (CHCl$_3$), $v_{max}$ cm$^{-1}$: 3380, 3300, 3200, 2970, 2830, 1610.

PREPARATION 61'

1-(2-Aminoethyl)-4-[α-(2-pyridyl)-4-trifluoromethylbenzyl]piperazine

The title compound was prepared in a quantitative yield in a similar manner to that described in Preparation 15' by reacting 4-[α-(2-pyridyl)-4-trifluoromethylbenzyl]-1-(2-phthalimidoethyl)piperazine (prepared as described in Preparation 52') and hydrazine hydrate.

Infrared Absorption Spectrum (CHCl$_3$), $v_{max}$ cm$^{-1}$: 3380, 3300, 3200, 2960, 2830, 1620.

PREPARATION 62'

1-(2-Aminoethyl)-4-[α-(2-pyridyl)benzyl]piperazine

The title compound was prepared in a yield of 52% in a similar manner to that described in Preparation 15' by reacting 4-[α-(2-pyridyl)benzyl]-1-(2-phthalimido-ethyl)piperazine (prepared as described in Preparation 53') and hydrazine hydrate.

Infrared Absorption Spectrum (CHCl$_3$), $v_{max}$ cm$^{-1}$: 3400, 3000, 2850, 1640.

PREPARATION 63'

1-(3-Aminopropyl)-4-[α-(2-thienyl)-benzylidene]piperidine

The title compound was prepared in a yield of 92% in a similar manner to that described in Preparation 15' by reacting 4-[α-(2-thienyl)benzylidene]-1-(3-phthalimidopropyl) piperidine (prepared as described in Preparation 54') and hydrazine hydrate.

Infrared Absorption Spectrum (CHCl$_3$), $v_{max}$ cm$^{-1}$: 3200, 3030, 2950, 2800, 1660, 1595.

We claim:
1. A compound of formula (I):

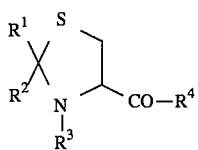

wherein:
R$^1$ represents a pyridyl group which is unsubstituted or is substituted by at least one substituent selected from the group consisting of alkyl groups having from 1 to 4 carbon atoms and alkoxy groups having from 1 to 4 carbon atoms;

R$^2$ represents a hydrogen atom, or a pyridyl group which is unsubstituted or is substituted by at least one substituent selected from the group consisting of alkyl groups having from 1 to 4 carbon atoms and alkoxy groups having from 1 to 4 carbon atoms;

R$^3$ represents a hydrogen atom or an alkyl group having from 1 to 4 carbon atoms;

R$^4$ represents a group of formula (II), (III), (IV), (V) or (VI):

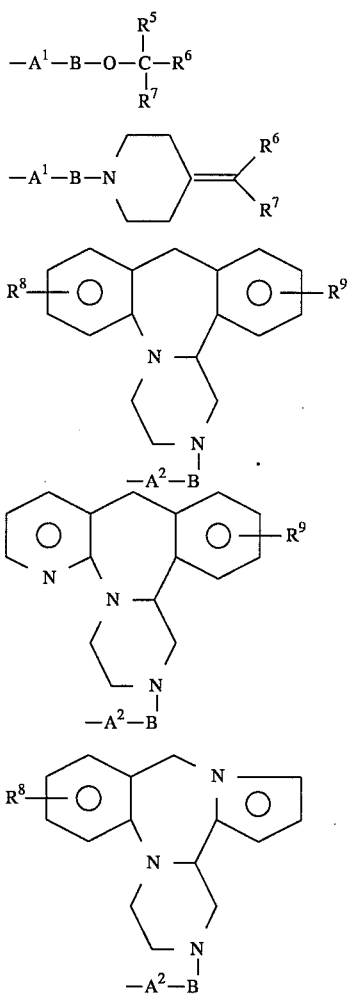

wherein:
R$^5$ represents a hydrogen atom or an alkyl group having from 1 to 4 carbon atoms;

R$^6$ and R$^7$ are independently selected from the group consisting of:
unsubstituted phenyl groups,
substituted phenyl groups which are substituted by at least one substituent selected from the group consisting of alkyl groups having from 1 to 4 carbon atoms, haloalkyl groups having 1 to 4 carbon atoms and having at least one halogen atom, alkoxy groups having from 1 to 4 carbon atoms and halogen atoms,
cycloalkyl groups having from 3 to 6 ring carbon atoms, and
aromatic heterocyclic groups having 5 or 6 ring atoms of which from 1 to 3 are hetero-atoms selected from the group consisting of nitrogen, oxygen and sulfur atoms and the remainder are carbon atoms;

R$^8$ and R$^9$ are independently from the group consisting of hydrogen atoms, alkyl groups having from 1 to 4 carbon atoms, haloalkyl groups having from 1 to 4 carbon atoms and having at least one halogen atom, alkoxy groups having from 1 to 4 carbon atoms, hydroxy groups and halogen atoms;

A$^1$ represents a group of formula (VII) or (VIII):

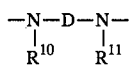

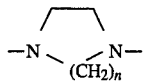

where:
R$^1$ and R$^{11}$ are independently selected from the group consisting of hydrogen atoms and alkyl groups having from 1 to 4 carbon atoms;

D represents an alkylene or alkylidene group having from 2 to 5 carbon atoms; and n is 2 or 3;

A$^2$ represents a group of formula (VIII), above, or (IX):

where R$^{10}$ is as defined above; and

B represents an alkylene or alkylidene group having from 2 to 4 carbon atoms; or —A$^2$—B—represents a single bond;
or a pharmaceutically acceptable salt thereof.

2. The compound of claim 1 wherein R$^4$ is

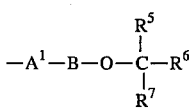

in which the group of formula (X) defined below

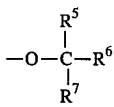

represents a bis(o-, m- or p- fluorophenyl) methoxy, α-(o-, m- or p-chlorophenyl)-benzyloxy, bis(o-, m- or p-fluorophenyl)methoxy, α,α-diphenylmethoxy, α-(o-, m- or p-fluorophenyl)benzyloxy, α-(o-, m- or p-methylphenyl)benzyloxy, α-(2-, 3- or 4-pyridyl)benzyloxy, 4-[α-(2- or 3-thienyl)-α-phenylmethylene]piperidinyl or 4-[α,α-bis(o-, m- or p-fluorophenyl)methylene]-piperidinyl group.

3. The compound of claim 1, wherein $R^4$ represents a group of formula (IV), (V) or (VI), wherein $R^8$, $R^9$, $A^2$ and B are as defined in claim 1.

4. The compound of claim 1, wherein $R^1$ represents a pyridyl group.

5. The compound of claim 1, wherein $R^2$ represents a hydrogen atom, a methyl group or a pyridyl group.

6. The compound of claim 5, wherein $R^2$ represents a hydrogen atom.

7. The compound of claim 1, wherein $R^3$ represents a hydrogen atom or a methyl group.

8. The compound of claim 7, wherein $R^3$ represents a hydrogen atom.

9. The compound of claim 1, wherein $A^1$ represents a group of formula (VII) or (VIII), wherein $R^{10}$ and $R^{11}$ are the same or different, and each represents a methyl group or an ethyl group; D represents an ethylene, trimethylene or tetramethylene group; and n is 2 or 3.

10. The compound of claim 9, wherein $R^{10}$ and $R^{11}$ are the same and each represents a methyl group; D represents an ethylene group or a trimethylene group; and n is 2.

11. The compound of claim 1, wherein B represents an ethylene group or a trimethylene group.

12. The compound of claim 11, wherein B represents an ethylene group.

13. The compound of claim 2, wherein the group of formula (X) represents a bis (4-fluorophenyl) methoxy, α-(4-chlorophenyl)benzyloxy, α-(4-fluorophenyl)-benzyloxy, α-(4-methylphenyl)benzloxy, bis(4-fluorophenyl)methoxy, diphenylmethoxy or α-(2-pyridyl)-benzyloxy group.

14. The compound of claim 1, wherein $R^4$ represents a group of formula (IV) or (VI), wherein $R^8$ and $R^9$ are the same or different, and each represents a hydrogen atom or a halogen atom.

15. The compound of claim 14, wherein $R^4$ represents a group of formula (IV), wherein $R^8$ and $R^9$ are the same or different and each represents a hydrogen atom, a fluorine atom or a chlorine atom.

16. The compound of claim 1, wherein $A^2$ represents a group of formula (IX) or (XI):

—N—         —N     N—
 |                \___/
 $R^{10}$ (IX)            (XI)

wherein $R^{10}$ represents a hydrogen atom or an alkyl group having from 1 to 4 carbon atoms.

17. The compound of claim 16, wherein $A^2$ represents a group of formula (IX), wherein $R^{10}$ represents a hydrogen atom or a methyl group.

18. The compound of claim 1, wherein B represents an ethylene group or a trimethylene group, or —$A^2$—B— represents a single bond.

19. The compound of claim 18, wherein B represents an ethylene group.

20. The compound of claim 1, wherein:

$R^1$ represents a pyridyl group;

$R^2$ represents a hydrogen atom, a methyl group or a pyridyl group;

$R^3$ represents a hydrogen atom or a methyl group;

$A^1$ represents a group of formula (VII) or (VIII), wherein $R^{10}$ and $R^{11}$ are the same or different, and each represent a methyl group or an ethyl group; D represents an ethylene, trimethylene or tetramethylene group; and n is 2 or 3;

B represents an ethylene group or a trimethylene group;

$R^4$ represents a group of formula (IV) or (VI), wherein $R^8$ and $R^9$ are the same or different, and each represents a hydrogen atom or a halogen atom.

21. The compound of claim 1, wherein:

$R^1$ represents a pyridyl group;

$R^2$ represents a hydrogen atom, a methyl group or a pyridyl group;

$R^3$ represents a hydrogen atom or a methyl group;

$A^2$ represents a group of formula (IX) or (XI):

—N—         —N     N—
 |                \___/
 $R^{10}$ (IX)            (XI)

wherein $R^{10}$ represents a hydrogen atom or an alkyl group having from 1 to 4 carbon atoms; and B represents an ethylene group or a trimethylene group, or —$A^2$—B—represents a single bond.

22. The compound of claim 1, wherein $R^4$ represents a group of formula (II) or (III).

23. The compound of claim 1, selected from the group consisting of N-methyl-N-{3-{N-[2-bis(4-fluorophenyl)methoxyethyl]-N-methylamino}propyl}-2-(3-pyridyl)thiazolidine-4-carboxamide and salts thereof.

24. The compound of claim 1, selected from the group consisting of N-methyl-N-{3-[N-(2-diphenylmethoxyethyl)-N-methylamino]propyl}-2-(3-pyridyl)thiazolidine-4-carboxamide and salts thereof.

25. The compound of claim 1, selected from the group consisting of N-methyl-N-{2-[N-(2-diphenylmethoxyethyl)-N-methylamino]ethyl}-2-(3-pyridyl)thiazolidine-4-carboxamide and salts thereof.

26. The compound of claim 1, selected from the group consisting of 1-[2-bis(4-fluorophenyl)methoxyethyl]-4-[2-(3-pyridyl)thiazolidin-4-ylcarbonyl]piperazine and salts thereof.

27. The compound of claim 1, selected from the group consisting of 1-(2-diphenylmethoxyethyl)-4-[2-(3-pyridyl)thiazolidin-4-ylcarbonyl]homopiperazine and salts thereof.

28. The compound of claim 1, selected from the group consisting of 1-{2-[bis(4-fluorophenyl)methoxy]-ethyl}-4-[2-(3-pyridyl)thiazolidin-4-ylcarbonyl]homopiperazine and salts thereof.

29. The compound of claim 1, selected from the group consisting of 1-{2-[α-(4-methylphenyl)benzyloxy]-ethyl}-4-[2-(3-pyridyl)thiazolidin-4-ylcarbonyl]-piperazine and salts thereof.

30. The compound of claim 1, selected from the group consisting of 1-[2-(α-cyclohexylbenzyloxy)ethyl]-4-[2-(3-pyridyl)thiazolidin-4-ylcarbonyl]piperazine and salts thereof.

31. The compound of claim 1, selected from the group consisting of 1-(2-diphenylmethoxyethyl)-4-[2-(3-pyridyl)thiazolidin-4-ylcarbonyl]piperazine and salts thereof.

32. The compound of claim 1, selected from the group consisting of 1-{2-α-(4-chlorophenyl)benzyloxy]-ethyl]-4-[2-(3-pyridyl)thiazolidin-4-ylcarbonyl]-piperazine and salts thereof.

33. The compound of claim 1, selected from the group consisting of 1-[2-(1,1-diphenylethoxy)ethyl]-4-[2-(3-pyridyl)thiazolidin-4-ylcarbonyl]homopiperazine and salts thereof.

34. The compound of claim 1, selected from the group consisting of 1-{2-[1,1-bis(4-fluorophenyl)ethoxy]-ethyl}-4-[2-(3-pyridyl)thiazolidin-4-ylcarbonyl]homopiperazine and salts thereof.

35. The compound of claim 1, selected from the group consisting of 1-[2-(1,1-diphenylethoxy)ethyl]-4-[2-(3-pyridyl)thiazolidin-4-ylcarbonyl]piperazine and salts thereof.

36. The compound of claim 1, selected from the group consisting of 1-{2-[1-(4-chlorophenyl)-1-phenylethoxy]ethyl}-4-[2-(3-pyridyl)thiazolidin-4-ylcarbonyl]piperazine and salts thereof.

37. The compound of claim 1, selected from the group consisting of 1-{2-[1,1-bis(4-fluorophenyl)ethoxy]-ethyl}-4-[2-(3-pyridyl)thiazolidin-4-ylcarbonyl]-piperazine and salts thereof.

38. This compound of claim 1, selected from the group consisting of 1-{2-[4-(diphenylmethylene)-1-piperidinyl]ethyl}-4-[2-(3-pyridyl)thiazolidin-4-ylcarbonyl]piperazine and salts thereof.

39. The compound of claim 1, selected from the group consisting of N-{2-(1,2,3,4,10,14b-hexahydrodibenzo[c,f]pyrazino[1,2-a]azepin-2-yl)ethyl}-2-(3-pyridyl)-thiazolidine-4-carboxamide and salts thereof.

40. The compound of claim 1, selected from the group consisting of N-{2-(1,2,3,4,10,14b-hexahydrodibenzo-[c,f]pyrazino[1,2-a]azepin-2-yl)ethyl}-N-methyl-2-(3-pyridyl)-4-carboxamide and salts thereof.

41. The compound of claim 1, selected from the group consisting of N-{2-(8-fluoro-1,2,3,4,10,14b-hexahydrodibenzo[c,f]pyrazino[1,2-a]azepin-2-yl)ethyl}-2-(3-pyridyl)thiazolidine-4-carboxamide and salts thereof.

42. The compound of claim 1, selected from the group consisting of N-{2-(8-chloro-1,2,3,4,10,14b-hexahydrodibenzo[c,f]pyrazino[1,2-a]azepin-2-yl)ethyl}-2-(3-pyridy)thiazolidine-4-carboxamide and salts thereof.

43. The compound of claim 1, selected from the group consisting of N-{3-(1,2,3,4,10,14b-hexahydrodibenzo[c,f]pyrazino[1,2-a]azepin-2-yl)butyl}-2-(3-pyridyl)-thiazolidine-4-carboxamide and salts thereof.

44. The compound of claim 1, selected from the group consisting of N-{4-(1,2,3,4,10,14b-hexahydrodibenzo-[c,f]pyrazino[1,2-a]azepin-2-yl)butyl}-2-(3-pyridyl)-thiazolidine4-carboxamide and salts thereof.

45. The compound of claim 1, selected from the group consisting of 2-[2-(3-pyridyl)thiazolidin-4-ylcarbonyl]-1,2,3,4,10,14b-hexahydrodibenzo[c,f]pyrazino [1,2-a]-azepine and salts thereof.

46. The compound of claim 1, selected from the group consisting of N-{2-[1,2,3,4,10,14b-hexahydropyrazino-[2,1-a]pyrido[2,3-c][2]benzoazepin-2-yl]ethyl}-2-(3-pyridyl)thiazolidine-4-carboxamide and salts thereof.

47. The compound of claim 1, selected from the group consisting of N-{2-[1,2,3,4,10,14b-hexahydropyrazino[1,2-a]pyrrolo[2,1-c][1,4]benzodiazepin-2-yl]ethyl}-2-(3-pyridyl)thiazolidine-4-carboxamide and salts thereof.

48. The compound of claim 1, selected from the group consisting of 1-{2-[1,2,3,4,10,14b-hexahydrodibenzo[c,f]pyrazino[1,2-a]azepin-2-yl]ethyl}-4-[2-(3-pyridyl)-thiazolidin-4-ylcarbonyl]piperazine and salts thereof.

49. A composition for the treatment or prophylaxis of histamine- or PAF-related disorders in a mammal, which comprises an effective amount of an anti-histamine or anti-PAF agent in admixture with a pharmaceutically acceptable carrier or diluent, wherein the anti-histamine or anti-PAF agent is at least one compound selected from the group consisting of compounds of formula (I) and pharmaceutically acceptable salts thereof, as claimed in claim 1.

50. The composition of claim 49, wherein:

$R^1$ represents a pyridyl group;

$R^2$ represents a hydrogen atom, a methyl group or a pyridyl group;

$R^3$ represents a hydrogen atom or a methyl group;

$A^1$ represents a group of formula (VII) or (VIII), wherein $R^{10}$ and $R^{11}$ are the same or different, and each represent a methyl group or an ethyl group; D represents an ethylene, trimethylene or tetramethylene group; and n is 2 or 3;

B represents an ethylene group or a trimethylene group;

$R^4$ represents a group of formula (IV) or (VI), wherein $R^8$ and $R^9$ are the same or different, and each represents a hydrogen atom or a halogen atom.

51. The composition of claim 49, wherein:

$R^1$ represents a pyridyl group;

$R^2$ represents a hydrogen atom, a methyl group or a pyridyl group;

$R^3$ represents a hydrogen atom or a methyl group;

$A^2$ represents a group of formula (IX) or (XI):

$$-\underset{R^{10}}{N}- \qquad -N\diagup\!\diagdown N-$$

(IX)        (XI)

wherein $R^{10}$ represents a hydrogen atom or an alkyl group having from 1 to 4 carbon atoms; and B represents an ethylene group or a trimethylene group, or —$A^2$—B—represents a single bond.

52. The composition of claim 49, wherein said anti-histamine or anti-PAF agent is selected from the group consisting of:

N-methyl-N-{3-{N-[2-bis(4-fluorophenyl)methoxyethyl]-N-methylamino}propyl}-2-(3-pyridyl)thiazolidine-4-carboxamide;

N-methyl-N-{3-[N-(2-diphenylmethoxyethyl)-N-methylamino]propyl}-2-(3-pyridyl)thiazolidine-4-carboxamide;

N-methyl-N-{2-[N-(2-diphenylmethoxyethyl)-N-methylamino]ethyl}-2-(3-pyridyl)thiazolidine-4-carboxamide;

1-[2-bis(4-fluorophenyl)methoxyethyl]-4-[2-(3-pyridyl)-thiazolidin-4-ylcarbonyl]piperazine;

1-[2-diphenylmethoxyethyl)-4-[2-(3-pyridyl)thiazolidin-4-ylcarbonyl]homopiperazine;

1-{2-[bis(4-fluorophenyl)methoxy]ethyl}-4-[2-(3-pyridyl)thiazolidin-4-ylcarbonyl]homopiperazine;

1-{2-[α-(4-methylphenyl)benzyloxy]ethyl}-4-[2-(3-pyridyl)thiazolidin-4-ylcarbonyl]piperazine;

1-[2-(α-cyclohexylbenzyloxy)ethyl]-4-[2-(3-pyridyl)thiazolidin-4-ylcarbonyl]piperazine;

1-t 2-diphenylmethoxyethyl)-4-[2-(3-pyridyl)thiazolidin-4-ylcarbonyl]piperazine;

1-{2-[α-(4-chlorphenyl)benzyloxy]ethyl}-4-[2-(3-pyridyl)thiazolidin-4-ylcarbonyl]piperazine;

1-[2-(1,1-diphenylethoxy)ethyl]-4-[2-(3pyridyl)thiazoli-
din-4-ylcarbonyl]homopiperazine;

1-{2-[1,1-bit(4-fluorophenyl)ethoxy]ethyl}-4-[2-(3-py-
ridyl)thiazolidin-4-ylcarbonyl]homopiperazine;

1-[2-(1,1-diphenylethoxy)ethyl]-4-[2-(3-pyridyl)thiazoli-
din-4-ylcarbonyl]piperazine;

1-{2-[1-(4-chlorophenyl)-1-phenylethoxy]ethyl}-4-[2-
(3-pyridyl)thiazolidin-4-ylcarbanyl]piperazine;

1-{2-[1,1-bis(4-fluorophenyl)ethoxy]ethyl}-4-[2-(3-py-
ridyl)thiazolidin-4-ylcarbonyl]piperazine;

1-{2-[4-(diphenylmethylene)-1-piperidinyl]ethyl}-4-[2-
(3-pyridyl)thiazolidin-4-ylcarbonyl]piperazine;

N-{2-(1,2,3,4,10,14b-hexahydrodibenzo[c,f]pyramino-
[1,2-a]azepin-2-yl)ethyl}-2-(3-pyridyl)thiazolidine-4-
carboxamide;

N-{2-(1,2,3,4,10,14b-hexahydrodibenzo[c,f]pyrazine-[1,
2-a]azepin-2-yl)ethyl}-N-methyl-2-(3-pyridyl)thiazo-
lidine-4-carboxamide;

N-{2-(8-fluoro-1,2,3,4,10,14b-hexahydrodibenzo[c,f]-
pyrazino[1,2-a]azepin-2-yl)ethyl}-2-(3-pyridyl)thiazo-
lidine-4-carboxamide;

N-{2-(8-chloro-1,2,3,4,10,14b-hexahydrodibenzo[c,f]-
pyrazino[1,2-a]azepin-2-yl)ethyl}-2-(3-pyridyl)thiazo-
lidine-4-carboxamide;

N-{3-(1,2,3,4,10,14b-hexahydrodibenzo[c,f]pyrazino-[1,
2-a]azepin-2-yl)propyl}-2-(3-pyridyl)thiazolidine-4-
carboxamide;

N-{4-(1,2,3,4,10,14b-hexahydrodibenzo[c,f]pyrazino-[1,
2-a]azepin-2-yl)butyl}-2-(3-pyridyl)thiazolidine-4car-
boxamide;

2-[2-(3-pyridyl)thiazolidin-4-ylcarbonyl]-1,2,3,4,10,14b-
hexahydrodibenzo[c,f]pyrazino[1,2-a]azepine;

N-{2-(1,2,3,4,10,14b-hexahydropyrazino[2,1-a]pyrido-
[2,3-c][2]benzoazepin-2-yl]ethyl}-2-(3-pyridyl)thiazo-
lidine-4-carboxamide;

N-{2-[1,2,3,4,10,14b-hexahydropyrazino[1,2-a]pyrrolo
[2,1-c][1,4]benzodiazepin-2-yl]ethyl}-2-(3-py-
ridyl)thiazolidine-4-carboxamide;

1-{2-[1,2,3,4,10,14b-hexahydrodibenzo[c,f]pyrazino-[1,
2-a]azepin-2-yl]ethyl}-4-[2-(3-pyridyl)thiazolidin-4-
ylcarbonyl]piperazine;

and pharmaceutically acceptable salts thereof.

53. A method for the treatment or prophyaxis of hsita-
mine-related disorders in a mammal, which comprises
administering to said mammal an effective amount of an
anti-histamine, wherein the anti-histamine is at least one
compound selected from the group consisting of compounds
of formula (I) and pharmaceutically acceptable salts thereof,
as claimed in claim 1.

54. The method of claim 53, wherein:

$R^1$ represents a pyridyl group;

$R^2$ represents a hydrogen atom, a methyl group or a pyridyl group;

$R^3$ represents a hydrogen atom or a methyl group;

$A^1$ represents a group of formula (VII) or (VIII), wherein $R^{10}$ and $R^{11}$ are the same or different, and each represent a methyl group of an ethyl group; D represents an ethylene, trimethylene or tetramethylene group; and n is 2 or 3;

B represents an ethylene group or a trimethylene group; and $R^4$ represents a group of formula (IV) or (VI), wherein $R^8$ and $R^9$ are the same or different, and each represents a hydrogen atom or a halogen atom.

55. The method of claim 53, wherein:

$R^1$ represents a pyridyl group;

$R^2$ represents a hydrogen atom, a methyl group or a pyridyl group;

$R^3$ represents a hydrogen atom or a methyl group;

$A^2$ represents a group of formula (IX) or (XI):

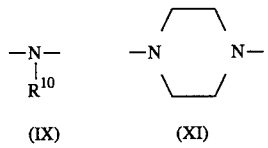

wherein $R^{10}$ represents a hydrogen atom or an alkyl group having from 1 to 4 carbon atoms; and 3 represents an ethylene group or a trimethylene group, or —$A^2$—3—represents a single bond.

56. The method of claim 53, wherein said compound is selected from the group consisting of:

N-methyl-N-{3-{N-[2-bis(4-fluorophenyl)methoxyethyl]
-N-methylamino}propyl}-2-(3-pyridyl)thiazolidine-4-
carboxamide;

N-methyl-N-{3-[N-(2-diphenylmethoxyethyl)-N-methy-
lamino]propyl}-2-(3-pyridyl)thiazolidine-4-carboxam-
ide;

N-methyl-N-{2-[N-(2-diphenylmethoxyethyl)-N-methy-
lamino]ethyl}-2-(3-pyridyl)thiazolidine-4-carboxam-
ide;

1-[2-bis(4-fluorophenyl)methoxyethyl]-4-[2-(3-py-
ridyl)thiazolidin-4-ylcarbonyl]piperazine;

1-(2-diphenylmethoxyethyl)-4-[2-(3-pyridyl)thiazolidin-
4-ylcarbonyl]homopiperazine;

1-{2-[bis(4-fluorophenyl)methoxy]ethoxy}-4-[2-(3-py-
ridyl)thiazolidin-4-ylcarbonyl]homopiperazine;

1-{2-[α-(4-methylphenyl)benzyloxy]ethyl}-4-[2-(3-py-
ridyl)thiazolidin-4-ylcarbonyl]piperazine;

1-[2-(α-cyclohexylbenzyloxy)ethyl]-4-[2-(3-pyridyl)thi-
azolidin-4-ylcarbonyl]piperazine;

1-(2-diphenylmethoxyethyl)-4-[2-(3-pyridyl)thiazolidin-
4-ylcarbonyl]piperazine;

1-{2-[α-(4-chlorophenyl)benzyloxy]ethyl}-4-[2-(3-py-
ridyl)thiazolidin-4-ylcarbonyl]piperazine;

1-[2-(1,1-diphenylethoxy)ethyl]-4-[2-(3-pyridyl)-thiazo-
lidin-4-ylcarbonyl]homopiperazine;

1-{2-[1,1-bis(4-fluorophenyl)ethoxy]ethyl}-4-[2-(3-py-
ridyl)thiazolidin-4-ylcarbonyl]homopiperazine;

1-[2-(1,1-diphenylethoxy)ethyl]-4-[2-(3-pyridyl)-thiaz-
solidin-4-ylcarbonyl]piperazine;

1-{2-[1-(4-chlorophenyl)-1-phenylethoxy]ethyl}-4-[2-
(3-pyridyl)thiazolidin-4-ylcarbonyl]piperazine;

1-{2-[1,1-bis(4-fluorophenyl)ethoxy]ethyl}-4-[2-(3-py-
ridyl)thiazolidin-4-ylcarbonyl]piperazine;

1-{2-[4-(diphenylmethylene)-1-piperidinyl]ethyl}-4-[2-
(3-pyridyl)thiazolidin-4-thiazolidin-4-ylcarbonyl]pip-
erazine;

N-{2-(1,2,3,4,10,14b-hexahydrodibenzo[c,f]pyrazino-[1,
2-a]azepin-2-yl)ethyl}-2-(3-pyridyl)thiazolidine-4-car-
boxamide;

N-{2-(1,2,3,4,10,14b-hexahydrodibenzo[c,f]pyrazino-[1,
2-a]azepin-2-yl)ethyl}-N-methyl-2-(3-pyridyl)-thiazo-
lidine-4-carboxamide;

N-{2-(8-fluoro-1,2,3,4,10,14b-hexahydrodibenzo[c,f]-
pyrazino(1,2-a]azepin-2-yl)ethyl}-2-(3-pyridyl)-thia-
zolidine-4-carboxamide;

N-{2-(8-chloro-1,2,3,4,10,14b-hexahydrodibenzo[c,f]-
pyrazino(1,2-a]azepin-2-yl)ethyl}-2-(3-pyridyl)-thia-
zolidine-4-carboxamide;

N-{3-(1,2,3,4,10,14b-hexahydrodibenzo[c,f]pyrazino-[1,
2-a)azepin-2-yl)propyl}-2-(3-pyridyl)thiazolidine-4-
carboxamide;

N-{4-(1,2,3,4,10,14b-hexahydrodibenzo[c,f]pyrazino-[1,
2-a]azepin-2-yl)butyl}-2-(3-pyridyl)thiazolidine-4-
carboxamide;

2-[2-(3-pyridyl)thiazolidin-4-ylcarbonyl]-1,2,3,4,10,14b-
hexahydrodibenzo[c,f]pyrazino [1,2-a]aszepine;

N-{2-[1,2,3,4,10,14b-hexahydropyrazino[2,1-a]pyrido-
[2,3-c][2]benzoazepin-2-yl]ethyl}-2-(3-pyridyl)-thia-
zolidine-4-carboxamide;

N-{2-[1,2,3,4,10,14b-hexahydropyrazino[1,2-a]pyrrolo-
[2,1-c][1,4]benzodiazepin-2-yl]ethyl}-2-(3-pyridyl)-
thiazolidine-4-carboxamide;

1-{2-[1,2,3,4,10,14-b-hexahydrodibenzo[c,f]pyrazino-[1,
2-a]azepin-2-yl]ethyl}-4-[2-(3-pyridyl)thiazolidin-4-
ylcarbonyl]piperazine;

and pharmaceutically acceptable salts thereof.

57. Compounds of formula (I):

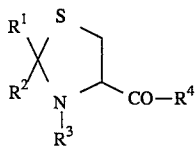

wherein:

$R^1$ represents a pyridyl group which is unsubstituted or is substituted by at least one substituent selected from the group consisting of alkyl groups having from 1 to 4 carbon atoms and alkoxy groups having from 1 to 4 carbon atoms;

$R^2$ represents a hydrogen atom, an alkyl group having from 1 to 4 carbon atoms, or a pyridyl group which is unsubstituted or which is substituted by at least one substituent selected from the group consisting of alkyl groups having from 1 to 4 carbon atoms and alkoxy groups having from 1 to 4 carbon atoms;

$R^3$ represents a hydrogen atom, an alkyl group having from 1 to 4 carbon atoms, an alkoxycarbonyl group having from 2 to 5 carbon atoms, an aralkyloxycarbonyl group in which the alkyl part has from 1 to 4 carbon atoms and the aryl part is as defined below, an aryloxycarbonyl group in which the aryl part is as defined below, an aliphatic carboxylic acyl group having from 1 to 5 carbon atoms, an aliphatic carboxylic acyl group which has from 2 to 5 carbon atoms and which is substituted by at least one halogen atom, an arylcarbonyl group in which the aryl part is as defined below, an alkylsulfonyl group having from 1 to 4 carbon atoms, an arylsulfonyl group in which the aryl part is as defined below, or a group formula -B'-NR$^{5'}$R$^{6'}$, in which B' represents an alkylene or alkylidene group having from 2 to 4 carbon atoms; and R$^{5'}$ and R$^{6'}$ are independently selected from the group consisting of hydrogen atoms and alkyl groups having from 1 to 4 carbon atoms;

said aryl groups have from 6 to 10 ring atoms and are unsubstituted or are substituted by at least one substituent selected from the group consisting of alkyl groups having from 1 to 4 carbon atoms, alkoxy groups having from 1 to 4 carbon atoms and halogen atoms;

$R^4$ represents a group of formula (VI)':

R$^{4'}$ represents a hydrogen atom or an alkyl group having from 1 to 4 carbon atoms;

A' represents an alkylene or alkylidene group having from 2 to 7 carbon atoms; and Z' represents a group of formula:

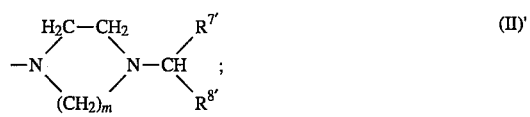

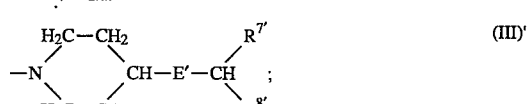

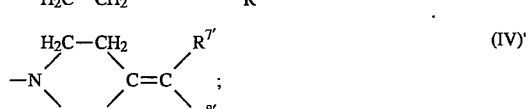

or

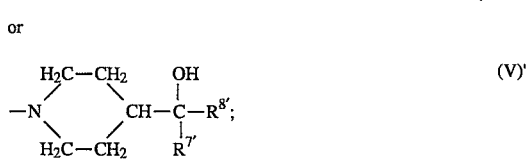

or a group of formulae (II)', (III)', (IV)' or (V)' in which one or more of the ring atoms is substituted by an alkyl group having from 1 to 4 carbon atoms;

in which:

R$^{7'}$ and R$^{8'}$ are independently selected from the group consisting of unsubstituted phenyl groups, substituted phenyl groups which are substituted by at least one substituent selected from the group consisting of substituents (a), defined below, and aromatic heterocyclic groups which have 5 or 6 ring atoms of which 1 or 2 are hetero-atoms selected from the group consisting of nitrogen, oxygen and sulfur heteroatoms, said aromatic heterocyclic groups being unsubstituted or being substituted by at least one substituent selected from the group consisting of substituents (a), defined below;

said substituents (a) are selected from the group consisting of alkyl groups having from 1 to 4 carbon atoms, alkoxy groups having from 1 to 4 carbon atoms, halogen atoms and haloalkyl groups having from 1 to 4 carbon atoms;

E' represents a direct carbon-carbon single bond or an oxygen atom; and m is 2 or 3;

or a pharmaceutically acceptable salt thereof.

58. The compound of claim 57 wherein $R^1$ represents an unsubstituted pyridyl group or a substituted pyridyl group having at least one substituent selected from the group consisting of alkyl groups which have from 1 to 4 carbon atoms.

59. The compound of claim 57, wherein $R^2$ represents a hydrogen atom.

60. The compound of claim 57, wherein $R^3$ represents a hydrogen atom, an alkyl group having from 1 to 4 carbon atoms, an alkoycarbonyl group having from 2 to 5 carbon atoms or an aliphatic carboxylic acyl group having from 1 to 5 carbon atoms.

61. The compound of claim 55, wherein $R^3$ represents a hydrogen atom.

62. The compound of claim 57, wherein $R^{4'}$ represents a hydrogen atom.

63. The compound of claim 57, wherein Z' represents a 4-(diphenylmethyl)-1-piperazinyl, 4-[α-(chlorophenyl)benzyl]-1-piperazinyl, 4-[bis(fluorophenyl)-methyl]-1-piperazinyl, 4-[α-(chlorophenyl)-o-, m- or o-fluorobenzyl]-1-piperazinyl, 4-[bis(chlorophenyl)-methyl]-1-piperazinyl, 4-(diphenylmethyl)-1-piperidyl, 4-[bis(fluorophenyl)methyl]-1-piperidyl, 4-[α-(chlorophenyl)benzyl]-1-piperidyl, 4-diphenylmethoxy)-1-piperidyl, 4-[α-(fluorophenyl)benzyloxy]-1-piperidyl, 4-[bis(fluorophenyl)methoxy]-1-piperidyl, 4-[α-(chlorophenyl)benzyloxy]-1-piperidyl, 4-(diphenyl-methylene)-1-piperidyl, 4-[α-(fluorophenyl)benzylidene]-1-piperidyl, 4-[bis(fluorophenyl)methylene]-1-piperidyl, 4-[α-(chlorophenyl)benzylidene]-1-piperidyl, 4-(α-hydroxydiphenylmethyl)-1-piperidyl, 4-[α-fluorophenyl)-α-hydroxybenzyl]-1-piperidyl, 4-[bis(fluorophenyl)-α-hydroxymethyl]-1-piperidyl or 4-[α-(chlorophenyl)-α-hydroxybenzyl]-1-piperidyl group.

64. The compound of claim 57, wherein:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 7 carbon atoms; and Z' represents a group of formula (II)', (III)', (IV)' or (V)', as defined in claim 61, in which:

$R^{7'}$ and $R^{8'}$ are independently selected from the group consisting of unsubstituted phenyl groups, substituted phenyl groups which are substituted by at least one substituent selected from the group consisting of substituents (a'), defined below, and aromatic heterocyclic groups which have 5 or 6 ring atoms of which 1 is a hetero-atom selected from the group consisting of nitrogen, oxygen and sulfur hetero-atoms, said aromatic heterocyclic groups being unsubstituted or being substituted by at least one substituent selected from the group consisting of alkyl groups having from 1 to 4 carbon atoms;

said substituents (a') are selected from the group consisting of alkyl groups having from 1 to 4 carbon atoms, halogen atoms and trifluoromethyl groups;

E' represents an oxygen atom; and m is 2.

65. The compound of claim 57, wherein:

$R^1$ represents an unsubstituted pyridyl group;

$R^2$ represents a hydrogen atom;

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a group of formula (II)', (III)', (IV)' or (V)', as defined in claim 61, in which:

$R^{7'}$ and $R^{8'}$ are independently selected from the group consisting of unsubstituted phenyl groups, substituted phenyl groups which are substituted by at least one substituent selected from the group consisting of substituents (a''), defined below, pyridyl groups and thienyl groups;

said substituents (a'') are selected from the group consisting of methyl groups, fluorine atoms and chlorine atoms;

E' represents an oxygen atom; and m is 2.

66. The compound of claim 57, wherein:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 6 carbon atoms; and Z' represents a group of formula (II)', (III)', (IV)' or (V)', in which:

$R^{7'}$ and $R^{8'}$ are independently selected from the group consisting of unsubstituted phenyl groups and substituted phenyl groups which are substituted by at least one substituent selected from the group consisting of substituents (a'''), defined below;

said substituents (a''') are selected from the group consisting of alkyl groups having from 1 to 4 carbon atoms and halogen atoms;

E' represents a direct carbon-carbon single bond or an oxygen atom; and m is 2 or 3.

67. The compound of claim 57, wherein:

$R^1$ represents an unsubstituted pyridyl group;

$R^2$ represents a hydrogen atom;

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a group of formula (II)', (III)', (IV)' or (V)', in which:

$R^{7'}$ and $R^{8'}$ are independently selected from the group consisting of unsubstituted phenyl groups and substituted phenyl groups which are substituted by at least one substituent selected from the group consisting of substituents (a''), defined below;

said substituents (a'') are selected from the group consisting of methyl groups, fluorine atoms and chlorine atoms;

E' represents an oxygen atom; and m is 2.

68. The compound of claim 57, wherein:

$R^1$ represents an unsubstituted pyridyl group;

$R^2$ represents a hydrogen atom;

131

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a 4-[α-(chlorophenyl)benzyl]-1-piperazinyl, 4-[bis(fluorophenyl)methyl]-1-piperazinyl, 4-(diphenylmethylene)-1-piperidyl, 4-[bis(fluorophenyl)-methoxy]-1-piperidyl or 4-(α-hydroxydiphenylmethyl)-1-piperidyl group.

69. The compound of claim 57, selected from the group consisting of {3-[4-bis(4-fluorophenyl)methyl-1-piperazinyl]propylcarbamoyl}-2-(3-pyridyl)thiazolidine and salts thereof.

70. The compound of claim 57, selected from the group consisting of {3-[4-(α-2-pyridylbenzyl)-1-piperazinyl]propylcarbamoyl}-2-(3-pyridyl)thiazolidine and salts thereof.

71. The compound of claim 57, selected from the group consisting of [2-(4-diphenylmethyl-1-piperazinyl)ethyl-carbamoyl]-2-(3-pyridyl)thiazolidine and salts thereof.

72. The compound of claim 57, selected from the group consisting of [3-{4-[α-(4-chlorophenyl)benzyl]-1-piperazinyl}propylcarbamoyl]-2-(3-pyridyl)thiazolidine and salts thereof.

73. The compound of claim 57, selected from the group consisting of [2-{4-[α-(4-chlorophenyl)benzyl]-1-piperazinyl}ethylcarbamoyl]-2-(3-pyridyl)thiazolidine and salts thereof.

74. The compound of claim 57, selected from the group consisting of {3-[4-bis(4-fluorophenyl)methoxy-1-piperidyl]propylcarbamoyl}-2-(3-pyridyl)thiazolidine and salts thereof.

75. The compound of claim 57, selected from the group consisting of {2-[4-(diphenylmethyl)-1-piperidyl]-ethylcarbamoyl}-2-(3-pyridyl)thiazolidine and salts thereof.

76. The compound of claim 57, selected from the group consisting of {3-[4-(diphenylmethylene)-1-piperidyl]-propylcarbamoyl}-2-(3-pyridyl)thiazolidine and salts thereof.

77. The compound of claim 57, selected from the group consisting of {4-[4-(diphenylmethylene)-1-piperidyl]-butylcarbamopyl}-2-(3-pyridyl)thiazolidine and salts thereof.

78. The compound of claim 57, selected from the group consisting of [3-{4-[bis(4-fluorophenyl)methylene]-1-piperidyl}propylcarbamoyl]-2-(3-pyridyl)thiazolidine and salts thereof.

79. The compound of claim 57, selected from the group consisting of }3-[4-(α-2-thienyl)benzylidene-1-piperidyl] propylcarbamoyl}-2-(3-pyridyl)thiazolidine and salts thereof.

80. The compound of claim 57, selected from the group consisting of [N-{3-[4-diphenylmethylene-1-piperidyl]-propyl}-N-ethylcarbamoyl]-2-(3-pyridyl)thiazolidine and salts thereof.

81. The compound of claim 57, selected from the group consisting of [N-{2-[4-diphenylmethylene-1-piperidyl]-ethyl}-N-methylcarbamoyl]-2-(3-pyridyl)thiazolidine and salts thereof.

82. The compound of claim 57, selected from the group consisting of {2-[4-(α-hydroydiphenylmethyl)-1-piperidyl] ethylcarbamoyl}-2-(3-pyridyl)thiazolidine and salts thereof.

83. A composition for the treatment or prophylaxis of histamine- or PAF- related disorders in a mammal, which comprises an effective amount of an anti-histamine or anti-PAF agent in admixture with a pharmaceutically acceptable carrier or diluent, wherein the anti-histamine or anti-PAF agent is at least one compound selected from the group consisting of compounds of formula (I) and pharmaceutically acceptable salts thereof, as claimed in claim 57.

84. The composition of claim 83, wherein:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 7 carbon atoms; and Z' represents a group of formula (II)', (III)', (IV)' or (V)', in which:

$R^{7'}$ and $R^8$ are independently selected from the group consisting of unsubstituted phenyl groups, substituted phenyl groups which are substituted by at least one substituent selected from the group consisting of substituents (a'), defined below, and aromatic heterocyclic groups which have 5 or 6 ring atoms of which 1 is a hetero-atom selected from the group consisting of nitrogen, oxygen and sulfur hetero-atoms, said aromatic heterocyclic groups being unsubstituted or being substituted by at least one substituent selected from the group consisting of alkyl group having from 1 to 4 carbon atoms;

said substituents (a') are selected from the group consisting of alkyl groups having from 1 to 4 carbon atoms, halogen atoms and trifluoromethyl groups;

E' represents an oygen atom; and m is 2.

85. The composition of claim 83, wherein:

$R^1$ represents an unsubstituted pyridyl group;

$R^2$ represents a hydrogen atom;

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a 4-[α-(chlorophenyl)benzyl-1-piperazinyl, 4-[bis(fluorophenyl)methyl]-1-piperazinyl, 4-(diphenylmethylene)-1-piperidyl, 4-[bis(fluorophenyl)-methoxy]-1-piperidyl or 4-(α-hydroxydiphenylmethyl)-1-piperidyl group.

86. The composition of claim 83, wherein the active compound is selected from the group consisting of:

{3-[4-bis(4-fluorophenyl)methyl-1-piperazinyl]-propylcarbamoyl}-2-(3-pyridyl)thiazolidine;

{3-[4-(α-2-pyridylbenzyl)-1-piperazinyl]propylcarbamoyl}-2-(3-pyridyl)thiazolidine;

[2-(4-diphenylmethyl-1-piperazinyl)ethylcarbamoyl]-2-(3-pyridyl)thiazolidine;

[3-{4-[α-(4-chlorophenyl)benzyl]-1-piperazinyl}-propylcarbamoyl]-2-(3-pyridyl)thiazolidine;

[2-{4-[α-(4-chlorophenyl)benzyl]-1-piperazinyl}-ethylcarbamoyl]-2-(3-pyridyl)thiazolidine;

{3-[4-bis(4-fluorophenyl)methoxy-1-piperidyl]propylcarbamoyl}-2-(3-pyridyl)thiazolidine;

{2-[4-(diphenylmethylene)-1-piperidyl]ethylcarbamoyl}-2-(3-pyridyl)thiazolidine;

{3-[4-(diphenylmethylene)-1-piperidyl]propylcarbamoyl}-2-(3-pyridyl)thiazolidine;

{4-[4-(diphenylmethylene)-1-piperidyl]butylcarbamoyl}-2-(3-pyridyl)thiazolidine;

[3-{-4-[bis(4-fluorophenyl)methylene]-1-piperidyl}-propylcarbamoyl]-2-(3-pyridyl)thiazolidine;

{3-[4-(α-2-thienyl)benzylidene-1-piperidyl]propylcarbamoyl}-2-(3-pyridyl)thiazolidine;

[N-{3-[4-diphenylmethylene-1-piperidyl]propyl}-N-ethylcarbamoyl]-2-(3-pyridyl)thiazolidine;

[N-{2-[4-diphenylmethylene-1-piperidyl]ethyl}-N-methylcarbamoyl]-2-(3-pyridyl)thiazolidine; and {2-[4-(α-hydroxydiphenylmethyl)-1-piperidyl]ethylcarbamoyl}-2-(3-pyridyl)thiazolidine;

and salts thereof.

87. A method for the treatment or prophylaxis of histamine-related disorders in a mammal, which comprises administering to said mammal an effective amount of an anti-histamine, wherein the anti-histamine is at least one compound selected from the group consisting of compounds of formula (I) and pharmaceutically acceptable salts thereof, as claimed in claim 57.

88. The method of claim 87, wherein:

$R^1$ represents a pyridyl group which is unsubstituted or which is substituted by at least one substituent selected from the group consisting of alkyl groups having from 1 to 4 carbon atoms;

$R^2$ represents a hydrogen atom;

$R^3$ represents a hydrogen atom, an alkyl group having from 1 to 4 carbon atoms, an alkoxycarbonyl group having from 2 to 5 carbon atoms or an aliphatic carboxylic acyl group having from 1 to 5 carbon atoms;

$R^{4'}$ represents a hydrogen atom or an alkyl group having from 1 to 4 carbon atoms;

A' represents an alkylene or alkylidene group having from 2 to 7 carbon atoms; and Z' represents a group of formula (II)', (III)', (IV)' or (V)', in which:

$R^{7'}$ and $R^{8'}$ are independently selected from the group consisting of unsubstituted phenyl groups, substituted phenyl groups which are substituted by at least one substituent selected from the group consisting of substituents (a'), defined below, and aromatic heterocyclic groups which have 5 or 6 ring atoms of which 1 is a hetero-atom selected from the group consisting of nitrogen, oxygen and sulfur hetero-atoms, said aromatic heterocyclic groups being unsubstituted or being substituted by at least one substituent selected from the group consisting of alkyl groups having from 1 to 4 carbon atoms;

said substituents (a') are selected from the group consisting of alkyl groups having from 1 to 4 carbon atoms, halogen atoms and trifluoromethyl groups;

E' represents an oxygen atom; and m is 2.

89. The method of claim 87, wherein:

$R^1$ represents an unsubstituted pyridyl group;

$R^2$ represents a hydrogen atom;

$R^3$ represents a hydrogen atom;

$R^{4'}$ represents a hydrogen atom or a methyl or ethyl group;

A' represents an alkylene or alkylidene group having from 2 to 4 carbon atoms; and Z' represents a 4-[α-(chlorophenyl)benzyl]-1-piperazinyl, 4-[bis(fluorophenyl)methyl]-1-piperazinyl, 4-(diphenylmethylene)-1-piperidyl, 4-[bis(fluorophenyl)-methoxy]-1-piperidyl or 4-(α-hydroxydiphenylmethyl)-1-piperidyl group.

90. The method of claim 87, wherein the active compound is selected from the group consisting of:

{3-[4-bis(4-fluorophenyl)methyl-1-piperazinyl]-propylcarbamoyl}-2-(3-pyridyl)thiazolidine;

{3-[4-(α-2-pyridylbenzyl)-1-piperazinyl]propylcarbamoyl}-2-(3-pyridyl)thiazolidine;

[2-(4-diphenylmethyl-1-piperazinyl)ethylcarbamoyl]-2-(3-pyridyl)thiazolidine;

[3-{4-[α-(4-chlorophenyl)benzyl]-1-piperazinyl}-propylcarbamoyl]-2-(3-pyridyl)thiazolidine;

[2-{4-[α-(4-chlorophenyl)benzyl]-1-piperazinyl}-ethylcarbamoyl]-2-(3-pyridyl)thiazolidine;

{3-[4-bis(4-fluorophenyl)methoxy-1-piperidyl]propylcarbamoyl}-2(3-pyridyl)thiazolidine;

{2-[4-(diphenylmethylene)-1-piperidyl]ethylcarbamoyl}-2-(3-pyridyl)thiazolidine;

{3-[4-(diphenylmethylene)-1-piperidyl]propylcarbamoyl}-2-(3-pyridyl)thiazolidine;

{4-[4-(diphenylmethylene)-1-piperidyl]butylcarbamoyl}-2-(3-pyridyl)thiazolidine;

[3-{4-[bis(4-fluorophenyl)methylene]-1-piperidyl}-propylcarbamoyl]-2-(3-pyridyl)thiazolidine;

{3-[4-(α-2-thienyl)benzylidene-1-piperidyl]propylcarbamoyl}-2-(3-pyridyl)thiazolidine;

[N-{3-[4-diphenylmethylene-1-piperidyl]propyl}-N-ethylcarbamoyl]-2-(3-pyridyl)thiazolidine;

[N-{2-[4-diphenylmethylene-1-piperidyl]ethyl}-N-methylcarbamoyl]-2-(3-pyridyl)thiazolidine; and {2-[4(α-hydroxydiphenylmethyl)-1-piperidyl]ethylcarbamoyl}-2-(3-pyridyl)thiazolidine;

and salts thereof.

\* \* \* \* \*